United States Patent
Rao et al.

(10) Patent No.: US 11,679,168 B2
(45) Date of Patent: Jun. 20, 2023

(54) CASPASE-3-TRIGGERED MOLECULAR SELF-ASSEMBLING PET PROBES AND USES THEREOF

(71) Applicant: The Board of Trustees of the Leland Stanford Junior University, Palo Alto, CA (US)

(72) Inventors: Jianghong Rao, Palo Alto, CA (US); Yunfeng Cheng, Stanford, CA (US); Min Chen, Stanford, CA (US); Jianghang Xie, Fremont, CA (US); Zixin Chen, Stanford, CA (US)

(73) Assignee: The Board of Trustees of Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/570,228

(22) Filed: Sep. 13, 2019

(65) Prior Publication Data
US 2020/0085980 A1    Mar. 19, 2020

Related U.S. Application Data

(60) Provisional application No. 62/842,173, filed on May 2, 2019, provisional application No. 62/731,469, filed on Sep. 14, 2018.

(51) Int. Cl.
*A61K 51/08* (2006.01)
*C07K 5/113* (2006.01)
*C07K 5/103* (2006.01)

(52) U.S. Cl.
CPC ........... *A61K 51/088* (2013.01); *C07K 5/101* (2013.01); *C07K 5/1021* (2013.01)

(58) Field of Classification Search
CPC ...... A61K 51/00; A61K 51/08; A61K 51/088; A61K 2121/00; A61K 2123/00; A61K 49/00; A61K 49/0021; A61K 49/0056; A61K 49/0032; C07K 5/1021; C07K 5/101; C07K 7/02; C07K 5/081; C07K 5/1013
USPC .......... 424/1.11, 1.49, 1.65, 1.69, 1.81, 1.85, 424/1.89, 9.1, 9.2, 9.3, 9.4, 9.5, 9.6
See application file for complete search history.

(56) References Cited

U.S. PATENT DOCUMENTS

2010/0297009 A1* 11/2010 Olson .................. C07D 401/08
424/490

OTHER PUBLICATIONS

Ye et al, Angew. Chem. Int. Ed., vol. 50, pp. 2275-2279 (Year: 2011).*
Stratech, "Peptide Labeling Reagents", peptide-labeling-reagents.pdf (aatbio.com); pp. 1-48 (Year: 2018).*
Chen, Zixin, et al. "Exploring the Condensation Reaction between Aromatic Nitriles and Amino Thiols To Optimize In Situ Nanoparticle Formation for the Imaging of Proteases and Glycosidases in Cells." Angewandte Chemie 132.8 (2020): 3298-3305.
Lai, Shinn-Liang; et al. "p53 gene status modulates the chemosensitivity of non-small cell lung cancer cells." Journal of biomedical science 7.1 (2000): 64-70.
Blackman, Melissa L; et al. "Tetrazine ligation: fast bioconjugation based on inverse-electron-demand Diels-Alder reactivity." Journal of the American Chemical Society 130.41 (2008): 13518-13519.
Biankin, Andrew V; et al. "Patient-centric trials for therapeutic development in precision oncology." Nature 526.7573 (2015): 361-370.
Vargas, Ashley J.; et al. "Biomarker development in the precision medicine era: lung cancer as a case study." Nature Reviews Cancer 16.8 (2016): 525.
Eisenhauer, Elizabeth A., et al. "New response evaluation criteria in solid tumours: revised RECIST guideline (version 1.1)." European journal of cancer 45.2 (2009): 228-247.
Kummar, Shivaani, et al. "Drug development in oncology: classical cytotoxics and molecularly targeted agents." British Journal of clinical pharmacology 62.1 (2006): 15-26.
Fox, Elizabeth; et al. "Clinical trial design for target-based therapy." The oncologist 7.5 (2002): 401-409.
Venneti, Sriram, et al. "Glutamine-based PET imaging facilitates enhanced metabolic evaluation of gliomas in vivo." Science translational medicine 7.274 (2015): 274ra17-274ra17.
Weber, Wolfgang A. "Assessing tumor response to therapy." J Nucl Med 50.Suppl 1 (2009): 1S-10S.
Rankin, Sheila. "PET/CT for staging and monitoring non small cell lung cancer." Cancer Imaging 8.Spec Iss A (2008): S27.
Weber, Wolfgang A., et al. "Positron emission tomography in non-small-cell lung cancer: prediction of response to chemotherapy by quantitative assessment of glucose use." Journal of Clinical Oncology 21.14 (2003): 2651-2657.
Schelling, M., et al. "Positron emission tomography using [18F] fluorodeoxyglucose for monitoring primary chemotherapy in breast cancer." Journal of Clinical Oncology 18.8 (2000): 1689-1695.
Avril, Stefanie, et al. "18F-FDG PET/CT for monitoring of treatment response in breast cancer." Journal of nuclear medicine: official publication, Society of Nuclear Medicine 57.Suppl 1 (2016): 34S.
Wahl, Richard L., et al. "From RECIST to PERCIST: evolving considerations for PET response criteria in solid tumors." Journal of nuclear medicine: official publication, Society of Nuclear Medicine 50.Suppl 1 (2009): 122S.
Ertay, Türkan, et al. "18F-FDG-PET/CT in Initiation and Progression of Inflammation and Infection." Molecular Imaging and Radionuclide Therapy 26.2 (2017): 47.

(Continued)

*Primary Examiner* — D. L. Jones
(74) *Attorney, Agent, or Firm* — Thomas | Horstemeyer, LLP

(57) ABSTRACT

Embodiments of the synthesis, radiolabeling and biological applications of an activatable tracer that undergoes intramolecular cyclization and aggregation upon activation by cleavage of a blocking moiety are provided. The probes of the disclosure allow for target-controlled self-assembly of small molecules in living subjects for imaging and drug delivery. The aggregated nanoprobes of the disclosure may be detectable optically, by PET detection, magnetic resonance imaging, and the like depending on the detectable reporter attached to the nanoprobe.

3 Claims, 62 Drawing Sheets

(56) References Cited

OTHER PUBLICATIONS

Li, Xiao-Feng, et al. "18F-Fluorodeoxyglucose uptake and tumor hypoxia: revisit 18F-fluorodeoxyglucose in oncology application." Translational oncology 7.2 (2014): 240-247.
Burgman, Paul, et al. "Hypoxia-induced increase in FDG uptake in MCF7 cells." Journal of Nuclear Medicine 42.1 (2001): 170-175.
Hassan, Mohamed, et al. "Apoptosis and molecular targeting therapy in cancer." BioMed research international 2014 (2014).
Blankenberg, Francis G. "In vivo detection of apoptosis." The Journal of Nuclear Medicine 49 (2008): 81S.
Brindle, Kevin. "New approaches for imaging tumour responses to treatment." Nature Reviews Cancer 8.2 (2008): 94-107.
De Saint-Hubert, Marijke, et al. "Molecular imaging of cell death." Methods 48.2 (2009): 178-187.
Okada, Hitoshi, and Tak W. Mak. "Pathways of apoptotic and non-apoptotic death in tumour cells." Nature Reviews Cancer 4.8 (2004): 592-603.
Blankenberg, Francis G., et al. "Imaging of Apoptosis (Programmed Cell Death) with 99mTc Annexin V." (1999).
Kartachova, Marina, et al. "In vivo imaging of apoptosis by 99mTc-Annexin V scintigraphy: visual analysis in relation to treatment response." Radiotherapy and oncology 72.3 (2004): 333-339.
Reshef, Ayelet, et al. "Small-molecule biomarkers for clinical PET imaging of apoptosis." Journal of Nuclear Medicine 51.6 (2010): 837-840.
Grimberg, Hagit, et al. "Monitoring of tumor response to chemotherapy in vivo by a novel small-molecule detector of apoptosis." Apoptosis 14.3 (2009): 257-267.
Reshef, Ayelet, et al. "Molecular imaging of neurovascular cell death in experimental cerebral stroke by PET." Journal of Nuclear Medicine 49.9 (2008): 1520-1528.
Höglund, Johanna, et al. "18F-ML-10, a PET tracer for apoptosis: first human study." Journal of Nuclear Medicine 52.5 (2011): 720-725.
Madar, Igal, et al. "Detection and quantification of the evolution dynamics of apoptosis using the PET voltage sensor 18F-fluorobenzyl triphenyl phosphonium." Journal of Nuclear Medicine 50.5 (2009): 774-780.
Madar, Igai, et al. "Characterization of membrane potential-dependent uptake of the novel PET tracer 18 F-fluorobenzyl triphenylphosphonium cation." European journal of nuclear medicine and molecular imaging 34.12 (2007):2057-2065.
Porter, Alan G.; et al. "Emerging roles of caspase-3 in apoptosis." Cell death & differentiation 6.2 (1999): 99-104.
Bedner, Elzbieta, et al. "Activation of caspases measured in situ by binding of fluorochrome-labeled inhibitors of caspases (FLICA): correlation with DNA fragmentation." Experimental cell research 259.1 (2000): 308-313.
Chen, Delphine L., et al. "Radiolabeled isatin binding to caspase-3 activation induced by anti-Fas antibody." Nuclear medicine and biology 39.1 (2012): 137-144.
Méthot, Nathalie, et al. "A caspase active site probe reveals high fractional inhibition needed to block DNA fragmentation." Journal of Biological Chemistry 279.27 (2004): 27905-27914.
Villa, Pascal; et al. "Caspases and caspase inhibitors." Trends in biochemical sciences 22.10 (1997): 388-393.
Rapic, Sara, et al. "Evaluation of [18 F] CP18 as a Substrate-Based Apoptosis Imaging Agent for the Assessment of Early Treatment Response in Oncology." Molecular Imaging and Biology 19.4 (2017): 560-569.
Doss, Mohan, et al. "Biodistribution and radiation dosimetry of 18F-CP-18, a potential apoptosis imaging agent, as determined from PET/CT scans in healthy volunteers." Journal of Nuclear Medicine 54.12 (2013): 2087-2092.
Ye, Deju, et al. "Bioorthogonal cyclization-mediated in situ self-assembly of small-molecule probes for imaging caspase activity in vivo." Nature chemistry 6.6 (2014): 519.
Shen, Bin, et al. "Positron emission tomography imaging of drug-induced tumor apoptosis with a caspase-triggered nanoaggregation probe." Angewandte Chemie International Edition 52.40 (2013): 10511-10514.
Palner, Mikael, et al. "Preclinical kinetic analysis of the caspase-3/7 PET tracer 18F-C-SNAT: quantifying the changes in blood flow and tumor retention after chemotherapy." Journal of Nuclear Medicine 56.9 (2015): 1415-1421.
Hartshorn, Christopher M., et al. "Nanotechnology strategies to advance outcomes in clinical cancer care." ACS nano 12.1 (2018): 24-43.
Witney, Timothy H., et al. "A systematic comparison of 18F-C-SNAT to established radiotracer imaging agents for the detection of tumor response to treatment." Clinical Cancer Research 21.17 (2015): 3896-3905.
Harvey, E. Newton. "The oxidation-reduction potential of the luciferin-oxyluciferin system." The Journal of general physiology 10.3 (1927): 385-393.
Niitani, Hisanobu; et al. "Cisplatin/carboplatin therapy in non-small cell lung cancer." Oncology 49.Suppl. 1 (1992): 51-56.
Xu, Xiao-Man, et al. "Combined anticancer activity of osthole and cisplatin in NCI-H460 lung cancer cells in vitro." Experimental and therapeutic medicine 5.3 (2013): 707-710.
Hientz, Karin, et al. "The role of p53 in cancer drug resistance and targeted chemotherapy." Oncotarget 8.5 (2017): 8921.
Vogelstein, Bert; et al. "Surfing the p53 network." Nature 408.6810 (2000): 307-310.
Cai, Yang, et al. "The predictive value of ERCC1 and p53 for the effect of panobinostat and cisplatin combination treatment in NSCLC." Oncotarget 6.22 (2015): 18997.
Cai, Lisheng; et al. "Chemistry with [18F] fluoride ion." European Journal of Organic Chemistry 2008.17 (2008): 2853-2873.
Huiban, Mickael, et al. "A broadly applicable [18 F] trifluoromethylation of aryl and heteroaryl iodides for PET imaging." Nature chemistry 5.11 (2013): 941-944.
Jacobson, Orit; et al. "Fluorine-18 radiochemistry, labeling strategies and synthetic routes." Bioconjugate chemistry 26.1 (2015): 1-18.
Shi, Jinjun, et al. "Cancer nanomedicine: progress, challenges and opportunities." Nature Reviews Cancer 17.1 (2017): 20.
Xie, Jinghang, et al. "Differential suppression of the aryl hydrocarbon receptor nuclear translocator-dependent function by an aryl hydrocarbon receptor PAS-A-derived inhibitory molecule." Biochemical pharmacology 88.2 (2014): 253-265.
Litwin, Mark S.; et al. "The diagnosis and treatment of prostate cancer: a review." Jama 317.24 (2017): 2532-2542.
Sathianathen, Niranjan J., et al. "Landmarks in prostate cancer." Nature Reviews Urology 15.10 (2018): 627-642.
Li, Roger, et al. "The use of PET/CT in prostate cancer." Prostate cancer and prostatic diseases 21.1 (2018): 4-21.
Evans, Jaden D., et al. "Prostate cancer-specific PET radiotracers: A review on the clinical utility in recurrent disease." Practical radiation oncology 8.1 (2018): 28-39.
Parimi, Vamsi, et al. "Neuroendocrine differentiation of prostate cancer: a review." American journal of clinical and experimental urology 2.4 (2014): 273.
Sheikhbahaei, Sara, et al. "Prostate-specific membrane antigen (PSMA)-targeted PET imaging of prostate cancer: an update on important ptlfalls." Seminars in nuclear medicine. vol. 49. No. 4. WB Saunders, 2019.
Moghanaki, Drew, et al. "Advances in prostate cancer magnetic resonance imaging and positron emission tomography-computed tomography for staging and radiotherapy treatment planning." Seminars in radiation oncology. vol. 27. No. 1. WB Saunders, 2017.
Li, Xuan; et al. "Amino-terminal protein processing in *Saccharomyces cerevisiae* is an essential function that requires two distinct methionine aminopeptidases." Proceedings of the National Academy of Sciences 92.26 (1995): 12357-12361.
Tucker, L. A., et al. "Ectopic expression of methionine aminopeptidase-2 causes cell transformation and stimulates proliferation." Oncogene 27.28 (2008): 3967-3976.

(56) References Cited

OTHER PUBLICATIONS

Sin, Ny, et al. "The anti-angiogenic agent fumagillin covalently binds and inhibits the methionine aminopeptidase, MetAP-2." Proceedings of the National Academy of Sciences 94.12 (1997): 6099-6103.
Güflith, Eric C., et al. "Molecular recognition of angiogenesis inhibitors fumagillin and ovalicin by methionine aminopeptidase 2." Proceedings of the National Academy of Sciences 95.26 (1998): 15183-15188.
Ingber, Donald, et al. "Synthetic analogues of fumagillin that inhibit angiogenesis and suppress tumour growth." Nature 348.6301 (1990): 555-557.
Cheruvallath, Zacharia, et al. "Discovery of potent, reversible MetAP2 inhibitors via fragment based drug discovery and structure based drug design—Part 1." Bioorganic & Medicinal Chemistry Letters 26.12 (2016): 2774-2778.
Heinrich, Timo, et al. "Discovery and structure-based optimization of next-generation reversible methionine Aminopeptidase-2 (MetAP-2) inhibitors." Journal of medicinal chemistry 62.10 (2019): 5025-5039.
Weidner, Noel, et al. "Tumor angiogenesis correlates with metastasis in invasive prostate carcinoma." The American Journal of pathology 143.2 (1993): 401.
Yamaoka, Masuo, et al. "Angiogenesis inhibitor TNP-470 (AGM-1470) potently inhibits the tumor growth of hormone-independent human breast and prostate carcinoma cell lines." Cancer research 53.21 (1993): 5233-5236.
Goldstein, Andrew S., et al. "Purification and direct transformation of epithelial progenitor cells from primary human prostate." Nature protocols 6.5 (2011): 656-667.
Mickey, Don D., et al. "Heterotransplantation of a human prostatic adenocarcinoma cell line in nude mice." Cancer Research 37.11 (1977): 4049-4058.
Stone, Kenneth R., et al. "Isolation of a human prostate carcinoma cell line (DU 145)." International journal of cancer 21.3 (1978): 274-281.
Sramkoski, R. Michael, et al. "A new human prostate carcinoma cell line, 22Rv1." In Vitro Cellular & Developmental Biology—Animal 35.7 (1999): 403-409.
Arfin, Stuart M., et al. "Eukaryotic methionyl aminopeptidases: two classes of cobalt-dependent enzymes." Proceedings of the National Academy of Sciences 92.17 (1995): 7714-7718.
Bradshaw, Ralph A; et al. "N-terminal processing: the methionine aminopeptidase and Na-acetyl transferase families." Trends in biochemical sciences 23.7 (1998): 263-267.
Agard, Nicholas J; et al. "A strain-promoted [3+ 2] azide-alkyne cycloaddition for covalent modification of biomolecules in living systems." Journal of the American Chemical Society 126.46 (2004): 15046-15047.
Baskin, Jeremy M., et al. "Copper-free click chemistry for dynamic in vivo imaging." Proceedings of the National Academy of Sciences 104.43 (2007): 16793-16797.
Ning, Xinghai, et al. "Visualizing metabolically labeled glycoconjugates of living cells by copper-free and fast Huisgen cycloadditions." Angewandte Chemie 120.12 (2008): 2285-2287.
Nikic, Ivana, et al. "Minimal tags for rapid dual-color live-cell labeling and super-resolution microscopy." Angewandte Chemie International Edition 53.8 (2014): 2245-2249.
Liang, Gaolin; et al. "A biocompatible condensation reaction for controlled assembly of nanostructures in living cells." Nature chemistry 2.1 (2010): 54-60.
Ren, Hongjun, et al. "A biocompatible condensation reaction for the labeling of terminal cysteine residues on proteins." Angewandte Chemie International Edition 48.51 (2009): 9658-9662.
Nguyen, Duy P., et al. "Genetically encoded 1, 2-aminothiols facilitate rapid and site-specific protein labeling via a bio-orthogonal cyanobenzothiazole condensation." Journal of the American Chemical Society 133.30 (2011): 11418-11421.
Ramil, Carlo P., et al. "Sequence-specific 2-cyanobenzothiazole ligation." Journal of the American Chemical Society 138.17 (2016): 5499-5502.
Liang, Gaolin, et al. "Controlled Self-Assembling of Gadolinium Nanoparticles as Smart Molecular Magnetic Resonance Imaging Contrast Agents." Angewandte Chemie International Edition 50.28 (2011): 6283-6286.
Dragulescu-Andrasi, Anca, et al. "Activatable oligomerizable imaging agents for photoacoustic imaging of furin-like activity in living subjects." Journal of the American Chemical Society 135.30 (2013): 11015-11022.
Liu, Shuang, et al. "Oligomeric Hydrogels Self-Assembled from Reduction-Controlled Condensation." Angewandte Chemie International Edition 54.12 (2015): 3639-3642.
Ai, Xiangzhao, et al. "In vivo covalent cross-linking of photon-converted rare-earth nanostructures for tumour localization and theranostics." Nature communications 7.1 (2016): 1-9.
Zheng, Zhen, et al. "Cell environment-differentiated self-assembly of nanofibers." Journal of the American Chemical Society 138.35 (2016): 11128-11131.
Park, Sunny; et al. "High levels of intracellular cysteine promote oxidative DNA damage by driving the fenton reaction." Journal of bacteriology 185.6 (2003): 1942-1950.
Stipanuk, Martha H., et al. "Mammalian cysteine metabolism: new insights into regulation of cysteine metabolism." The Journal of nutrition 136.6(2006): 1652S-1659S.
Ye, Deju, et al. "Controlling intracellular macrocyclization for the imaging of protease activity." Angewandte Chemie 123.10 (2011): 2323-2327.
Ye, Deju, et al. "Redox-triggered self-assembly of gadolinium-based MRI probes for sensing reducing environment." Bioconjugate chemistry 25.8 (2014): 1526-1536.
Ye, Deju, et al. "Caspase-responsive smart gadolinium-based contrast agent for magnetic resonance imaging of drug-induced apoptosis." Chemical science 5.10 (2014): 3845-3852.
Shuhendler, Adam J., et al. "Molecular magnetic resonance imaging of tumor response to therapy." Scientific reports 5.1 (2015): 1-14.
Gao, Yuan, et al. "Imaging enzyme-triggered self-assembly of small molecules inside live cells." Nature communications 3.1 (2012): 1-8.
Bosmann, H. Bruce; et al. "Enzyme activity in invasive tumors of human breast and colon." Proceedings of the National Academy of Sciences 71.5 (1974): 1833-1837.
Debacq-Chainiaux, Florence, et al. "Protocols to detect senescence-associated beta-galactosidase (SA-ßgal) activity, a biomarker of senescent cells in culture and in vivo" Nature protocols 4.12 (2009): 1798.
Bullok, Kristin; et al. "Synthesis and characterization of a small, membrane-permeant, caspase-activatable far-red fluorescent peptide for imaging apoptosis." Journal of medicinal chemistry 48.17 (2005): 5404-5407.
Challapalli, Amarnath, et al. "18F-ICMT-11, a caspase-3-specific PET tracer for apoptosis: biodistribution and radiation dosimetry." Journal of Nuclear Medicine 54.9 (2013): 1551-1556.
Chen, Delphine L., et al. "Imaging caspase-3 activation as a marker of apoptosis-targeted treatment response in cancer." Molecular Imaging and Biology 17.3 (2015): 384-393.
McIlwain, David R.; et al. "Caspase functions in cell death and disease." Cold Spring Harbor perspectives in biology 5.4 (2013): a008656.
Smith, Bryan A.; et al. "Biomarkers and molecular probes for cell death imaging and targeted therapeutics." Bioconjugate chemistry 23.10 (2012): 1989-2006.

\* cited by examiner

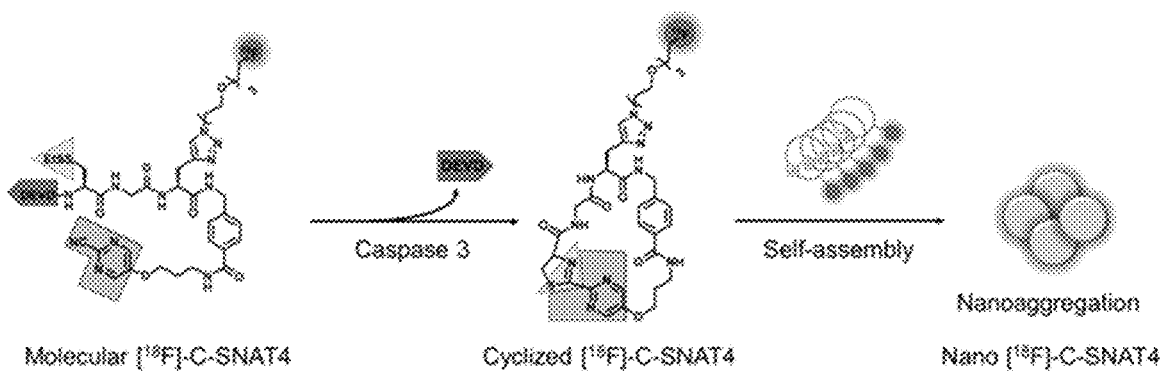
Fig. 1A
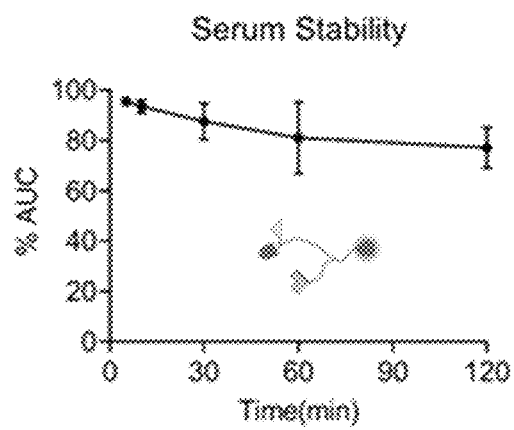
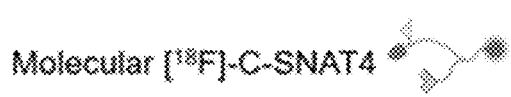
Fig. 1B
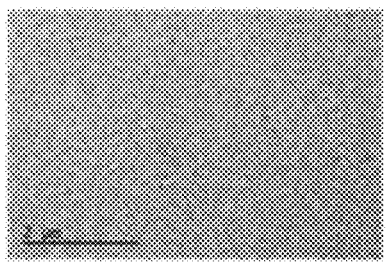
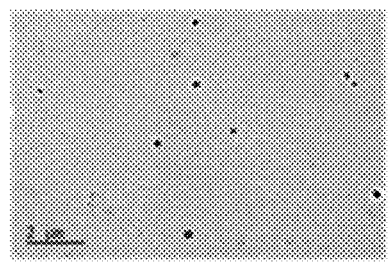
Fig. 1C

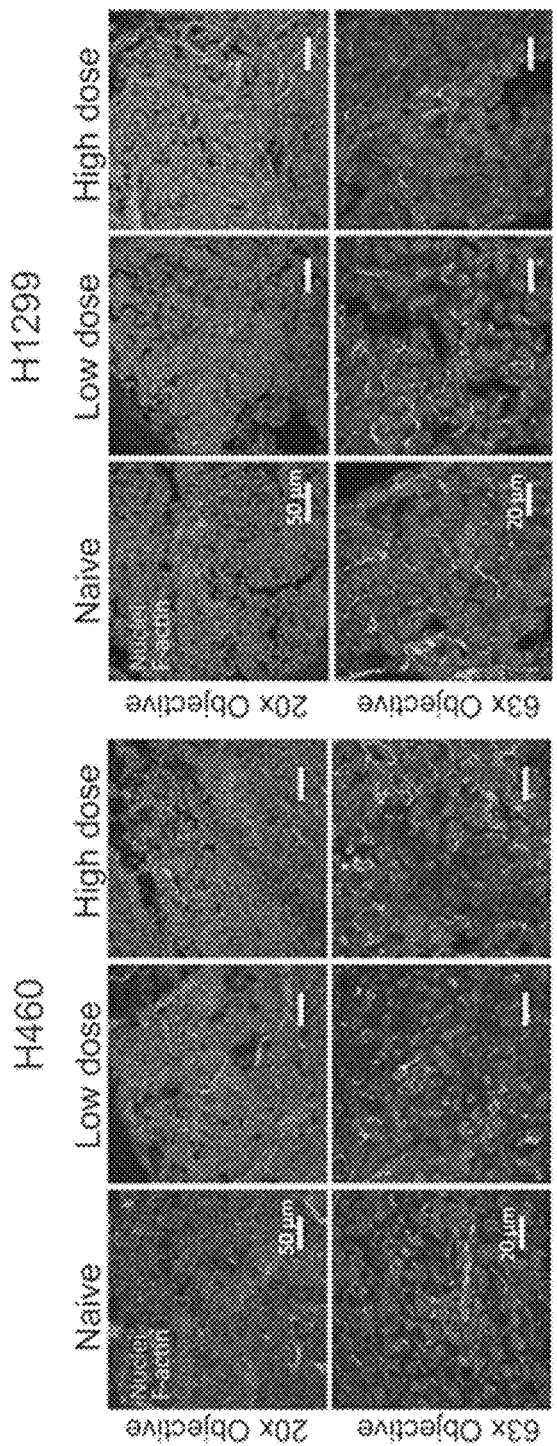
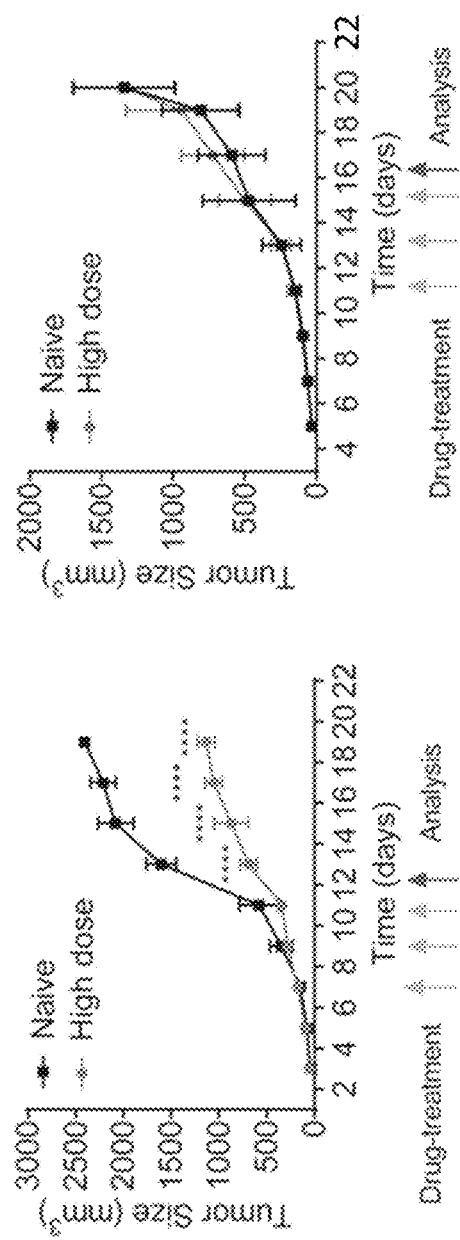
Fig. 5A
Fig. 5B

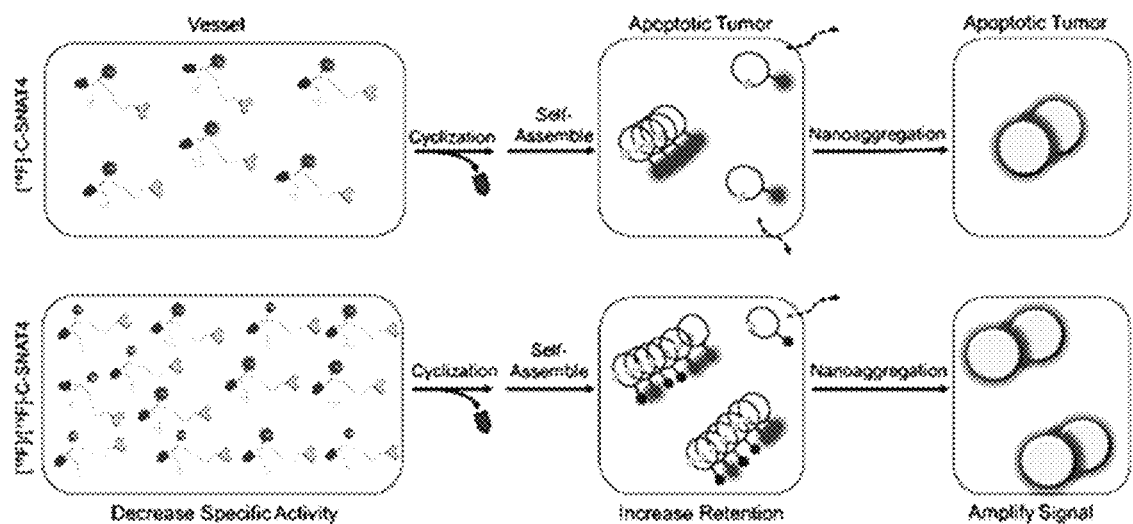
Fig. 6A
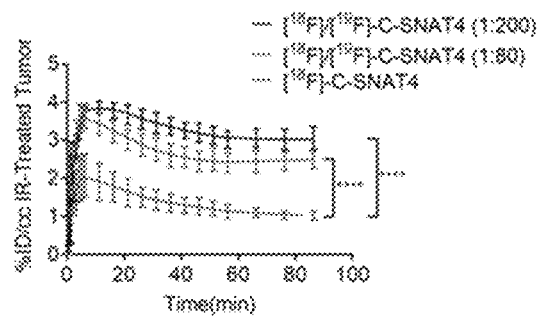
Fig. 6B
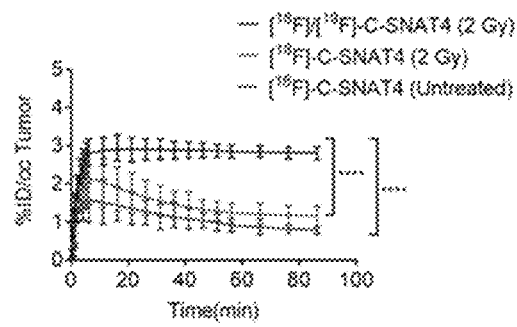
Fig. 6C
Fig. 6D
Fig. 6E

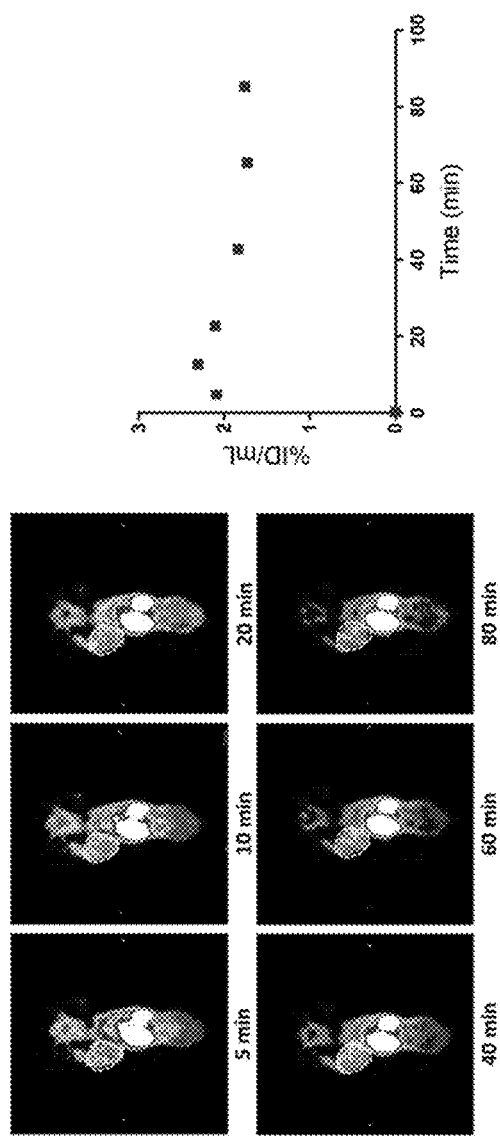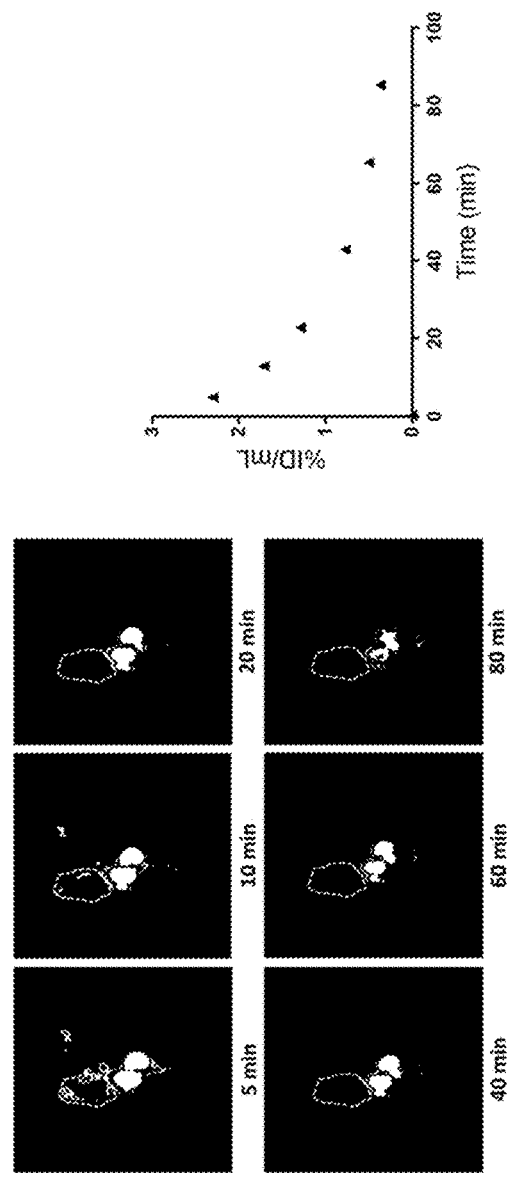

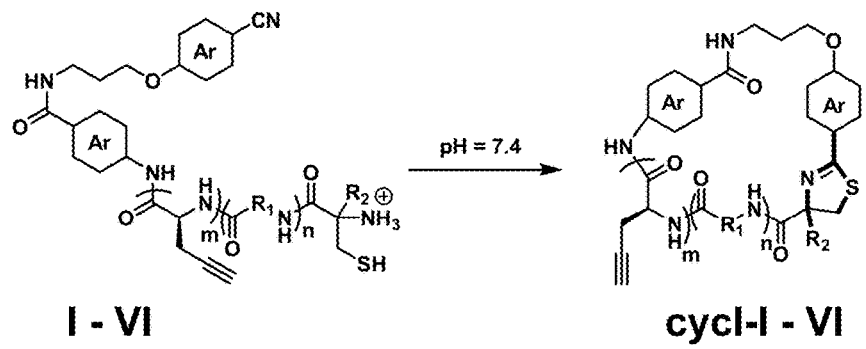

| | Aromatic nitriles | Aromatic linker | m, n, R$_1$, R$_2$ | 1$^{st}$ order rate constant k (s$^{-1}$) |
|---|---|---|---|---|
| SNAT | quinoline-CN | benzothiazole-thiazoline | m = 0, n = 1, R$_1$ = CH$_2$, R$_2$ = H | 5.8 ± 0.5 × 10$^{-3\ a}$ |
| I | quinoline-CN | phenyl | m = 0, n = 0, R$_2$ = H | 0.2 ± 0.02 × 10$^{-3}$ |
| II | quinoline-CN | phenyl | m = 1, n = 0, R$_2$ = H | 1.2 ± 0.04 × 10$^{-3}$ |
| III | pyrimidine-CN | phenyl | m = 1, n = 0, R$_2$ = H | 0.9 ± 0.02 × 10$^{-3}$ |
| IV | pyrimidine-CN | phenyl | m = 1, n = 1, R$_1$ = CH$_2$, R$_2$ = H | 2.1 ± 0.07 × 10$^{-3}$ |
| V | pyrimidine-CN | phenyl | m = 1, n = 1, R$_1$ = (CH$_2$)$_2$, R$_2$ = H | 0.8 ± 0.06 × 10$^{-3}$ |
| VI | pyrimidine-CN | phenyl-CH$_2$ | m = 1, n = 1, R$_1$ = CH$_2$, R$_2$ = CH$_3$ | 2.7 ± 0.1 × 10$^{-3}$ |

*Fig. 26A*

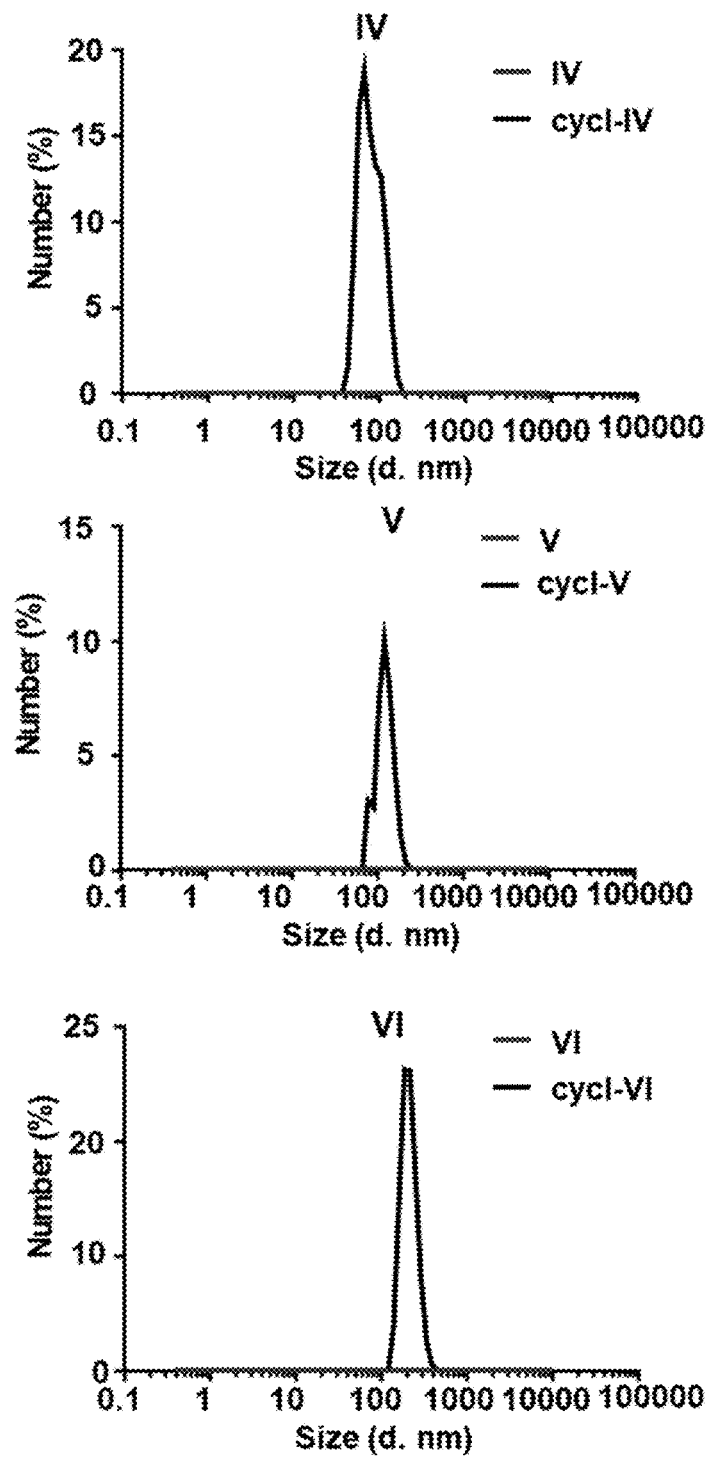
Fig. 26B-cont'd

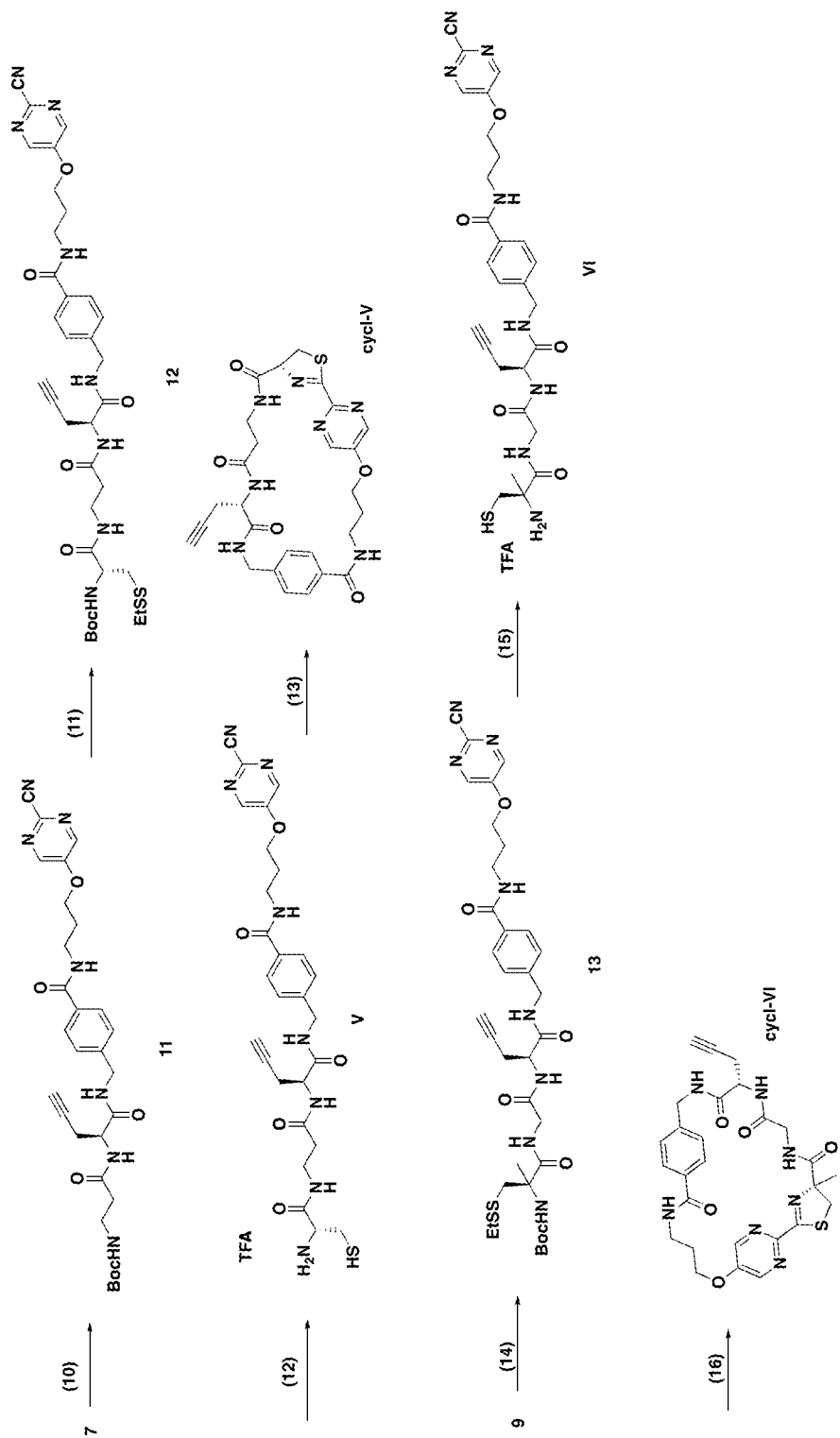
Fig. 38-cont'd

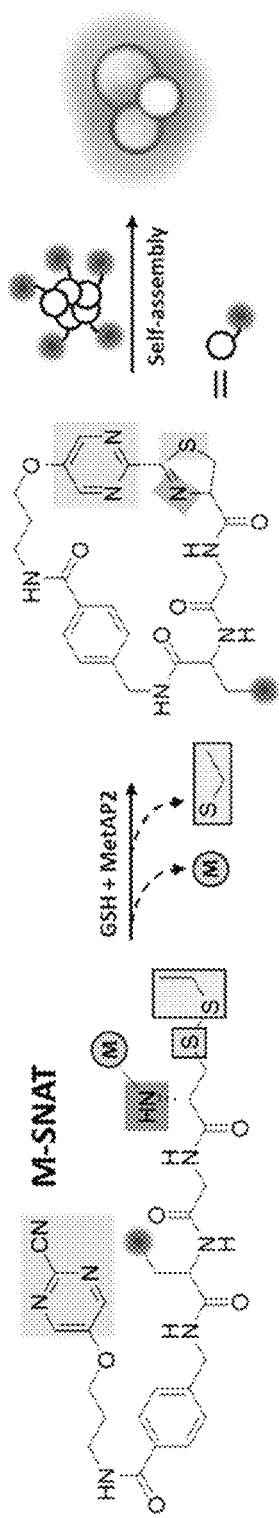
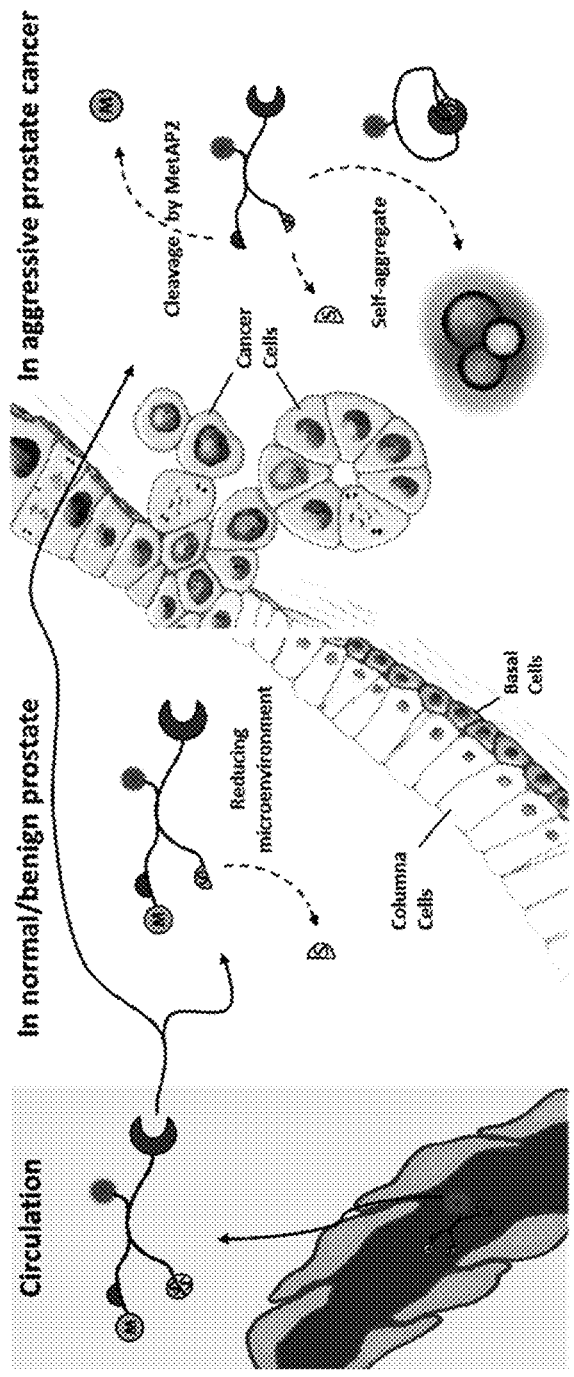
Fig. 43A
Fig. 43B

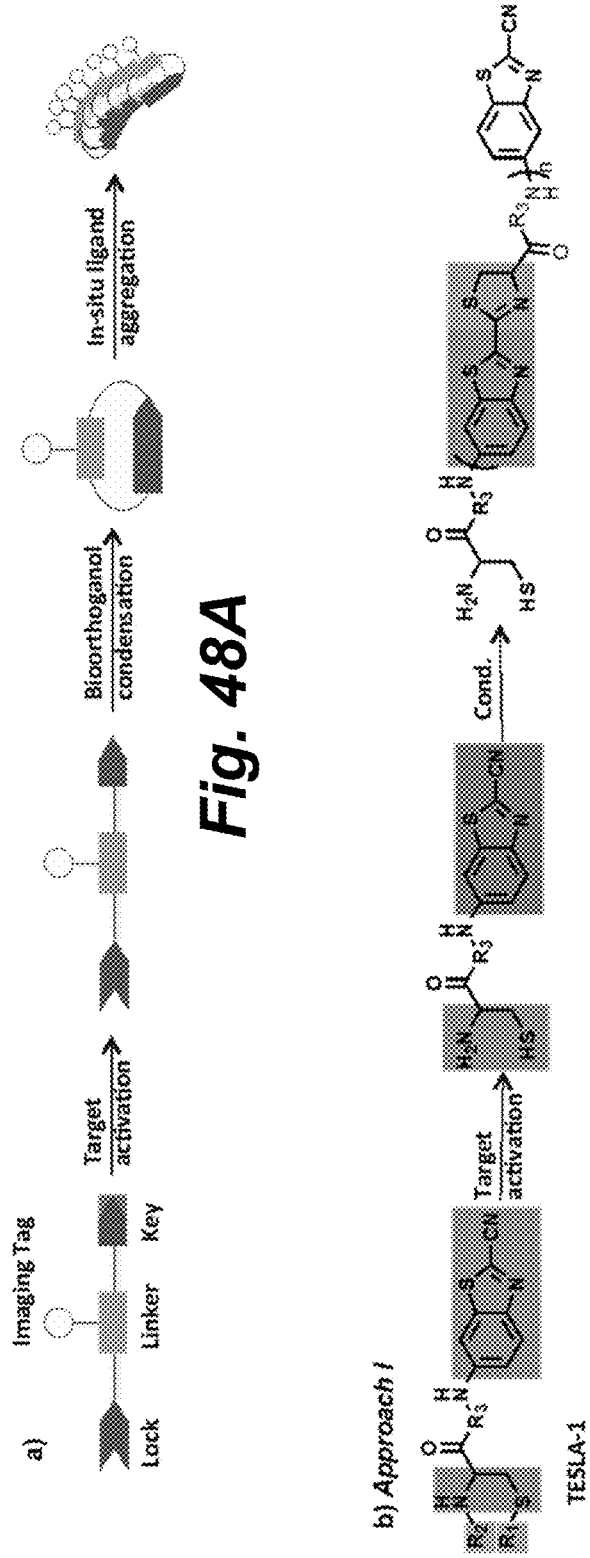
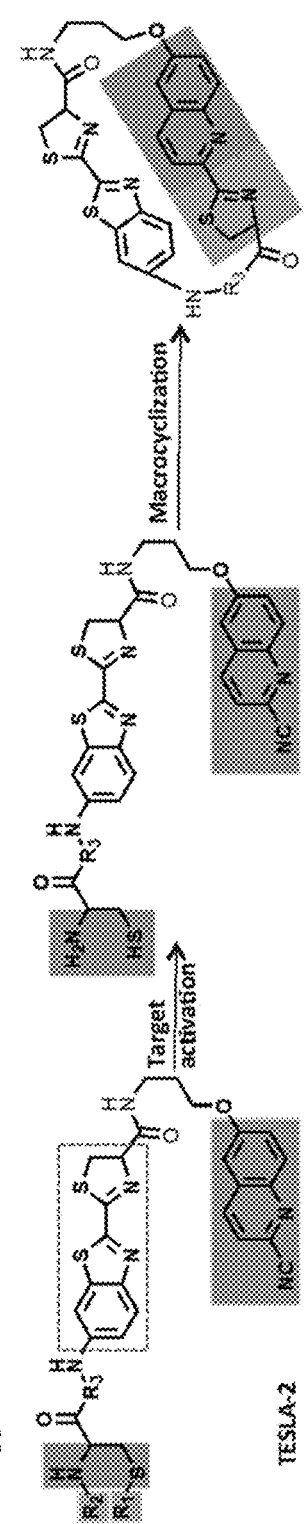
Fig. 48A
Fig. 48B

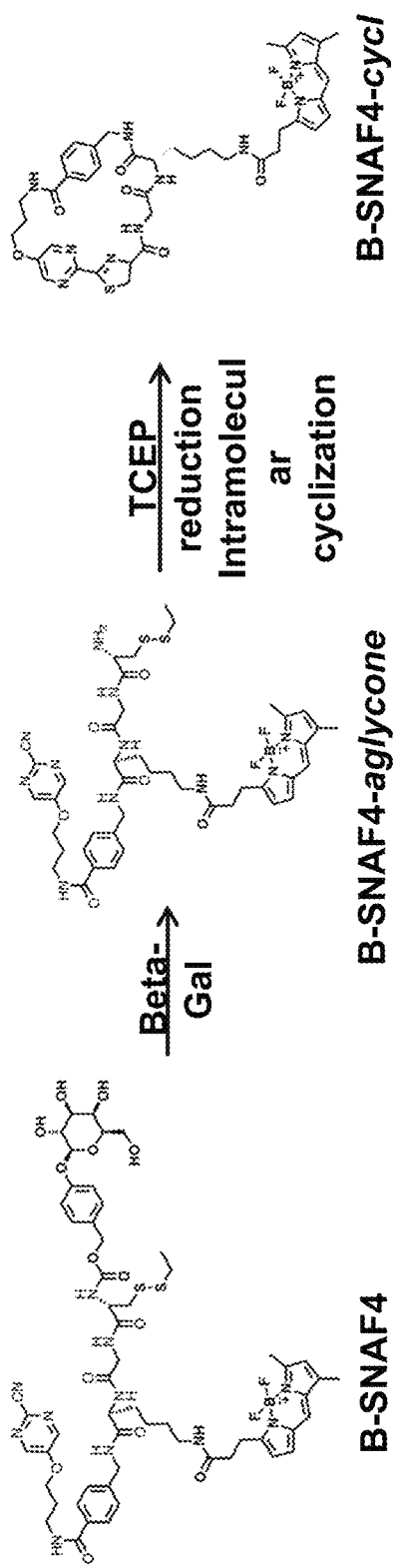
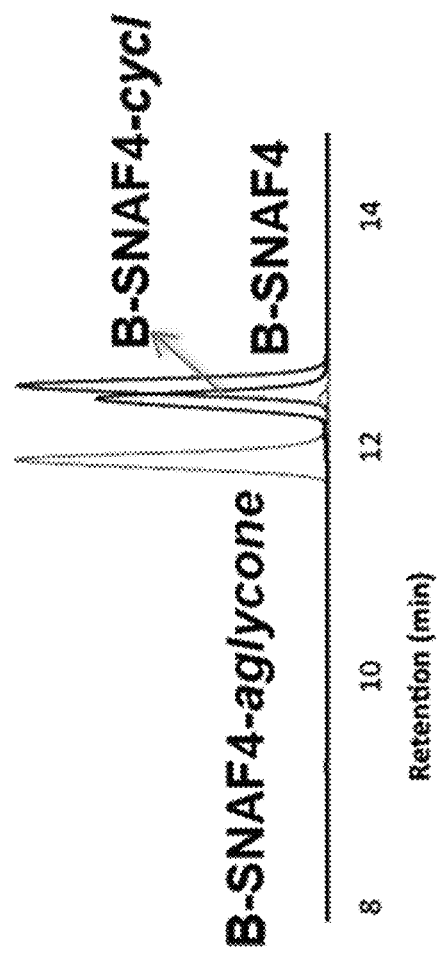
Fig. 52A
Fig. 52B

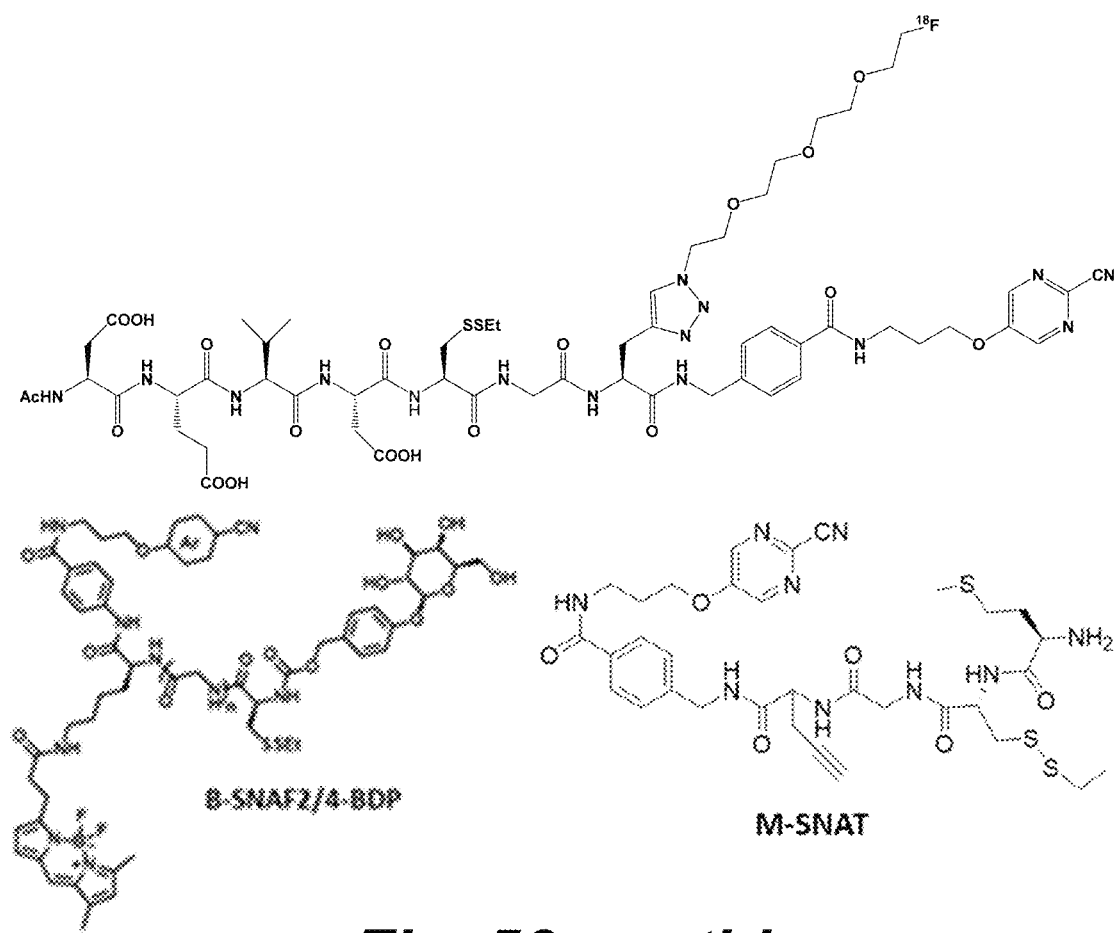
Fig. 56-cont'd

CASPASE-3-TRIGGERED MOLECULAR SELF-ASSEMBLING PET PROBES AND USES THEREOF

CROSS-REFERENCE TO RELATED APPLICATIONS

This application claims priority to U.S. Provisional Patent Application Ser. No. 62/731,496 entitled "CASPASE-3-TRIGGERED MOLECULAR SELF-ASSEMBLING PET PROBES AND USES THEREOF" filed on Sep. 14, 2018, and to U.S. Provisional Application 62/842,173 filed May 2, 2019, the entireties of which are hereby incorporated by reference.

STATEMENT OF GOVERNMENT SUPPORT

This invention was made with Government support under contract CA151459 awarded by the National Institutes of Health. The Government has certain rights in the invention.

FIELD OF THE DISCLOSURE

The present disclosure relates to positron emission tomography (PET) self-assembling nanoaggregation probes for the detection of apoptotic cells and tissues. The present disclosure further relates to methods of detecting and imaging cells and tissues.

BACKGROUND

Personalized cancer medicine requires early detection of tumor response to enable effective patient management, allowing rapid treatment decisions, minimizing deleterious side effects and reducing health care costs. In the clinic, the current approach for monitoring response is rely on measuring changes in tumor size to detect response according to the guidelines of the Response Evaluation Criteria in Solid Tumors (RECIST) criteria (Eisenhauer et al., Eur J. Cancer 45: 228-247 (2009)). However, this approach lacks sensitivity and it may take many weeks when there is evidence on tumor volume shrinkage. Positron emission tomography (PET) and PET/computed tomography (CT) are emerging as important techniques in clinical application owing to their high specificity and sensitivity (Sriram Venneti et al., Science Translat. Medi. 7: 1-11 (2015); Weber W. J. Nucl. Med. 50 Suppl 1: 1S-10S (2009); Rankin S. Cancer Imaging 8 Spec No A: S27-31 (2008)). Imaging with the glucose analog 2-$^{18}$F-fluoro-2-deoxy-D-glucose ($^{18}$F-FDG) used PET technology is a representative approach for assessing the effects of therapy objectively and quantitatively in a range of tumor types (Weber et al., J. Clin. Oncol. 21:2651-2657 (2003); Schelling et al., J. Clinical Oncol. 18: 1689-1695 (2000); Avril et al., J. Nucl. Med. 57 Suppl 1: 34S-39S (2016)), while it lacks specificity for cell death and cannot differentiate among treatment outcomes.

The cell death detection remains one of the most important unsolved problems in clinical molecular imaging (Weber W. J. Nucl. Med. 50 Suppl 1: 1S-10S (2009)). Effective anticancer therapy induces tumor cell death through apoptosis, the so-called programmed cell death, which is a highly regulated biological process and associated with the cell fate (Hassan et al., Biomed. Res. Int. (2014)). Non-invasive monitoring of apoptosis during therapy can provide predictive outcome information in the context of routine patient management and early clinical trials. Therefore, an early read-out of therapeutic efficacy via non-invasive imaging of apoptosis into routine clinical practice is an important step toward its anticipated role in patient care (Blankenberg F. G. J. Nucl. Med. 49 Suppl 2: 81S-95S (2008); Brindle K. Nat. Rev. Cancer. 8: 94-107 (2008)).

Efforts have been expended to develop PET probes for monitoring tumor response to therapy based on the well-defined biochemical changes for apoptosis. For example, $^{99m}$Tc-HYNIC-labeled Annexin V ($^{99m}$Tc Annexin V) that binds to phosphatidylserine (PS) has been used to image drug-induced cell death in widely types of cancer (Kartachova et al., Radiother. Oncol. 72: 333-339 (2004)). However, it has failed to process beyond phase II/III clinical trials due to its poor biodistribution profile (Reshef et al., J. Nucl. Med. 51: 837-840 (2010)). As direct mediators of the early stages of apoptosis, the direct imaging biomarker caspase-3/7 has become an attractive biomarker of apoptosis and shown promise for the non-invasive detection of cell death (Porter A. G Cell Death Different. 6: 99-104 (1999)). The corresponding radiopharmaceuticals such as, the small-molecule caspase-3/-7 inhibitor $^{18}$F-ICMT-II has shown promise for the early detection of drug-induced tumor apoptosis on a wide scope of disease (Challapalli et al., J. Nucl. Med. 54: 1551-1556 (2013)). Caspase-3/-7 are proteases, and their substrate for processing can be used as readout of enzyme activity. The substrate sequence most commonly used, the tetra-peptide substrate Asp-Glu-Val-Asp (DEVD), is efficiently recognized by Caspase-3/7 (Chen et al., Mal. Imaging Biol. 17: 384-393 (2015); Mcilwain et al., Cold Spring Harb. Perspect. Biol. 5 (2013)). The first substrate-based caspase-3/7 radiotracer for PET imaging of apoptosis, $^{18}$F-CP18, has been under clinical investigations (Su et al., Mal. Imaging Biol. 15: 739-747 (2013); Xia et al., Mal. Imaging Biol. 15: 748-757 (2013); Rapic et al., Mal. Imaging Biol. 19: 560 569 (2017)).

Recently, on such radiotracer $^{18}$F-labeled caspase-sensitive nanoaggregation PET tracer ([$^{18}$F]-C-SNAT) has been shown to detect early response to therapy in tumors by PET via the so-called caspase-3 targeted enable in situ ligand aggregation (TESLA) mechanism (Shen et al., Angew. Chem. Int. 52: 10511 10514 (2013); Witney et al., Clin. Cancer Res. 21: 3896-3905 (2015)). However, these probes have limitations of serum stability.

SUMMARY

One aspect of the disclosure, therefore, encompasses embodiments of a compound comprising a terminal aromatic nitrile group, a phenyl or a substituted phenyl, a cysteine, and a thiol cysteine blocking group having the structure (—S—$R_3$), wherein (i) the terminal aromatic nitrile group and the phenyl or substituted phenyl can be connected by a linker 1, (ii) the phenyl or substituted phenyl and the cysteine can be connected by linker 2, and (iii) the cysteine blocking group can be conjugated to the cysteine to form a disulfide bond, wherein the compound can have the formula A:

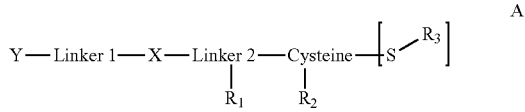

wherein: $R_1$ can be a detectable label; $R_2$ can be a moiety specifically cleavable from the scaffold by an enzyme; and $R_3$ can be an unsubstituted or substituted straight-chain alkyl group, an unsubstituted or substituted branched-chain group, an aromatic group, or a substituted aromatic group.

In some embodiments of this aspect of the disclosure, the compound can have the formula I:

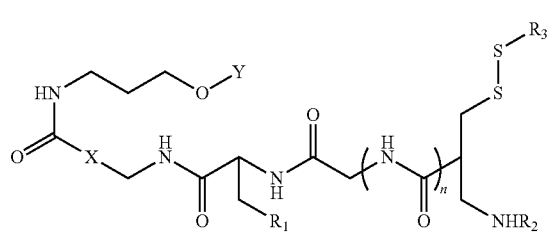

I wherein the scaffold can comprise a terminal aromatic nitrile group and a disulfide group, and wherein: n=0-6, $R_1$ can be a detectable label; $R_2$ can be a moiety specifically cleavable from the scaffold by an enzyme; $R_3$ can be an unsubstituted or substituted straight-chain alkyl group, an unsubstituted or substituted branched-chain group; X can be a phenyl or a substituted phenyl; and Y can an aromatic nitrile group.

In some embodiments of this aspect of the disclosure, X can be a phenyl group.

In some embodiments of this aspect of the disclosure, Y can be a pyrimidine nitrile group.

In some embodiments of this aspect of the disclosure, n=0-6, X can be a phenyl group, Y can be a pyrimidine nitrile group, and the scaffold has the formula II:

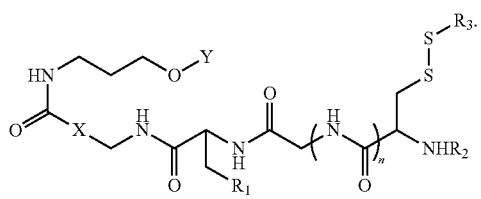

II

In some embodiments of this aspect of the disclosure, $R_1$ can be selected from a fluorescent dye, a positron emission tomography (PET) detectable moiety, and a magnetic resonance detectable moiety.

In some embodiments of this aspect of the disclosure, fluorescent dye can be a cyanine dye.

In some embodiments of this aspect of the disclosure, cyanine dye is Cy5 or Cy5.5.

In some embodiments of this aspect of the disclosure, the PET detectable moiety is an $^{18}F$-labelled moiety.

In some embodiments of this aspect of the disclosure, $R_3$ can be $(CH_2)_m$—CHs, wherein m=0-6.

In some embodiments of this aspect of the disclosure, magnetic resonance detectable moiety can be a gadolinium ion, and wherein the gadolinium ion can be attached to the scaffold by a metal chelating group.

In some embodiments of this aspect of the disclosure, $R_2$ can be a peptide having the amino acid sequence Aspartate-Glutamate-Valine-Aspartate (DEVD) and is specifically cleavable from the scaffold by caspase 3/7, a peptide having the amino acid sequence Isoleucine-Glutamate-Phenylalanine-Aspartate (IEFD) or the amino acid sequence Isoleucine-Glutamate-Proline-Aspartate (IEPD) and specifically cleavable from the scaffold by granzyme-B, a β-galactosidase-cleavable-moiety, or methionine.

In some embodiments of this aspect of the disclosure, $R_2$ can be a glycoside specifically cleavable from the scaffold by β-galactosidase.

In some embodiments of this aspect of the disclosure, compound can be admixed with a pharmaceutically acceptable carrier.

Another aspect of the disclosure encompasses embodiments of a composition comprising at least one molecule of a self-aggregating compound having formula III:

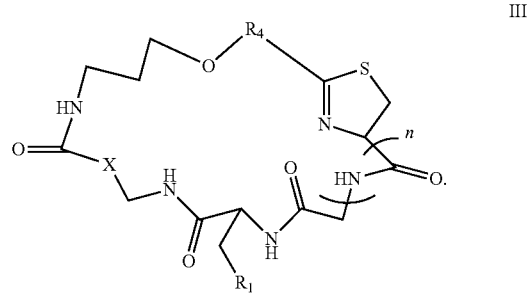

III wherein: $R_1$ is a detectable label; $R_2$ is a moiety specifically cleavable from the scaffold by an enzyme; $R_4$ can be an aromatic group; and X is a phenyl or a substituted phenyl.

In some embodiments of this aspect of the disclosure, the composition can have the formula IV:

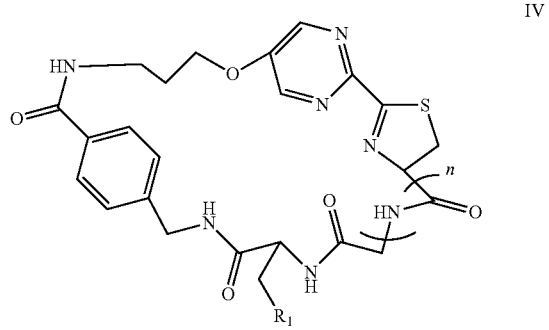

IV

In some embodiments of this aspect of the disclosure, a plurality of molecules of the compound having formula III are self-aggregated to form a nanoaggregate.

In some embodiments of this aspect of the disclosure, $R_1$ can be selected from a fluorescent dye, a positron emission tomography (PET) detectable moiety, and a magnetic resonance detectable moiety.

In some embodiments of this aspect of the disclosure, fluorescent dye can be a cyanine dye.

In some embodiments of this aspect of the disclosure, the PET detectable moiety can be $^{18}F$.

In some embodiments of this aspect of the disclosure, $R_2$ is a peptide having the amino acid sequence Aspartate-Glutamate-Valine-Aspartate (DEVD) and is specifically cleavable from the scaffold by caspase 3/7, a peptide having the amino acid sequence Isoleucine-Glutamate-Phenylalanine-Aspartate (IEFD) or the amino acid sequence Isoleucine-Glutamate-Proline-Aspartate (IEPD) and specifically cleavable from the scaffold by granzyme-B, a glycoside specifically cleavable from the scaffold by β-galactosidase, or methionine.

Yet another aspect of the disclosure encompasses embodiments of a method of generating an image of a tissue in an animal or human subject, the method comprising the steps of: (i) administering to an animal or human subject a pharmaceutically acceptable composition comprising a terminal aromatic nitrile group, a phenyl or a substituted phenyl, a cysteine, and a thiol cysteine blocking group having the structure (—S—$R_3$), wherein (i) the terminal aromatic nitrile group and the phenyl or substituted phenyl can be connected by a linker 1, (ii) the phenyl or substituted phenyl and the cysteine can be connected by linker 2, and (iii) the cysteine blocking group can be conjugated to the cysteine to form a disulfide bond, wherein the compound can have the formula A:

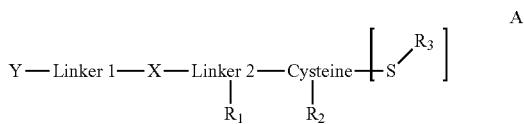

wherein: $R_1$ can be a detectable label; $R_2$ can be a moiety specifically cleavable from the scaffold by an enzyme; and $R_3$ can be an unsubstituted or substituted straight-chain alkyl group, an unsubstituted or substituted branched-chain group, an aromatic group, or a substituted aromatic group; and (ii) obtaining an image of the location of nanoaggregates of the compound in a tissue of the animal or human subject.

In some embodiments of this aspect of the disclosure, the compound can have the formula I:

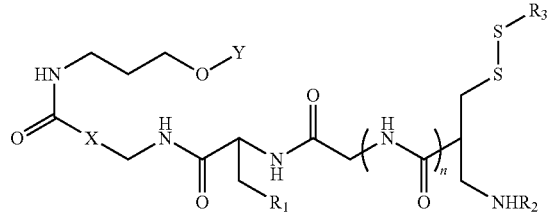

wherein the compound comprises a terminal aromatic nitrile group and a disulfide group, and wherein: n=0-6; $R_1$ can be a detectable label; $R_2$ can be a moiety specifically cleavable from the scaffold by an enzyme; $R_3$ can be an unsubstituted or substituted straight-chain alkyl group, an unsubstituted or substituted branched-chain group; X is a phenyl or a substituted phenyl; and Y is an aromatic nitrile group; and (ii) obtaining an image of the location of nanoaggregates of the compound in a tissue of the animal or human subject.

In some embodiments of this aspect of the disclosure, n=0-6, X can be a phenyl group, Y can be a pyrimidine nitrile group, and the scaffold can have the formula II:

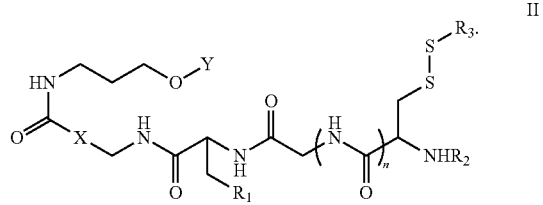

In some embodiments of this aspect of the disclosure, $R_1$ can be selected from a fluorescent dye, a positron emission tomography (PET) detectable moiety, and a magnetic resonance detectable moiety.

In some embodiments of this aspect of the disclosure, the fluorescent dye can be a cyanine dye.

In some embodiments of this aspect of the disclosure, the cyanine dye can be Cy5 or Cy5.5.

In some embodiments of this aspect of the disclosure, the PET detectable moiety can be an $^{18}$F-labelled moiety.

In some embodiments of this aspect of the disclosure, a fraction of the $^{18}$F can be replaced by $^{19}$F.

In some embodiments of this aspect of the disclosure, the magnetic resonance detectable moiety is a gadolinium ion, and wherein the gadolinium ion is attached to the scaffold by a metal chelating group.

In some embodiments of this aspect of the disclosure, $R_2$ can be a peptide having the amino acid sequence Aspartate-Glutamate-Valine-Aspartate (DEVD) and can be specifically cleavable from the scaffold by caspase 3/7, a peptide having the amino acid sequence Isoleucine-Glutamate-Phenylalanine-Aspartate (IEFD) or the amino acid sequence Isoleucine-Glutamate-Proline-Aspartate (IEPD) and specifically cleavable from the scaffold by granzyme-B, a β-galactosidase-cleavable-moiety, or methionine.

In some embodiments of this aspect of the disclosure, $R_2$ can be a glycoside specifically cleavable from the scaffold by β-galactosidase.

BRIEF DESCRIPTION OF THE DRAWINGS

Many aspects of the disclosure can be better understood with reference to the following drawings.

FIGS. 1A-1C illustrate the mechanism of PET imaging by [$^{18}$F]-C-SNAT4 of caspase-3 activity in human tumor xenograft mouse model and serum stability of [$^{18}$F]-C-SNAT4.

FIG. 1A illustrates the structure of an [$^{18}$F]-C-SNAT4 tracer and caspase-3/7 and reduction-controlled conversion of molecular C-SNAT4 into cyclized [$^{18}$F]-C-SNAT4 through the targeted-enable in situ ligand aggregation, followed by self-assembly into nanoaggregation (Nano [$^{18}$F]-C-SNAT4).

FIG. 1B illustrates the serum stability of [$^{18}$F]-C-SNAT4 in mouse serum. [$^{18}$F]-C-SNAT4 was incubated in serum at 37° C. and analyzed by HPLC.

FIG. 1C illustrates the TEM images of [$^{19}$F]-C-SNAT4 before and after addition of active caspase-3 (Casp3) enzyme. [$^{19}$F]-C-SNAT4 (20 μM) was incubated with caspase-3 (2×10$^{-3}$U mL$^{-1}$, human, recombinant from E. coli, Sigma) in caspase buffer at 37° C. overnight.

FIG. 3A illustrates a flow cytometric analysis of vehicle or different ratios of drug-to-vehicle-treated cells in NCI-H460 cells. 100% cisplatin-treated cells were treated with 10 μM cisplatin for 24 hours. Cell death was detected with FITC-Annexin V (λ Ex/Em=488/535) and PI staining (λ Ex/Em=488/636). Q1=viable; Q2=early apoptotic; Q3=late apoptotic; Q4=Necrotic.

FIG. 3B illustrates a correlation between cisplatin-induced cell death and radiotracer accumulation in H460 cells. Flow cytometric quantitation of cell death was compared with cell-associated radioactivity for [$^{18}$F]-C-SNAT4 in cell mixtures. Mean±SD (n=3 per group); ***, P<0.005.

FIGS. 4A and 4D illustrate representative 55- to 60-min axial and sagittal fused PET/CT images. Nude mice received approximately 200 μCi of [18F]-C-SNAT4 via tail vein injection, with PET/CT images acquired at 55 to 60 min after injection. Arrowheads indicate the tumor, identified from the CT images. H460 and H1299 tumor bearing mice were naïve, or 24 h following last dose of cisplatin treatment (Low dose: 3 mg/kg every other day for three times; high dose: 9 mg/kg every other day for three times).

FIGS. 4B and 4E illustrate time-activity curves (TAC) of [$^{18}$F]-C-SNAT4 in naïve and drug-treated tumors.

FIGS. 4C and 4F illustrate the area under the curve (AUC) was shown from t=0 to t=85 min for TAC in FIGS. 4B and 4E. For all TAC points represent mean±S.D. (n=3-4 per group).

FIGS. 5A and 5B illustrate the characterization of Cisplatin-therapy response in H460 (left) and H1299 tumors.

FIG. 5A illustrates an ex vivo investigation of cell death following tumors without or with drug treatment. Mice bearing drug-sensitive tumor H460 or drug-resistant tumor H1299 were untreated or were excised 24 h following last dose of cisplatin treatment. Caspase-3 activity was detected through immunofluorescence. Tissue sections are shown at 20×(top row) or 63×(bottom row) objective. Scale bars: 20×=50 μm, 63×=20 μm.

FIG. 5B illustrates caliper measurement of H460 and H1299 tumor volumes in saline and drug-treated mice. Measurements are time after cell implantation, with high dose of cisplatin-treated (Intravenous injection, 9 mg/kg every other day for three times) in H460 and in H1299 tumor-bearing mice as arrow indicated (arrow). n=5 for each group.

FIGS. 6A-6E illustrate that a mixture tracer [$^{18}$F]/[$^{19}$F]-C-SNAT4 can increase tumor uptake and improve imaging sensitivity in radiotherapeutic tumor-bearing mice.

FIG. 6A illustrates a schematic mechanism of increasing the sensitivity via [$^{18}$F]-C-SNAT4 mixing with [$^{19}$F]-C-SNAT4.

FIGS. 6B and 6C illustrate representative axial PET images of tumors at 48 hs after radiation treatment at the dose of 5 Gy (FIG. 6B) and 2 Gy (FIG. 6C) after injection of 200 μCi mixture tracers [$^{18}$F]/[$^{19}$F]-C-SNAT4 or 200 μCi of hot tracer [$^{18}$F]-C-SNAT4.

FIGS. 6D and 6E illustrate time-activity curves (TAC) illustrating H460 tumor uptake of mixture tracer [$^{18}$F]/[$^{19}$F]-C-SNAT4 compared to [$^{18}$F]-C-SNAT4 after radiation treatment. Dotted cycle indicates the tumor location. T=Tumor. Statistical significance was determined by two-sided analysis of variance (ANOVA), ****P<0.0001, n=3 per group.

FIG. 18A illustrates a representative PET images of drug-sensitive H460 tumor-bearing mouse imaged 24 h following cisplatin treatment (intravenous injection, 9 mg/kg every other day for three times) with intravenous injection of approximately 200 μCi [$^{18}$F]-C-SNAT4.

FIG. 18B illustrates images data was quantified for tumor uptake of [$^{18}$F]-C-SNAT4 corresponds to the time-points shown in (a). Tumors are outlined in white dashed lines.

FIG. 19A illustrates representative PET images of drug-resistant H1299 tumor-bearing mouse imaged 24 hours following cisplatin treatment (intravenous injection, 9 mg/kg every other day for three times) with intravenous injection of approximately 200 μCi [$^{18}$F]-C-SNAT4.

FIG. 19B illustrates image data was quantified for tumor uptake of [$^{18}$F]-C-SNAT4 corresponds to the time-points shown in (a). Tumors are outlined in white dashed lines.

FIG. 24A illustrates representative PET images of H460 tumor bearing mice imaged post IR treatment at 60 min post-injection of approximately 200 μCi tracer of [$^{18}$F]/[$^{19}$F]-C-SNAT4 or hot tracer [$^{18}$F]-C-SNAT4.

FIG. 24B illustrates a time activity curve of [$^{18}$F]/[$^{19}$F]-C-SNAT4 (1:200) or [$^{18}$F]-C-SNAT4 in high dose (9 mg/kg every other day for three times) treated-tumors or [$^{18}$F]-C-SNAT4 in naïve tumors.

FIG. 24C illustrates that the area under the curve (AUC) was shown from t=0 to t=85 min for TAC. Dotted cycle indicates the tumor location. Statistical significance was determined by two-sided ANOVA. For all TAC points represent mean±S.D. (* P<0.05, *P<0.005, **P<0.0001, n=3 for each group). T=Tumor; K=Kidney.

FIG. 25A illustrates representative 55- to 60-min axial and sagittal fused PET/CT images. Nude mice received about 200 μCi of [$^{18}$F]-C-SNAT4 or mixed tracer [$^{18}$F]/[$^{19}$F]-C-SNAT4 via tail vein injection, with PET/CT images acquired 55 to 60 min after injection. Arrowheads indicate the tumor, identified from the CT mice.

FIG. 25B illustrates a time-activity curve (TAC) of [$^{18}$F]/[$^{19}$F]-C-SNAT4 (mixture ratio at 1:80 or 1:200) or [$^{18}$F]-C-SNAT4 in naïve tumors.

FIG. 25C illustrates the area under the curve (AUC) was showed from t=0 to t=85 min for TAC in (FIG. 25B). For all TAC points represent mean±S.D. (n=4 for each group). Dotted cycle indicates the tumor location. Statistical significance was determined by two-sided ANOVA.

FIGS. 26A-26B illustrates an analysis of cyclization reaction rates and their cyclic products.

FIG. 26A illustrates an analysis of cyclization reaction by modulating condensation reaction substrate pair, different linkers and different ring sizes. $1^{st}$ Order rate constants for the intramolecular cyclization were measured in PBS buffer at room temperature using HPLC assay.

FIG. 26B illustrates dynamic light scattering (DLS) analysis of the hydrodynamic radius of I-VI and nanoaggregates of cycl-I to cycl-VI.

FIG. 27A illustrates in-gel fluorescence and Coomassie stain analysis of SNAT2 (lane 1) and SNAT4 (lane 2) after they were incubated in HeLa lysate (37° C., 6 hours) followed by click reaction with Cy5-azide. BSA was first labeled by 6-heptynoic NHS ester before subjecting to click reaction with Cy5-azide as a positive control (lane 3).

FIG. 27B illustrates an HPLC analysis of HeLa lysate after incubation of disulfide caged SNAT4 in live HeLa cells (37° C., 6 h). HeLa lysate without (bottom) and with (top) incubation with disulfide caged SNAT4.

FIG. 27C illustrates an HPLC analysis of HeLa lysate after incubation of disulfide caged SNAT4 in HeLa lysate (37° C., 6 h). HeLa lysate without (bottom) and with (top) incubation with disulfide caged SNAT4. * Cyclized product.

FIG. 28A illustrates β-galactosidase and reduction-initiated conversion of B-SNAF2/4-BDP into B-SNAF2/4-BDP-aglycone and cycl-SNAF2/4-BDP via enzyme activation and intramolecular cyclization followed by self-assembly into nanoaggregation in situ.

FIGS. 28B-28E illustrates DLS and TEM analyses of cycl-SNAF2-BDP (FIGS. 3B and 3C) or cycl-SNAF4-BDP (FIGS. 3D and 3E) following β-galactosidase activation in vitro.

FIG. 28F illustrates live cell imaging of β-galactosidase activity in LacZ-transfected 9L cells using B-SNAF2/4-BDP (2 μM, 2 h). Cells were stained with nuclear dye Hoechst 33342. Scale bar: 50 μm.

FIG. 28G illustrates a flow cytometry analysis of 9L/LacZ and 9L/Luc cells stained with B-SNAF2-BDP or B-SNAF4-BDP.

FIG. 29A illustrates caspase-3 and reduction-initiated conversion of C-SNAF4-Cy5 into cycl-SNAF4-Cy5 via intramolecular cyclization, followed by self-assembly into nanoaggregation in situ.

FIGS. 29B and 29C illustrate DLS and TEM analyses of cycl-SNAF4-Cy5 following caspase-3 activation in vitro.

FIG. 29D illustrates cell imaging of caspase-3 activity in cisplatin-induced (10 μM, 24 hours) H460 apoptotic cells using C-SNAF4-Cy5 (scale bar: 20 μm). H460 cells were treated with or without cisplatin or with additional caspase inhibitor Z-VAD-fmk (50 μM). Cells were stained with nuclear dye Hoechst 33342.

FIG. 35A illustrates Western blot studies performed on untreated or cisplatin-treated NCI-H460 (10 μM, 24 hours). A 35-kD band indicates procaspase-3, a 17-kD band indicates caspase-3 and β-Actin was used as control.

FIG. 35B illustrates quantification of the percent gel intensity observed from Western blot for procaspase-3 or active caspase-3.

FIG. 42A illustrates a Western blot analysis of MetAP2 in cells and tumor xenografts; 40 μg of each whole cell or tumor lysate were loaded.

FIG. 42B illustrates a Western blot analysis of androgen receptor (AR), PSMA and MetAP2 in tumor xenografts; 40 μg of each whole cell or tumor lysate were loaded.

FIG. 42C illustrates IHC staining of prostate cancer patients' biopsies showing the overexpression of MetAP2 in both low- and high-grade tumors but not benign regions. Scale bar: 500 μm left, 100 μm right.

FIG. 42D illustrates the intensity of the staining of patients' biopsy scored from 0 to 3 (0: negative; 1: uncertain/excluded; 2: weakly positive; 3: strongly positive). Percentage of patients with none (0), low (average>1 & ≤2) and high (average>2) MetAP2 staining were presented within each group of biopsies (BPH, n=104; Benign, n=105; 3+3 to 3+4, n=248; 4+3 to 5+4, n=56).

FIG. 42E illustrates a graph showing the months to biochemical recurrence of IHC analyzed patients (n=212) in TMAs within 9 years. The top curve indicated the patients with at least 2 of the 3 biopsy cores scored as 3 (MetAP2 overexpression). The bottom curve represented all the other patients.

FIGS. 43A-43C illustrate the mechanism of in vivo imaging of MetAP2 activity by $^{18}$F-M-SNAT in human prostate cancer.

FIG. 43A illustrates MetAP2 and cellular glutathione (GSH)-controlled conversion of M-SNAT into M-SNAT-cycl through the bioorthogonal intramolecular cyclization reaction, followed by self-assembly into nanoaggregates in situ.

FIG. 43A schematically illustrates that after intravenous administration, M-SNAT extravasates into tumor tissue because of its small size. In normal or benign tissue that express minimal amount of MetAP2, the methionine mostly remains and M-SNAT can diffuse away freely, which leads to low signal. In aggressive tumor tissue overexpressing MetAP2, after methionine cleavage, M-SNAT undergoes macrocyclization and in situ nanoaggregation, leading to enhanced probe retention and high radioactive signal.

FIG. 43C illustrates the structures of $^{18}$F-M-SNAT, M-SNAT and M-SNAT-Ctrl in this study.

FIG. 44A illustrates HPLC traces of M-SNAT and the product of the incubation of M-SNAT (10 μM) with recombinant human MetAP2 (7.5 μg/ml) at 37° C. in reaction buffer for 24 h.

FIG. 44B illustrates DLS analysis shows the formation of nanoparticles with an average diameter of 861 nM (531-1281 nM).

FIG. 44C illustrates TEM image of nanoaggregates after incubation of M-SNAT (10 μM) with MetAP2.

FIG. 45A illustrates post click labeling of MetAP2 activated intramolecular cyclization and self-nanoaggregation by Cy5.

FIG. 45B illustrates fluorescence microscopy imaging of cy5 post-labeled M-SNAT (20 μM) with or without TNP470 and M-SNAT-ctrl (20 μM) in PC3 cells. Permealized cells were also stained with DAPI (blue).

FIG. 46A illustrates an SR-SIM image of self-aggregated fluorescent nanoparticles in PC3 cells incubated with M-SNAT (20 μM) and post-labeled by Cy5. Cells were co-stained with DAPI. The yellow box indicates the enlarged area.

FIG. 46B illustrates an enlarged SR-SIM image of the single cell in a. Arrow points to an aggregation structure in the cell. The box indicates the enlarged area.

FIG. 46C illustrates an enlarged SR-SIM image of the aggregation structures. Arrow points to an aggregation structure in the cell.

FIG. 47A illustrates images after 90 min programed PET/CT scan; n=4. About 150 μCi $^{18}$F-M-SNAT were injected. White and gray indicate CT signal; a thresholding method was utilized to mask the relatively high uptake in liver, spleen, kideney and bladder.

FIG. 47B illustrates curves of the percentage of tumor retained injection dosage per cc acquired by defining the volumes of interest (VOI) in software.

FIG. 47C illustrates the biodistribution of $^{18}$F-M-SNAT in PBS treated mice acquired by defining the volumes of interest in software.

FIG. 48A illustrates the mechanism of target enabled in-situ ligand aggregation (TESLA).

FIG. 48B illustrates approach I through intermolecular bioorthogonal condensation of CBT with cysteine, and approach II via intramolecular cyclization of CHQ with cysteine.

FIG. 49A illustrates (left) structure of compound I; middle, HPLC analysis of the first-order reaction rate of the compound; (top right) a digital image of an aqueous solution of compound I (200 μM) at acidic and neutral pH; (bottom right) a graph showing dynamic light scattering of compound 1 (10 μM).

FIG. 49B illustrates (left) structure of compound II; middle, HPLC analysis of the first-order reaction rate of the compound; (top right) a digital image of an aqueous solution of compound 11 (200 μM) at acidic and neutral pH; (bottom right) a graph showing dynamic light scattering of compound 11 (10 μM).

FIG. 50A illustrates the second-order reaction rate of cyano-substituted aromatics with cysteine at phosphate-buffered saline (pH=7.4).

FIG. 50B illustrates the second-order reaction rate of 2-cyanobenzothiazole (CBT) with substituted cysteine analogues.

FIG. 50C illustrates the structures and first-order reaction rates of designed compounds III to VI.

FIG. 50D illustrates graphs showing the dynamic light scattering of designed compound (10 μM) after pH change.

FIGS. 51A-51C illustrate the imaging of caspase-3/7 activity in cisplatin-treated cancer cells with C-SNAF-Cy5 analogues.

FIG. 51A illustrates a caspase-3 and reduction-initiated conversion of C-SNAF4-Cy5 into C-SNAF-Cy5-cycl via intramolecular cyclization, followed by self-assembly into nanoaggregation in situ.

FIG. 51B illustrates a DLS analysis of C-SNAF4-Cy5 (20 μM) incubated with caspase-3 (1 μg/ml) in caspase buffer (pH 7.4) at 37° C. for 6 h.

Figure 51A:
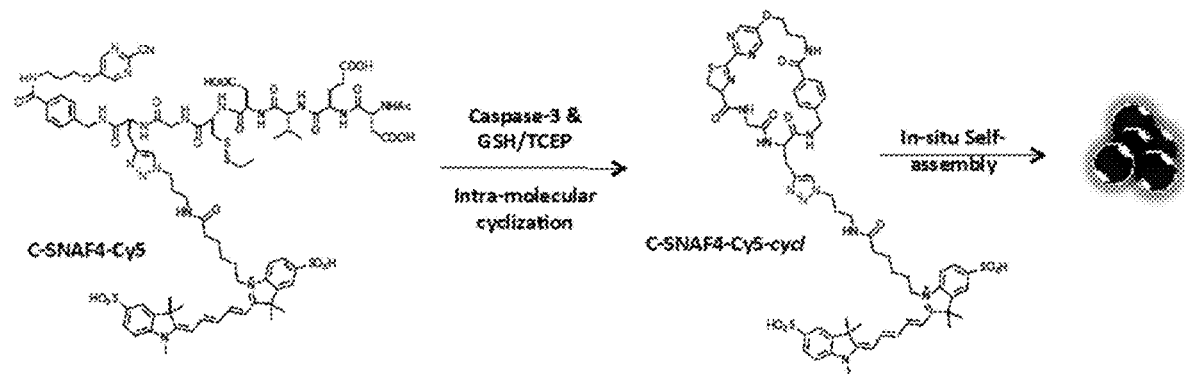
Figure 51B:
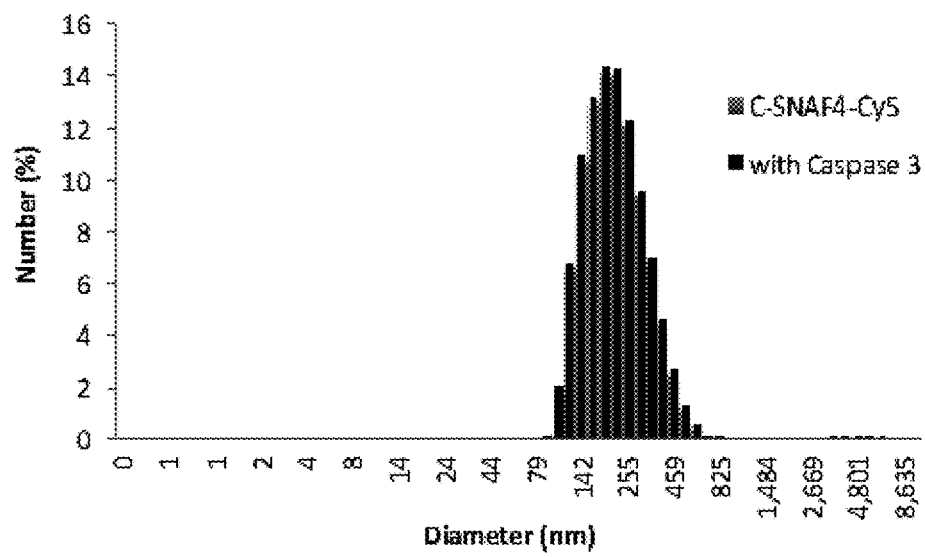
Figure 51C:
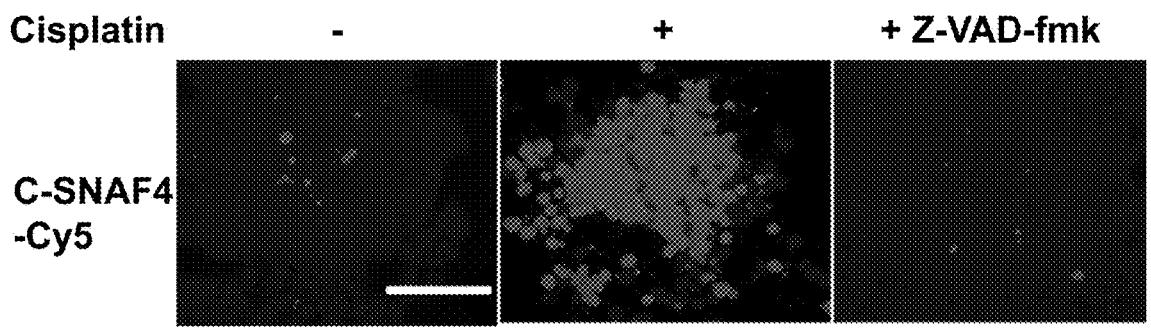

FIG. 51C illustrates a cell imaging of C-SNAF4-Cy5 probe for imaging caspase-3 activity in cisplatin-induced (10 μM; 24 h) H460 apoptotic cell modeling. H460 cells were labeled with or without C-SNAF4-Cy5 (2 μM) or with additional caspase inhibitor Z-VAD-fmk (50 μM). Cells were stained with nuclear dye Hoechst 33342. Scale bar: 20 μm.

FIGS. 52A-52D illustrate imaging of β-galactosidase activity in cells with B-SNAF4.

FIG. 52A illustrates β-galactosidase and reduction-induced conversion of B-SNAF4 into B-SNAF-cycl.

FIG. 52B illustrates an HPLC characterization of B-SNAF4 upon enzyme and TCEP treatment.

Figure 52C:
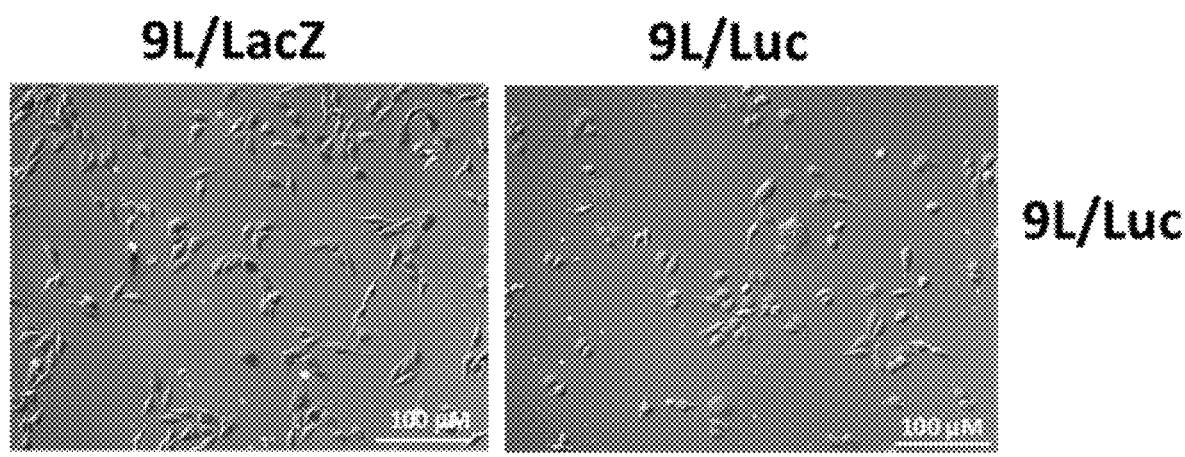

FIG. 52C illustrates LacZ staining with X-gal of 6L/LaZ and 9L/Luc cell lines.

Figure 52D:
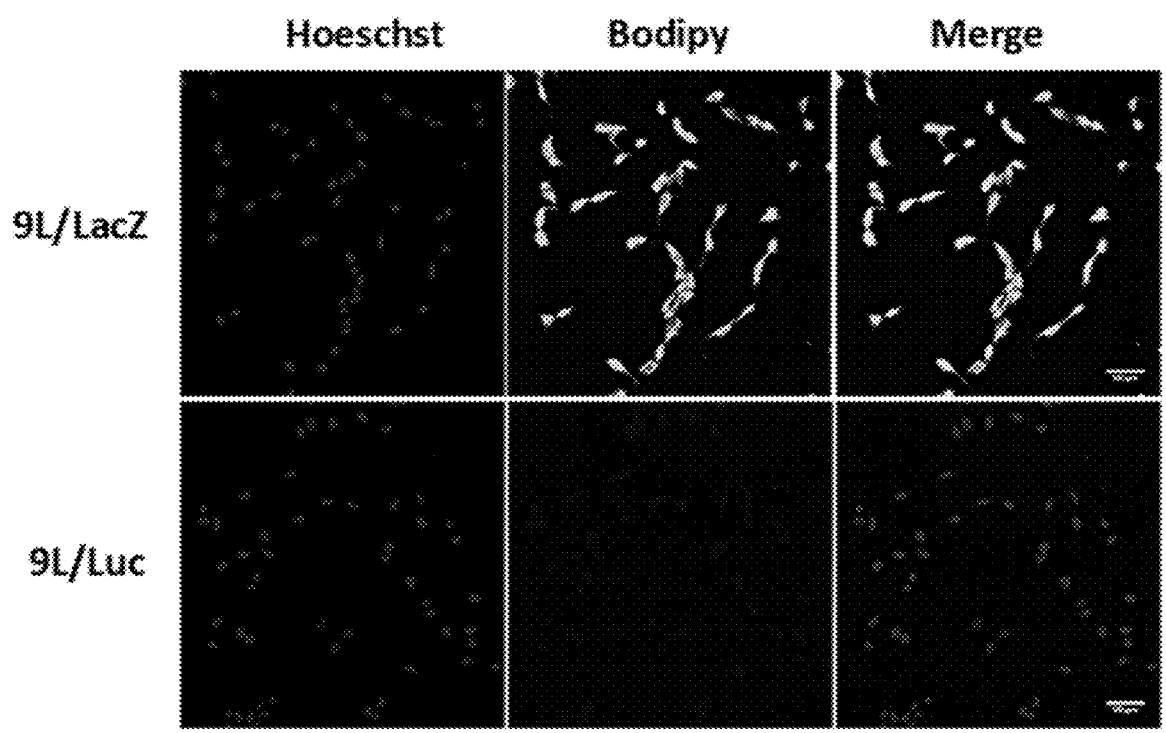

FIG. 52D illustrates fluorescence microscopy of B-SNAF (2 μM) at 37° C. for 2 h for imaging β-galactosidase activity. Cells were stained with nuclear dye Hoechst 33342. Scale bar: 50 μm.

Figure 53:
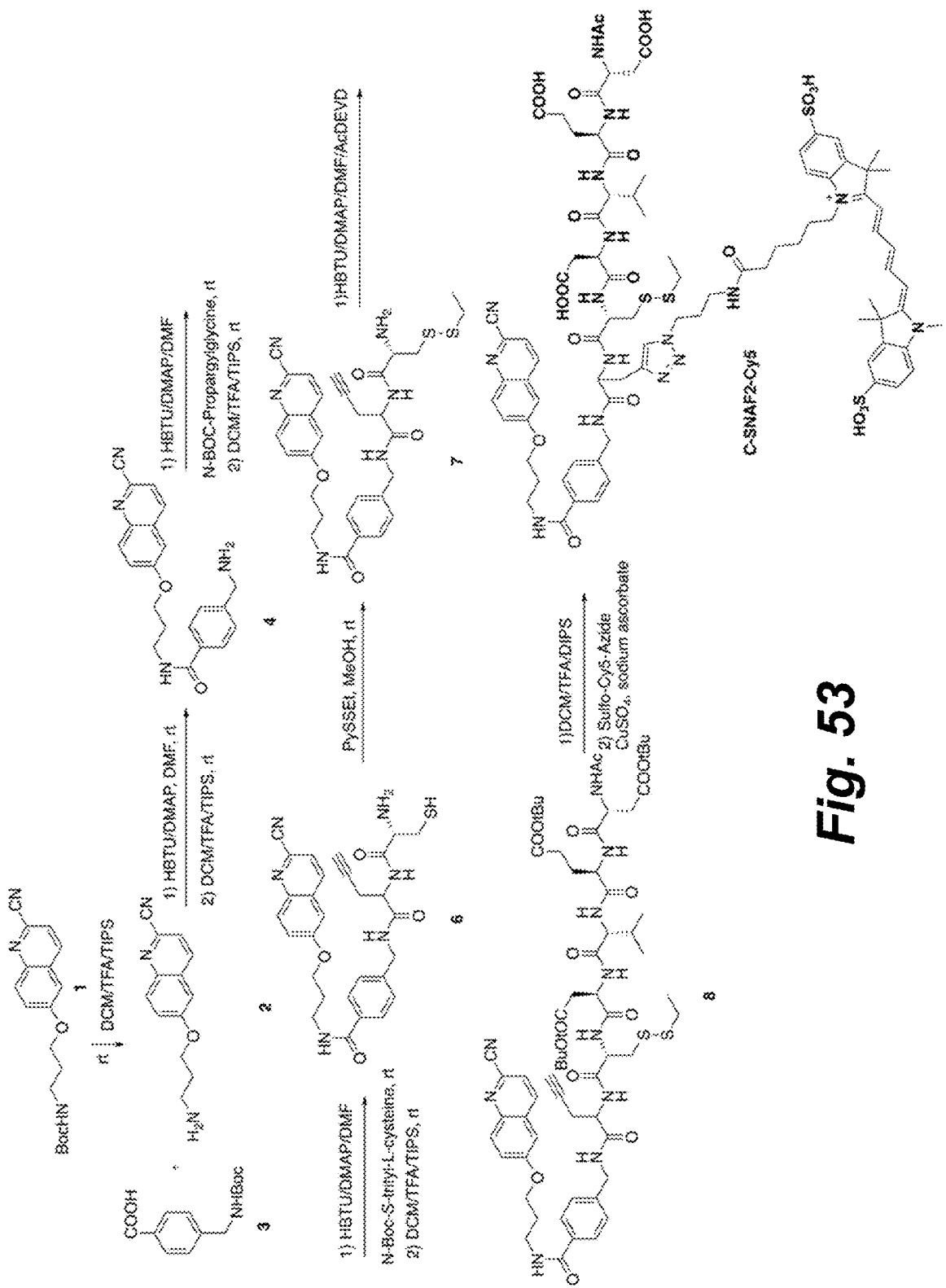

FIG. 53 illustrates Scheme 1 for the synthesis of C-SNAF2-Cy5.

Figure 54:
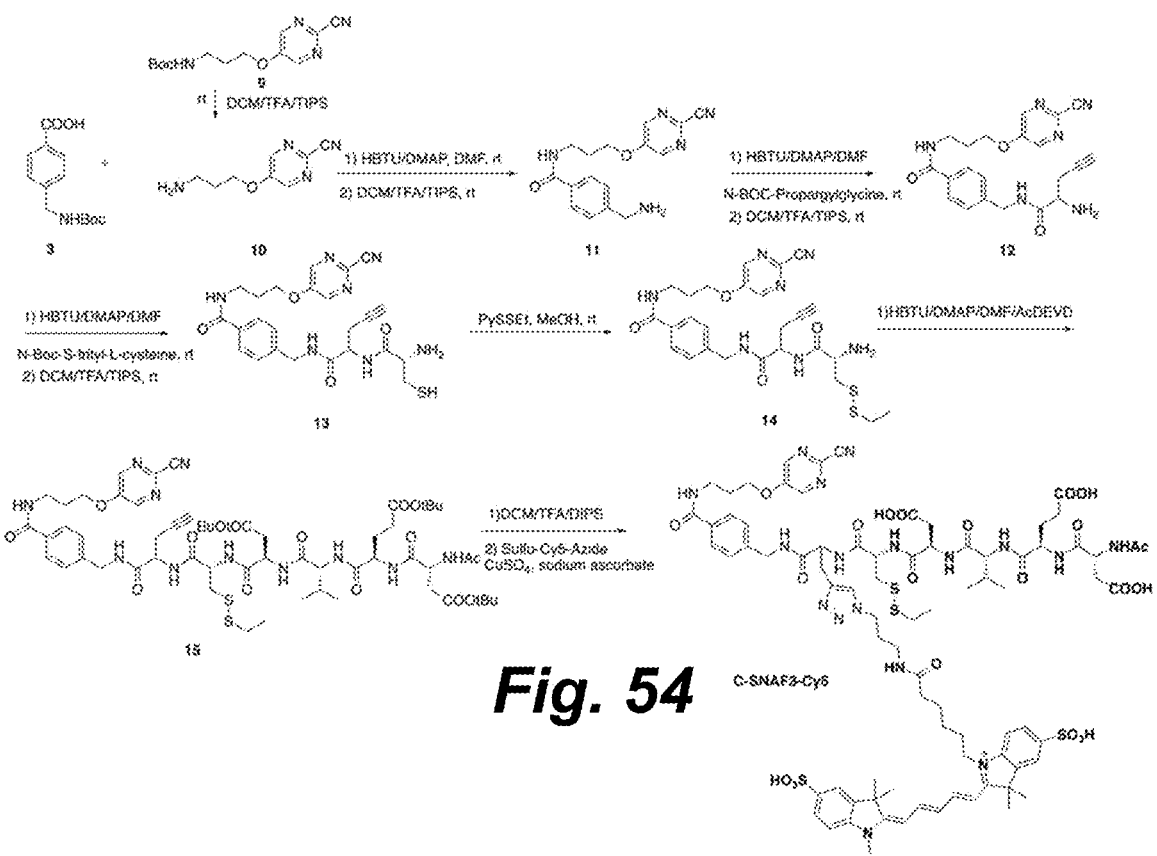

FIG. 54 illustrates Scheme 2 for the synthesis of C-SNAF3-Cy5.

Figure 55:
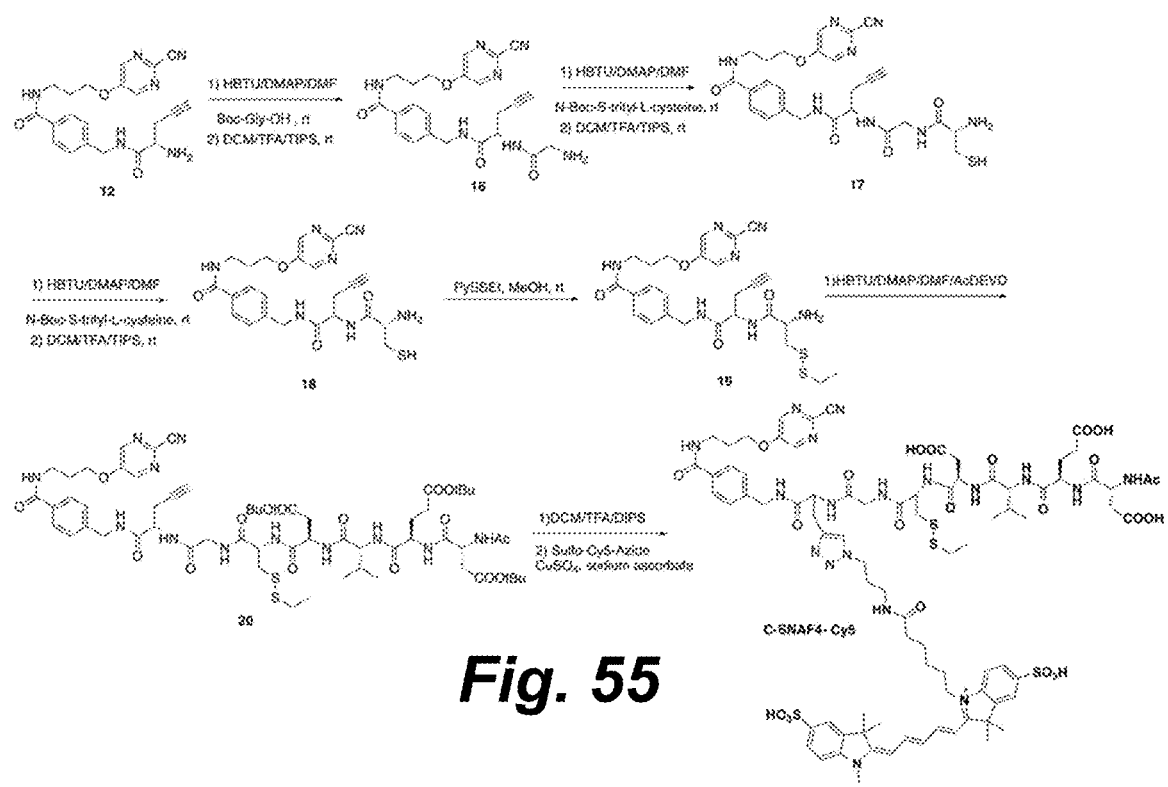

FIG. 55 illustrates Scheme 3 for the synthesis of C-SNAF4-Cy5.

Figure 56:
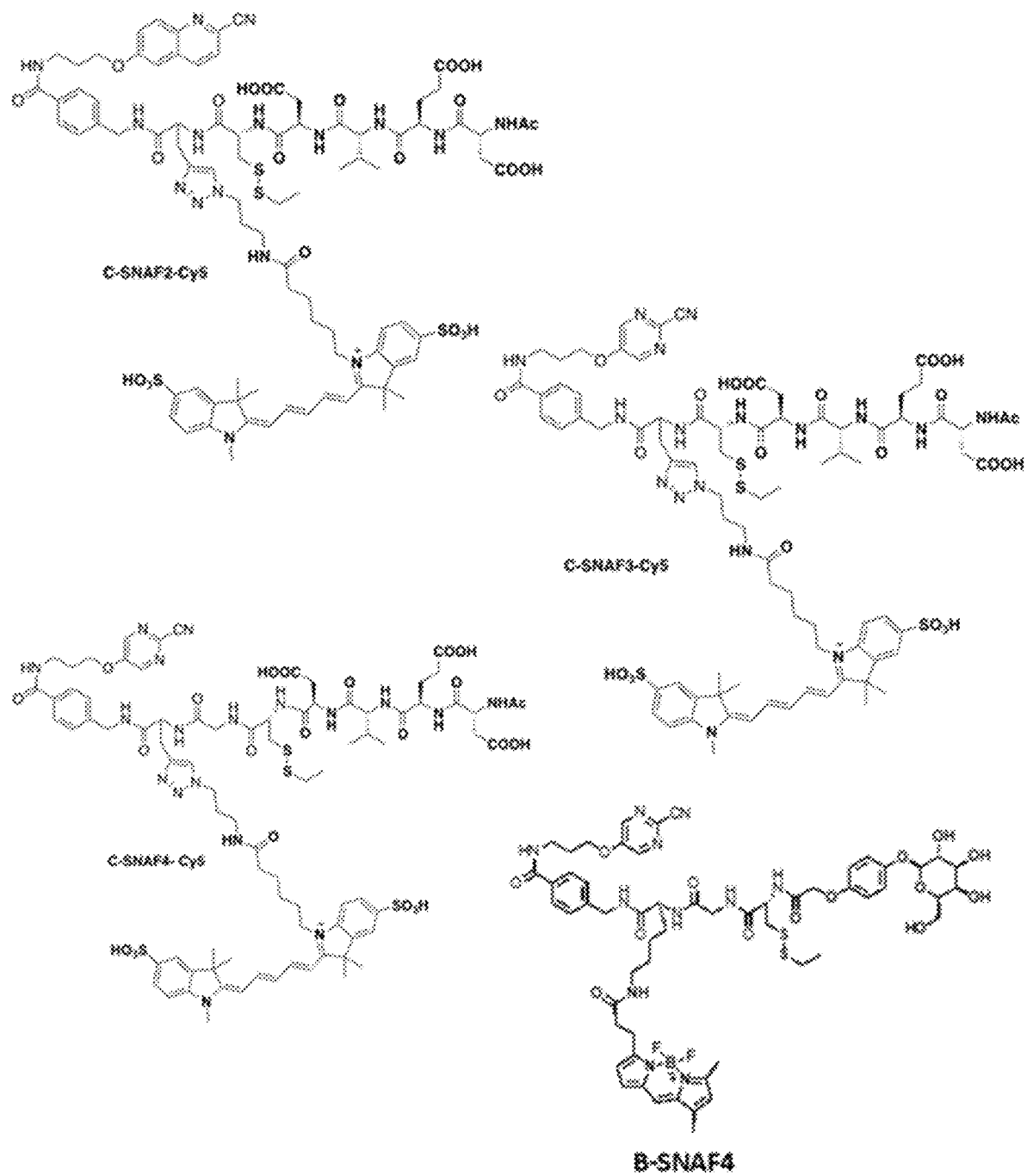

FIG. 56 illustrates representative embodiments of probes of the disclosure.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

C-SNAF: caspase-sensitive nanoaggregation fluorescent probe; C-SNAT: caspase-sensitive nanoaggregation tracer probe.

Definitions

The term "positron emission tomography" as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 (about 20 min), nitrogen-13 (about 10 min), oxygen-15 (about 2 min), and fluorine-18 (about 110 min). PET technology can be used to trace the biologic pathway of any compound in living humans (and many other species as well), provided it can be radiolabeled with a PET isotope. The half-life of fluorine-18 is long enough such that fluorine-18 labeled radiotracers can be manufactured commercially at an offsite location.

The term "Magnetic Resonance Imaging" (MRI) as used herein is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

The term "activatable probe" as used herein refers to a probe monomer of the disclosure that includes a blocking, or capping, moiety such as a peptide that can be cleaved from the probe. Upon cleavage, the probe may then cyclize and aggregate to generate a non-aggregation probe structure.

The term "detachable capping moiety" as used herein refers to a structure such as a peptide that when attached to the probe prevents self-cyclization of the probe and subsequent aggregation to form nanoaggregation probes.

The term "chelator" as used herein refers to a molecular moiety that may form ionic bonds to an anion and in particular to metallic ions that have at least two positive charges thereon. Chelating agents containing paramagnetic metals for use in magnetic resonance imaging can also be employed as ancillary agents. Typically, a chelating agent containing a paramagnetic metal is associated with a coating on the nanoparticles. The chelating agent can be coupled directly to one or more of components of the coating layer, such as a polyaspartate coat. Suitable chelating agents include a variety of multi-dentate compounds including EDTA, DPTA, DOTA, and the like. These chelating agents can be coupled directly to functional amino groups of a polyaspartate coat of the nanoparticles.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "nanoparticle" as used herein refers to a particle having a diameter of between about 1 and about 1000 nm. Similarly, by the term "nanoparticles" is meant a plurality of particles having an average diameter of between about 1 and about 1000 nm.

It will be understood by one of ordinary skill in the art that when referring to a population of nanoparticles as being of a particular "size", what is meant is that the population is made up of a distribution of sizes around the stated "size". Unless otherwise stated, the "size" used to describe a particular population of nanoparticles will be the mode of the size distribution (i.e., the peak size). By reference to the "size" of a nanoparticle is meant the length of the largest straight dimension of the nanoparticle. For example, the size of a perfectly spherical nanoparticle is its diameter.

The term "detectable signal emitter", for the purposes of the specification or claims, means a label molecule that is incorporated indirectly or directly into a nanoparticle, wherein the label molecule facilitates the detection of the nanoparticle in which it is incorporated. Thus, "detectable signal emitter" is used synonymously with "label molecule."

The term "detectable" refers to the ability to detect a signal over the background signal. The detectable signal is defined as an amount sufficient to yield an acceptable image using equipment that is available for pre-clinical use. A detectable signal maybe generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The term "optical energy" as used herein refers to electromagnetic radiation between the wavelengths of about 350 nm to about 800 nm and which can be absorbed by the dyes or cellulose-based nanoparticles of the embodiments of the photoacoustic probes of the disclosure. The term "optical energy" may be construed to include laser light energy or non-laser energy.

The term "detectable imaging moiety" or "label" as used herein refers to an atom, or radioactive atom detectable by such methods as γ-radiation detection, positron emission transmission, and the like, or to an inorganic or organic molecule that may be detected by an optical method, for example by fluorescence detection, light absorbance and the like. It should be noted that reference to detecting a signal from a probe also includes detecting a signal from a plurality of probes. In some embodiments, a signal may only be detected that is produced by a plurality of probes. Additional details regarding detecting signals (e.g., acoustic signals) are described below.

The "imaging moiety" may be detected either externally to a subject human or non-human animal body or via use of detectors designed for use in vivo, such as intravascular radiation or optical detectors such as endoscopes, or radiation detectors designed for intra-operative use. The imaging moiety is preferably chosen from, but is not limited to, a positron-emitting radioactive non-metal or a reporter suitable for in vivo optical imaging. It is contemplated, however, that other detectable labels may be incorporated into the probes of the disclosure including, but not limited to, a radioactive nuclide. When the imaging moiety is a radioactive metal ion, i.e. a radiometal, suitable radiometals can be either positron emitters such as $^{64}$Cu, $^{48}$V, $^{52}$Fe, $^{55}$Co, $^{94m}$Tc or $^{68}$Ga or γ-emitters such as 99mTc, $^{111}$In, $^{113}$In, $^{67}$Ga. When the imaging moiety is a positron-emitting radioactive non-metal, suitable such positron emitters can include: $^{11}$C, $^{13}$N, $^{15}$O, $^{17}$F, $^{18}$F, $^{76}$Br, $^{76}$Br or $^{124}$I.

The term "imaging moiety" as used herein may further refer to a reporter suitable for in vivo optical imaging and the reporter is any moiety capable of detection either directly or indirectly in an optical imaging procedure. The reporter can be a light scatterer (e.g. a colored or uncolored particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most advantageously, the reporter has fluorescent properties.

Organic chromophoric and fluorophoric reporters suitable for use in the probes of the disclosure include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoaniline dyes, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful.

Particular examples of chromophores which may be used include: fluorescein, sulforhodamine 101 (Texas Red), rhodamine B, rhodamine 6G, rhodamine 19, indocyanine green, Cy2, Cy3, Cy3B, Cy3.5, Cy5, Cy5.5, Cy7, Cy7.5, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750.

Particularly advantageous are dyes which have absorption maxima in the visible or near infrared (NIR) region, between 400 nm and 3 µm, particularly between 600 and 1300 nm. Optical imaging modalities and measurement techniques include, but are not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarization, luminescence, fluorescence lifetime, quantum yield, and quenching.

The term "fluorophore" as used herein refers to a component of a molecule that causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorophores for use in the compositions of the disclosure include, but are not limited to, fluorescein isothiocyanate (FITC), a reactive derivative of fluorescein, which has been one of the most common fluorophores chemically attached to other, non-fluorescent, and molecules to create new fluorescent molecules for a variety of applications. Other historically common fluorophores are derivatives of rhodamine (TRITC), coumarin, and cyanine. Newer generations of fluorophores such as the ALEXA FLUORS™ and the DYLIGHT FLUORS™ are generally more photostable, brighter, and less sensitive than other standard dyes of comparable excitation and emission.

The term "contrast agent" as used herein refers to an agent that when delivered to an animal or human subject can improve the image obtained by a method such as magnetic resonance imaging (MRI). Such agents may include, but are not limited to, gadolinium, iron oxide, manganese and magnesium salts, and the like that may be formulated into pharmaceutically acceptable compositions for administering in vivo with limited and acceptable degrees of undesirable side effects. One suitable MRI contrast agent for incorporation into the liposomal nanoparticle delivery vehicles of the disclosure is gadolinium (Gd), and derivatized variants thereof. A particularly useful such derivative, but not intended to be limiting, is Gadofluorine (GdF, Bayer Schering Pharma AG), a gadolinium analogue that is an amphiphilic, macrocyclic, gadolinium-containing complex. It is a derivative of Gd-DO3A containing a perfluorooctyl side chain and a mannose moiety. Other Gd derivatives for use as an MRI contrast agent are, but not limited to, Carbocyanine-labelled GdF (cc-GdF), Gd-DTPA (MAGNEVIST™, Bayer Schering Pharma, Berlin, Germany), Gd-DO3A and the like.

The term "selectively cleavable" as used herein refers to when a linker is not cleaved by certain reactions conditions, but selectively cleavable by different reaction conditions. The selectively cleavable peptide of the probes of the disclosure will include a peptide bond that can be cleaved by peptidase the activity of which is to be detected by the probe, but not cleaved by other peptidases. For example, but not intended to be limiting, the targeted peptidase can be a caspase 3 or 7 (hereinafter caspase 3/7) that is induced by the onset of apoptosis in a cell and cleaves a peptide bond at the C-terminus of the peptide L-asparate-glutamate-valine-aspartate, whereas same peptide bond is not cleaved by a different peptidase. Further non-limiting examples of selective cleavage may be specific cleavage by b-galactosidase or Granzyme B.

The term "caspase" as used herein refers to a family of cysteine-aspartic proteases or cysteine-dependent aspartate-directed proteases that are a family of cysteine proteases that play essential roles in apoptosis (programmed cell death), necrosis, and inflammation. Failure of apoptosis is one of the main contributions to tumor development and autoimmune diseases; this, coupled with the unwanted apoptosis that occurs with ischemia or Alzheimer's disease, has stimulated interest in caspases as potential therapeutic targets. Effector caspases (e.g., CASP3, CASP6, and CASP7) cleave protein substrates within the cell to trigger the apoptotic process. The initiation of this cascade reaction is regulated by caspase inhibitors. Caspases are first synthesized as inactive pro-caspases that consist of a prodomain, a small subunit and a large subunit. Granzyme B (released by cytotoxic T lymphocytes and NK cells) is known to activate caspase-3 and -7.

The term "alkyl", either alone or within other terms such as "thioalkyl" and "arylalkyl", means a monovalent, saturated hydrocarbon group that may be a straight chain (i.e. linear) or a branched chain. An alkyl group for use in the present disclosure generally comprises from about 1 to 20 carbon atoms, particularly from about 1 to 10, 1 to 8 or 1 to 7, more particularly about 1 to 6 carbon atoms, or 3 to 6. In certain aspects of the disclosure an alkyl group is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl group may be optionally substituted with substituents at positions that do not significantly interfere with the preparation of compounds of the disclosure and do not significantly reduce the efficacy of the compounds. In certain aspects of the disclosure, an alkyl group can be substituted with one to five substituents including, but not limited to, halo, lower alkoxy, lower aliphatic, a substituted lower aliphatic, hydroxy, nitro, thio, amino, keto, aldehyde, ester, amide, substituted amino, carboxyl, sulfonyl, sulfuryl, sulfenyl, sulfate, sulfoxide, substituted carboxyl, or halogenated lower alkyl (e.g. $CF_3$). Substituents on an alkyl group may themselves be substituted.

The term "substituted phenyl" as used herein includes an aromatic ring, or fused aromatic ring system consisting of no more than three fused rings at least one of which is aromatic, and where at least one of the hydrogen atoms on a ring carbon has been replaced by a halogen, an amino, a hydroxy, a nitro, a thio, an alkyl, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl, chlorphenyl and the like.

The term "aryl", alone or in combination, as used herein refers to a carbocyclic aromatic system containing one, two or three rings wherein such rings may be attached together in a pendant manner or may be fused. In aspects of the disclosure an aryl radical comprises 4 to 24 carbon atoms, in particular 4 to 10, 4 to 8, or 4 to 6 carbon atoms. Illustrative "aryl" radicals includes without limitation aromatic radicals such as phenyl, benzyl, naphthyl, preferably phenyl.

An aryl radical may be optionally substituted with groups as disclosed herein, in particular hydroxyl, alkyl, carbonyl, carboxyl, thiol, amino, and/or halo, in particular a substituted aryl includes without limitation arylamine and arylalkylamine.

The term "thioalkyl" as used herein, alone or in combination, refers to a chemical functional group where a sulfur atom is bonded to an alkyl, straight-chain or branched, which may be substituted. Examples of thioalkyl groups are thiomethyl, thioethyl, and thiopropyl. A thioalkyl may be substituted with a substituted or unsubstituted carboxyl, aryl, heterocylic, carbonyl, or heterocyclic.

The term "thioaryl" as used herein, alone or in combination, refers to a chemical functional group where a sulfur atom (S) is bonded to an aryl group and having the general chemical formula —S—R where R is aryl that may be substituted. Illustrative examples of thioaryl groups and substituted thioaryl groups are thiophenyl, chlorothiophenol, para-chlorothiophenol, thiobenzyl, 4-methoxy-thiophenyl, 4-nitro-thiophenyl, and para-nitrothiobenzyl.

The term "thiol cysteine blocking group" as used here in refers to a thiolaklyl or thioaryl group that, when attached to a cysteine of the compounds of the disclosure, generates a disulfide group.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

Description

The present disclosure encompasses embodiments of a compound generally comprising a terminal aromatic nitrile group Y, a phenyl or a substituted phenyl X, a cysteine, and a cysteine blocking group. The terminal aromatic nitrile group I connected to the phenyl or substituted phenyl by conjugation to a first linker 1. The phenyl or a substituted phenyl is further connected to the cysteine via conjugation to a second linker 2. The cysteine further comprises a cysteine blocking group (—S—$R_3$) conjugated to the cysteine by the formation of a disulfide bond. Accordingly, the compounds of the disclosure have the general formula A:

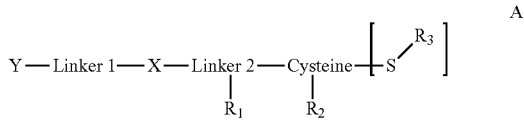

wherein $R_1$ is a detectable label conjugated to the linker 2, $R_2$ is a moiety specifically cleavable from the scaffold by an enzyme. $R_3$ is the cysteine blocking group that can be an unsubstituted or substituted straight-chain alkyl group, an unsubstituted or substituted branched-chain group, an aromatic group, or a substituted aromatic group.

The first and second linkers may be any structure that allows the cyclization of the compound after cleavage of the $R_2$ moiety from the compound which generate an amine group that can interact with the disulfide under reducing conditions. In embodiments of the disclosure, the $R_3$ moiety of the cysteine blocking group can be any aliphatic or aromatic group that does not substantially impede the entry of the compound into an intracellular environment. Upon entry into the reducing intracellular environment. In one preferred embodiment, for example, $R_3$ can be an ethyl group.

The compounds of the disclosure can be usefully employed as detectable probes. The choice of the detectable label $R_1$ allows for applicability to a wide selection of detection methods including, but not limited to PET imaging, MRI, fluorescent imaging, and the like. The intensity of the imaging signal can be increased by the aggregation of the cyclized compound, after entry into a target cell, to form nanoaggregates. Further, the cleavable moiety $R_2$ may be selected such that a particular cell or tissue having an elevated concentration of a cleaving enzyme may be selectively imaged. For example, but not intended to be limiting, $R_2$ may be selectively cleaved by a caspase or a β-galactosidase to selectively target an apoptotic cell or one containing the β-galactosidase, respectively.

Structure Optimization of TESLA-2

The Target-Enabled in-situ Ligand Aggregation (TESLA) strategy of the disclosure is based on a chemical reaction which can lead to the self-assembly of nanoaggregates in vitro and in vivo. Through modification of the linker and cyan-substituted aromatics of the TESLA-2 scaffold, the newly designed scaffold a more streamlined synthesis, smaller size, better water solubility, comparable kinetics were achieved, while avoiding the scaffold oxidation, thus assuring its increased serum stability. By varying reactive groups used to mask the presence of the molecular template, C-SNAF-Cy5 (for caspase) and B-SNAF (β-galactosidase) were designed as targeting probes for visualization of TESLA in cells. The retention contrast of the TESLA platform was generated through controlled-cyclization, followed by self-assembly into nanoaggregates in situ, which demonstrates its great potential in biology and clinical translation, such as controlled drug-delivery and PET imaging (cross-reference).

Probe TESLA-2 (FIGS. 48A and 48B) may be dissected into three parts: two condensation reacting groups, CBQ, a cysteine derivative, and the linking group between them, such as a luciferin unit. It was determined, for example, whether the luciferin unit in the linker (dashed rectangle, FIG. 48A) was required for the cyclization and nanoaggregation. Previously it has been shown that when the luciferin is replaced by a PEG linker, the resulting macrocyclics did not aggregate. Also tested was whether the luciferin unit could be replaced with a phenyl group, the smallest and simplest aromatic ring. To make the comparison, the cysteine and 2-cyano-6-hydroxylquinoline (CHQ) units were retained as the "key and lock" pair.

Figure 49A:
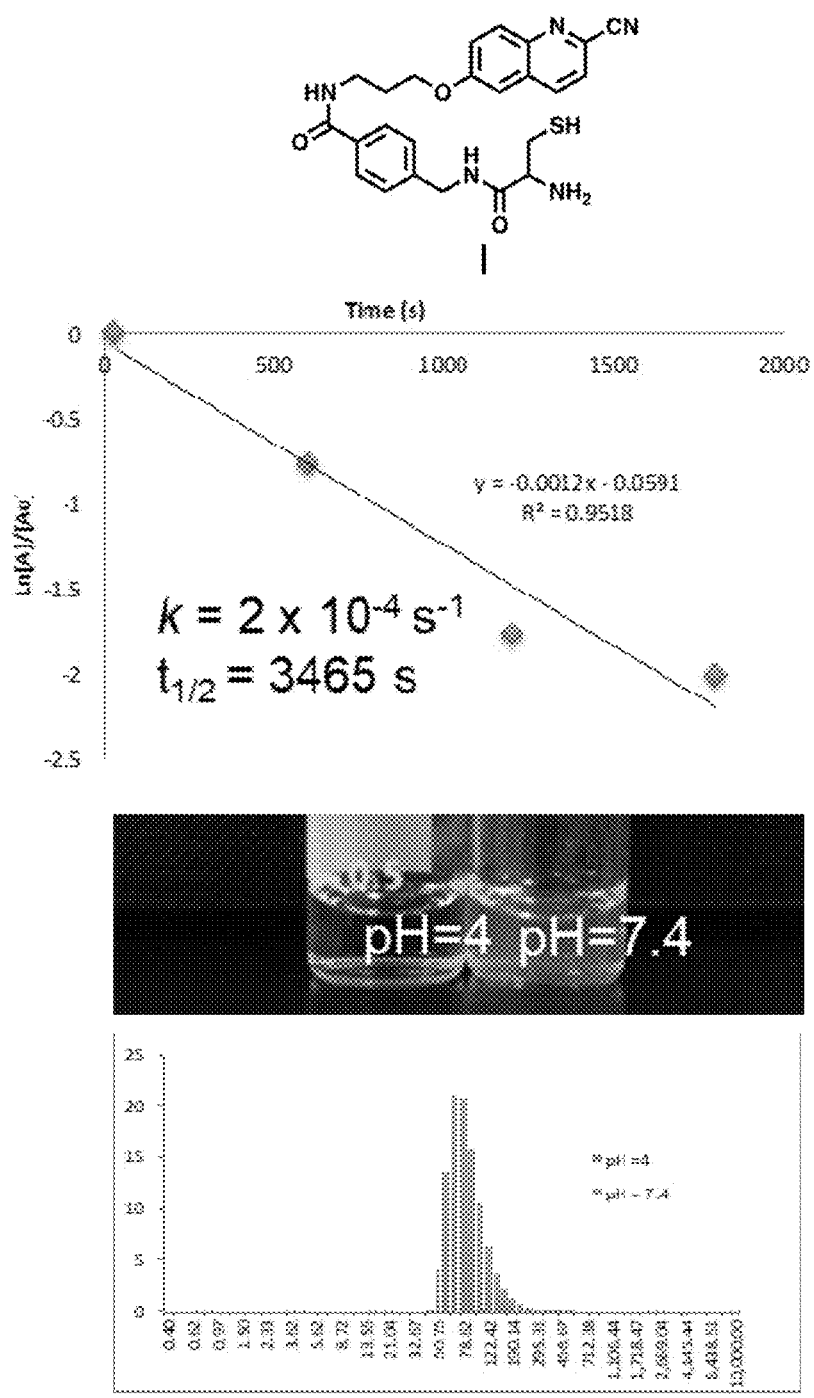
FIGS. 49A and 49B illustrate pH-controlled intramolecular cyclization and self-assembly of cyclized product.
Figure 49B:
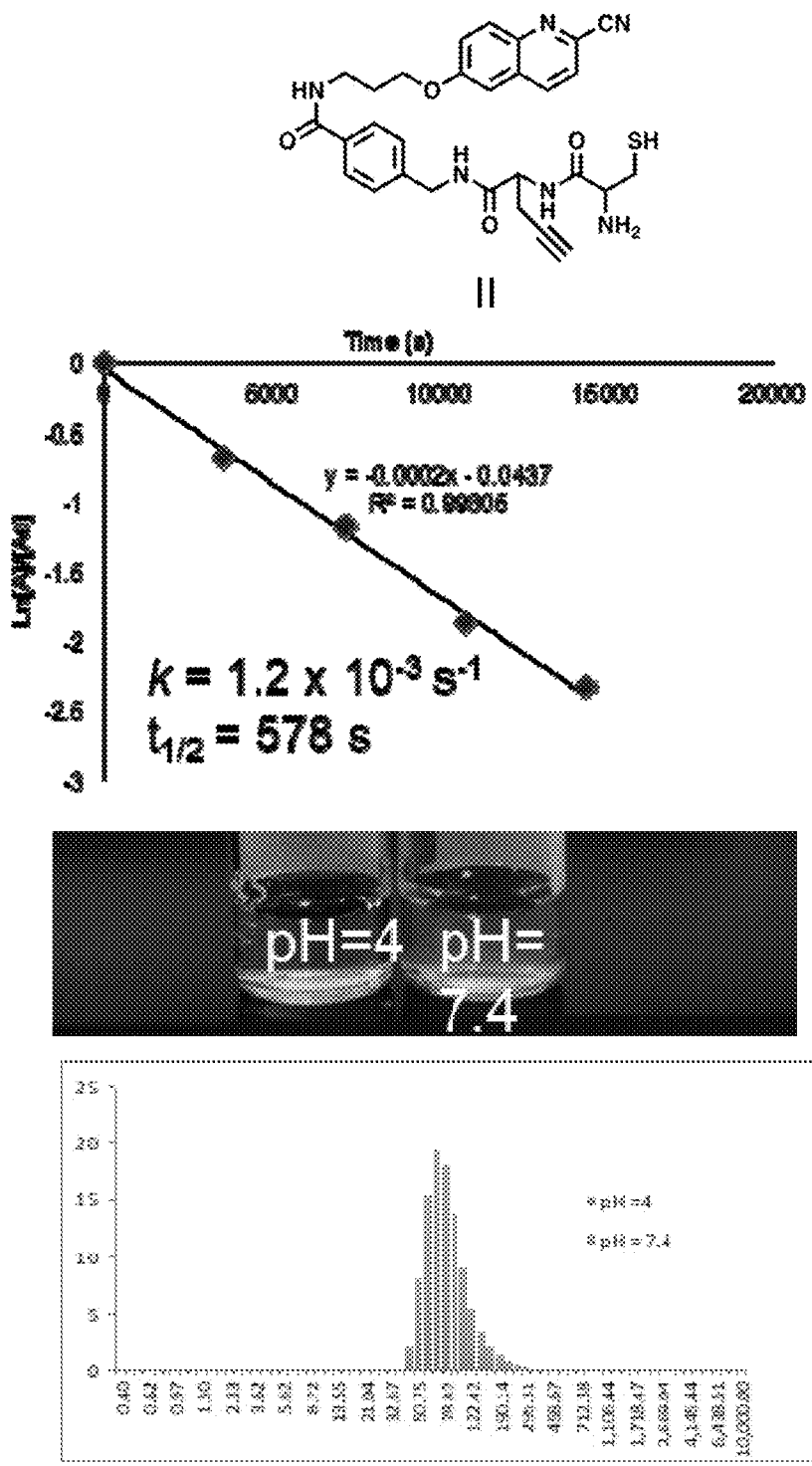

Compounds I and II that include an alkyne handle for imaging the tag were synthesized, and an HPLC assay used to measure the reaction rate of the intramolecular cyclization, as shown in FIGS. 49A and 49B. Upon the adjustment of the pH value from 4 to 7.4 the two analogues both afforded cyclized products. The first order reaction rate for compounds I and II was $2\times10^{-4}$ s$^{-1}$ and $1.2\times10^{-3}$ s$^{-1}$, respectively, which is comparable to TESLA-2 analogue with similar ring size ($3.2\times10^{-4}$ s$^{-1}$, $5.8\times10^{-3}$ s$^{-1}$), and consistent with a previous report that the intramolecular condensation reaction rate is affected by the size of the macrocyclic ring formed (Ye et al., (2011) *Angew. Chem.-Int. Edit.* 50: 2275-2279).

After examining the reaction rate, the ability of compound I and II to assemble into nanoaggregates after cyclization was evaluated. As shown in FIGS. 49A and 49B, aqueous solutions of compounds I and 11 (200 μM) turned from clear into homogenously cloudy once the pH was raised from 4 to 7.4, which indicated the formation of nanoaggregates. The results were further confirmed by dynamic light scattering (DLS) showing that, after raising the pH from acidic to 7.4 the compounds I and II (10 μM) self-assembled into nanoparticles with a mean diameter of 80 nm.

The key and lock part of the probes of the disclosure were examined to determine whether the CHQ could be replaced with a cyano substituted mono aromatic ring structure. For structure optimization of the lock part (FIGS. 48A and 48B), the intermolecular reaction rates for a series of cyano-substituted aromatic compounds with L-cysteine in phosphate-buffered saline (pH=7.4), were determined while minimizing interference from endogenous free cysteine (20-100 μM). (Park & Imlay (2003) *J. Bacteriol.* 185: 1942-1950). As shown in FIG. 49A, the 2-cyanobenzothiazole (CBT) analogue of TESLA-1 (FIGS. 48A and 48B) has a second-order reaction rate of 3.2 M$^{-1}$ s$^{-1}$, and can quickly react with cysteine (100 μM), which indicates potential competition from endogenous cysteine. However, 2-cyano-6-hydroxyquinoline (CHQ) as in TESLA-2 (FIGS. 48A and 48B) has a second-order reaction rate of 0.019 M$^{-1}$ s$^{-1}$, and can tolerate cysteine as high as 4 mM.

To further minimize the structure size, 4-methyl-2-thiazolecarbonitrile was considered as a potential candidate since it contains one heterocyclic aromatic ring and has a second-order reaction rate of 0.7 M$^{-1}$ s$^{-1}$. (Ye et al., (2011) *Angew. Chem.-Int. Edit.* 50: 2275-2279). From a detailed literature search of the reactivity of cyano-substituted aromatic compounds, pyrimidine-2-carbonitrile was considered as advantageous with a second-order reaction rate of 0.17 M$^{-1}$ s$^{-1}$. The reactivity of 4-bromo-pyrimidine-2-carbonitrile with an electron-withdrawing group at the para-position gave an increased second-order reaction rate (0.58 M$^{-1}$ s$^{-1}$). The reaction rate of both was slower than that of 4-methyl-2-thiazolecarbonitrile but faster than that of CHQ, indicating that pyrimidine-2-carbonitrile and its para-electron donating analogue were advantageous for structure modification of TESLA-2.

Also tested were modifications of the "key" part (cysteine highlighted as a rectangle in both in TESLA-1 and TESLA-2, FIGS. 48A and 48B). Specifically, the second-order reaction rate of substituted cysteines were compared. 2-methyl-L-cysteine has a faster second-order reaction rate (5.7 M$^{-1}$ s$^{-1}$) compared to most often used cysteine (3.2 M$^{-1}$ s$^{-1}$), and showed the possibility to be tethered into newly designed scaffold for increased kinetics. Another analogue, 3,3-dimethyl cysteine showed slower kinetics (0.06 M$^{-1}$ s$^{-1}$), indicating that the steric hindrance in the 3-position can dramatically affect its reaction with cyano-substituted aromatic compound.

Figure 50A:
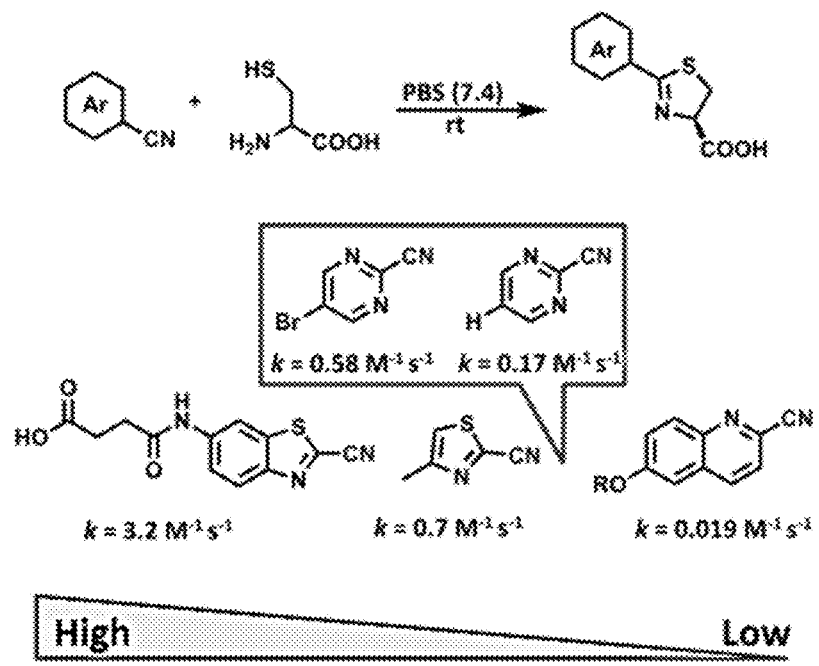
FIGS. 50A-50D illustrate the reactivity screening of cyano-substituted aromatics and cysteine analogues.
Figure 50B:
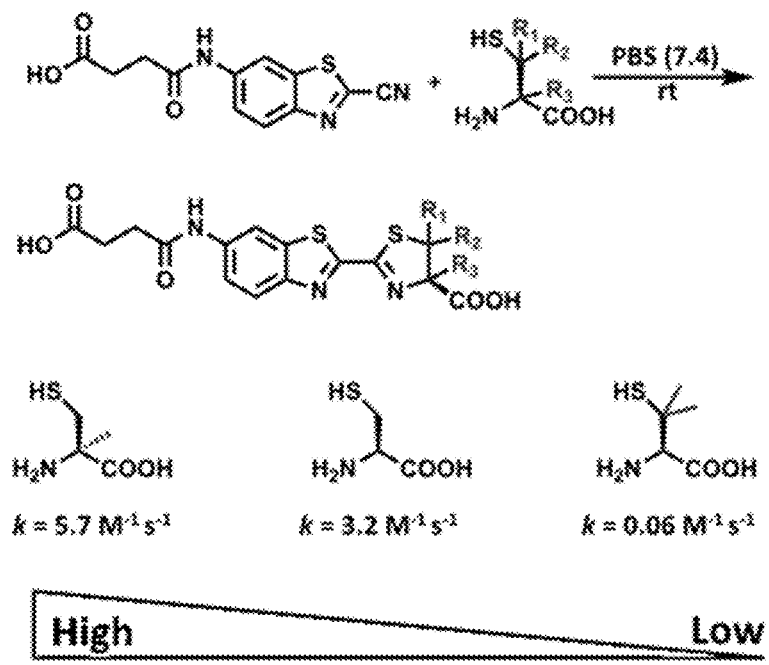
Figure 50C:
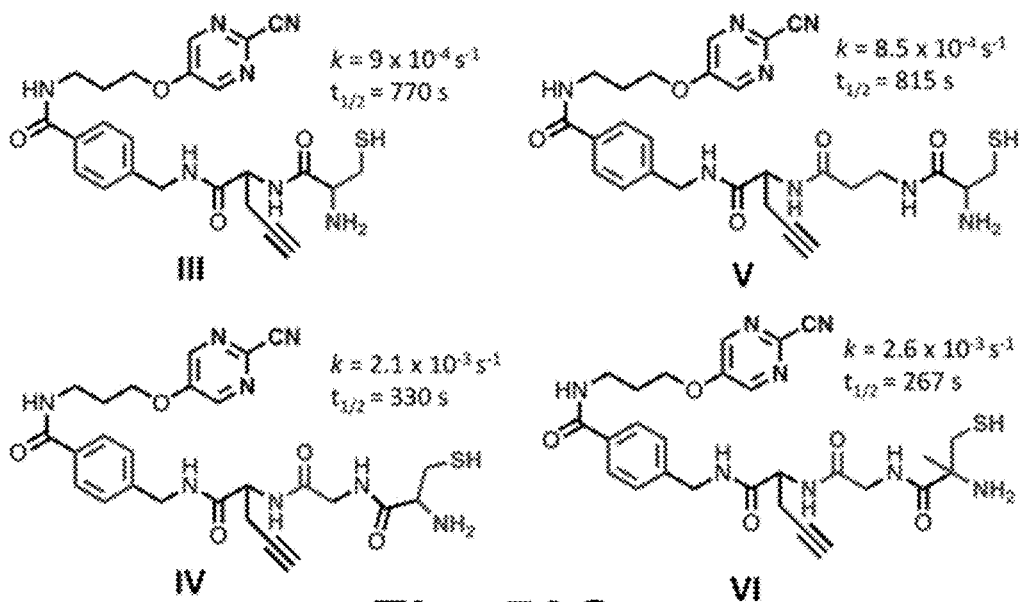
Figure 50D:
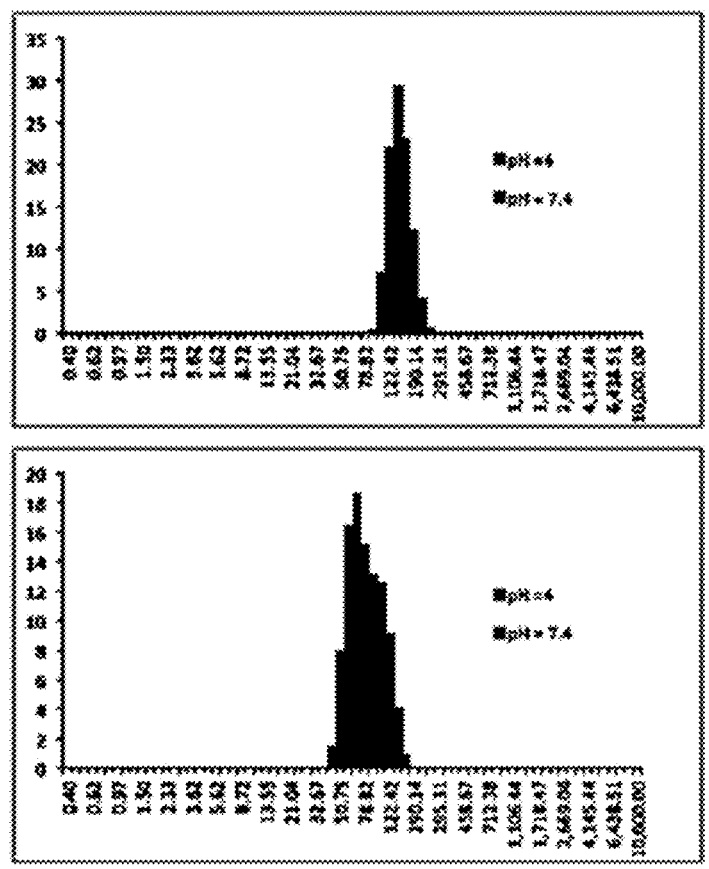

Accordingly, both key and lock part of the structure of compounds III, IV, V, and VI were generated, replacing the luciferin linker with a phenyl ring, and CHQ with an alkoxy-substituted pyrimidine-2-carbonitrile, and L-cysteine with 2-methyl-L-cysteine. The first order reaction rates of III and IV were determined as $9\times10^{-4}$ s$^{-1}$ and $2.1\times10^{-3}$ s$^{-1}$, respectively, which is comparable to TESLA-2 ($5.8\times10^{-3}$ s$^{-1}$). Most advantageously, both III and IV formed intramolecular cyclized products after raising pH from 4 to 7.4. Furthermore cyclized monomer was self-assembled into nanoparticles, confirmed by dynamic light scattering as having a mean of diameter of 130 and 80 nm for compound III and IV respectively (FIG. 50D). By lengthening of the linker with one more carbon, the analogue V showed slower kinetics ($8\times10^{-4}$ s$^{-1}$ vs $2.1\times10^{-3}$s$^{-1}$ of IV), indicating that linker length is significant for analogue design to obtain optimum kinetics. Replacing the L-cysteine of IV with a more reactive 2-methyl-L-cysteine, compound VI showed kinetics with a second-order reaction rate of $2.1\times10^{-3}$s$^{-1}$.

Visualization of TESLA in Cells

TESLA-2 can be used for imaging caspase activity in vitro and in vivo, can undergo caspase-3 and GSH-triggered DEVD and disulfide uncaging, intra-molecular cyclization and self-assembly (Ye et al. (2014) *Nat. Chem.* 6: 519-526). It was also investigated whether a targeting-incorporated scaffold could also be used for the visualization of TESLA in cells. DEVD and disulfide were thus incorporated into the structure IV.

Caspase-sensitive nanoaggregation fluorescent probes were designed and synthesized according to Schemes 1-3, FIGS. 53-55, respectively). The mechanism of C-SNAFs-Cy5 is shown in FIG. 51A.

After cleavage of the DEVD by caspase under reducing conditions, intramolecular cyclization occurred between the terminal cysteine and pyrimidine-2-carbonitrile, followed by the bioorthogonal intra-molecular cyclization. In vitro validations were performed by incubating C-SNAF-Cy5 with caspase-3 and reducing agent TCEP simultaneously (FIG. 51A). DLS analysis of C-SNAF4-Cy5 (20 μM) following incubating with caspase-3 in caspase buffer after 6 h further confirmed the in situ forming of nanoaggregates with an average diameter of 200 nm. The retention of C-SNAF-Cy5 in cisplatin-induced H460 apoptotic cells was investigated further by fluorescence microscopy. As shown in FIG. 51C, C-SNAFs-Cy5 accumulated extensively in cisplatin-treated apoptotic cells, while negligible fluorescence was observed in viable cells without cisplatin treatment. Fluorescence abolishment after pan-caspase inhibitor Z-VAD-fmk treatment confirmed the activation of C-SNAF4-Cy5 by effector caspase.

Embodiments of the scaffold of the disclosure are also advantageous for imaging targets having other than caspase-3. For example, β-galactosidase has been widely used as a gene reporter and identified as a biomarker in various disease events such as tumor metastasis and cellular senescence (Bernacki et al., (1985) *Cancer metastasis reviews* 4: 81-101; Bosmann & Hall (1974) *Proc. Nat. Acad. Sci. U.S.A.* 71: 1833-1837; Debacq-Chainiaux et al., (2009) *Nat. Protoc.* 4: 1798-1806). The design of B-SNAF4 and its mechanism for imaging β-galactosidase is shown in FIG. 52A. After cleavage of the glycoside by β-galactosidase under reducing environment, the linker self-immolates in the form of quinone methide and carbon dioxide to generate available cysteine that undergoes the same bioorthogonal intra-molecular cyclization with pyrimidine-2-carbonitrile. In vitro validations were performed by incubating B-SNAF4 with β-galactosidase alone and with β-galactosidase with reducing agent TCEP. The enzyme cleavage product and cyclization product were confirmed by HPLC and mass analysis (FIG. 52B).

To demonstrate the selective retention of B-SNAF4 in LacZ-expressed cell line, a fluorescent assay was used to compare the uptake of this probe in 9L/LacZ rat gliosarcoma cell line with the uptake in 9L/Luc cell line. LacZ gene expression in 9L/LacZ, and the control cell line 9L/luc were first confirmed through X-Gal staining, a widely used colorimetric essay to detect β-galactosidase activity (FIG. 52C). Fluorescent imaging was subsequently performed for the two cell lines when incubated with B-SNAF4. 9L/LacZ showed significantly higher retention of fluorescent signal than 9L/Luc, indicating that the intramolecular cyclization and aggregation of the probe was sufficient to generate selective retention of the probe in cells having the target enzyme present.

One aspect of the disclosure, therefore, encompasses embodiments of a compound comprising a terminal aromatic nitrile group, a phenyl or a substituted phenyl, a cysteine, and a thiol cysteine blocking group having the structure (—S—$R_3$), wherein (i) the terminal aromatic nitrile group and the phenyl or substituted phenyl can be connected by a linker 1, (ii) the phenyl or substituted phenyl and the cysteine can be connected by linker 2, and (iii) the cysteine blocking group can be conjugated to the cysteine to form a disulfide bond, wherein the compound can have the formula A:

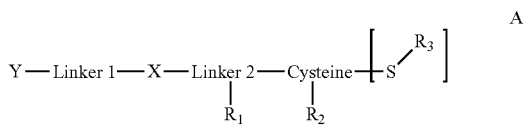

wherein: $R_1$ can be a detectable label; $R_2$ can be a moiety specifically cleavable from the scaffold by an enzyme; and $R_3$ can be an unsubstituted or substituted straight-chain alkyl group, an unsubstituted or substituted branched-chain alkyl group, an aromatic group, or a substituted aromatic group.

In some embodiments of this aspect of the disclosure, the compound can have the formula I:

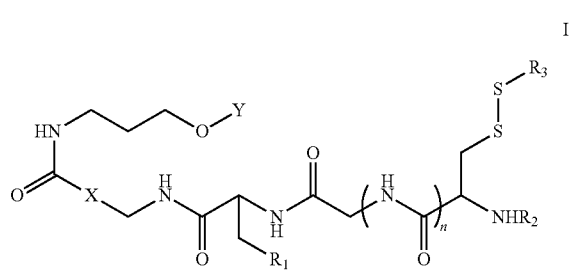

wherein the scaffold can comprise a terminal aromatic nitrile group and a disulfide group, and wherein: n=0-6, $R_1$ can be a detectable label; $R_2$ can be a moiety specifically cleavable from the scaffold by an enzyme; $R_3$ can be an unsubstituted or substituted straight-chain alkyl group, an unsubstituted or substituted branched-chain group; X can be a phenyl or a substituted phenyl; and Y can an aromatic nitrile group.

In some embodiments of this aspect of the disclosure, X can be a phenyl group.

In some embodiments of this aspect of the disclosure, Y can be a pyrimidine nitrile group.

In some embodiments of this aspect of the disclosure, n=0-6, X can be a phenyl group, Y can be a pyrimidine nitrile group, and the compound can have the formula II:

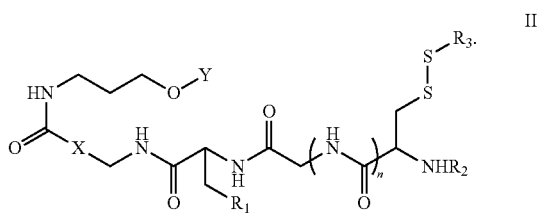

In some embodiments of this aspect of the disclosure, $R_1$ can be selected from a fluorescent dye, a positron emission tomography (PET) detectable moiety, and a magnetic resonance detectable moiety.

In some embodiments of this aspect of the disclosure, fluorescent dye can be a cyanine dye.

In some embodiments of this aspect of the disclosure, cyanine dye is Cy5 or Cy5.5.

In some embodiments of this aspect of the disclosure, the PET detectable moiety is an $^{18}$F-labelled moiety.

In some embodiments of this aspect of the disclosure, $R_3$ can be $(CH_2)_m$—$CH_3$, wherein m=0-6.

In some embodiments of this aspect of the disclosure, magnetic resonance detectable moiety can be a gadolinium ion, and wherein the gadolinium ion can be attached to the scaffold by a metal chelating group.

In some embodiments of this aspect of the disclosure, $R_2$ can be a peptide having the amino acid sequence Aspartate-Glutamate-Valine-Aspartate (DEVD) and is specifically cleavable from the scaffold by caspase 3/7, a peptide having the amino acid sequence Isoleucine-Glutamate-Phenylalanine-Aspartate (IEFD) or the amino acid sequence Isoleucine-Glutamate-Proline-Aspartate (IEPD) and specifically cleavable from the scaffold by granzyme-B, a β-galactosidase-cleavable-moiety, or methionine.

In some embodiments of this aspect of the disclosure, $R_2$ can be a glycoside specifically cleavable from the scaffold by β-galactosidase.

In some embodiments of this aspect of the disclosure, the glycoside can have the structure:

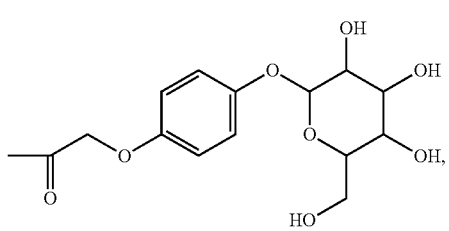 [SMILES: CC(=O)COc1ccc(OC2OC(CO)C(O)C(O)C2O)cc1]

In some embodiments of this aspect of the disclosure, the compound can have a formula selected from the group consisting of:

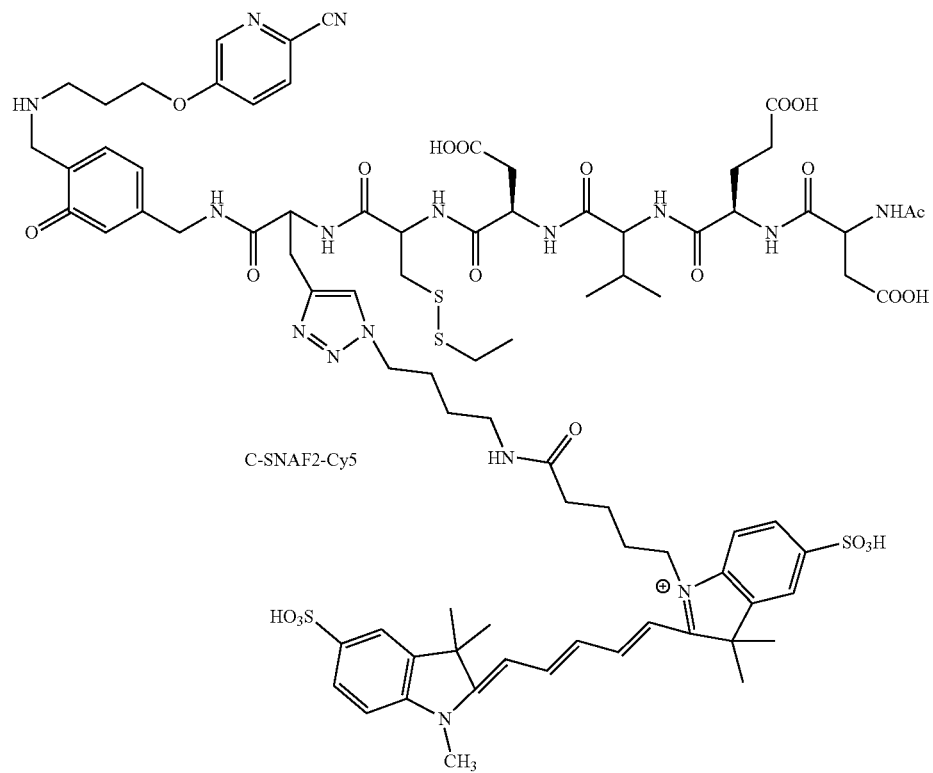
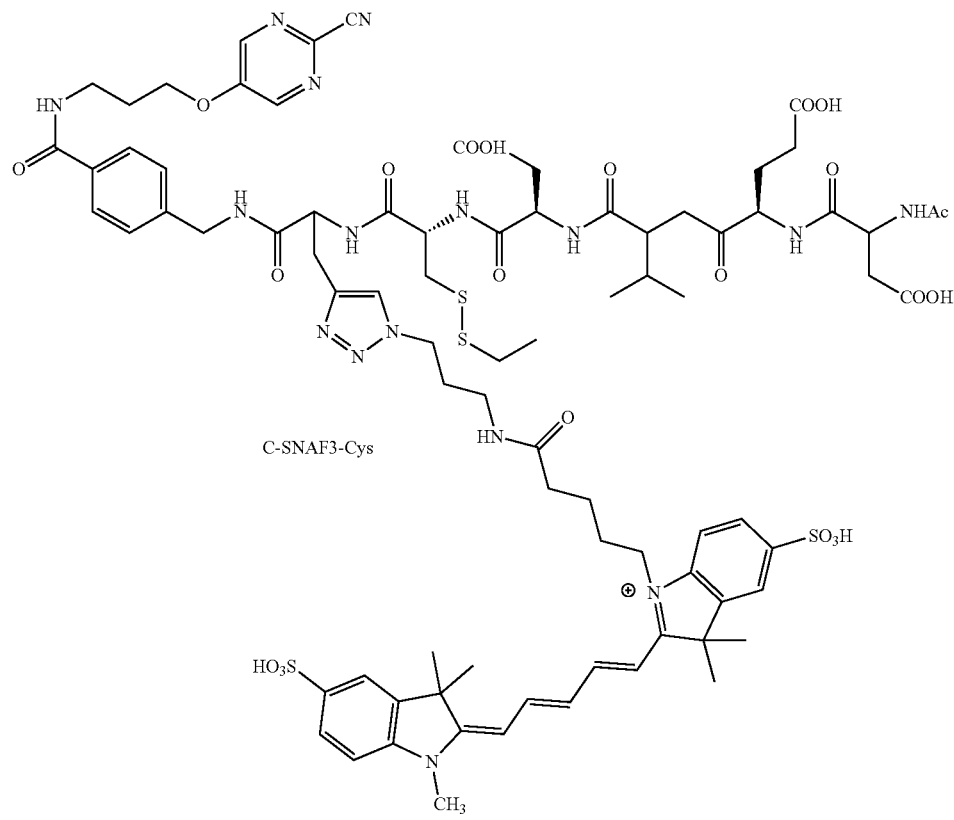

-continued
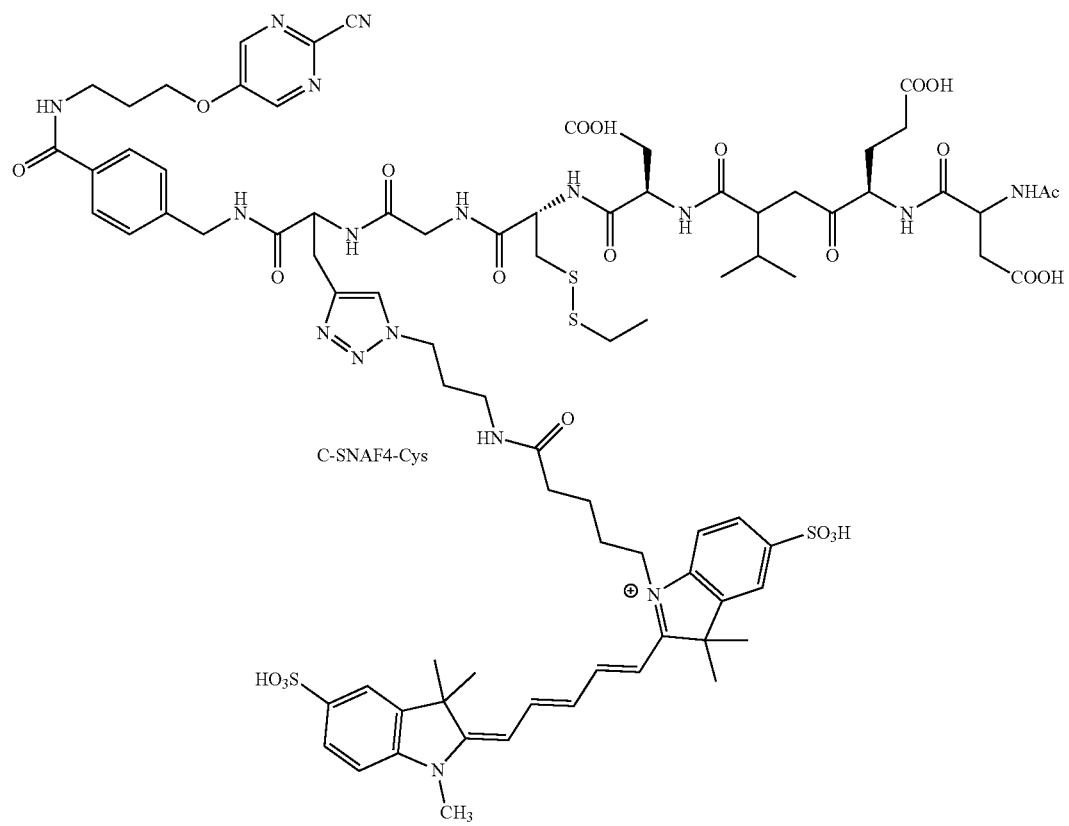
C-SNAF4-Cys
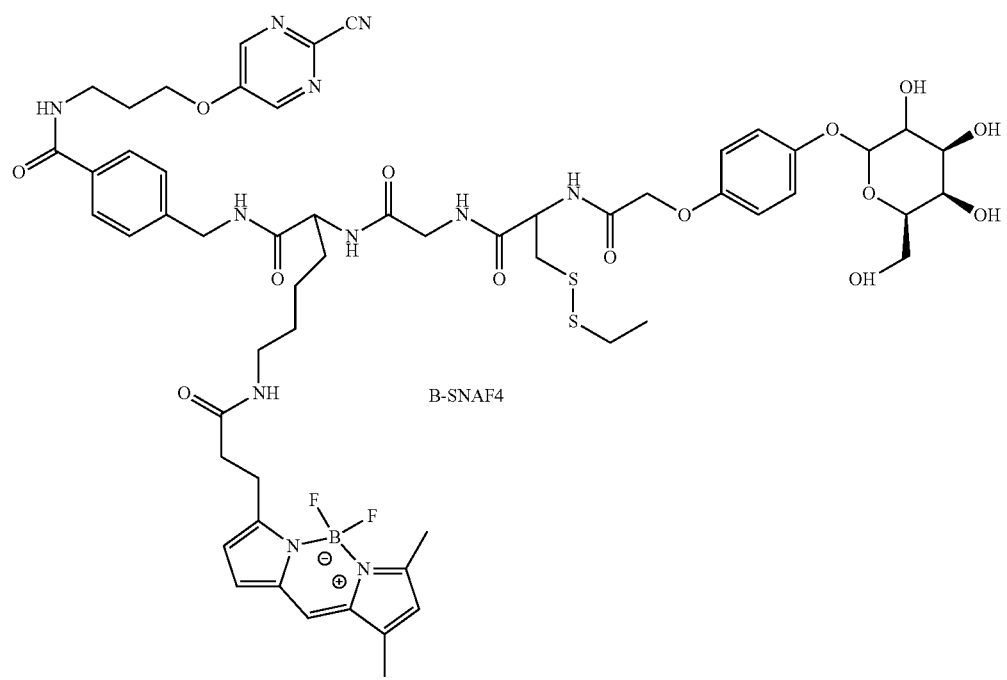
B-SNAF4

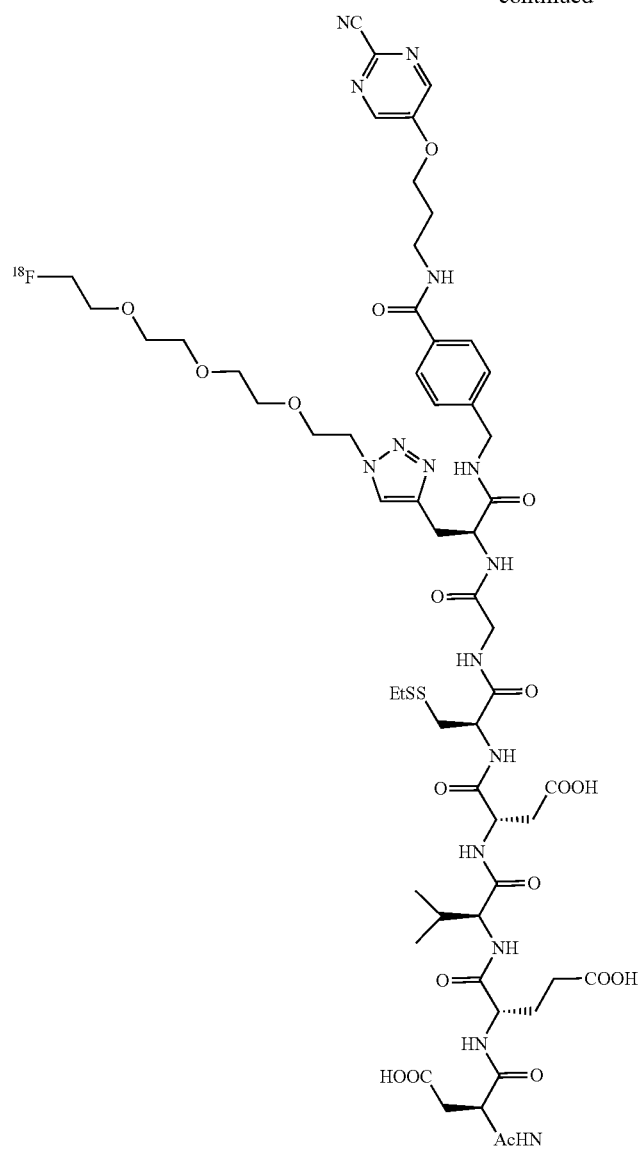
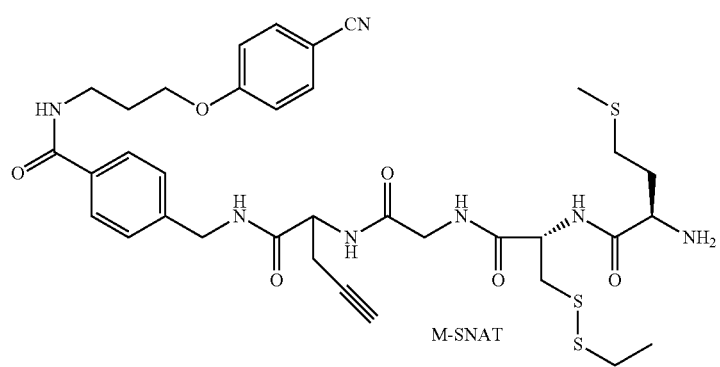
M-SNAT

In some embodiments of this aspect of the disclosure, compound can be admixed with a pharmaceutically acceptable carrier.

Another aspect of the disclosure encompasses embodiments of a composition comprising at least one molecule of a self-aggregating compound having formula III:

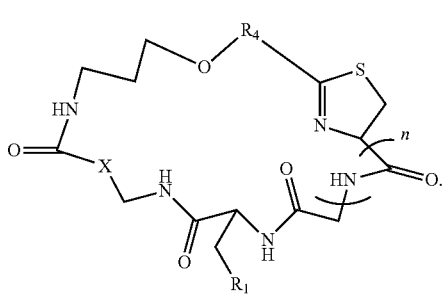

wherein: $R_1$ is a detectable label; $R_2$ is a moiety specifically cleavable from the scaffold by an enzyme; $R_4$ can be an aromatic group; and X is a phenyl or a substituted phenyl.

In some embodiments of this aspect of the disclosure, the composition can have the formula IV:

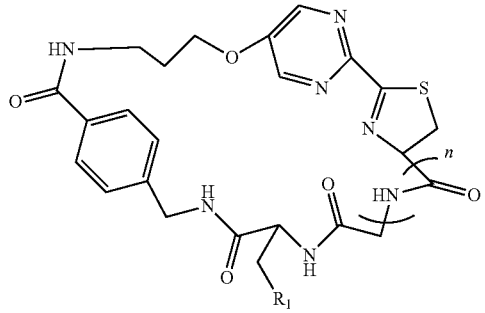

In some embodiments of this aspect of the disclosure, a plurality of molecules of the compound having the formula III are self-aggregated to form a nanoaggregate.

In some embodiments of this aspect of the disclosure, $R_1$ can be selected from a fluorescent dye, a positron emission tomography (PET) detectable moiety, and a magnetic resonance detectable moiety.

In some embodiments of this aspect of the disclosure, fluorescent dye can be a cyanine dye.

In some embodiments of this aspect of the disclosure, the PET detectable moiety can be $^{18}F$.

In some embodiments of this aspect of the disclosure, $R_2$ is a peptide having the amino acid sequence Aspartate-Glutamate-Valine-Aspartate (DEVD) and is specifically cleavable from the scaffold by caspase 3/7, a peptide having the amino acid sequence Isoleucine-Glutamate-Phenylalanine-Aspartate (IEFD) or the amino acid sequence Isoleucine-Glutamate-Proline-Aspartate (IEPD) and specifically cleavable from the scaffold by granzyme-B, a glycoside specifically cleavable from the scaffold by β-galactosidase, or methionine.

Yet another aspect of the disclosure encompasses embodiments of a method of generating an image of a tissue in an animal or human subject, the method comprising the steps of: (i) administering to an animal or human subject a pharmaceutically acceptable composition comprising a terminal aromatic nitrile group, a phenyl or a substituted phenyl, a cysteine, and a thiol cysteine blocking group having the structure (—S—$R_3$), wherein (i) the terminal aromatic nitrile group and the phenyl or substituted phenyl can be connected by a linker 1, (ii) the phenyl or substituted phenyl and the cysteine can be connected by linker 2, and (iii) the cysteine blocking group can be conjugated to the cysteine to form a disulfide bond, wherein the compound can have the formula A:

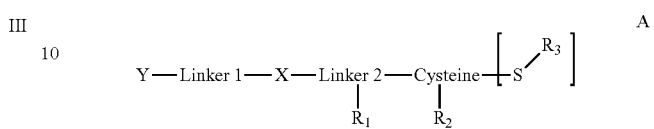

wherein: $R_1$ can be a detectable label; $R_2$ can be a moiety specifically cleavable from the scaffold by an enzyme; and $R_3$ can be an unsubstituted or substituted straight-chain alkyl group, an unsubstituted or substituted branched-chain group, an aromatic group, or a substituted aromatic group; and (ii) obtaining an image of the location of nanoaggregates of the compound in a tissue of the animal or human subject.

In some embodiments of this aspect of the disclosure, the compound can have the formula I:

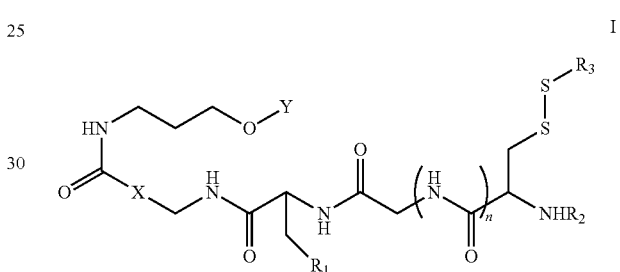

wherein the compound comprises a terminal aromatic nitrile group and a disulfide group, and wherein: n=0-6; $R_1$ can be a detectable label; $R_2$ can be a moiety specifically cleavable from the scaffold by an enzyme; $R_3$ can be an unsubstituted or substituted straight-chain alkyl group, an unsubstituted or substituted branched-chain group; X is a phenyl or a substituted phenyl; and Y is an aromatic nitrile group; and (ii) obtaining an image of the location of nanoaggregates of the compound in a tissue of the animal or human subject.

In some embodiments of this aspect of the disclosure, n=0-6, X can be a phenyl group, Y can be a pyrimidine nitrile group, and the scaffold can have the formula II:

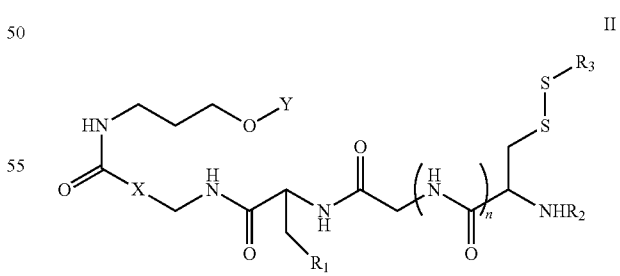

In some embodiments of this aspect of the disclosure, $R_1$ can be selected from a fluorescent dye, a positron emission tomography (PET) detectable moiety, and a magnetic resonance detectable moiety.

In some embodiments of this aspect of the disclosure, fluorescent dye can be a cyanine dye.

In some embodiments of this aspect of the disclosure, the cyanine dye can be Cy5 or Cy5.5.

In some embodiments of this aspect of the disclosure, the PET detectable moiety can be an $^{18}$F-labelled moiety.

In some embodiments of this aspect of the disclosure, a fraction of the $^{18}$F can be replaced by [19]F.

In some embodiments of this aspect of the disclosure, the magnetic resonance detectable moiety can be a gadolinium ion, and wherein the gadolinium ion is attached to the scaffold by a metal chelating group.

In some embodiments of this aspect of the disclosure, $R_2$ can be a peptide having the amino acid sequence Aspartate-Glutamate-Valine-Aspartate (DEVD) and can be specifically cleavable from the scaffold by caspase 3/7, a peptide having the amino acid sequence Isoleucine-Glutamate-Phenylalanine-Aspartate (IEFD) or the amino acid sequence Isoleucine-Glutamate-Proline-Aspartate (IEPD) and specifically cleavable from the scaffold by granzyme-B, a β-galactosidase-cleavable-moiety, or methionine.

In some embodiments of this aspect of the disclosure, $R_2$ can be a glycoside specifically cleavable from the scaffold by β-galactosidase.

In some embodiments of this aspect of the disclosure, the glycoside can have the structure:

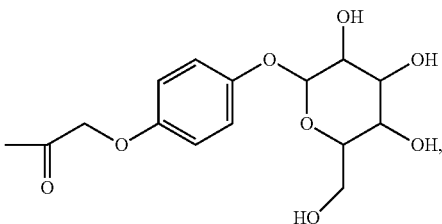 [SMILES: CC(=O)COc1ccc(OC2OC(CO)C(O)C(O)C2O)cc1]

In some embodiments of this aspect of the disclosure, the compound having the formula A can be selected from the group consisting of:

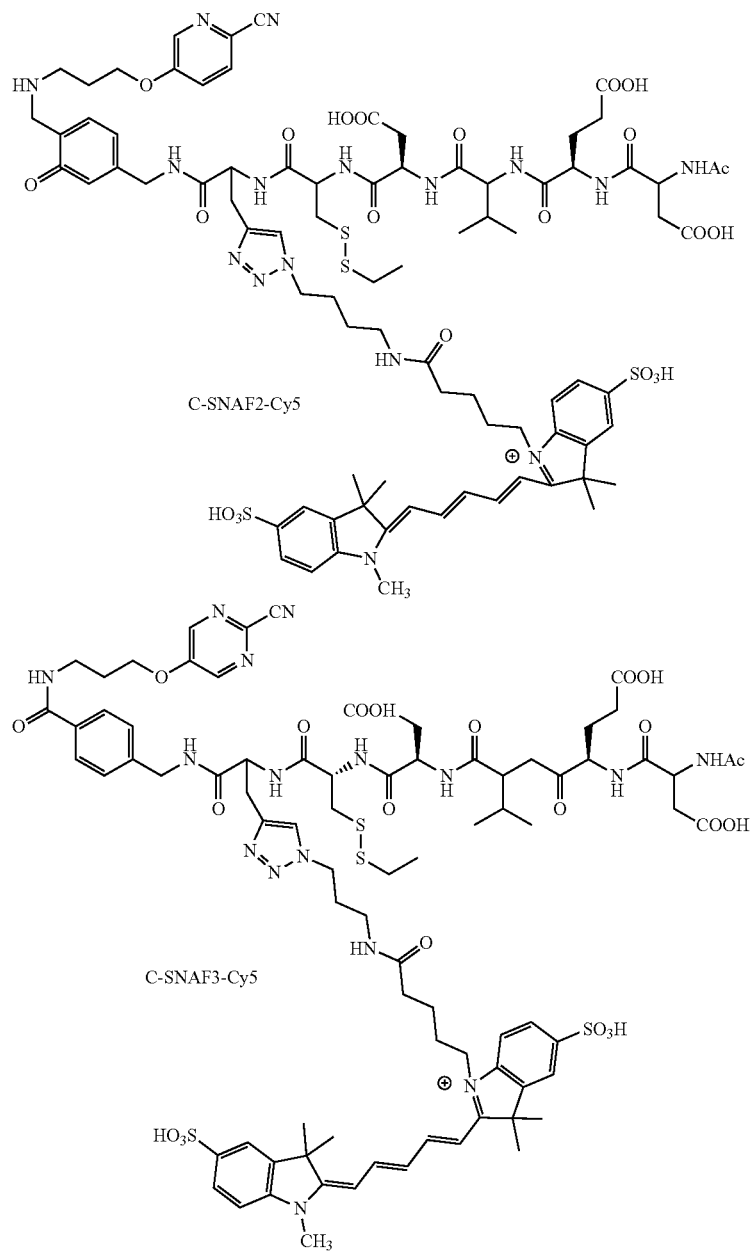

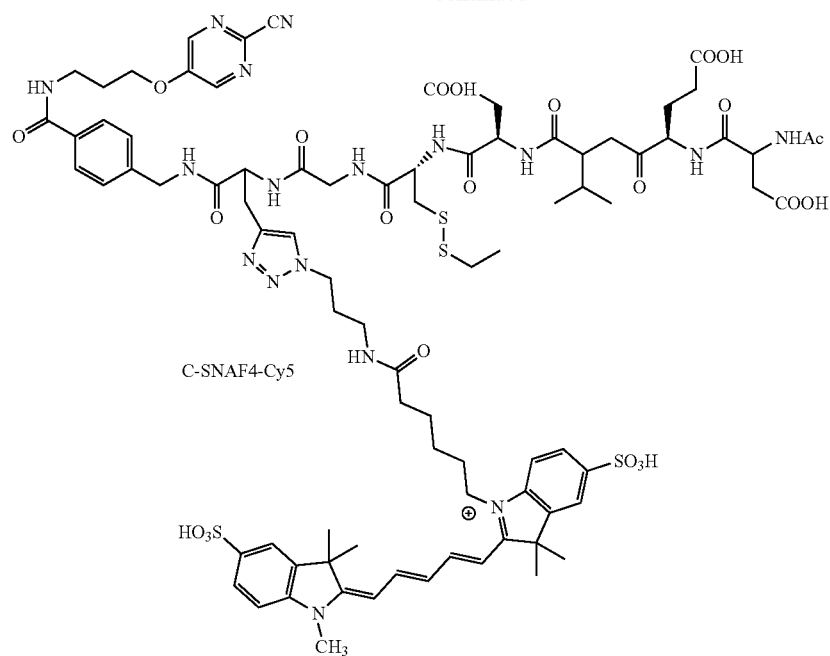
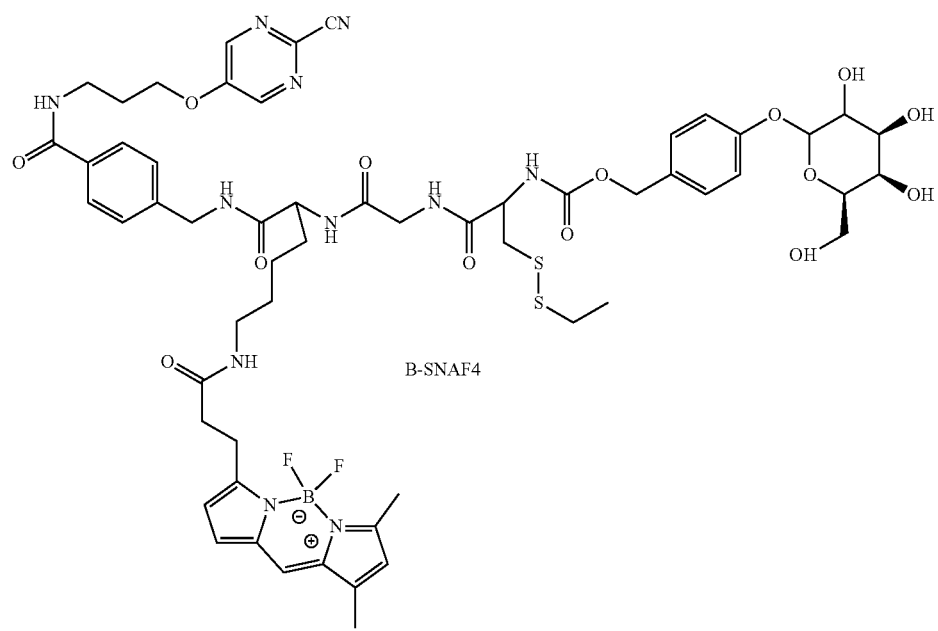

-continued
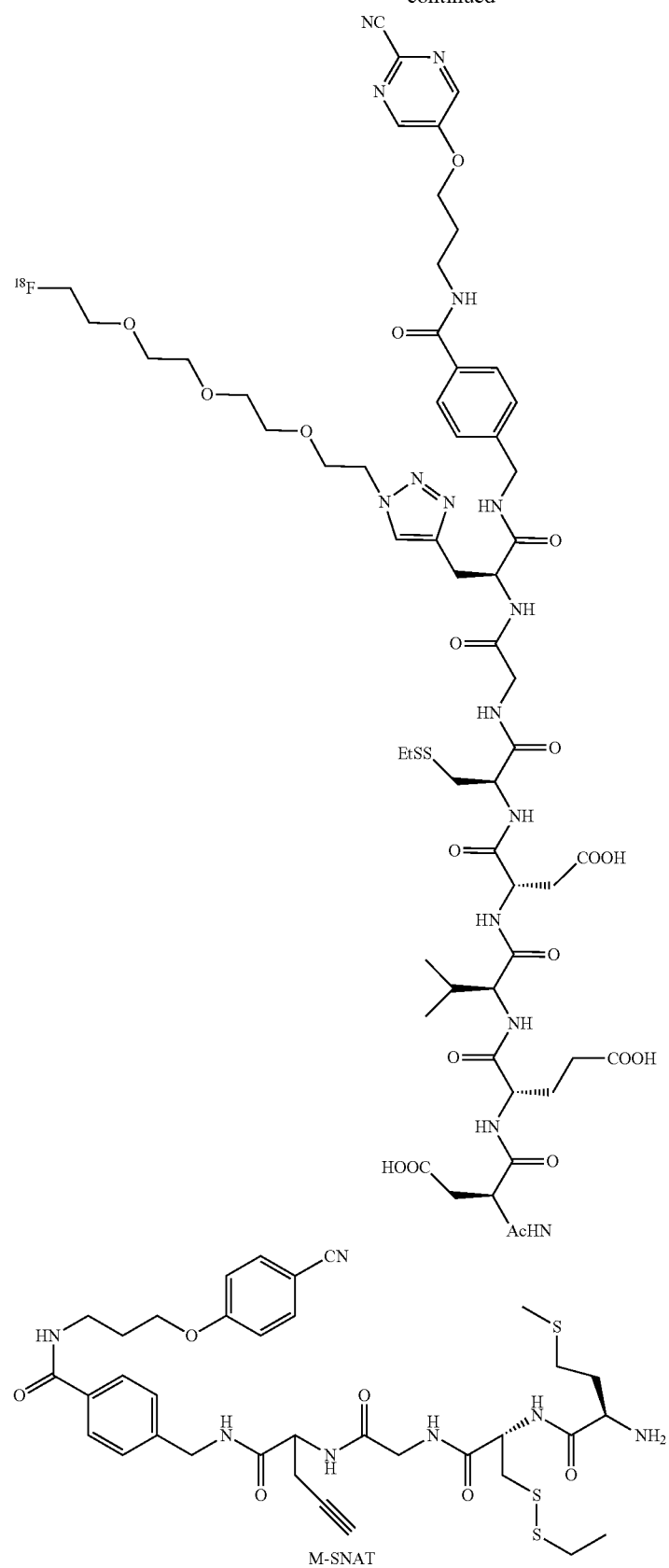

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

PET Imaging of Therapeutic Responses in Non-Small Cell Lung Cancer with a Caspase 3-Targeted Tracer
Caspase-3/7 Activated Nanoaggregation PET Probe ([$^{18}$F]-C-SNAT4)

An early assessment of treatment response is crucial for the development of novel therapies since patients with similar tumor types frequently respond differently to the same therapy. Advances in molecular imaging in cancer have made in vivo detection of therapeutic outcome possible. PET imaging of apoptosis in vivo provides powerful tool to rapidly select the most effective treatment. The probe [$^{18}$F]-C-SNAT4 of the disclosure shows advantages for imaging treatment outcomes, including the enhanced retention of $^{18}$F-activity and the utilization of small molecular probe. This probe can circumvent the safety concerns generally limiting the use of nanoparticles in clinical imaging. Application of caspase-3-sensitive nanoaggregation probes [$^{18}$F]-C-SNAT4 for monitoring caspase-3 activity and apoptotic changes in vitro and in vivo using PET imaging. [$^{18}$F]-C-SNAT4 radiotracer permitted assessment of the molecular characteristics of tumor death based on caspase-3 activation. Thus, [$^{18}$F]-C-SNAT4 can be advantageous for preclinical detection of treatment response in two types of non-small cell lung cancer both in vitro and in vivo.

The cellular uptake study (FIGS. 2-3B) showed selective uptake by apoptotic cells in correlation with the apoptotic percentage, which indicated that efficient monitoring of apoptosis for [$^{18}$F]-C-SNAT4. PET imaging in vivo (FIGS. 4A-4F) showed that the clearance of [$^{18}$F]-C-SNAT4 radiotracer was mainly through renal clearance, accompanied by long-retention in treated tumor. The rapid clearance and low nonspecific uptake of [$^{18}$F]-C-SNAT4 provided specific imaging of caspase-3/7 activity in tumors. Moreover, PET imaging using mixture with [$^{19}$F]-C-SNAT4 (FIGS. 6A-6E) confirmed that the mixture strategy can increase the retention of $^{18}$F signal, ultimately improve the PET imaging sensitivity both in radiotherapy and chemotherapy animal models (FIGS. 6A-6E and 24A-24C). This mixture strategy efficiently increased the tumor uptake of [$^{18}$F]-C-SNAT4 and improved imaging sensitivity of therapeutic outcomes.

Figure 20:
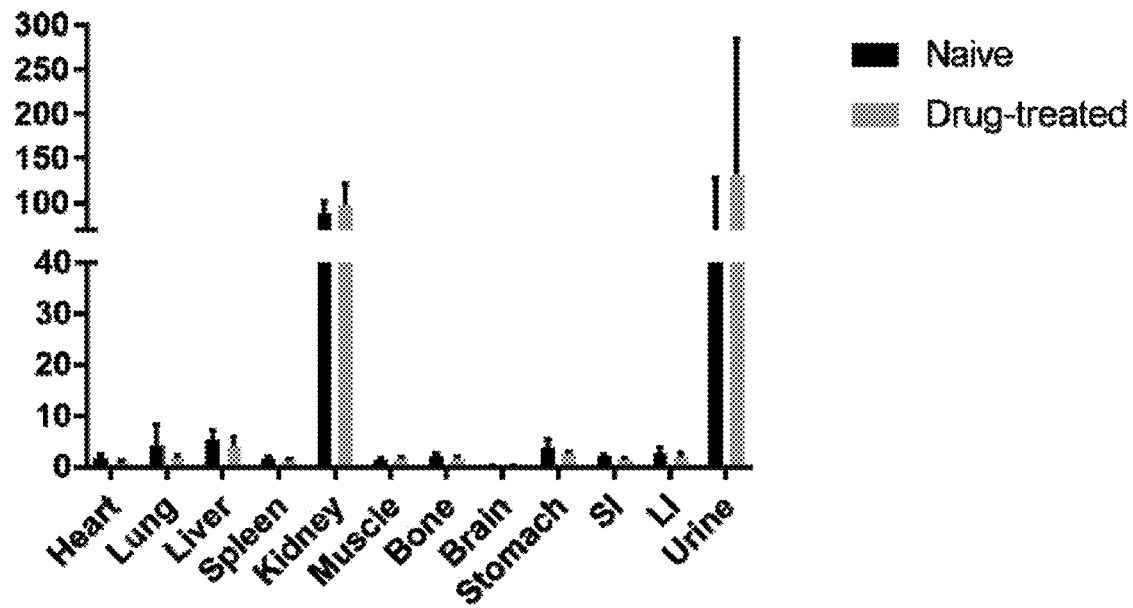
FIG. 20 illustrates biodistribution of [$^{18}$F]-C-SNAT4 in H460 tumor-bearing female nude mice. Mice were administered approximately 200 μCi [$^{18}$F]-C-SNAT4, animal were exsanguinated through the left ventricle and indicated tissues were excised at 2 hours post-injection in mice bearing naïve-tumor (black) or drug-treated tumor (gray). Data represent the mean±S.D. (n=4 animals per groups)

The scaffold C-SNAT4 of the disclosure is advantageous as having a simple synthesis, rapid radiolabeling, high serum stability for clinical application. The [$^{18}$F]-C-SNAT4 radiopharmaceuticals can be produced for human applications. Secondly, the tracer manifests high selectivity and specificity for apoptotic cells in the early stages of the cell death process, and preferably monitoring therapeutic responses in vitro and in vivo, providing insight of tumor microenvironment between drug-sensitive and-resistant states (FIGS. 2 and 4A-4F). Thirdly, the PET tracer is suitable for using in vivo for its adequate biodistribution on intravenous administration, with high retention in treated tumor and rapid clearance through renal pathway (FIG. 20).

After validation of efficacy, safety and dosimetry studies, [$^{18}$F]-C-SNAT4 has been approved for use in humans by FDA eIND as PET tracer for caspase-3 targeted imaging of therapeutic outcomes in cancer.

Caspase-3/7-activated nanoaggregation PET probes of the disclosure comprise, in the scaffold, a 2-pyrimidine carbonitrile and a benzyl linker to build the probe [$^{18}$F]-C-SNAT4 (FIG. 1A). Upon cleavage by caspases-3/7 and glutathione in cells, the free cysteine and pyrimidine carbon nitrile undergo condensation reaction to form the hydrophobic cyclic product, which self-assembles in situ to form nanoaggregates to prolong retention of $^{18}$F activity and enhance PET imaging contrast.

Figure 7:
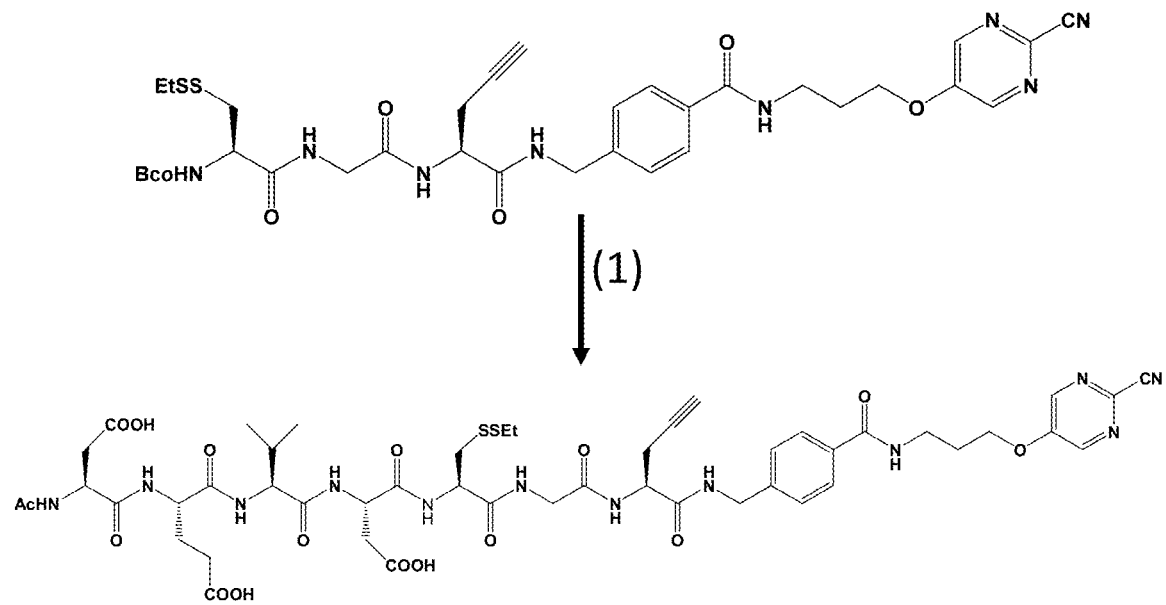
FIG. 7 illustrates synthesis of precursor C-SNAT4. (1) (i) 1:4 TFA/DCM, r.t., 30 min; (ii) Ac-DEVD-OH peptide, HBTU, DIPEA, DMF, r.t., 2 h; (iii) 1:1:0.05 TFA/DCM/TIPS, r.t. 2 h.
Figure 8:
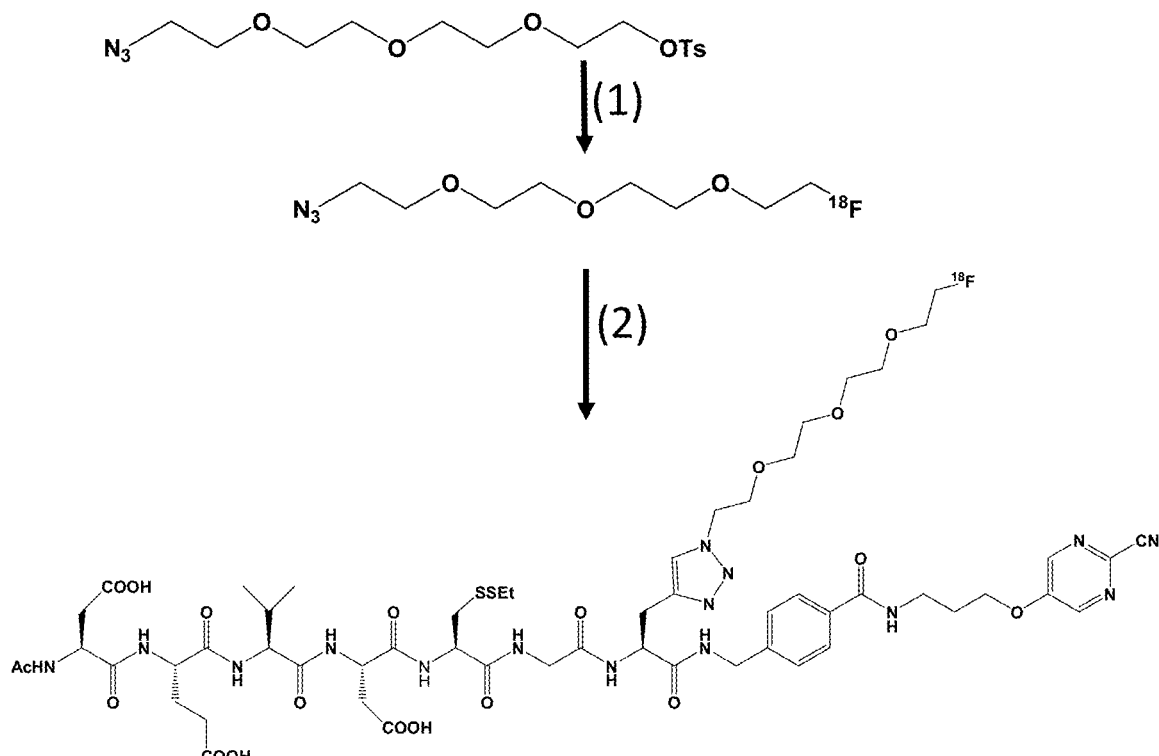
FIG. 8 illustrates radiosynthesis of [$^{18}$F]-C-SNAT4. (1)$^{18}$F/Kryptofix 222/K$_2$CO$_3$, DMSO, 110° C., 20 min; (2)C-SNAT4, CuSO$_4$, sodium ascorbate, (BimC$_4$A)$_3$.
Figure 9A:
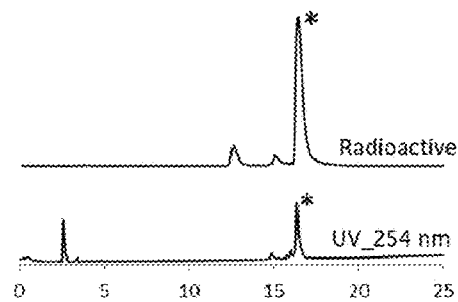
FIG. 9A illustrates a representative analytical HPLC chromatogram (radioactive and UV at 254 nm) of crude [$^{18}$F/$^{19}$F]C-SNAT4 for monitoring click reaction. An aliquot of the reaction solution was taken out 20 min after reaction started.
Figure 9B:
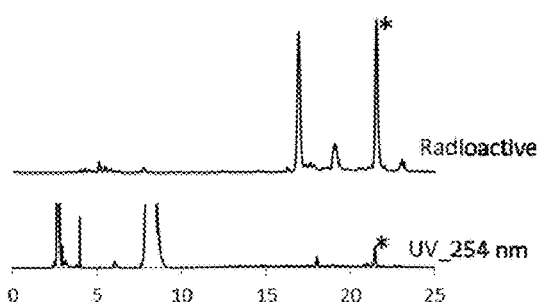
FIG. 9B illustrates a representative semi-preparative HPLC chromatogram (radioactive and UV at 254 nm) of crude [$^{18}$F/$^{19}$F]C-SNAT4 after click reaction.
Figure 9C:
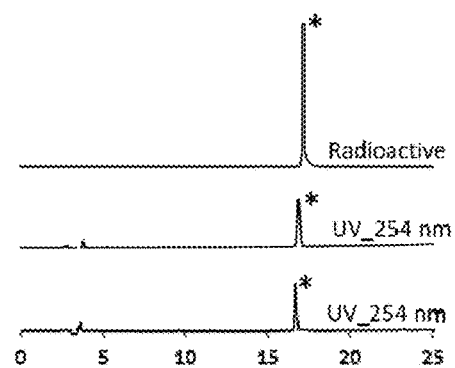
FIG. 9C illustrates a representative analytical HPLC chromatogram (radioactive and UV at 254 nm) of purified [$^{18}$F/$^{19}$F]C-SNAT4 and [$^{19}$F]C-SNAT4 standard (bottom).
Figure 9D:
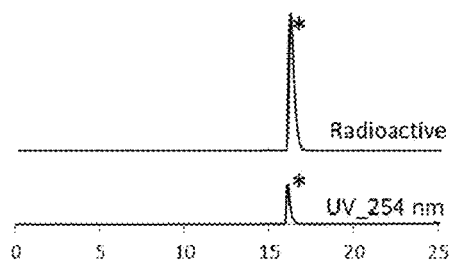
FIG. 9D illustrates an analytical HPLC chromatogram (radioactive and UV at 254 nm) of co-injection of purified [$^{18}$F/$^{19}$F]C-SNAT4 and [$^{19}$F]C-SNAT4 standard. * [$^{18}$F/$^{19}$F] C-SNAT4.
Figure 10:
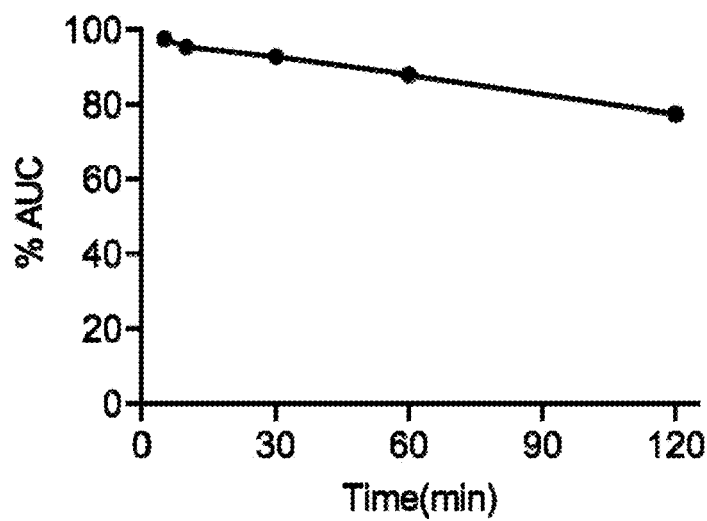
FIG. 10 illustrates serum stability of [$^{18}$F]-C-SNAT4 in human serum. [$^{18}$F]-C-SNAT4 was incubated in serum at 37° C. and analyzed by HPLC.

Radiosynthesis of [$^{18}$F]-C-SNAT4 proceeded through click reaction. Briefly, [$^{18}$F] fluoride generated from a cyclotron first displaced the tosyl-group on azide-PEG$_3$-tosylate in a fully automated synthetic module (FIGS. 7 and 8). The resulting azide-PEG$_3$-$^{18}$F was then introduced onto C-SNAT4 precursor through copper catalyzed azide-alkyne-1, 3-cycloaddition (CuAAC) confirmed by HPLC (FIGS. 9A-9D). The radiochemical yield of [$^{18}$F]-C-SNAT4 was 6.6±5.0% with a specific activity of 2.3±1.1 Ci/µmol. The stability of [$^{18}$F]-C-SNAT4 in mouse serum (FIG. 1B) and in human serum (FIG. 10) was monitored by HPLC equipped with radiation detector.

The percentages of [$^{18}$F]-C-SNAT4 left were calculated at different time points and the results showed percentages of [$^{18}$F]-C-SNAT4 remained in mouse serum (77.2%) and in human serum (77.5%) over 2 h incubation, much improved over the first generation of [$^{18}$F]-C-SNAT.

Figure 11:
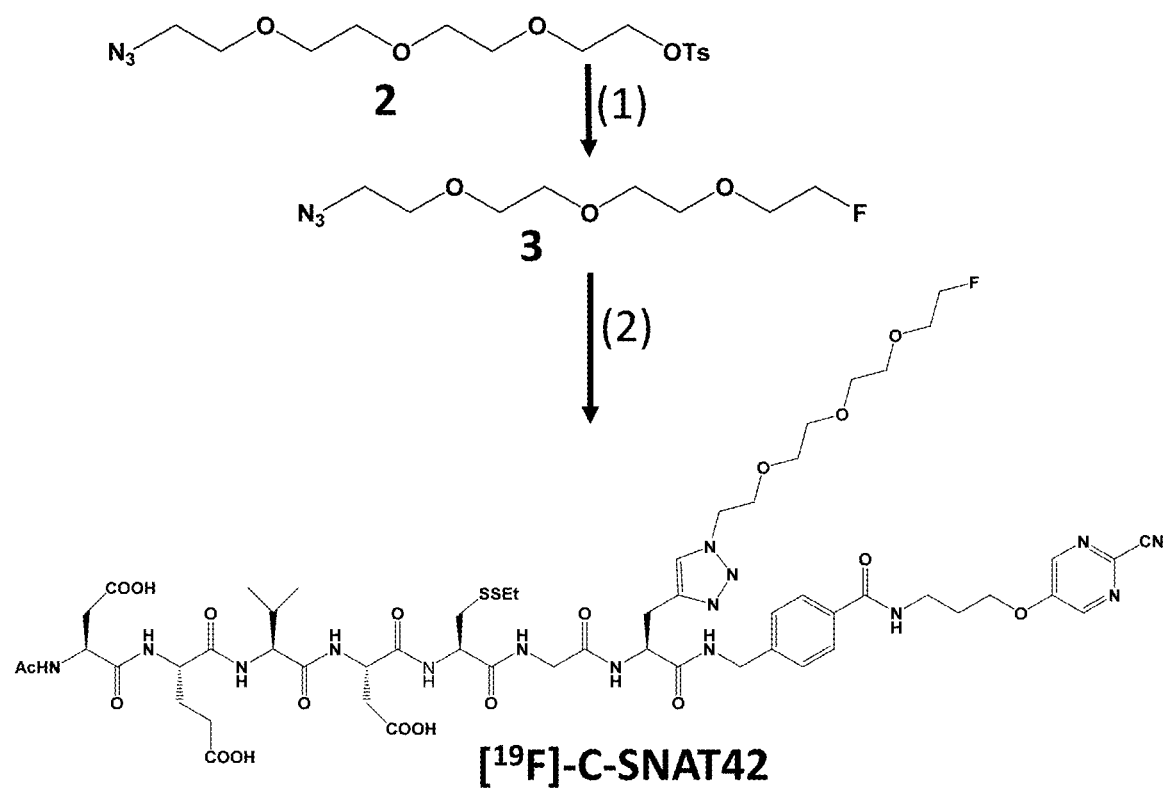
FIG. 11 illustrates synthesis of cold analog [$^{19}$F]-C-SNAT4. (1) TBAF, ACN, 80° C., overnight; (2)C-SNAT4, CuSO$_4$, sodium ascorbate, (BimC$_4$A)$_3$ ligand.
Figure 12:
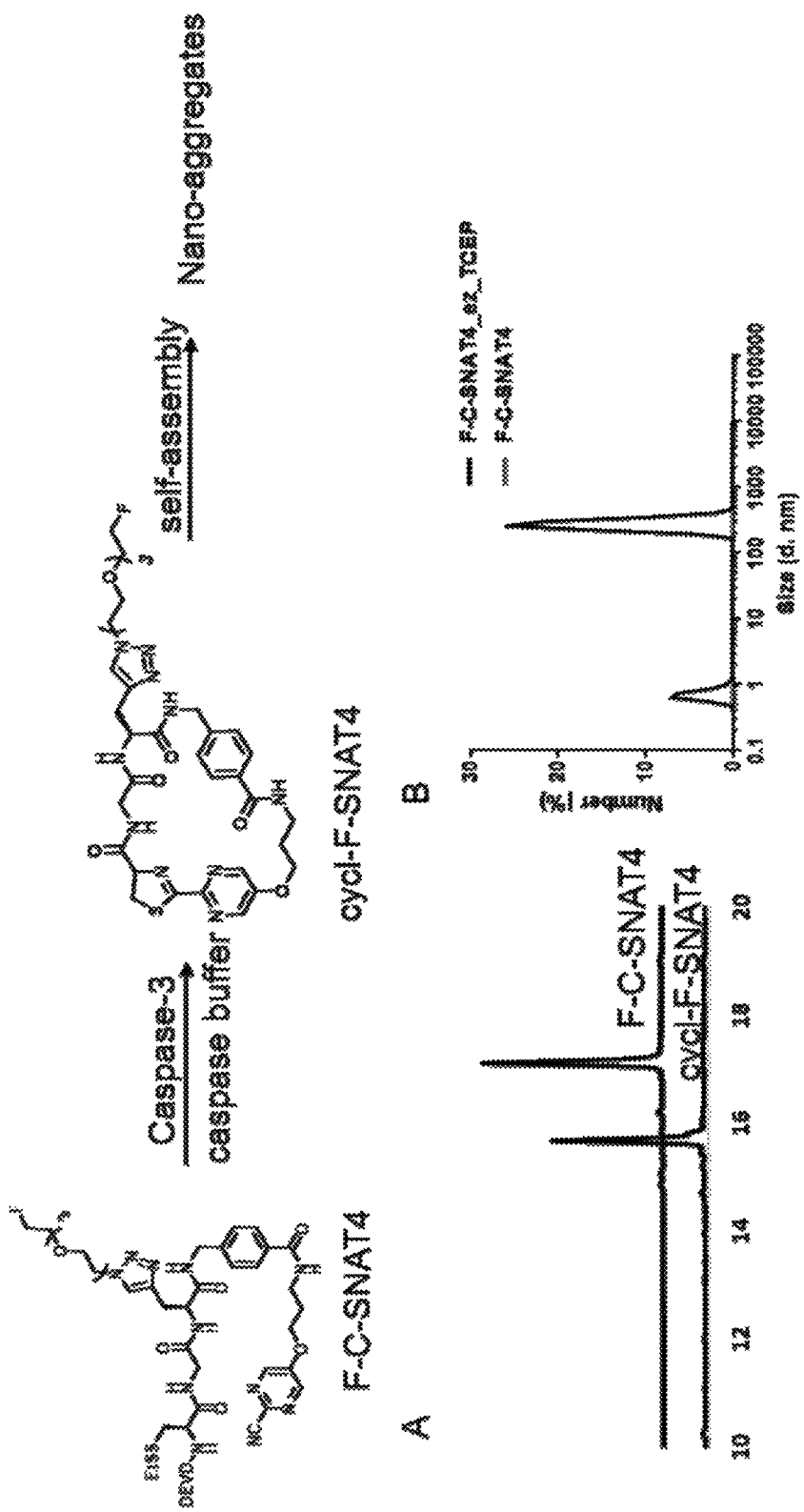
FIG. 12 illustrates in vitro validation and nanoaggregation characterization of [$^{19}$F]-C-SNAT4. [$^{19}$F]-C-SNAT4 and formation of cycl-[$^{19}$F]-SNAT4 after [$^{19}$F]-C-SNAT4 incubated with caspase-3 were analyzed by (A) HPLC, (B) DLS of [$^{19}$F]-C-SNAT4 without and with caspase-3 incubation. [$^{19}$F]-C-SNAT4 (20 μM) was incubated with caspase-3 (2×10$^{-3}$U mL$^{-1}$, human, recombinant from E. coli, Sigma) in caspase buffer (50 mM HEPES, 100 mM NaCl, 1 mM EDTA, 10 mM TCEP, 10% glycerol and 0.1% CHAPS at pH 7.4) at 37° C. overnight.
Figure 13:
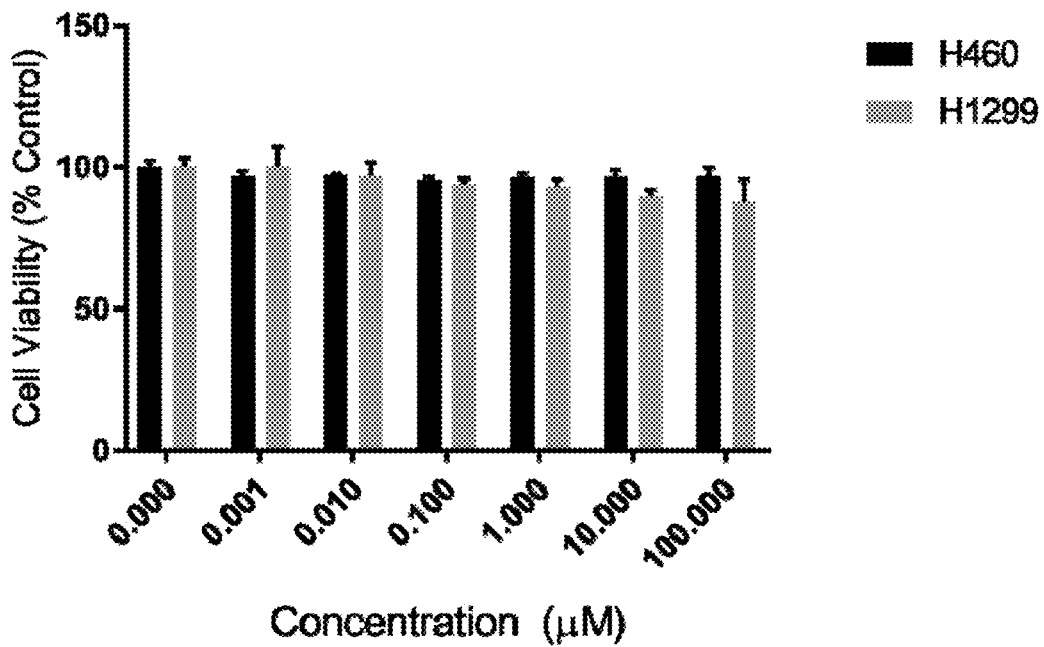
FIG. 13 illustrates cellular toxicity analysis in H460 and H1299 cells. Cells were incubated at different concentration of [$^{19}$F]-C-SNAT4 over 24 hours. The viability of cells was measured using an MTS assay.
Figure 14:
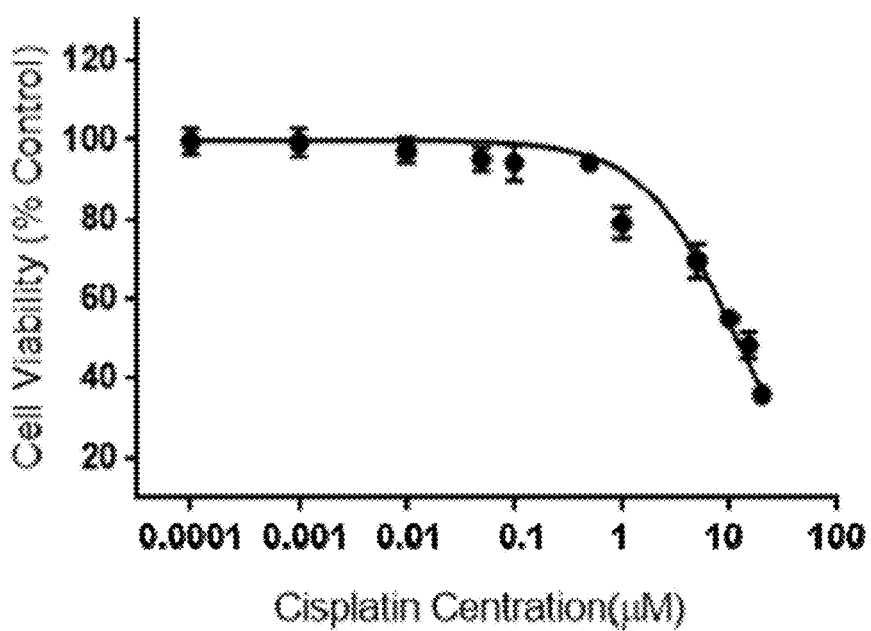
FIG. 14 illustrates a Cisplatin dose response curves were assessed in H460 cells by MTS assay. The curves generated by GraphPad Prism software. IC50 of cisplatin in H460 was 9.51 μM.

The cold analog [$^{19}$F]-C-SNAT4 was synthesized (FIG. 11) based on the precursor C-SNAT4 and dynamic light scattering (DLS) analysis (FIG. 12) showed that [$^{19}$F]-C-SNAT4 formed nanoparticles with an average size of around 200 nm after caspase-3 activation. The effective formation of [$^{19}$F]-C-SNAT4 nanoparticles were further confirmed by transmission electron microscopy (TEM) images (FIG. 1C). In vitro assessment of [$^{18}$F]-C-SNAT4 for monitoring the chemotherapy response: Cytotoxicity of [$^{19}$F]-C-SNAT4 was tested in two types of NSCLC cell (H460 and H1299) that showed no toxicity of cold probes up to 100 µM in two cell lines (FIG. 13). Apoptotic cell models using cisplatin treatment were built to assess $^{18}$F-C-SNAT4 in vitro. Cisplatin is a platinum-coordinated complex, which is widely used chemotherapeutic agents for the treatment of NSCLC in clinic. H460 is a cisplatin-sensitive NSCLC cell line, and rapidly undergoes caspase-3 mediated cell death following cisplatin treatment. Biochemical assays by MTS assay showed that the half-maximal inhibitory concentration (IC50) of cisplatin in H460 was 9.51 µM (FIG. 14).

Figure 2:
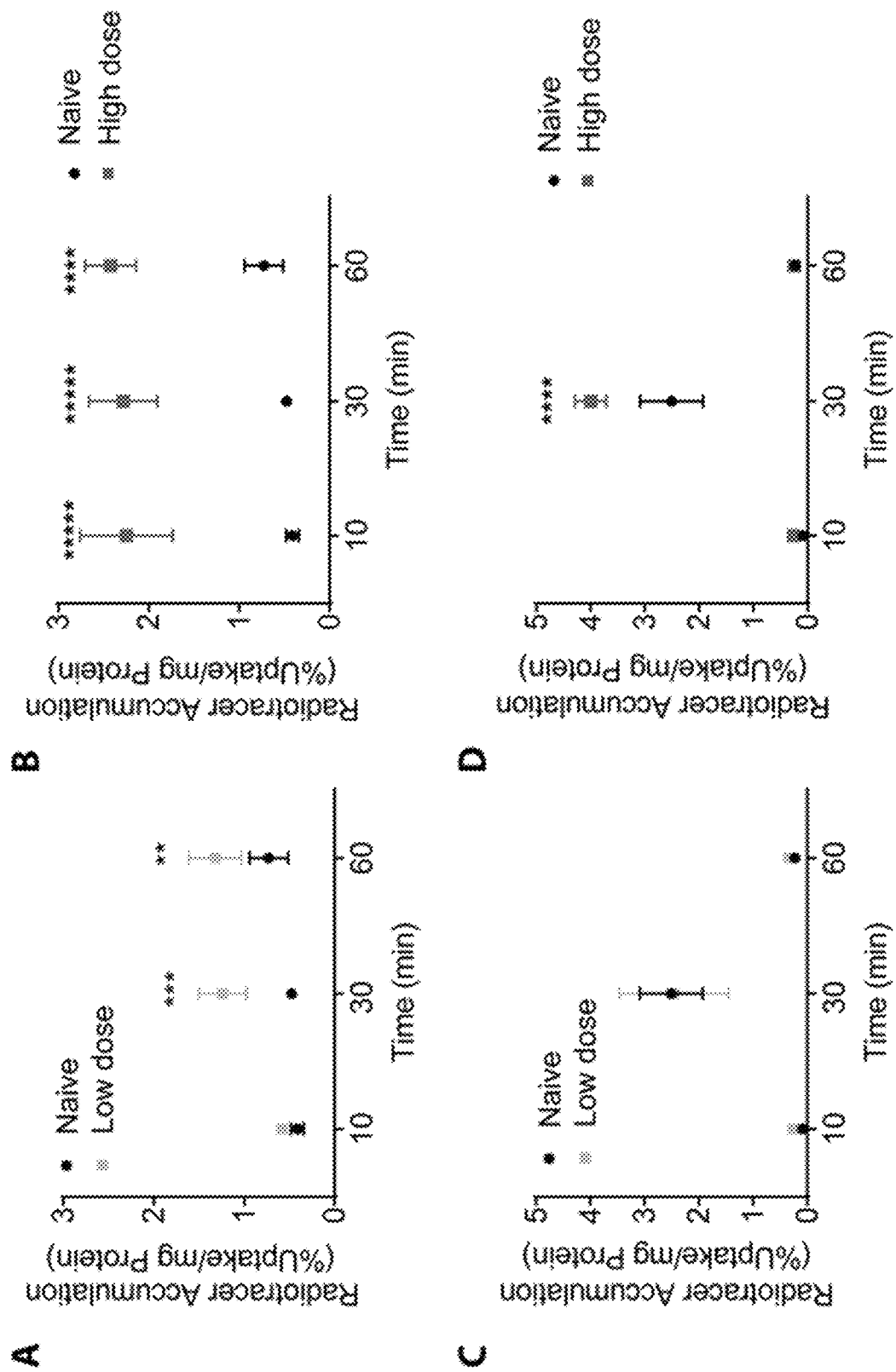
FIG. 2 illustrates the time course of [$^{18}$F]-C-SNAT4 uptake in cisplatin-treated (Low dose: 4.5 μM, 24 h; High dose: 13.5 μM, 24 h) and untreated human non-small cell lung cancer (Panels A and B) H460 and (Panels C and D) H1299 cells. Temporal changes in cell-associated radioactivity in drug-treated cells or vehicle cells were measured with [18F]-C-SNAT4. Data are means±SD (n=3 per group). *, P<0.05; , P<0.01; *, P<0.005; *****, P<0.0001.
Figure 15:
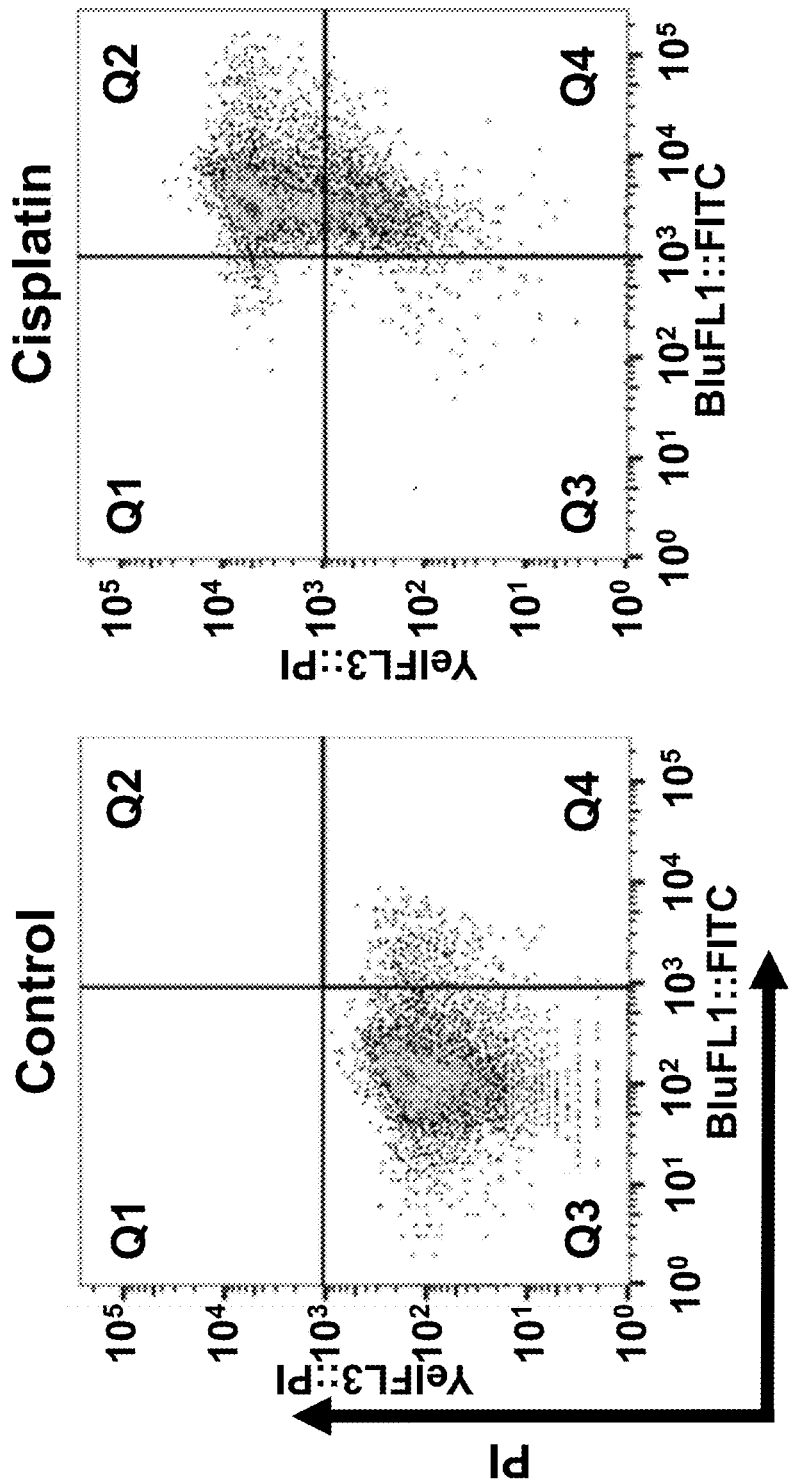
FIG. 15 illustrates a Cisplatin-induced apoptosis and activation of caspase-3 in H460 cells. Flow-cytometry analysis of control and cisplatin (10 μM)-induced apoptotic H460 cells stained with Annexin V (FITC) and PI. The quadrants Q are defined as Q1=FITC (−)/PI (+), Q2=FITC (+)/PI (+), Q3=FITC (+)/PI (−), Q4=FITC (−)/PI (−).

The data from flow cytometry using an Annexin V/Propidium Iodide (PI) apoptosis assay confirmed that 10 µM of cisplatin with 24 h of exposure can induce apoptosis in H460 (FIG. 15). The retention of [$^{18}$F]-C-SNAT4 in cisplatin-treated H460 and H1299 cells was assessed over 60 min (FIG. 2).

After cisplatin treatment at a low dose (4.5 µM, 24 h), the uptake of drug-treated H460 cells was 0.7±0.1% uptake/mg protein at 10 min and 1.45±0.11% radioactivity/mg protein at 60 min. In the untreated H460 cells, the uptake was 0.5±0.1% radioactivity/mg protein at 10 min and 0.4% uptake/mg protein at 60 min. The uptake of low dose-treated cells was 2.4-fold higher than control cells at 60 min post incubation (P<0.0001; n=3). In high dose-treated cells (13.5 µM, 24 h), the uptake was 2.3%±0.5% radioactivity/mg protein, which is 5.8-fold higher than in control cells (0.4±0.1% uptake/mg protein; P<0.001; n=3) at 10 min post incubation. These data indicated that the cellular uptake of [$^{18}$F]-C-SNAT4 is dose- and time-dependent of caspase-3 activation.

Figure 16:
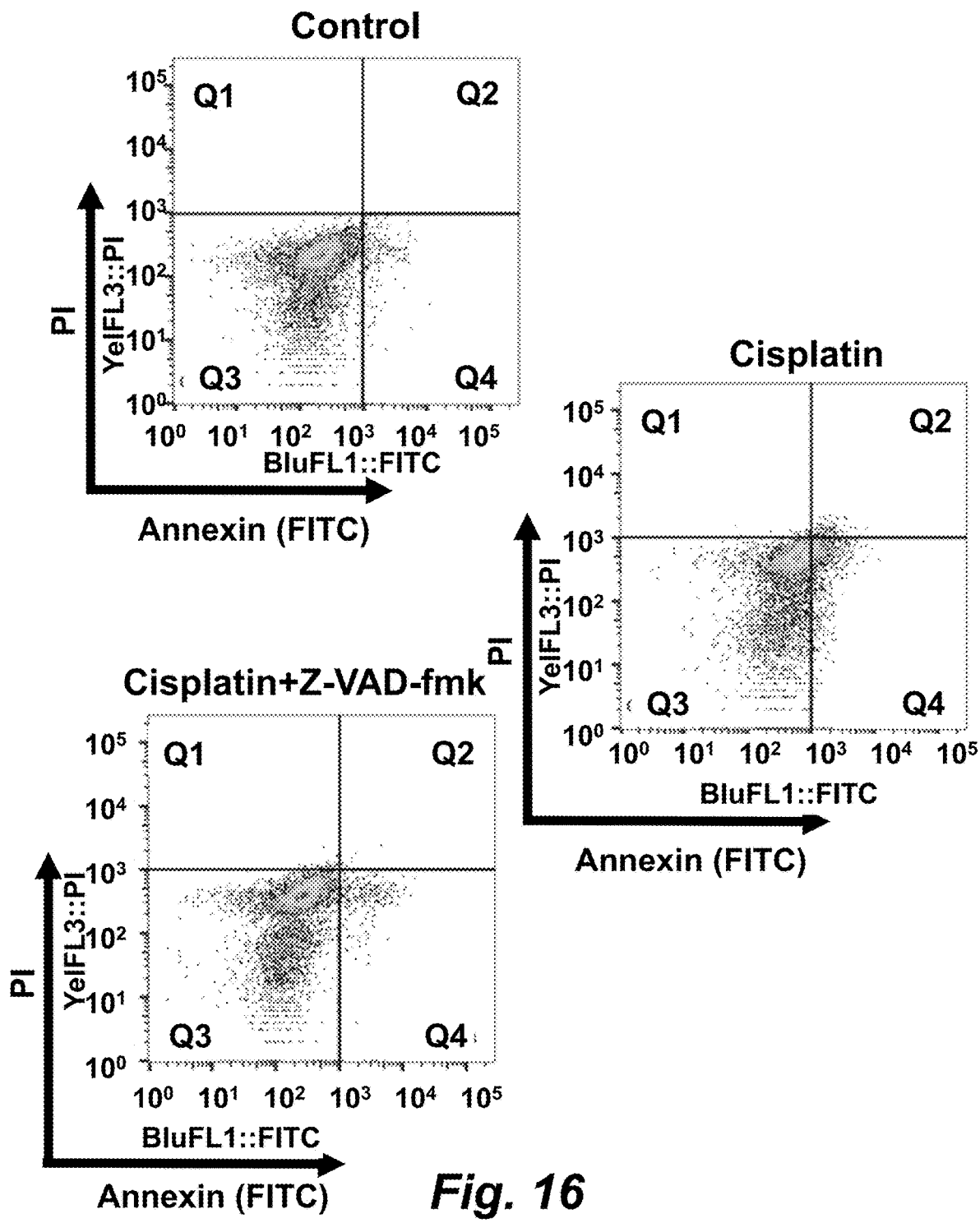
FIG. 16 illustrates Cisplatin-induced apoptosis and activation of caspase-3 in H1299 cells. Flow-cytometry analysis of control, cisplatin (10 μM)-induced apoptotic and inhibitors treated H1299 cells stained with Annexin V (FITC) and PI. The quadrants Q are defined as Q1=FITC (−)/PI (+), Q2=FITC (+)/PI (+), Q3=FITC (+)/PI (−), Q4=FITC (−)/PI (−).
Figure 17:
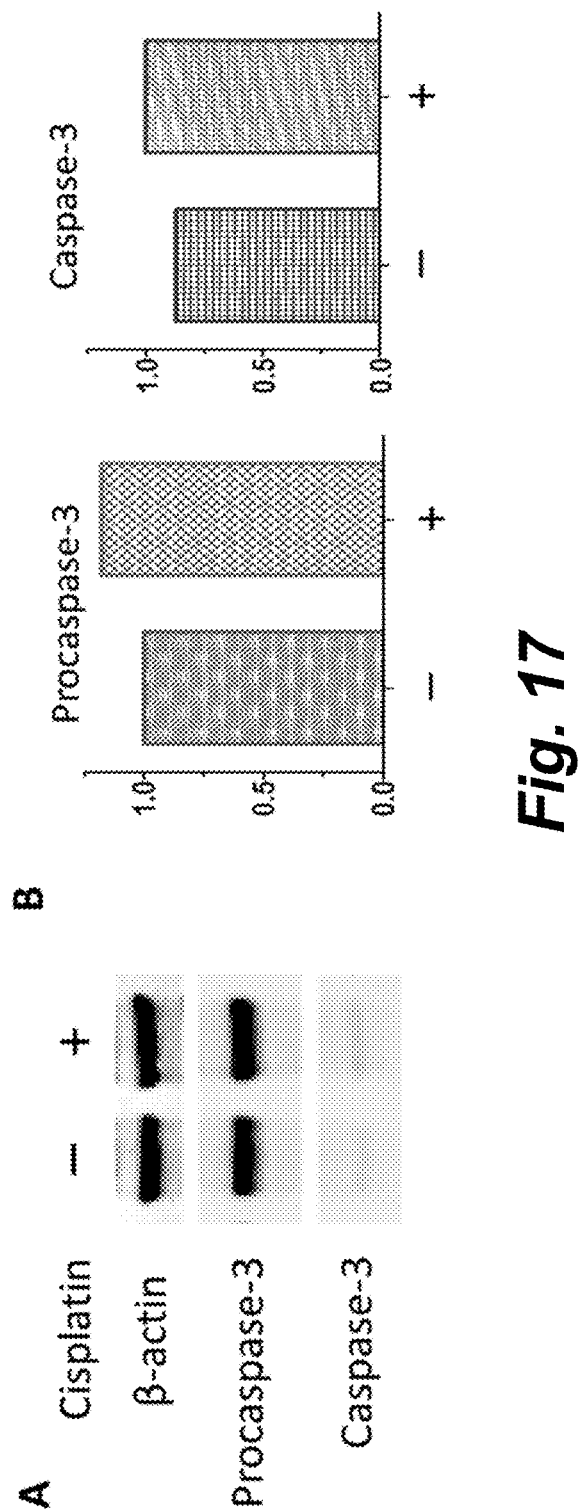
FIG. 17 illustrates analysis of Procaspase-3 and caspase-3 expressions in non-small lung cancer line H1299 cells. (A) Western blot studies were performed on untreated or cisplatin-treated H1299 cells (10 μM, 24 h). A 35-kD band of procaspase-3, a 17-kD band of caspase-3, β-Actin was the control. (B) Quantification of the percent gel intensity observed from panel Western blot Procaspase-3 or active caspase-3 band.

The p53-null lung carcinoma cell line H1299 is resistant to cisplatin therapy. To explore whether [$^{18}$F]-C-SNAT4 can report the treatment efficacy in drug-resistant cells, the cell model (FIGS. 16 and 17) was used to confirm the low-expression of caspase-3 after cisplatin-treatment and then assessed the tracer uptake both in naive and cisplatin treated H1299 cells. For the low dose treatment (4.5 µM, 24 h), [$^{18}$F]-C-SNAT4 uptake in drug-treated and naïve H1299 at 60 min was 0.3±0.1% and 0.2±0.1% uptake/mg protein, respectively (FIG. 2C), and there is no significant difference between two groups. For the high dose treatment (13.5 µM, 24 h), [$^{18}$F]-C-SNAT4 cellular uptake increased in both control group (2.5±0.6% radioactivity/mg protein) and drug-treated group (4.0±0.3% radioactivity/mg protein) at 30 min post incubation (FIG. 2D). At 60 min, [$^{18}$F]-C-SNAT4 cellular uptakes were decreased both in drug-treated and untreated. There was no difference between two groups (P>0.05; n=3). This data demonstrated quick washing happened in H1299 cells between 30 and 60 min after tracer incubation and there was low retention of [$^{18}$F]-C-SNAT4 in H1299 cells. These results indicated that [$^{18}$F]-C-SNAT4 can efficiently read out of chemotherapeutic outcomes both in drug-sensitive and resistant cells, as [$^{18}$F]-C-SNAT4 was specifically initiated by activated caspase-3 in the cellular environment.

Figure 3A:
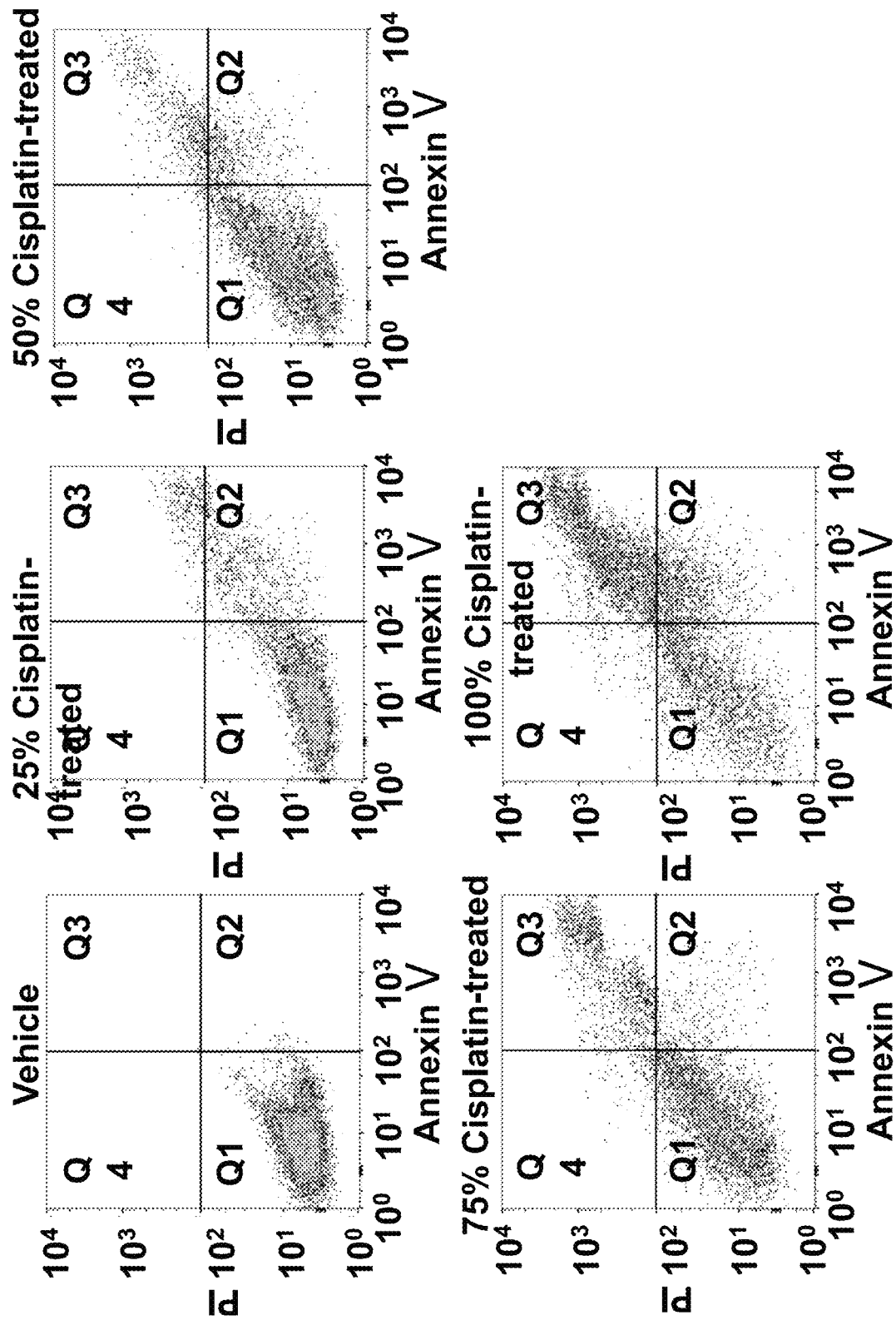
FIGS. 3A and 3B illustrate the specificity of [$^{18}$F]-C-SNAT4 for detecting cell death in cells.
Figure 3B:
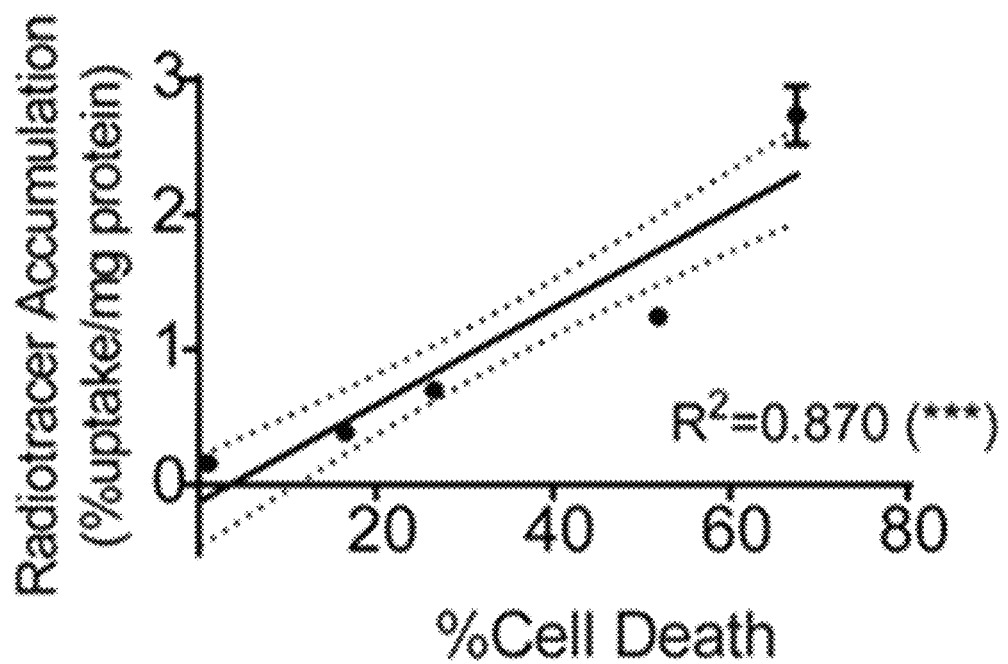

Radiotracer uptake was correlated to the level of drug-induced cell death in culture measured by the Annexin V/PI apoptosis assay. Since cisplatin treatment may induce early and late apoptotic/necrotic cells present in the samples, the combined staining by Annexin V and PI was used to identify the population of "dying cells." Different ratios of drug-treated H460 cells were combined with untreated cells to create a range of percentages of dying cells, from approximately 1.1% to 67.5% of the total cell population (FIG. 3A). Cell-associated radioactivity was compared with the percentage of cell death (FIG. 3B), revealing a strong correlation between the [$^{18}$F]-C-SNAF4 uptake in H460 and the level of cell death (Correlation coefficient $R^2$=0.87).

In vivo imaging of chemotherapeutic outcomes using [$^{18}$F]-C-SNAT4: Given the preferential retention and specificity of [$^{18}$F]-C-SNAT4 in apoptotic tumor cells, [$^{18}$F]-C-SNAT4 PET tracer in mouse model was evaluated for monitoring treatment efficacy. Xenografts of H460 (drug-sensitive) and H1299 (drug-resistant) were subcutaneously implanted in female nu/nu mice. When tumor size reached approximately 150 mm$^3$ (178.1±17.5 mm$^3$ for H460 tumors on the day 7 after implantation; 148.7±32.5 mm$^3$ for H1299 tumors on the day 11 after implantation), the tumor-bearing mice were treated with low doses of cisplatin (3 mg/kg every other day for three times, intravenous injection) or high doses of cisplatin (9 mg/kg every other day for three times, intravenous injection). The PET/CT imaging was performed at 24 h after the end of chemotherapy.

After administration of approximately 200 µCi [$^{18}$F]-C-SNAT4 in mice bearing H460 (FIG. 4A) or H1299 tumors (FIG. 4D), the dynamic PET/CT images were acquired. Quantitative PET/CT images were used to determine regions of interest for tumor tissue and time activity curves (TAC) for H460 (FIG. 4B) and H1299 (FIG. 4E) tumor-bearing mice were generated. The area under the TAC (AUC) was used as a metric of radiotracer uptake and retention between tumor treatment groups for drug-sensitive tumor H460, while quick washing was obtained in drug-resistant tumor H1299. Additionally, serial time points were analyzed between treatment groups of H460 (FIGS. 18A and 18B) and H1299 (FIGS. 19A and 19B) tumor models.

Figure 4C:
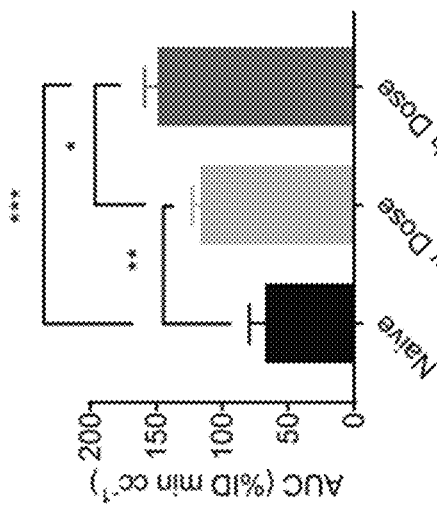
FIGS. 4A-4F illustrate in vivo monitoring of human xenograft tumors following chemotherapy with [18F]-C-SNAT4 in drug-sensitive tumor H460 and drug-resistant tumor H1299.
Figure 4B:
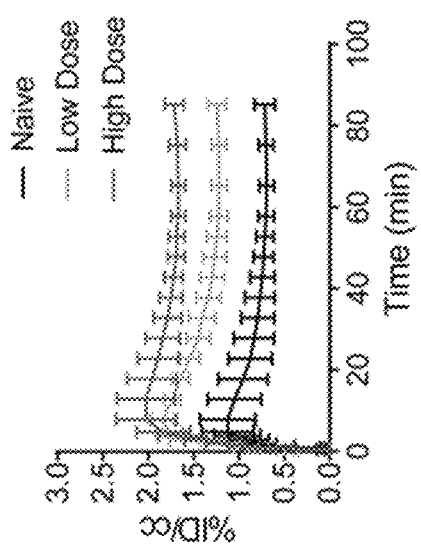
Figure 4A:
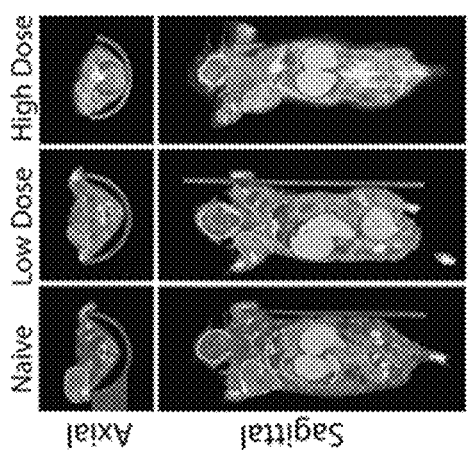
Figure 4F:
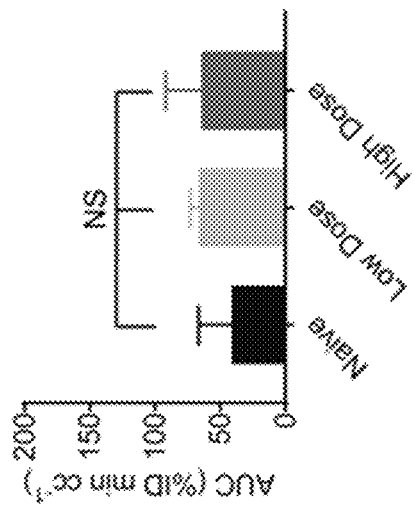
Figure 4E:
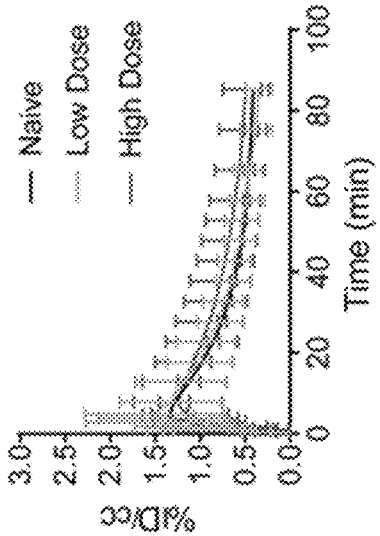
Figure 4D:
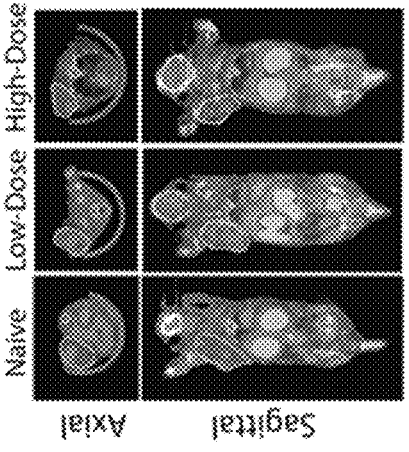

In drug-treated H460 tumor, [$^{18}$F]-C-SNAT4 uptake at 85 min post-injection were 1.2±0.1% ID/cc in low dose-treated animals and 1.7±0.1% ID/cc in high dose-treated animals. In contrast, the tumor uptake of [$^{18}$F]-C-SNAT4 in naïve animals was 0.7±0.11% ID/cc (P<0.05; n=4). AUC analysis in low dose-treated and high dose-treated tumors were 116.7±6.0% ID min/cc, and 148.9±10.1% ID min/cc, respectively. Both were significantly greater (p<0.05; n=4) than the value in naive tumor (67.5±12.0% ID min/cc). Rapid clearance of [$^{18}$F]-C-SNAT4 and no retention were observed in drug-resistant H1299 tumor, and there was no significant difference in the radioactivity retention at 85 min post-injection among three groups (0.4±0.2% ID/cc for low doses, 0.5±0.3% ID/cc for high doses and 0.4±0.1% ID/cc for saline, respectively). The analysis of AUC values showed similar pattern (66.0±6.8% ID min/cc for low doses, 64.2±27.8% ID min/cc for high doses and 41.2±25.4% ID min/cc for saline, respectively) (P>0.05; n=4) (FIG. 4F).

Figure 21:
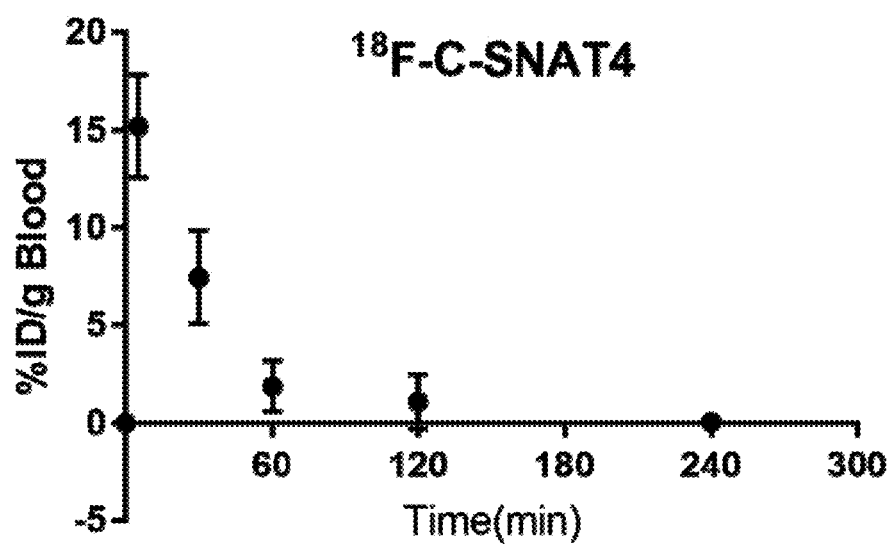
FIG. 21 illustrates blood half-life in healthy nude mice after intravenous injection of [$^{18}$F]-C-SNAT4 (n=4). The blood concentration peaked after 5 min (15.21±2.66% ID/g) and then cleared rapidly with a half-life of 0.36±0.11 hour.

Immunofluorescence staining was also used to validate the active cleaved caspases-3 levels in these cisplatin-treated tumors. Tumor tissues were collected at 2 h post PET imaging (FIG. 5A). It was shown that drug-treated H460 has intensive signals of caspase-3 and weak signal in untreated tumors. In comparison, H1299 tumor sections showed low expression of active caspase-3 in both cisplatin-treated and untreated tumors. The result was consistent with tumor uptake of [$^{18}$F]-C-SNAT4 in vivo. The tumor growth rate in high dose cisplatin-treated and naïve tumor is shown in FIG. 5B. The result showed high dose drug-treatment slowed down the tumor growth of H460 (690.8±88.6 mm$^3$) compared to the control group (1603.9±158.9 mm$^3$) on the day 13 after implantation. For H1299 model, there was no difference of tumor volumes in high dose drug-treated tumors (1348.5±356.0 mm$^3$) from the saline-treated tumors (1340.9±354.5 mm$^3$) on the day 21 after implantation. These data indicated that the tumor uptake of [$^{18}$F]-C-SNAT4 could reflect the caspase-3 activity and predict the chemotherapeutic outcomes in vivo. Ex vivo biodistribution profiles were collected to investigate the distribution of [$^{18}$F]-C-SNAT4 in individual organs at 2 h post injection of approximately 200 µCi [$^{18}$F]-C-SNAT4 (FIG. 20). High uptake in kidney and urine in H460 tumor-bearing mice indicated predominantly renal clearance of [$^{18}$F]-C-SNAT4. In healthy nude mice, [$^{18}$F]-C-SNAT4 cleared rapidly from the circulation with a blood life of 0.4±0.1 h and nearly complete elimination of [$^{18}$F]-C-SNAT4 from the blood had occurred by 2 h after administration (FIG. 21).

Improving sensitivity using mixture strategy: In experiments, the injected concentration of [$^{18}$F]-C-SNAT4 in vivo for PET imaging was around 58.8-166.7 pmol (calculated from injection dose of around 200 µCi and the average specific activity of 2.3±1.1 Ci/µmol). The self-aggregation process of caspase-activated [$^{18}$F]-C-SNAT4 is through non-covalent intermolecular interactions, which are concentration-dependent.

The concentration of [$^{18}$F]-C-SNAT4 in tumors may not be high enough to provide contrast when treatment effect is mild and produces low level of caspase-3 after low dose radiation treatment (FIG. 6A). In traditional PET imaging, the most common way to increase sensitivity is through increasing specific activity of the tracer. Because of the unique in-situ aggregation mechanism of the tracers of the disclosure, the sensitivity can be improved by reducing specific activity by mixing [$^{18}$F]-C-SNAT4 with cold [$^{19}$F]-C-SNAT4. Though the specific activity will be lower, the overall concentration will be higher, promoting the formation of more aggregates at the target site overall.

Figure 22:
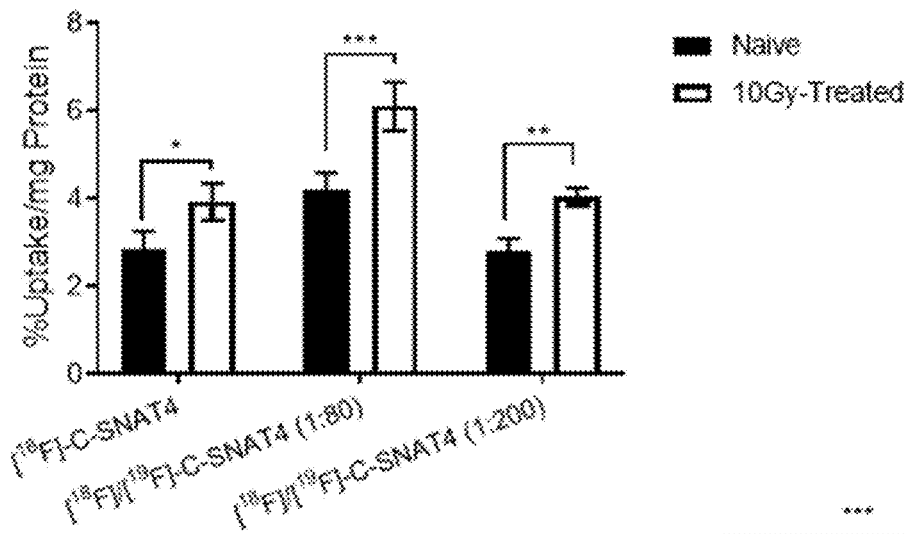
FIG. 22 illustrates that a mixture strategy enhances [$^{18}$F]-C-SNAT4 uptake in radiation (a single dose at 10 Gy) treated cells and vehicle human non-small cell lung cancer H460 cells. 40 μCi of mixture tracer [$^{18}$F]/[$^{19}$F]-C-SNAT4 (at ratio of 1:80 or 1:200) or 40 μCi [$^{18}$F]-C-SNAT4 were incubated in cells for 1 hour at 24 h post-IR treatment and radioactivity of [$^{18}$F] was measured using γ-counter. Data are means±SD (n=3 each group). *, P<0.05; , P<0.01; *, P<0.001.

Addition of cold [$^{19}$F]-C-SNAT4 leads to increased amount of substrate that will compete for the enzyme active site, which may result in target saturation and reduction of [$^{18}$F]-C-SNAT4 being activated. Optimization of the mixing ratio of [$^{18}$F]/[$^{19}$F]-C-SNAT4 was necessary for balance of aggregation and enzyme activation, providing the best signal retention. Different mixing ratios and two different concentrations of [$^{19}$F]-C-SNAT4 (0.9 nmol and 2.4 nmol) to mix with 40 µCi of [$^{18}$F]-C-SNAT4 in the radiation-induced apoptotic cells were tested (FIG. 22).

The respective mixing ratios of [$^{18}$F]/[$^{19}$F]-C-SNAT4 were calculated at 1:80 and 1:200 based on the specific activity of [$^{18}$F]-C-SNAT4 (3.4 Ci/µmol). At 24 h after 10 Gy radiation, the mixture tracers [$^{18}$F]/[$^{19}$F]-C-SNAT4 or hot tracer [$^{18}$F]-C-SNAT4 were incubated in IR-treated H460 cells for up to 1 h. In IR-treated cells, the group treated with [$^{18}$F]/[$^{19}$F]-C-SNAT4 (1:80) showed 6.1±0.5% uptake/mg protein, a 55.6% increase (P<0.005; n=3) compared to hot tracer only [$^{18}$F]-C-SNAT4 (3.9±0.4% uptake/mg protein). This result was consistent with the hypothesis that mixing the cold analogue with the radioactive tracer could improve self-aggregation and signal retention in treated cells. For mixture tracer [$^{18}$F]/[$^{19}$F]-C-SNAT4 (ratio at 1:200), the cell uptake was 4.0±0.2% uptake/mg protein, which has no significant increase compared to the hot tracer only group. The higher uptake of mixture ratio at 1:80 compared to the mixture ratio at 1:200 may be due to the overwhelming competition for the enzyme active site by the high amount of the cold analogue, which damped the activation of the radiotracer. For non-treated cells, there was no significant difference among the three groups (2.9±0.4% uptake/mg protein for mixture ratio at 1:80, 3.5±0.2% uptake/mg protein for mixture ratio at 1:200 or 2.8±0.3% uptake/mg protein for hot tracer only, respectively) (P>0.05; n=3). These data revealed that mixture strategy can increase cellular uptake of [$^{18}$F]-C-SNAT4 and improve the detection sensitivity in radiation treated cells but not increase the cellular uptake in vehicle cells.

Figure 23A:
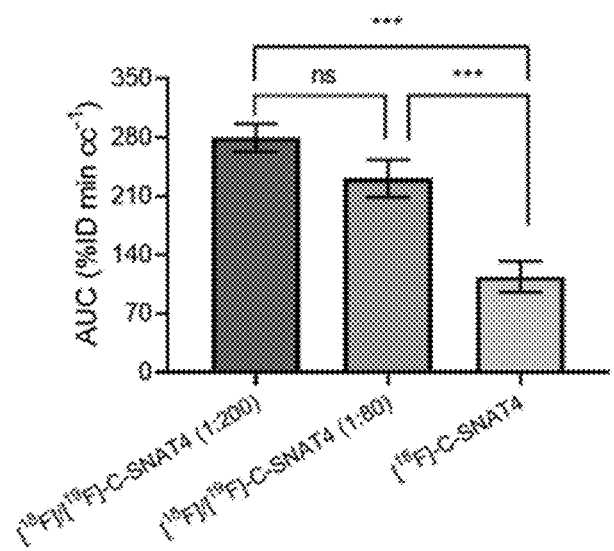
FIG. 23 (A): illustrates that area under the curve (AUC) was showed from t=0 to t=85 min for time activity of mixture tracer [$^{18}$F]/[$^{19}$F]-C-SNAT4 (1:200; 1:80) and hot tracer [$^{18}$F]/[$^{19}$F]-C-SNAT4 in two fractions of 5 Gy-treated tumors. (B): The area under the curve (AUC) showed from t=0 to t=85 min for time activity of mixture tracer [$^{18}$F]/[$^{19}$F]-C-SNAT4 (1:200) and hot tracer [$^{18}$F]-C-SNAT4 in two fractions of 2 Gy-treated tumors and hot tracer [$^{18}$F]-C-SNAT4 in naïve tumors.

The mixture strategy for monitoring radiotherapeutic outcomes in vivo was determined. Subcutaneous H460 tumor was implanted in nu/nu mice and when the tumor sizes reached approximately 150 mm$^3$, local radiation treatment at daily fraction of 5 Gy (10 Gy in total) were delivered in H460 tumor in vivo. At 24 h post IR-treatment, living mice were injected mixture tracer [$^{18}$F]/[$^{19}$F]-C-SNAT4 (at ratio of 1:80 or 1:200) or hot tracer only. The tumor uptakes of the three groups were performed by PET/CT imaging (FIG. 6B). As shown in the time activity curve (TAC), both groups injected with mixtures of tracer show higher uptake (3.0±0.3% ID/cc for mixture ratio at 1:200 and 2.5±0.3% ID/cc for mixture ratio at 1:80) than the group injected with only hot tracer (1.0±0.3% ID/cc) at 85 min post injection (FIG. 6D). The area under curve of TAC from t=0 to t=85 min (FIG. 23A) showed that the mixture groups (279.4±16.6% ID min/cc for 1:200 ratio; 230.9±22.4% ID min/cc for 1:80 ratio) had significant increase in uptake compared to hot tracer only (279.4±16.6% ID min/cc) (P<0.0001; n=3). There is no significant difference of uptake between two mixture groups.

Figure 23B:
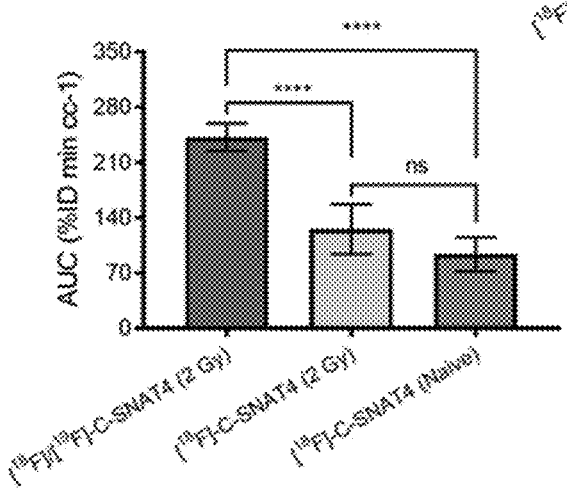

The finding that mixture strategy could improve the imaging sensitivity in 5 Gy-treated tumor model led us to validate this strategy in low dose radiation treatment (2 Gy), which induced low expression of caspase-3 activity. Mixture tracer [$^{18}$F]/[$^{19}$F]-C-SNAT4 (1:200) was used to image a treatment efficiency in a low-dose treatment using two fractions of 2 Gy-treatment for tumor-bearing mice (FIG. 6C). The TAC data (FIG. 6E) showed tracer uptake was significantly enhanced by 2.42-fold in tumor following injection of [$^{18}$F]/[$^{19}$F]-C-SNAT4 tracer at the ratio of 1:200 (2.8±0.2% ID/cc) compared to [$^{18}$F]-C-SNAT4 only (1.2±0.3% ID/cc) in 2 Gy-treated tumor-bearing mice. Using [$^{18}$F]-C-SNAT4 for PET imaging could not differentiate the treated tumor (1.2±0.3% ID/cc) from the untreated tumor (0.8±0.1% ID/cc) (P>0.05; n=3). The AUC value of mixture tracer [$^{18}$F]/[$^{19}$F]-C-SNAT4 (ratio at 1:200) uptake in treated tumor (FIG. 23B) was 242.0±17.2% ID min/cc, which was higher than AUC value of [$^{18}$F]-C-SNAT4 only in treated (123.6±30.9% ID min/cc) and naïve tumors (92.1±20.9% ID min/cc) (p<0.0001; n=4). The above in vitro and in vivo data support our hypothesis that using mixture strategy can enhance tracer uptake and improve sensitivity for monitoring the therapeutic efficacy after low-dose radiation treatment.

Figure 24A:
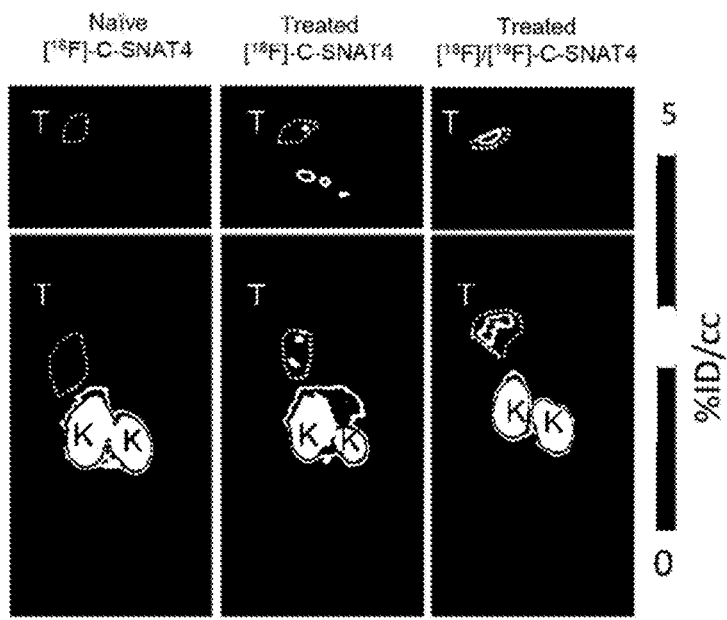
FIG. 24A-24C illustrate that mixed tracers of [$^{18}$F]/[$^{19}$F]-C-SNAT4 enhance tumor uptake in chemotherapeutic human xenograft tumors H460 tumor model.
Figure 24B:
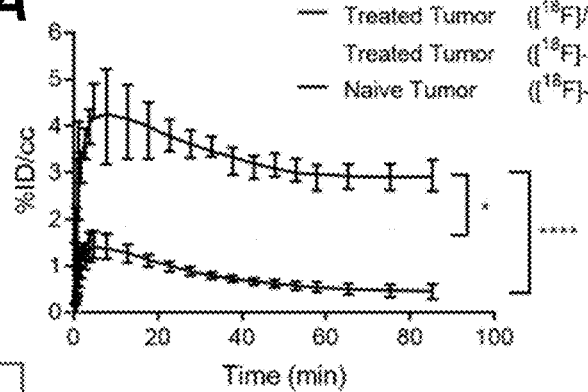
Figure 24C:
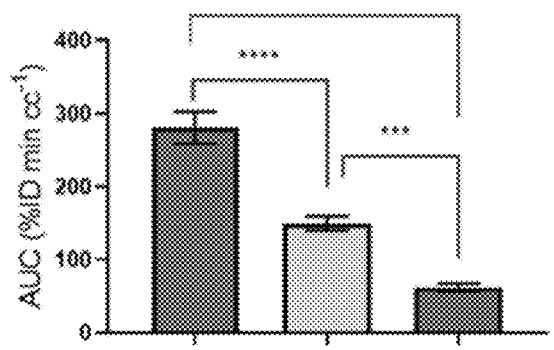
Figure 25A:
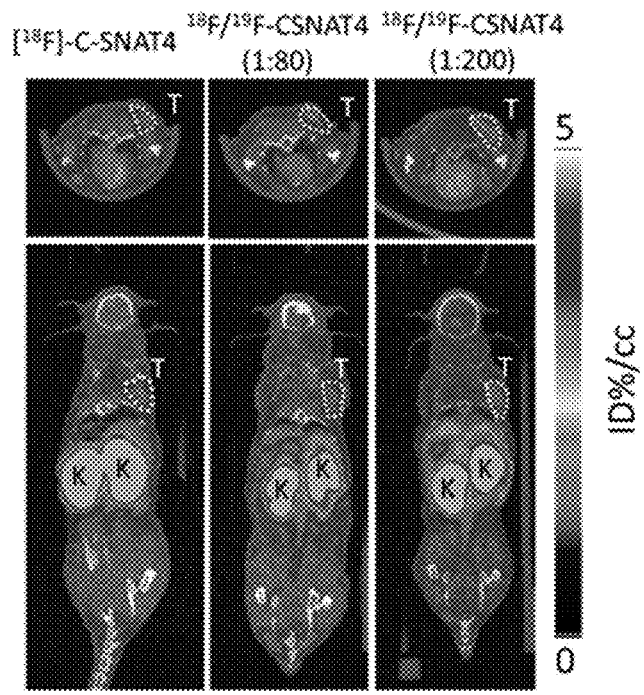
FIGS. 25A-25C illustrate that a mixed tracer of [$^{18}$F]/[$^{19}$F]-C-SNAT4 shows low uptake in naïve human xenograft tumors using PET/CT imaging.
Figure 25B:
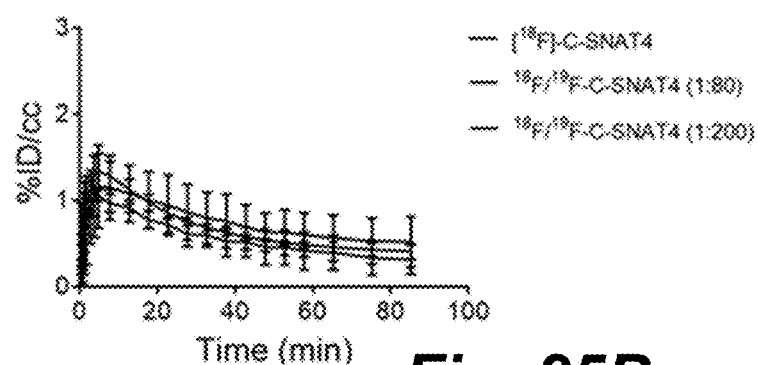
Figure 25C:
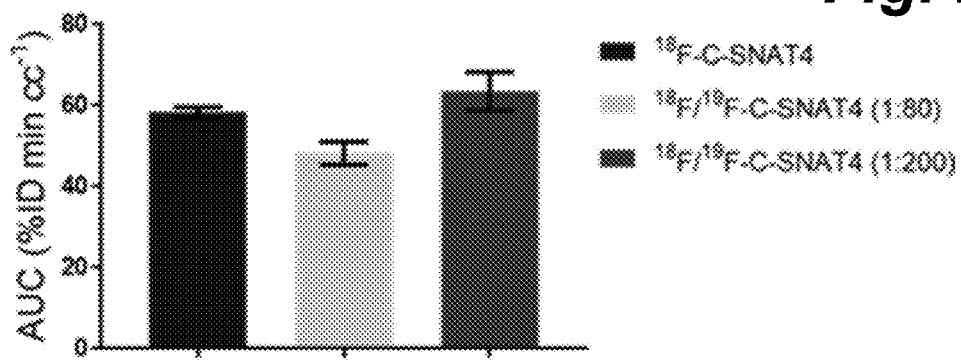

The mixture strategy was extend to the chemotherapeutic model underwent the same treatment as shown in FIG. 3A. At 24 h post treatment, mixture tracer of [$^{19}$F]-C-SNAT4 was injected with [$^{18}$F]-C-SNAT4 (mixture ratio at 1:200) through the tail vein for PET imaging (FIG. 24A-24C). For treated animal, tumor uptake of mixture tracer [$^{18}$F]/[$^{19}$F]-C-SNAT4 and [$^{18}$F]-C-SNAT4 were 2.9±0.3% ID/cc and 1.7±0.1% ID/cc, respectively at 85 min post injection. There was 1.7-fold increase of radioactivity in the mixture-treated mice. Overall, the uptake of [$^{18}$F]-C-SNAT4 was increased both in radiation and drug-treated tumors. In contrast, the tumor uptake of [$^{18}$F]/[$^{19}$F]-C-SNAT4 (ratio at 1:200) and [$^{18}$F]/[$^{19}$F]-C-SNAT4 (ratio at 1:80) in untreated tumor was 0.5±0.2% ID/cc and 0.3±0.2% ID/cc, respectively at 85 min after injection (FIG. 25A-25C), followed by a rapid signal decay back to baseline within a few minutes. There were no changes compared to the uptake of [$^{18}$F]-C-SNAT4 (0.4±0.1% ID/cc). These results demonstrated mixture tracer could not increase the non-specific uptake in naïve tumors and lack of radiotracer retention in naïve tumors was due to the absence of caspase-3 activity. Stability in mouse and human serum: The serum stability study was carried out using 1 ml of mouse or human serum was first equilibrated at 37° C. and was then added 100 ml of HPLC-purified [$^{18}$F]-C-SNAT4 (about 200 µCi). The serum was incubated at 37° C. and at each time point an aliquot of 100 µl were taken out and mixed with cold acetonitrile (200 µl). The sample was centrifuged at 13,400 g for 10 min and 100 ml of the resultant supernatant was diluted with 100 mL of water and analyzed on HPLC. % intact tracer was calculated as %=(peak area for tracer/total peak area on the HPLC chromatogram)×100.

Cell study: All cell lines were assessed to be pathogen-free prior to use in this study. Human H460 and H1299 lung adenocarcinoma cells non-small cell lung cancer H460 (ATCC) and H1299 (ATCC) were cultured in Dulbecco's modified Eagle's medium (DMEM) (Invitrogen), supplement with 10% v/v fetal bovine serum (Life Technologies Inc.) and 1% v/v penicillin-streptomycin (100 IU/ml, 100 mg/ml; Life Technologies Inc.) at 37° C. in a humidified atmosphere maintained at 5% $CO_2$. X-radiation was performed with an X-ray generator (0.2 mm Cu and 1 mm Al filter, 150 kV, Hitachi). The irradiation was carried out at room temperature at a dose rate of 0.2 Gy/min. Cell viability was assessed with CellTiter 96.RM AQueous One Solution Cell Proliferation Assay (MTS) kit from Promega (Madison, Wis., USA). Briefly, 100 µl aliquots of the treated or untreated cell suspension were seeded into 96-well polystyrene tissue culture plates and 20 µl of assay reagent was added to each well. After 60 min of incubation at 37° C., the absorbance was read at 490 nm with a 96 well plate reader from BMG LABTECH GmbH (Ortenberg, Germany).

Western blotting: Cells were lysed in radioimmunoprecipitation (RIPA) assay buffer according to the manufacturer's protocol (Sigma-Aldrich). Samples were centrifuged, the supernatants collected, and the protein content determined by Bradford Assay (Bio-Rad Inc.). Approximately 30 µg of protein was loaded per well and samples were run on 4-12% Bis-Tris Gel (NuPAGE®). Gels were transferred onto poly (vinylidene fluoride) membranes and blocked with 3% milk in tris-buffered saline with tween-20 (TBST). All primary antibodies were incubated in 3% milk in TBST overnight at 4° C. at the following dilutions: anti-cleaved caspase-3 at 1:1000 (D175, Cell Signaling Technology Inc., MA, USA), anti-pro-caspase-3 at 1:1000 (Cell Signaling Technology Inc., MA, USA), anti-actin antibody (1:2000, Sigma-Aldrich Co. Ltd.). Blots probed with secondary antibody conjugated to horseradish peroxidase (ab6721, Abcam®, UK), and protein bands were visualized by ECL western blotting substrate (Thermo Fisher Scientific Inc.) and HyBlot CL autoradiography film (Denville Scientific Inc., NJ, USA). Blots were scanned, and signal was quantified with ImageJ (National Institutes of Health).

Radiotracer uptake in cells: H460 and H1299 cells ($2\times10^5$) were plated in 6-well cell culture plates over night before [$^{18}$F]-C-SNAT4 uptake analysis. For chemotherapy, cells were incubated 10 µM of cisplatin over 24 h; for radiotherapy, cells were irradiated with a total of 10 Gy using a single 225 kV beam Kimtron IC 225 irradiator (Kimtron Medical, CT, USA). After 24 h treatment, fresh, prewarmed RPMI Medium 1640 containing 1.48 MBq (40 µCi) [$^{18}$F]-C-SNAT4 was added to individual wells (1 ml/well; 13.3 pmol). At post 10, 30, 60 min, medium was removed, cells were lifted by trypsinization, and washed three-times with cold PBS. Radioactivity contained in cell pellets was measured using a gamma counter, with counts normalized to total protein concentration as determined by cell digestion using RIPA buffer followed by protein quantitation by the Bradford method. The final radiotracer [$^{18}$F]-C-SNAT4 uptake concentration was expressed as µM of % uptake/mg protein. Results were normalized to a vehicle control (PBS for [$^{18}$F]-C-SNAT4 experiments at different time-points) which was washed.

Detection of cell death in vitro: Apoptosis and necrosis in cell mixtures containing 0% to 100% drug-treated cells were visualized by flow cytometry using a method adapted from reference[40], in parallel to cell uptake studies. Fluorescein isothiocyanate (FITC)-Annexin V (BioLegend) in combination with 7-amino-antinomycin D (7-ADD; BioLegend) were used for cell death determination. Early apoptotic cells were defined as cells death determination. Early apoptotic cells were defined as cells positively stained for FITC-Annexin V but not 7-ADD, with both late apoptotic and necrotic classified as cells positive for both stains. FlowJo (v.7.6.5; Tree Star, Inc.) was used for analysis.

Cell death correlation: To correlate cell-associated radioactivity with levels of drug-induced cell death, mixtures of vehicle and cisplatin-treated NCI-H460 cells were prepared 18 to 20 h after either vehicle or drug incubation. Mixtures contained 0%, 25%, 50%, 75%, and 100% v/v cisplatin-treated cells in 6 ml total volume, with the remaining volume made from vehicle-treated cell suspension. One million cells were subsequently collected for cell death analysis by flow cytometry, with the remaining cells used to assess cell-associated radioactivity 60 min after radio tracer addition, as described above.

Animal model and probe administration: For subcutaneous tumor models, H460 or H1299 ($2\times10^6$ cells in 100 µl of PBS) were injection subcutaneously on the back of female nu/nu nude mice (aged 6 to 8 weeks; Charles River Laboratories). Tumor dimensions were measured periodically using a caliper (by the same researcher), with tumor volumes calculated by the following equation: volume=a×b×c/2, where a, b, and c represent three orthogonal axis of the tumor. Treatment-response analysis was performed 24 h after drug treatment. For all other experiments, animals were culled 26 h after therapy and tissues excised for analysis. For chemotherapy mouse model, tumors were grown to about 150 $mm^3$, and then treatment that consisted of cisplatin (Sigma-Aldrich; Low dose: 3 mg/kg; high dose: 9 mg/kg) or saline was initiated through intravenous administration, every other day for three times. Total mouse body weight and tumor size were measured every other day. Treat or left untreated. For radiotherapy mouse model, treatment consisted of two fractions of 5 Gy or 2 Gy dose of radiation therapy delivered with a single 225 kV beam using the Kimtron IC 225 irradiator (Kimtron Medical, CT, USA).

Small-animal PET/CT imaging and analysis: PET/CT imaging was carried out on a docked Siemens Inveon PET/CT scanner (matrix size, 128×128×159; CT attenuation-corrected; non-scatter corrected) (Siemens Medical Solutions USA) following a bolus intravenous injection of approximately 200 µCi of [$^{18}$F]-C-SNAT4 into tumor-bearing mice (n=56, 3-4 mice per group). Dynamic scans were acquired in list mode format over 90 min, and sorted into 22 times of frames, 0.5-mm sinogram bins for image reconstruction (4×15 s, 4×60 s, 11×300 s, 3×600 s). Mice were anesthetized with 2% isoflurane near the center of the FOV to ensure the highest image resolution and sensitivity. Iterative reconstruction was performed using 3D ordered-subsets expectation maximization (3D-OSEM) followed by fast maximum a posteriori (fast MAP) with the following parameters: MAP OSEM iterations, 2; MAP subsets, 16; MAP iterations, 18. Siemens Inveon Research Workplace software v.4.0 was used for visualization of radiotracer uptake in the tumor, to define the three-dimensional (3D) volumes of interest (VOI) and for 3D-visualisation to create volume rendering technique (VRT) images. The relative tumor or organ radioactivity concentrations were from mean pixel values within the multiple ROI volumes. The radioactivity concentration within organs was obtained from mean pixel values with in the VOI and converted to counts per milliliter per min and then divided by the injected dose (ID) to obtain an imaging VOI-derived percentage of the injected radioactive dose per cubic centimeter of tissue (% ID/cc).

Biodistribution study: H460 or H1299 tumor-bearing female nude mice were administered approximately 7.4 MBq of [$^{18}$F]-C-SNAT4 via the tail vein (n=4-5 per group). Mice were maintained under anesthesia and warmed to 37° C. to replicate imaging conditions. At 90 min after [$^{18}$F]-C-SNAT4 injection, animals were sacrificed by exsanguination via cardiac puncture. For all animals, tumors were excised immediately upon death, weighed using pre-weighted tubes, and rapidly placed in 10% formalin (Fisher Scientific) for fixation. Tumor and tissue decay-corrected radioactivity was subsequently determined using a Cobra II Auto-Gamma counter (Packard Biosciences Co, UK.) Pre-defined 1.85 MBq (50 µCi) standards (50 µl) were also counter for data normalization to injected dose. Data were expressed as percent injected dose per gram of tissue (% ID/g).

Ex vivo analysis: Formalin-fixed tumors were embedded in paraffin, sectioned into 5-µm thick slices and placed on microscope slides according to standard procedures (Histo-Tec Laboratory). Sections were taken at regular intervals across the entire tumor volume. Section slides were fixed for 10 min in formalin, washed, permeabilized with 0.5% Triton X-100 in PBS, and blocked with 3% BSA and 3% goat serum, then stained with rabbit-derived anti-cleaved caspase-3 1:200 (Cell Signaling Technology Inc., MA, USA) overnight at 4° C., and then incubated in Alexa647-goat-anti-rabbit IgG secondary antibody (Life Technologies) and Alexa488-phalloidin conjugate (Life Technologies) for 1 hour at room temperature in the dark. Cover glass was mounted using SlowFade containing DAPI (Life Technologies), sealed, and slides were imaged using AxioObsever.Z1 confocal microscope (Carl Zeiss AG, Ltd.) with LSM 710 laser scanning module. Images were acquired with 405 nm (DAPI), 488 nm (Alexa 488), and 633 nm (Alexa 647) laser lines using 20× (Plan Apochromat, NA=0.8) and 63× oil immersion (Plan Apochromat, NA=0.19) objectives.

Statistics: The following statistical analyses were carried out using GraphPad.7 software, as detailed in figure legends. For two-group analysis, a two-tailed Student's t test was used to examine group differences. Two-way or one way ANOVA with post-hoc Bonferroni's correction. One-way ANOVA with post-hoc Tukey test and correlation analysis. Data were expressed as mean±SD. For statistically significance, it was determined using the Student t test and p values are indicated in figures and/or legends. A two-sided p value of <0.05 was considered statistically significant.

Synthesis of precursor C-SNAT4: Compound 1 was synthesized according to previously reported procedures. [SNAT4 paper] (i) A solution of 10 (14 mg, 0.019 mmol) in 2 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (1 mL) was added Ac-DEVD-OH (13.2 mg, 0.019 mmol), HBTU (11 mg, 0.029 mmol) and DIPEA (7 µL, 0.038 mmol). The reaction was stirred at room temperature for 2 h followed by extraction with ethyl acetate and water. The organic layer was dried over MgSO$_4$ and concentrated in vacuo. The crude product was used in the next step without further purification. (iii) The crude residue from previous step was dissolved in 5 mL of TFA/DCM/TIPS (1:1:0.05) and was stirred at room temperature for 2 h. The reaction was concentrated under reduced pressure and purified by preparative HPLC to afford the titled compound 14 (8 mg, 37.4%). HRMS: calc'd for $C_{48}H_{63}N_{12}O_{16}S_2^+[(M+H)^+]$: 1127.3921; found 1127.3923.

Radiochemistry: All chemicals unless otherwise stated were commercially available and used without further purification. Purification of 4 was carried on a high-performance liquid chromatography (HPLC) equipped with Dionex 680 pump (Dionex Corporation, USA) and KNAUER UV detector K-2001 (KNAUER, Germany) using a Phenomenex Gemini C18 column (250×10 mm, 5 µm) and gradient conditions (method 1): A: H$_2$O+0.1% TFA, B: CH$_3$CN+ 0.1% TFA; 0-2 min 10% B, 2-30 min 10-35% B, 30-40 min 95% B; 5.0 mL/min. [$^{18}$F]-C-SNAT4 was purified on a Dionex Ultimate 3000 chromatography system with a UVD 340U absorbance detector (Dionex Corporation, USA) and model 105S single-channel radiation detector (Carroll & Ramsey Associates, USA) using a Phenomenex Gemini C18 column (250×10 mm, 5 µm) and gradient conditions (method 2): A: H$_2$O+0.1% TFA, B: CH$_3$CN+0.1% TFA; 0-3 min 10% B, 3-26 min 10-50% B, 26-28 min 50-95% B; 5.0 mL/min. Analytical HPLC were performed on an Agilent 1200 Series HPLC system (Agilent Technology, USA) with ChemStation software (version B.04.02) equipped with a quaternary pump, UV diode array detector and model 105S single-channel radiation detector using a Phenomenex Gemini C18 column (250×4.6 mm, 5 µm) and gradient conditions: A: H$_2$O+0.1% TFA, B: CH$_3$CN+0.1% TFA; 0-3 min 20% B, 3-27 min 20-60% B, 27-29 min 95% B; 1.0 mL/min. The identity of the $^{18}$F-labeled products was confirmed by comparison with the analytical HPLC retention time of their non-radioactive reference compound [$^{19}$F]-C-SNAT4 or by co-injection with [$^{19}$F]-C-SNAT4 before administration to animals.

Synthesis of 4: Production of 4 was carried out in a fully-automated TRACERlab FX-FN module (GE Healthcare, USA). Briefly, no-carrier added [$^{18}$F] fluoride was produced via the $^{18}$O(p,n)$^{18}$F nuclear reaction by irradiation of enriched [$^{18}$O]H$_2$O in a PETtrace cyclotron (GE Healthcare, USA). [$^{18}$F]Fluoride was trapped on an anion-ex-

TABLE 1

Estimated radiation dose to an adult female and male (human) after tail vein injection of [$^{18}$F]-C-SNAT4 based on the PET/CT imaging data obtained in nu/nu mice (n = 3 for female mice; n = 3 for male mice), calculated using OLINDA software.

| Organ | Human total dose equivalent | | | |
|---|---|---|---|---|
| | Female | | Male | |
| | rem/mCi | rem/MBq | rem/mCi | rem/MBq |
| Adrenals | 4.35E-02 | 1.61 | 2.70E-02 | 1.00 |
| Brain | 1.35E-02 | 0.50 | 9.11E-03 | 0.34 |
| Breasts | 2.95E-02 | 1.09 | 1.87E-02 | 0.69 |
| Gallbladder Wall | 4.33E-02 | 1.60 | 3.10E-02 | 1.14 |
| Heart Wall | 3.99E-02 | 1.48 | 2.80E-02 | 1.04 |
| Kidneys | 1.37E-01 | 5.07 | 6.43E-02 | 2.38 |
| Liver | 3.81E-02 | 1.41 | 3.07E-02 | 1.14 |
| Lungs | 2.78E-02 | 1.03 | 2.11E-02 | 0.78 |
| Muscle | 2.45E-02 | 0.91 | 1.81E-02 | 0.67 |
| Ovaries | 4.11E-02 | 1.52 | 2.75E-02 | 1.02 |
| Pancreas | 4.57E-02 | 1.69 | 2.98E-02 | 1.10 |
| Red Marrow | 3.34E-02 | 1.24 | 2.98E-02 | 1.10 |
| Osteogenic Cells | 5.46E-02 | 2.02 | 3.32E-02 | 1.23 |
| Skin | 2.59E-02 | 0.96 | 1.65E-02 | 0.61 |
| Spleen | 1.38E-01 | 5.11 | 9.57E-02 | 3.54 |
| Testes | NR | NR | 2.15E-02 | 0.80 |
| Thyroid | 2.43E-02 | 0.90 | 1.86E-02 | 0.69 |
| Urinary Bladder Wall | 5.00E-02 | 1.85 | 5.80E-02 | 2.15 |
| Uterus | 3.08E-02 | 1.14 | NR | NR |
| Effective Dose | 4.93E-02 | 1.82 | 3.32E-02 | 1.23 | change resin cartridge (Macherey-Nagel Chromafix 30-PS-HCO$_3$ pre-conditioned with 1 mL of EtOH, 1 mL of H$_2$O and then blown dry). The cartridge was eluted with a solution of Kryptofix 222 (4,7,13,16,21,24-Hexaoxa-1,10-diazabicyclo [8.8.8] hexacosane, or K2.2.2) (15 mg) and potassium carbonate (3 mg) in H$_2$O (0.1 mL) and CH$_3$CN (0.9 mL). Following azeotropic drying, 2 (3.0 mg in 1.0 mL of anhydrous DMSO) was added to the K[$^{18}$F]F/K2.2.2 complex, and the mixture was heated for 20 min at 110° C. to yield 4. After cooling to room temperature, the reaction mixture was loaded onto a semi-prep HPLC (method 1). The fraction corresponding to the peak of the desired product was collected in a round bottom flask containing sterile water (20 mL), and then transferred to an adjacent customized module for solid phase extraction (SPE) using a C-18 Sep-Pak cartridge. 4 trapped on C-18 cartridge was eluted with diethyl ether (2 mL) through a Na$_2$SO$_4$ cartridge into a 5 mL V-vial with stirrer bar in the customized module. The diethyl ether was removed under helium stream at ambient temperature and the dried labeling agent was ready for further click chemistry.

Synthesis of [$^{18}$F]-C-SNAT4: To dried 4 from previous step was added a mixture of C-SANT4 (200 μL of 1 mg/mL stock solution in DMSO), 0.1 M HEPES solution (200 μL), CuSO$_4$ (5 μL of 0.1 M stock solution in water), (BimC$_4$A)$_3$ (5 μL of 30 mM stock solution in water) and sodium ascorbate (5 μL of 1 M stock solution in water, freshly prepared), and reaction mixture was kept at 40° C. for 20 min. The reaction mixture was diluted with 2 mL of water and injected onto a semi-preparative HPLC (method 2). Final product was formulated in saline with 10% ethanol by solid phase extraction with C-18 Sep-Pak light cartridge. The final product is confirmed on analytical HPLC by co-eluting with [$^{19}$F]-C-SNAT4 reference standard. Radiochemical yield was 6.6±5.0% and molar activity were 2.3±1.1 Ci/μmol, n=7, decay corrected to end of synthesis.

Synthesis of cold $^{19}$F-analogue [$^{19}$F]-C-SNAT4: 3 was first synthesized from 2 according to previously reported procedures[33]. To a solution of C-SNAT4 (10 mg, 0.009 mmol) in DMSO/0.1M HEPES buffer (2.5 mL/2.5 mL) was added 3 (17 mg, 0.045 mmol), CuSO$_4$ (20 μL of 0.1M stock solution in water), (BimC$_4$A)$_3$ (20 μL of 30 mM stock solution in water) and sodium ascorbate (20 μL of 1M stock solution in water, freshly prepared). The reaction was stirred at room temperature for 30 min and was subsequently purified by preparative HPLC to afford the final product (5 mg, 42%). HRMS: calc'd for C$_{56}$H$_{79}$FN$_{15}$O$_{19}$S$_2$$^+$ [(M+H)$^+$]: 1348.5097, found 1348.5097.

Synthesis of precursor C-SNAT4: Compound 1 was synthesized according to previously reported procedures. [SNAT4 paper] (i) A solution of 10 (14 mg, 0.019 mmol) in 2 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (1 mL) was added Ac-DEVD-OH (13.2 mg, 0.019 mmol), HBTU (11 mg, 0.029 mmol) and DIPEA (7 μL, 0.038 mmol). The reaction was stirred at room temperature for 2 h followed by extraction with ethyl acetate and water. The organic layer was dried over MgSO$_4$ and concentrated in vacuo. The crude product was used in the next step without further purification. (iii) The crude residue from previous step was dissolved in 5 mL of TFA/DCM/TIPS (1:1:0.05) and was stirred at room temperature for 2 h. The reaction was concentrated under reduced pressure and purified by preparative HPLC to afford the titled compound 14 (8 mg, 37.4%). HRMS: calc'd for C$_{48}$H$_{63}$N$_{12}$O$_{16}$S$_2$$^+$[(M+H)$^+$]: 1127.3921; found 1127.3923.

Radiochemistry: Purification of 4 was carried on a high-performance liquid chromatography (HPLC) equipped with Dionex 680 pump (Dionex Corporation, USA) and KNAUER UV detector K-2001 (KNAUER, Germany) using a Phenomenex Gemini C18 column (250×10 mm, 5 μm) and gradient conditions (method 1): A: H$_2$O+0.1% TFA, B: CH$_3$CN+0.1% TFA; 0-2 min 10% B, 2-30 min 10-35% B, 30-40 min 95% B; 5.0 mL/min. [$^{18}$F]-C-SNAT4 was purified on a Dionex Ultimate 3000 chromatography system with a UVD 340U absorbance detector (Dionex Corporation, USA) and model 105S single-channel radiation detector (Carroll & Ramsey Associates, USA) using a Phenomenex Gemini C18 column (250×10 mm, 5 μm) and gradient conditions (method 2): A: H$_2$O+0.1% TFA, B: CH$_3$CN+ 0.1% TFA; 0-3 min 10% B, 3-26 min 10-50% B, 26-28 min 50-95% B; 5.0 mL/min. Analytical HPLC were performed on an Agilent 1200 Series HPLC system (Agilent Technology, USA) with ChemStation software (version B.04.02) equipped with a quaternary pump, UV diode array detector and model 105S single-channel radiation detector using a Phenomenex Gemini C18 column (250×4.6 mm, 5 μm) and gradient conditions: A: H$_2$O+0.1% TFA, B: CH$_3$CN+0.1% TFA; 0-3 min 20% B, 3-27 min 20-60% B, 27-29 min 95% B; 1.0 mL/min. The identity of the $^{18}$F-labeled products was confirmed by comparison with the analytical HPLC retention time of their non-radioactive reference compound [$^{19}$F]-C-SNAT4 or by co-injection with [$^{19}$F]-C-SNAT4 before administration to animals.

Synthesis of 4: Production of 4 was carried out in a fully-automated TRACERlab FX-FN module (GE Healthcare, USA). Briefly, no-carrier added [$^{18}$F] fluoride was produced via the $^{18}$O(p,n)$^{18}$F nuclear reaction by irradiation of enriched [$^{18}$O]H$_2$O in a PETtrace cyclotron (GE Healthcare, USA). [$^{18}$F]Fluoride was trapped on an anion-exchange resin cartridge (Macherey-Nagel Chromafix 30-PS-HCO$_3$ pre-conditioned with 1 mL of EtOH, 1 mL of H$_2$O and then blown dry). The cartridge was eluted with a solution of Kryptofix 222 (4,7,13,16,21,24-Hexaoxa-1,10-diazabicyclo [8.8.8] hexacosane, or K2.2.2) (15 mg) and potassium carbonate (3 mg) in H$_2$O (0.1 mL) and CH$_3$CN (0.9 mL). Following azeotropic drying, 2 (3.0 mg in 1.0 mL of anhydrous DMSO) was added to the K[$^{18}$F]F/K2.2.2 complex, and the mixture was heated for 20 min at 110° C. to yield 4. After cooling to room temperature, the reaction mixture was loaded onto a semi-prep HPLC (method 1). The fraction corresponding to the peak of the desired product was collected in a round bottom flask containing sterile water (20 mL), and then transferred to an adjacent customized module for solid phase extraction (SPE) using a C-18 Sep-Pak cartridge. 4 trapped on C-18 cartridge was eluted with diethyl ether (2 mL) through a Na$_2$SO$_4$ cartridge into a 5 mL V-vial with stirrer bar in the customized module. The diethyl ether was removed under helium stream at ambient temperature and the dried labeling agent was ready for further click chemistry.

Synthesis of [$^{18}$F]-C-SNAT4. To dried 4 from previous step was added a mixture of C-SANT4 (200 μL of 1 mg/mL stock solution in DMSO), 0.1 M HEPES solution (200 μL), CuSO$_4$ (5 μL of 0.1 M stock solution in water), (BimC$_4$A)$_3$ (5 μL of 30 mM stock solution in water) and sodium ascorbate (5 μL of 1 M stock solution in water, freshly prepared), and reaction mixture was kept at 40° C. for 20 min. The reaction mixture was diluted with 2 mL of water and injected onto a semi-preparative HPLC (method 2).

Final product was formulated in saline with 10% ethanol by solid phase extraction with C-18 Sep-Pak light cartridge. The final product is confirmed on analytical HPLC by co-eluting with [$^{19}$F]-C-SNAT4 reference standard. Radiochemical yield was 6.6±5.0% and molar activity were 2.3±1.1 Ci/μmol, n=7, decay corrected to end of synthesis.

Synthesis of cold $^{19}$F-analog [$^{19}$F]-C-SNAT4. 3 was first synthesized from 2 according to previously reported procedures[33]. To a solution of C-SNAT4 (10 mg, 0.009 mmol) in DMSO/0.1M HEPES buffer (2.5 mL/2.5 mL) was added 3 (17 mg, 0.045 mmol), CuSO$_4$ (20 μL of 0.1M stock solution in water), (BimC$_4$A)$_3$ (20 μL of 30 mM stock solution in water) and sodium ascorbate (20 μL of 1M stock solution in water, freshly prepared). The reaction was stirred at room temperature for 30 min and was subsequently purified by preparative HPLC to afford the final product (5 mg, 42%). HRMS: calc'd for C$_{56}$H$_{79}$FN$_{15}$O$_{19}$S$_2^+$ [(M+H)$^+$]: 1348.5097, found 1348.5097.

Example 2

Bioorthogonal Condensation Substrate Pairs

Based on a condensation reaction between aromatic nitriles and aminothiols, the reactivity of the aromatic nitrile is affected by it electron density and number of heteroatoms in the aromatic ring. For example, for CBT, CHQ and 2-pyridinecarbonitrile (entries 1-3 in Table 2), no reaction was observed for 2-pyridinecarbonitrile while modest to fast reaction rates were observed for CHQ (0.059 M$^{-1}$ s$^{-1}$) and CBT (2.9 M$^{-1}$ s$^{-1}$). Comparison between the structures of CHQ and 2-pyridinecarbonitrile (entries 2 and 3, Table 2) reveals that adding one more aromatic ring in CHQ significantly increases the reactivity of aromatic nitrile by providing better electron delocalization in the fused aromatic ring system. Compare CBT with CHQ (entries 1 and 2 in Table 2), the presence of different heteroatoms like nitrogen or sulfur in the aromatic ring significantly changes the reactivity of the aromatic nitriles since heteroatoms have different electronegativity and number of unshared electron pairs from carbon. These observations prompted us to test if the reactivity of aromatic nitriles for the condensation reactions could be modulated by tuning the electronic properties or the heteroatoms on the aromatic ring. Starting from the unreactive 2-pyridinecarbonitrile (entry 3 in Table 2) reactive aromatic nitriles were designed by adding more nitrogen atoms onto the aromatic ring especially at 3 or 5-position and/or by adding electron-withdrawing groups such as halide. 2-pyrimidine-carbonitrile and 5-bromo-2-pyrimidinecarbonitrile were tested and their 2nd order rate constants measured with L-cysteine using an HPLC assay (entry 5 and 4 in Table 2): 0.99 M$^{-1}$ s$^{-1}$ for 2-pyrimidinecarbonitrile and 2.21 M$^{-1}$s$^{-1}$ for 5-bromo-2-pyrimidinecarbonitrile. An alkoxy-substituted 2-pyrimidinecarbonitrile (entry 6 in Table 2) was synthesized and tested its reactivity with L-cysteine. Since alkoxy substituents are electron-donating, its reactivity (0.01 M$^{-1}$ s$^{-1}$) is much lower than 2-pyrimidinecarbonitrile.

TABLE 2

Condensation reaction rate constants between the aromatic nitriles and aminothiols.

| Entry | Aromatic nitriles | Aminothiols | 2$^{nd}$ order rate constant k (M$^{-1}$s$^{-1}$) |
|---|---|---|---|
| 1 | HO-C(O)-CH$_2$CH$_2$-C(O)-NH-benzothiazole-CN | HS-CH$_2$-CH(NH$_2$)-COOH | 2.9 ± 0.3$^a$ |
| 2 | MeO-quinoline-2-CN | HS-CH$_2$-CH(NH$_2$)-COOH | 0.059 ± 0.017 |
| 3 | 2-pyridinecarbonitrile | HS-CH$_2$-CH(NH$_2$)-COOH | No Rxn$^a$ |
| 4 | 5-bromo-2-pyrimidinecarbonitrile | HS-CH$_2$-CH(NH$_2$)-COOH | 2.21 ± 0.037 |

TABLE 2-continued

Condensation reaction rate constants between the aromatic nitriles and aminothiols.

| Entry | Aromatic nitriles | Aminothiols | $2^{nd}$ order rate constant k $(M^{-1}s^{-1})$ |
|---|---|---|---|
| 5 | (pyrimidine-CN) | HS-CH2-CH(NH2)-COOH | 0.99 ± 0.17 |
| 6 | BocHN-(CH2)3-O-(pyrimidine)-CN | HS-CH2-CH(NH2)-COOH | 0.01 ± 0.0017 |
| 7 | HO-CO-(CH2)2-C(O)-NH-(benzothiazole)-CN | HS-C(Me)(Me)-CH(NH2)-COOH | 0.029 ± 0.003 |
| 8 | HO-CO-(CH2)2-C(O)-NH-(benzothiazole)-CN | HS-CH2-C(Me)(NH2)-COOH | 5.35 ± 0.8 |

$2^{nd}$ Order rate constants were measured in PBS buffer at room temperature using HPLC assay.
[a]The rate constants were reported in Reference[13].

The nucleophilicity of the aminothiol is another determining factor of the reaction rate. The reactivity of a series of aminothiols with different electronic and conformational properties found L-cysteine to be advantageous among all that were tested. The $2^{nd}$ order rate constant of the condensation between D-penicillamine (3,3-dimethyl D-cysteine) and CBT (entry 7 in Table 2) was determined to be 0.029 $M^{-1}$ $s^{-1}$, which was dramatically lowered than that of L-cysteine (2.9 $M^{-1}s^{-1}$). In spite of the "gem-dimethyl effect" on cysteine,[17] steric hindrance introduced by the two methyl groups around the thiol nucleophile lowers the rate of intermolecular nucleophilic attack. Interestingly, 2-methyl-L-cysteine showed a higher reaction rate constant (5.35 $M^{-1}$ $s^{-1}$, entry 8 in Table 2) than that of L-cysteine (2.9 $M^{-1}s^{-1}$).

Figure 26B:
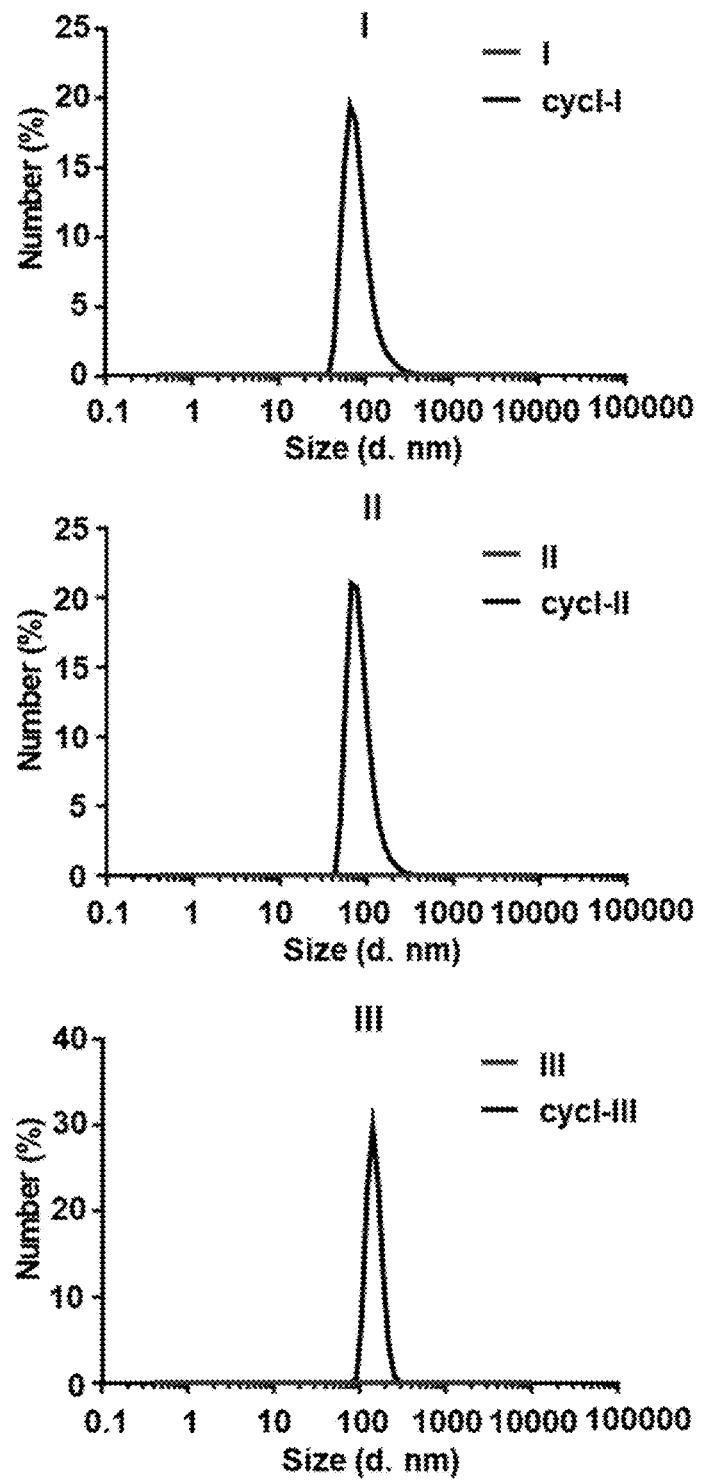

Structural Requirements for Linker to Promote Self-Assembly:

A replacement of the luciferin moiety in the previously reported scaffold by a non-aromatic, flexible PEG linker failed to produce nanoaggregates after condensation.[14] This indicated the role of the luciferin moiety in promoting self-assembly, however, it was unclear if other rigid aromatic structures besides the luciferin moiety could similarly promote assembly of the cyclization product. Compounds I and II, both of which use a benzyl group as the linker in place of the luciferin moiety were generated (FIG. 26A). Compound II differs from compound I in that there is one more amino acid residue in the linker so that the formed macrocyclic ring would have a similar size to that having the luciferin moiety. Upon adjustment of the pH value from 4 to 7.4, both I and II afforded cyclized products, as confirmed by HPLC and mass spectrometry. Their first-order reaction rate constants were determined by an HPLC assay: 0.2×10-3 s-1 for compound I and 1.2×10-3 s-1 for compound II; and dynamic light scattering (DLS) analysis of their cyclized products (cycl-I and cycl-II, FIG. 26B) showed formation of nanoaggregates with hydrodynamic sizes of around 80 nm for both compounds. These results suggest that like the luciferin moiety, aromatic functional groups as simple as a benzene ring can similarly promote assembly of cyclic products.

To test if the benzyl linker can promote macrocyclization and self-assembly of aromatic nitriles other than CBT and CHQ, compounds III, IV, V, and VI were designed, each of which has the luciferin-linker replaced by a benzyl linker, and CHQ by an alkoxy-substituted 2-pyrimidinecarbonitrile. As shown in FIGS. 26A and 26B, despite different cyclization kinetics and condensation substrate pairs, all their cyclic products were able to form nanoaggregates ranging from 80 nm to 250 nm in diameters, demonstrating the robustness of this simple aromatic linker in promoting self-assembly of cyclic products. Length of the linker is also important to the cyclization kinetics. From compound III and IV to V, the kinetics of IV ($2.7 \times 10^{-3}$ $s^{-1}$) is the fastest while the ring size of its macrocyclic product is between III ($0.9 \times 10^{-3}$ $s^{-1}$) and V ($0.8 \times 10^{-3}$ $s^{-1}$). When 2-methyl-L-cysteine moiety is introduced to replace cysteine moiety in compound IV, the resulted compound VI displayed a 1.3-fold increase in the cyclization kinetics ($2.7 \times 10^{-3} s^{-1}$) over IV ($2.1 \times 10^{-3} s^{-1}$), similar to the enhancement in the second order reaction rate constant observed between cysteine moiety and 2-methyl-cysteine moiety in their reaction to CBT (Table 2, entries 1 and 8). It is interesting to observe that despite different kinetics, all these compounds can undergo macrocyclization and self-assembly. This result suggests that the luciferin moiety in SNAT[38] is not indispensable for macrocyclization and self-assembly. Some aromatic functionalities are necessary, and they can be the luciferin moiety or as simple as a benzyl group.

New Molecular Scaffold for Nanoaggregation

Figure 30:
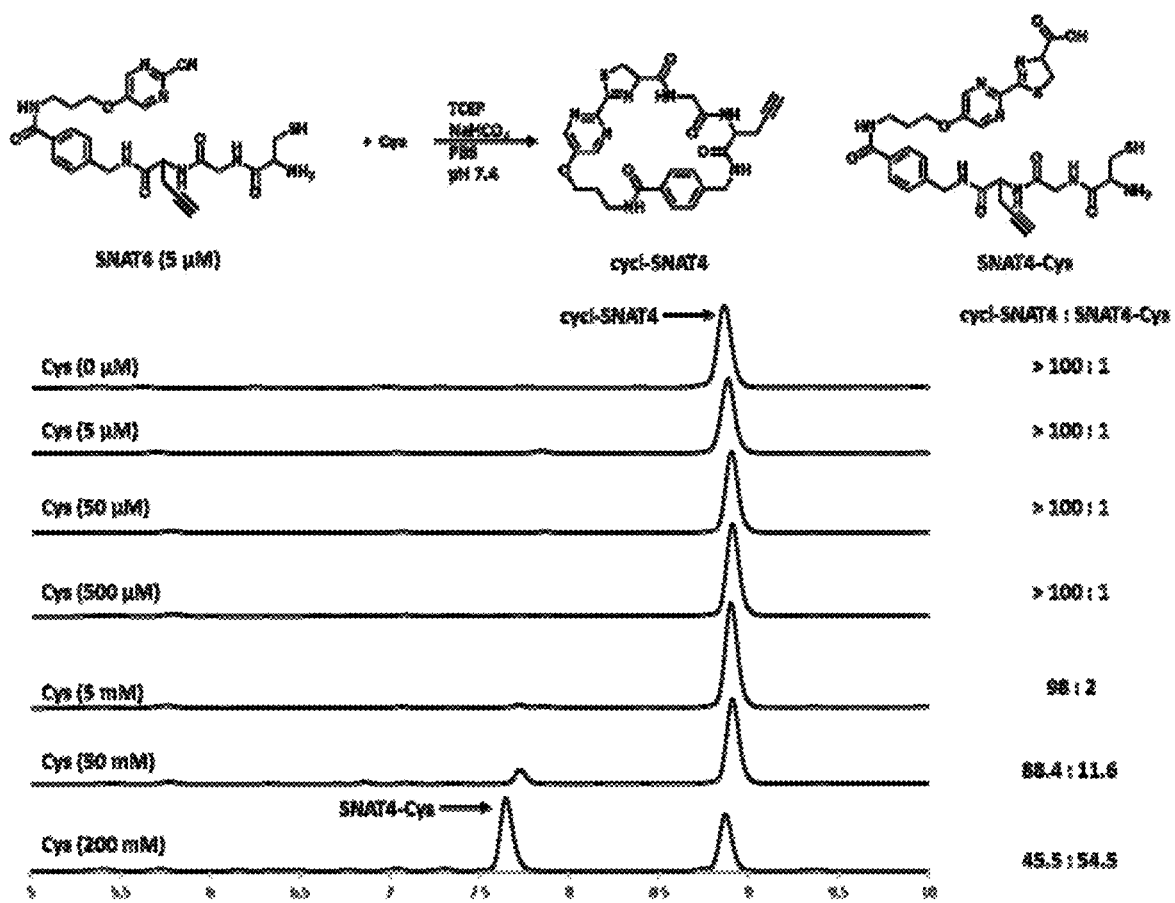
FIG. 30 illustrates an HPLC analysis of products ratio of intramolecular cyclization and intermolecular condensation in a mixture of SNAT4 with various concentrations of free cysteine.

Among the scaffolds tested in FIG. 26A, SNAT4 is of interest for macrocyclization promoted nanoaggregation because of its simplified structure and fast cyclization rate. Based on the condensation reaction rate between alkoxy-substituted 2-pyrimidinecarbonitrile ($0.01 M^{-1} s^{-1}$) and the intramolecular cyclization rate of compound IV ($2.1 \times 10^{-3} s^{-1}$), the intramolecular effective molarity was estimated to be around 210 mM, which is significantly higher than endogenous free cysteine in cells and plasma (usually around 20-100 µM). Consistent with this estimate, in a competitive HPLC assay using this new scaffold (FIG. 30), the ratio between the products of intramolecular cyclization and intermolecular condensation is about 45.5: 54.5 at 200 mM of free cysteine.

Figure 27A:
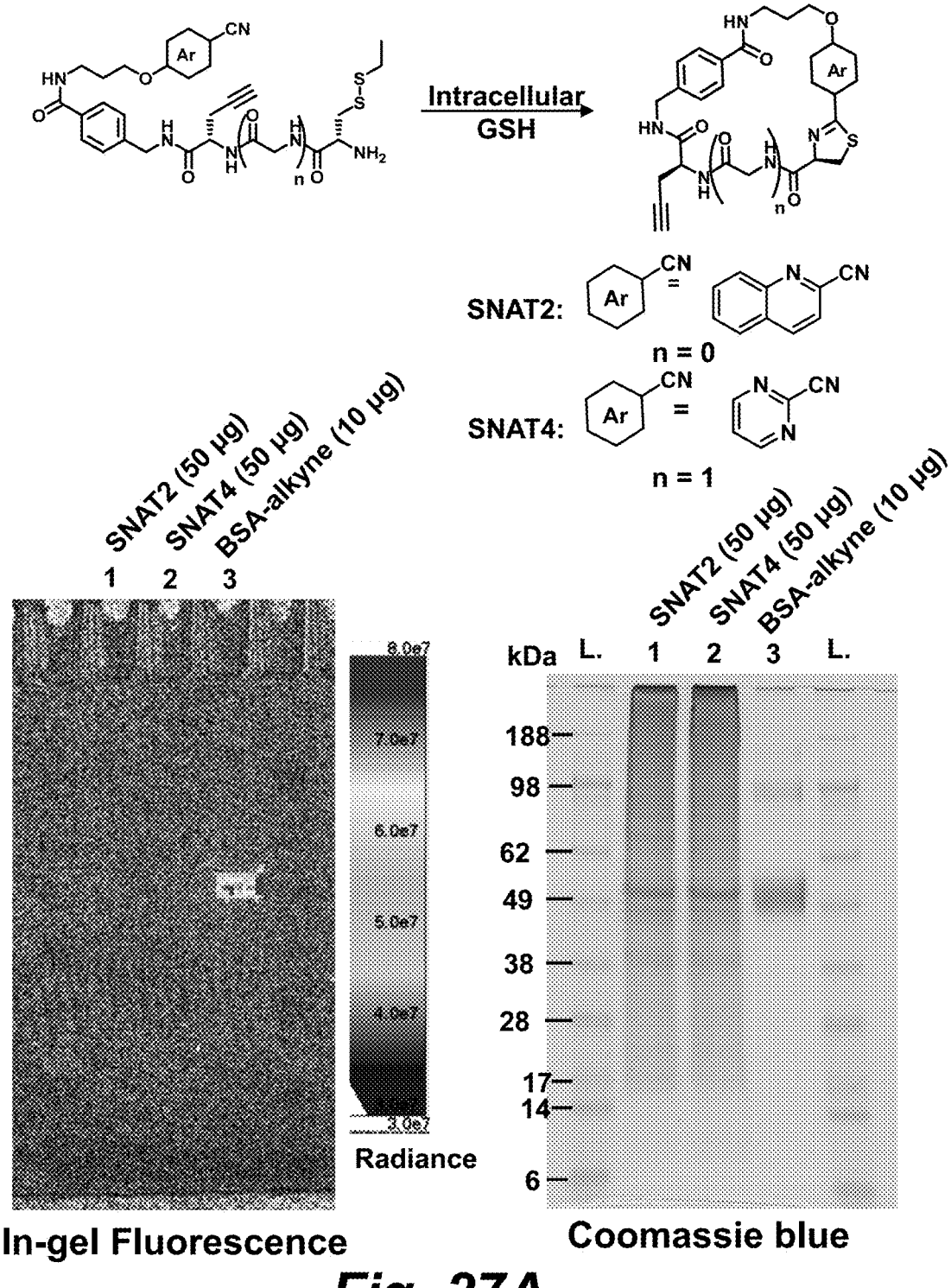
FIGS. 27A-27C illustrate the stability of SNAT2/4 and their cyclization products in cell lysate.
Figure 27B:
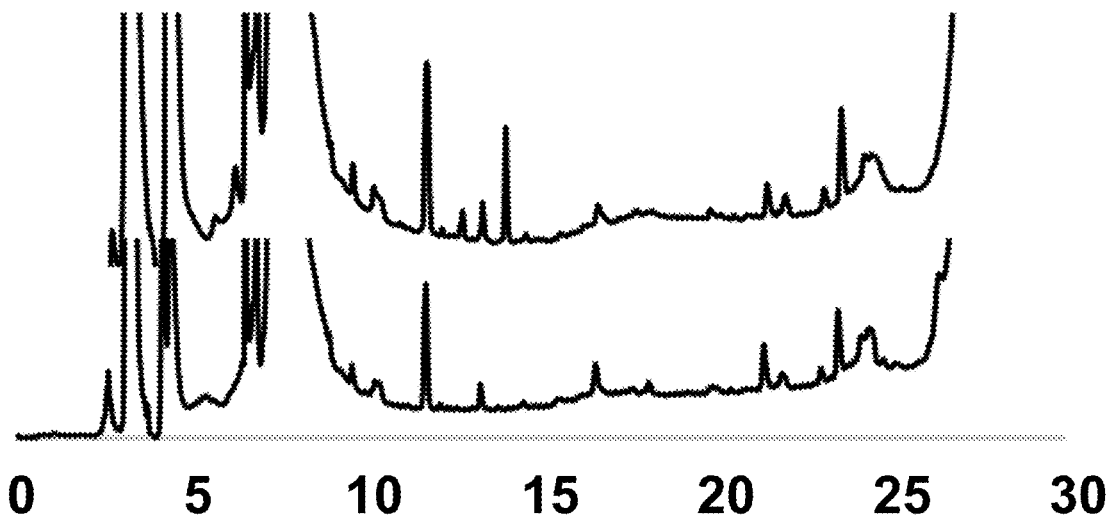
Figure 27C:
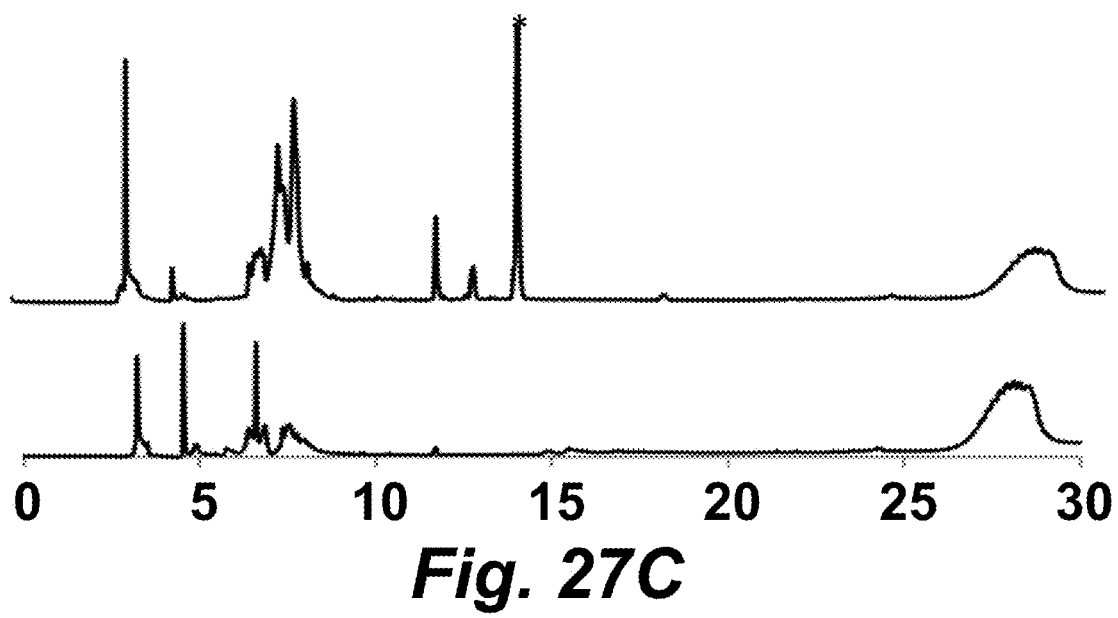

To examine any potential interactions between this new scaffold and intracellular proteins, disulfide caged SNAT4 was incubated in HeLa lysate at 100 µM at 37° C. for 6 hours. The cell lysates were first labeled with Cy5-azide through click reaction followed by being analyzed by SDS-Page for detection of SNAT4-protein conjugates. 6-heptynoic NHS ester was used to label BSA as the positive control to validate the in-gel labeling condition. BSA was labeled with 6-heptynoic NHS ester, followed by a similar Click reaction with Cy5-azide to provide a positive control. The in-gel fluorescence analysis did not show any significant protein labeling by SNAT4 (FIG. 27A) and HPLC analysis of the cell lysate showed the majority of SNAT4 were converted into the cyclized product (FIGS. 27B and 27C). These results suggest that the lack of reactions of SNAT4 with endogenous proteins. SNAT2 bearing CHQ was also included as a comparison, and consistent with previous report,[13] the CHQ didn't show any labeling of endogenous molecules either.

Imaging of Glycoside Hydrolase Activity in Live Cells

Figure 28A:
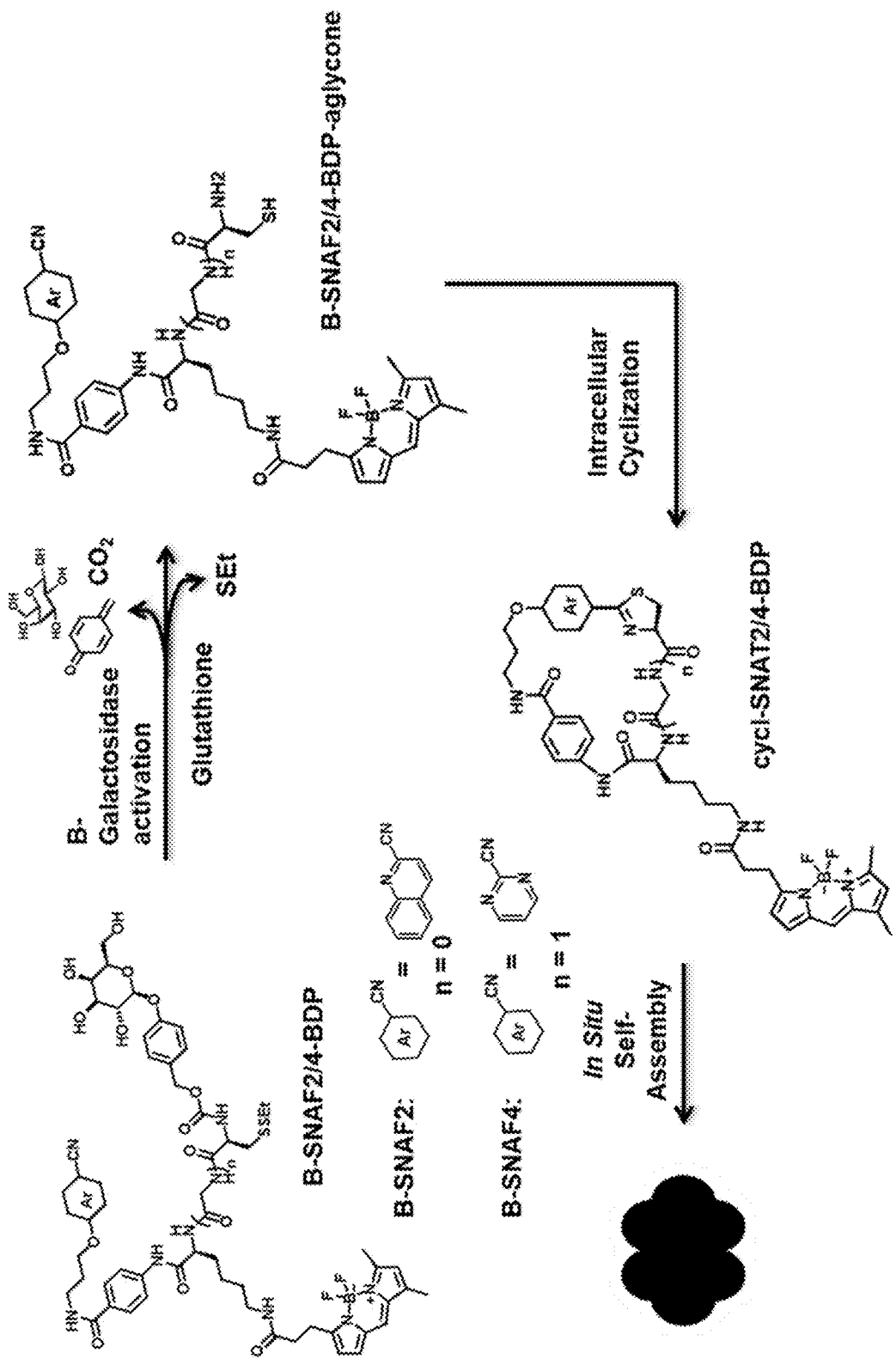
FIGS. 28A-28G illustrate in vitro and in cellulo validations of β-galactosidase imaging probes.
Figure 28B:
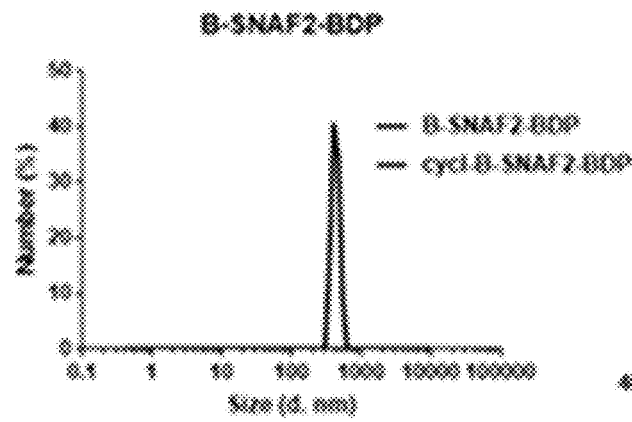
Figure 28C:
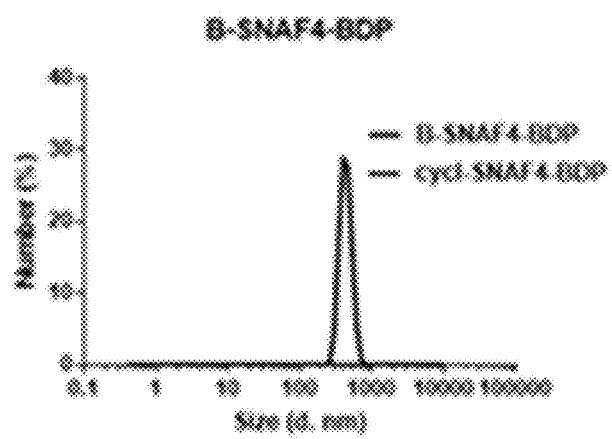
Figure 28D:
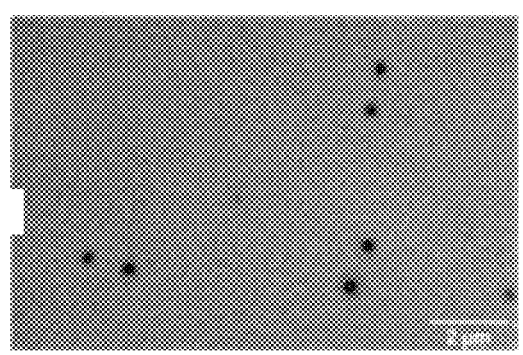
Figure 28E:
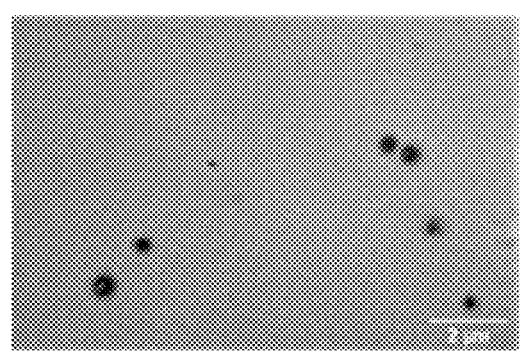
Figure 31A:
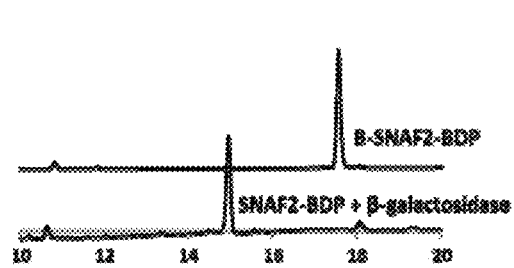
FIG. 31A illustrates an HPLC traces of B-SNAF2-BDP (10 μM) before (upper) and after (lower) incubation with β-galactosidase (1 unit) and TCEP (20 μM) at 37° C. for 2 hours.
Figure 31B:
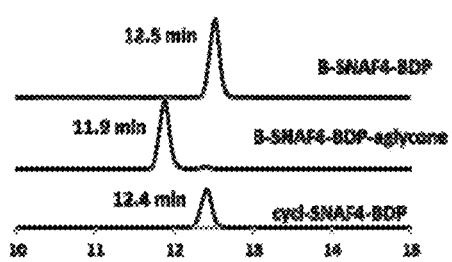
FIG. 31B illustrates HPLC traces of B-SNAF4-BDP (10 μM) before (upper) and after incubation with β-galactosidase only (middle) or with β-galactosidase (1 unit) and TCEP (20 μM) at 37° C. for 2 hours (lower).

The new scaffolds were tested to determine if they could be applied to image β-galactosidase, a widely used gene reporter and biomarker in various diseases and biological processes such as tumor metastasis and cellular senescence. [18] To image activity of β-galactosidase, a self-immolative group was introduced to link the C-1 hydroxyl group of the galactose to the amino group of the scaffold (FIG. 28A). After cleavage of the glycoside by β-galactosidase, the linker self-immolates in the form of quinone methide and carbon dioxide to afford the B-SNAF2/4-BDP-aglycone. Under reducing conditions, the disulfide is reduced followed by intramolecular cyclization between the terminal cysteine and aromatic nitrile and self-assembly into nanoaggregates. To verify this mechanism, B-SNAF2-BDP or B-SNAF4-BDP was incubated with β-galactosidase and TCEP together at 37° C. for 2 hours and the resulting products were confirmed by HPLC and LC-MS to be cycl-SNAF2-BDP or cycl-SNAF4-BDP (FIGS. 31A and 31B). The size of the nanoaggregates was measured by DLS and TEM to be around 300 nm for both cycl-SNAF2-BDP and cycl-SNAF4-BDP (FIGS. 28B-28E).

Figure 28F:
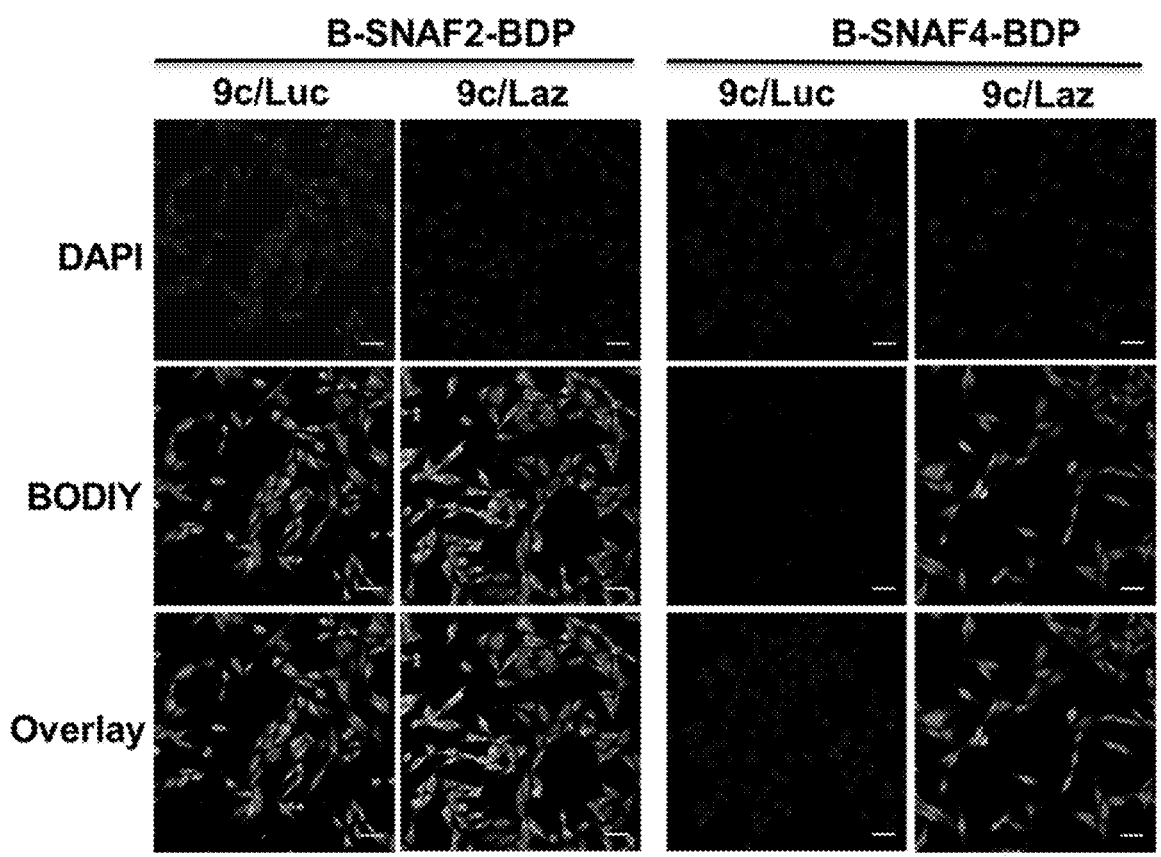
Figure 28G:
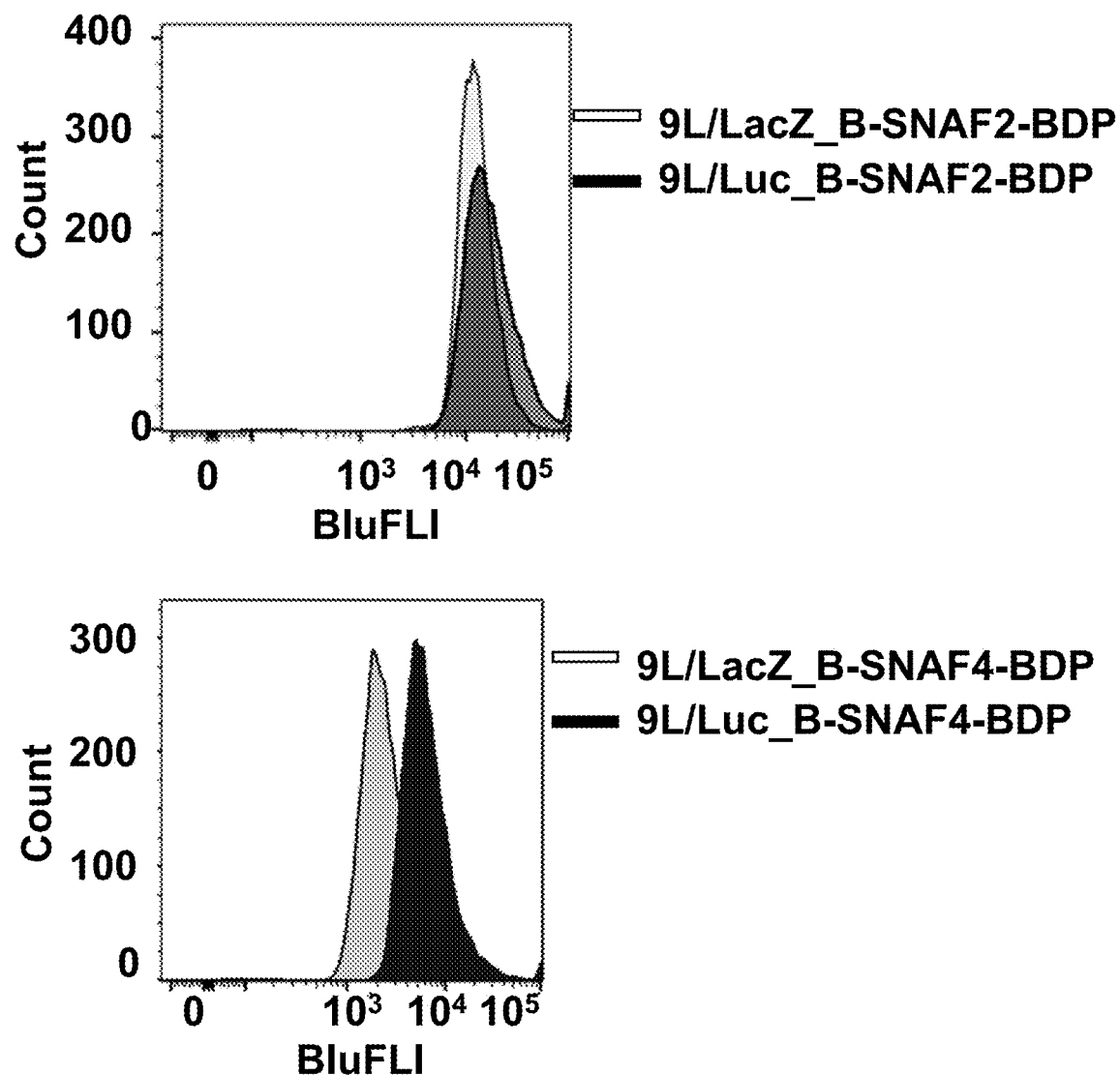
Figure 32:
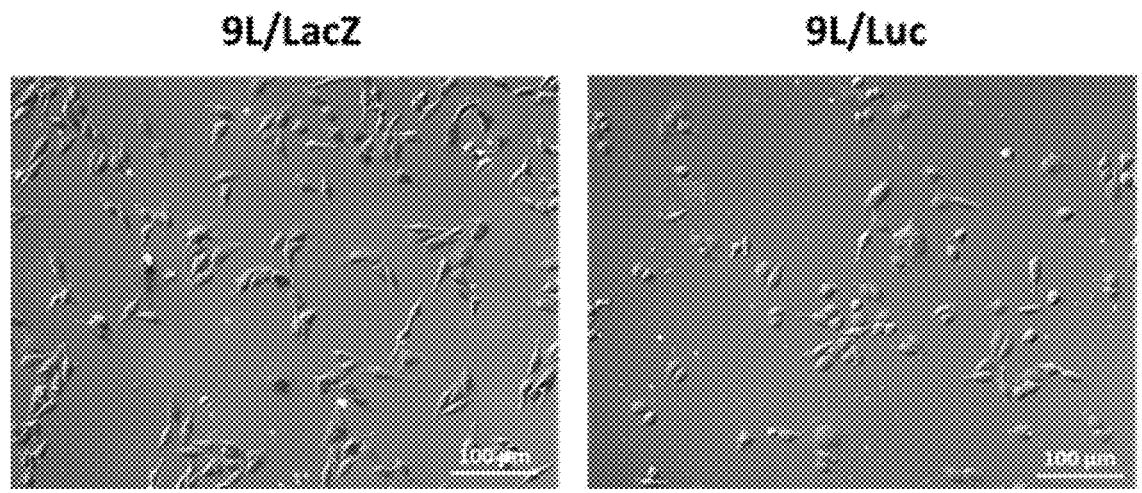
FIG. 32 illustrates 9L/LacZ (left) and 9L/Luc (right) after X-gal staining. Scale bar: 100 μm.
Figure 33:
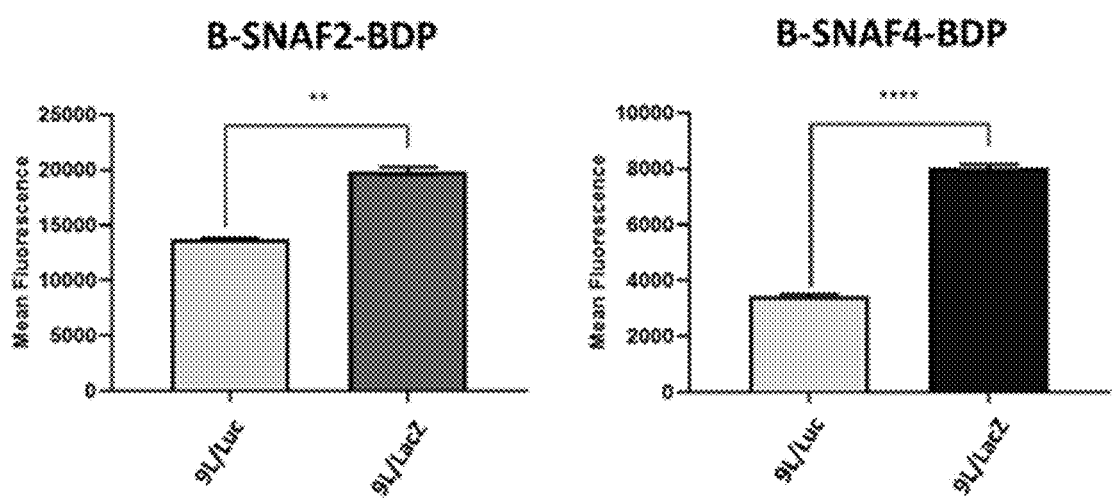
FIG. 33 illustrates quantification of fluorescent intensity in the flow cytometry data in FIG. 3G. 9L/LacZ and 9L/Luc were incubated with either B-SNAF2-BDP or B-SNAF4-BDP (2 μM) at 37° C. for 2 hours. , $P<0.01$; **, $P<0.001$.

To evaluate if B-SNAF2/4-BDP was selectively retained in LacZ-expressing living cells, it was tested in 9L rat gliosarcoma cells transfected with LacZ (9L/LacZ). LacZ expression in 9L/LacZ cell line was confirmed by X-Gal staining, a widely used colorimetric assay to detect β-galactosidase activity (FIG. 32). Both 9L/LacZ and control 9L cell lines (9L/Luc expressing luciferase) were incubated with B-SNAF2-BDP or B-SNAF4-BDP (2 µM at 37° C. for 2 hours) followed by nuclear staining with Hoechst. When incubated with B-SNAF4-BDP, 9L/LacZ showed 2.5-fold higher retention of fluorescent signal than 9L/Luc (FIGS. 28F and 33). For B-SNAF2-BDP, 9L/LacZ only showed slightly higher (1.3-fold) fluorescent signal than 9L/Luc (FIGS. 28G and 33). In addition, the uptake of B-SNAF2-BDP in both 9L/LacZ and 9L/Luc were higher than with B-SNAF4-BDP, which may come from higher hydrophobicity of B-SNAF2-BDP and stronger non-specific retention.

Imaging of Proteases Activity in Apoptotic Cells

Figure 29A:
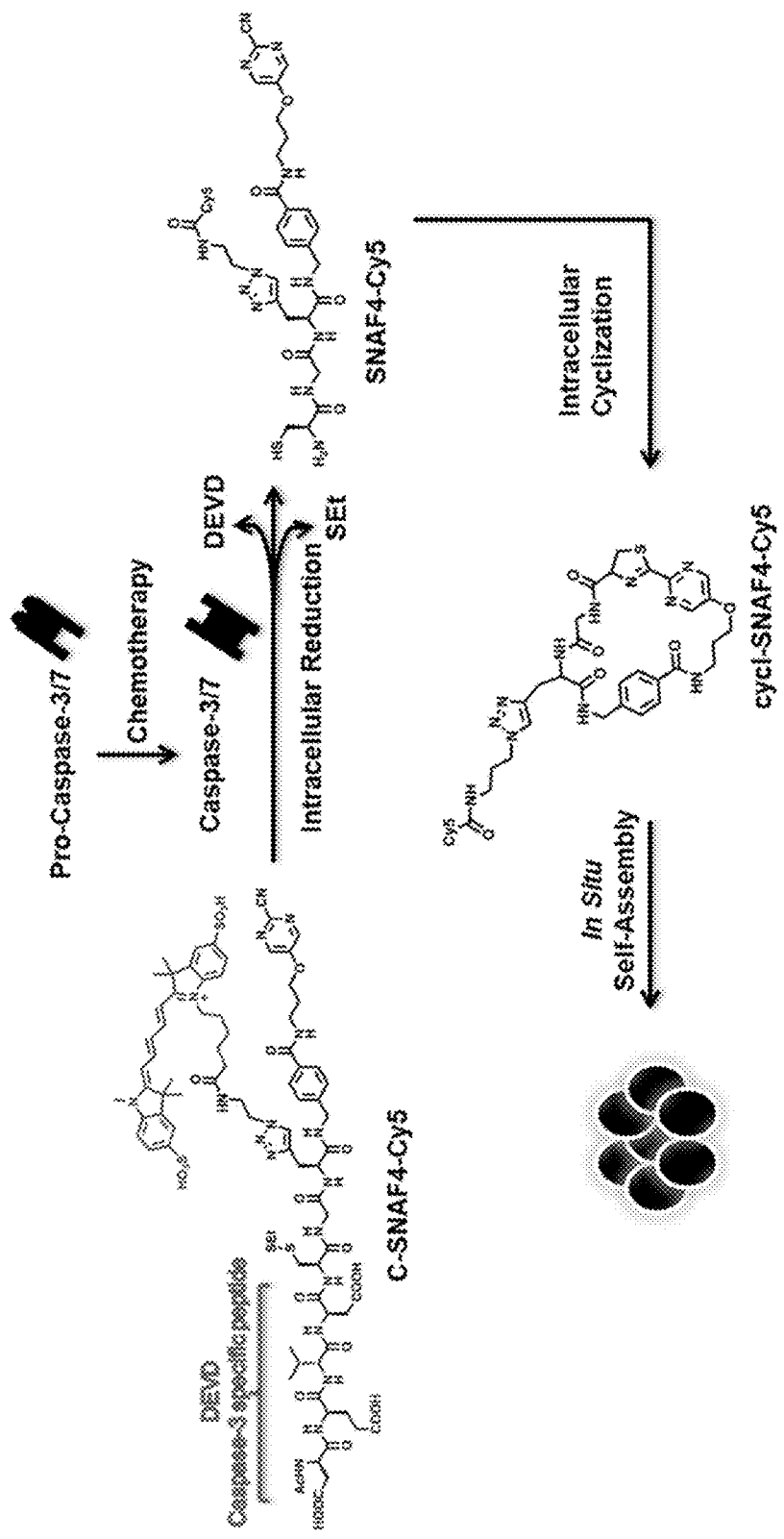
FIGS. 29A-29D illustrate in vitro and in cellulo validations of caspases-3/7 imaging probes.
Figure 29B:
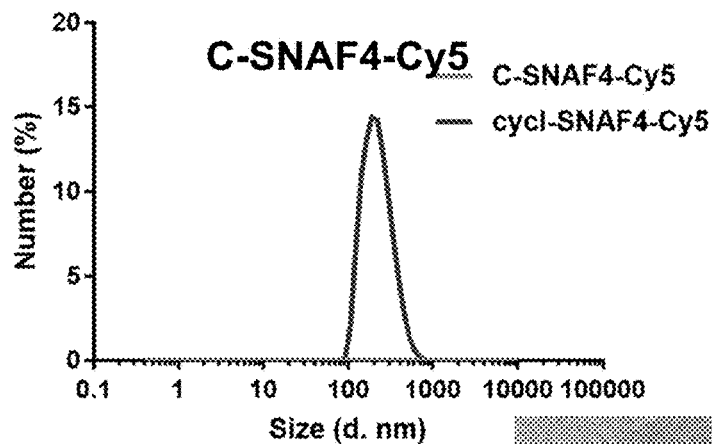
Figure 29C:
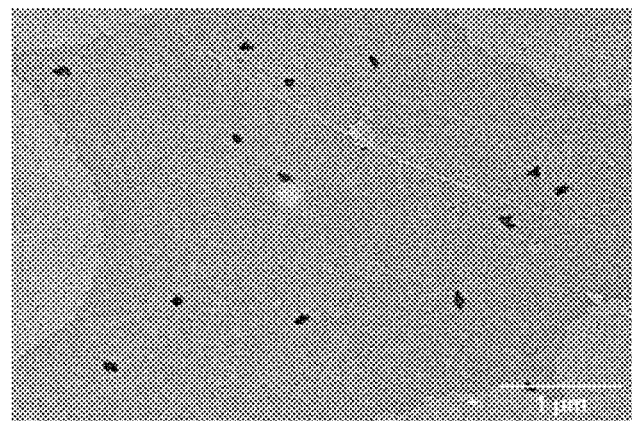
Figure 29D:
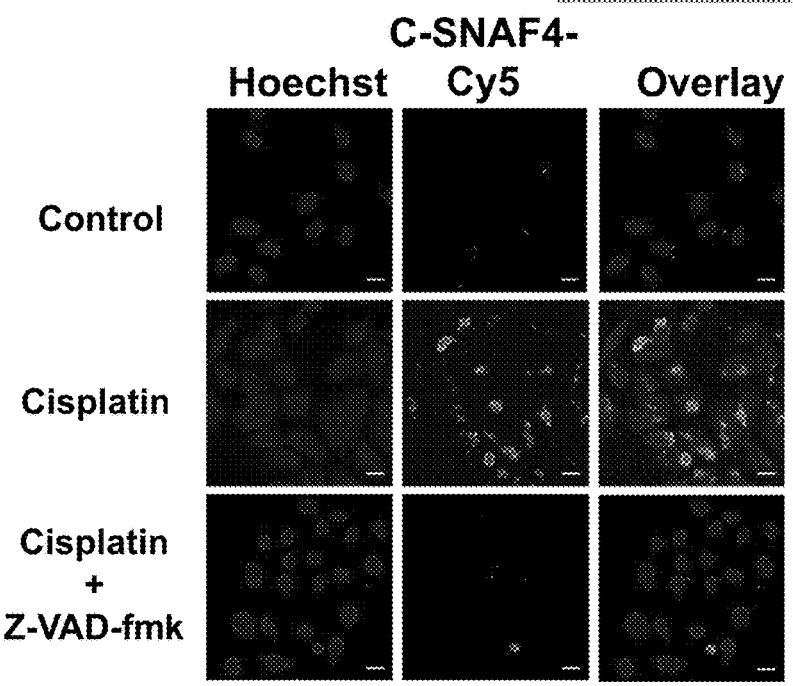
Figure 34B:
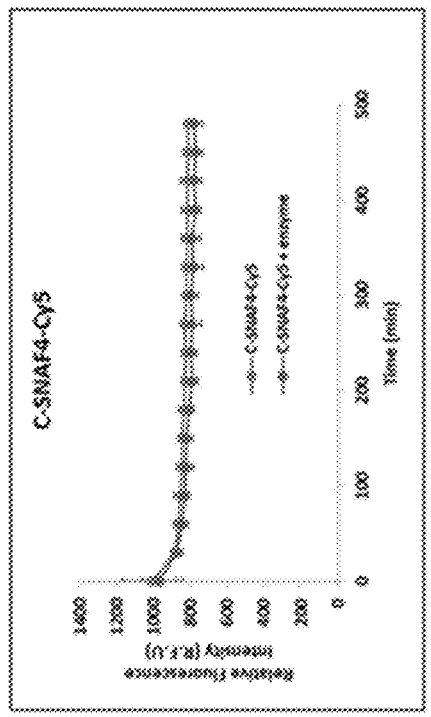
FIG. 34B illustrates fluorescent intensities of C-SNAF4-Cy5 monitored over time with and without incubation with caspase-3.
Figure 34A:
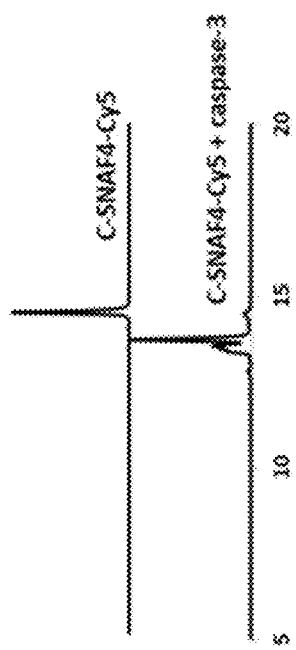
FIG. 34A illustrates HPLC traces of C-SNAF4-Cy5 before and after incubated with caspase-3 in caspase buffer at 37° C. overnight.
Figure 34D:
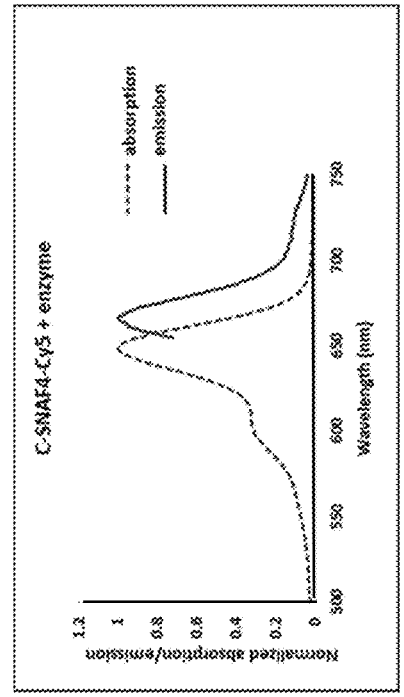
FIGS. 34C and 34D illustrate absorption and emission spectra of C-SNAF4-Cy5 before (FIG. 34C) and after (FIG. 34D) caspase-3 activation. Excitation (Amax)=645 nm, Emission (Amax)=670 nm.
Figure 34C:
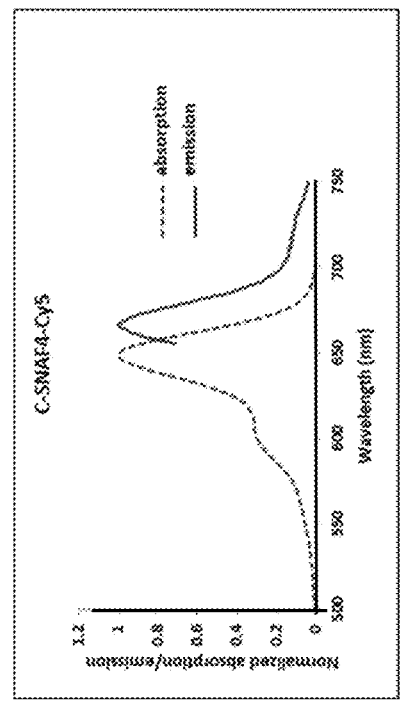
Figure 35A:
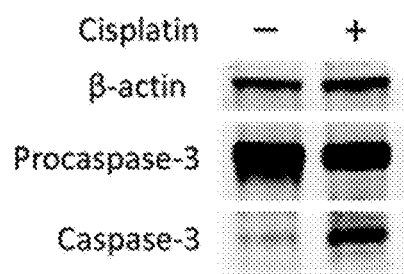
FIGS. 35A and 35B illustrate the analysis of procaspase-3 and caspase-3 expressions in non-small lung cancer cell line NCI-H460.
Figure 35B:
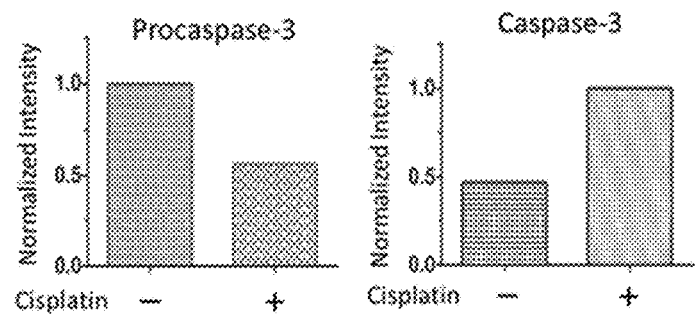
Figure 36A:
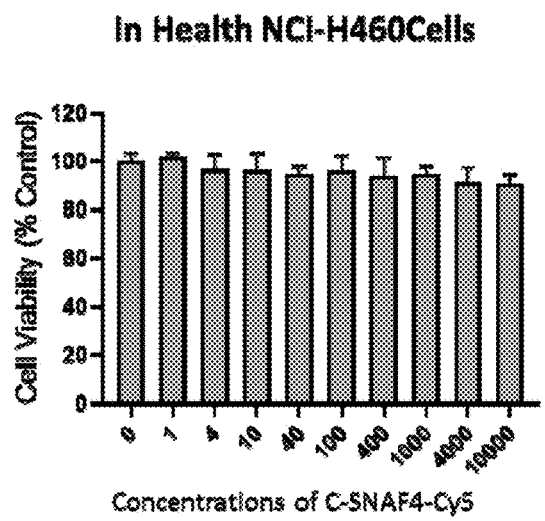
FIG. 36A illustrates the toxicity of C-SNAF4-Cy5 in heathy and apoptotic NCI-H460 measured with MTS assay (37° C., 24 h) in heathy H460 cells.
Figure 36B:
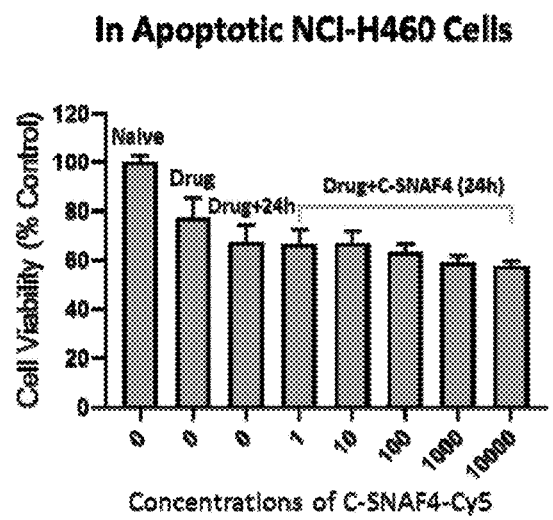
FIG. 36B illustrates the toxicity of C-SNAF4-Cy5 in H460 cells treated with cisplatin (1 μM, 24 hours) followed by incubation with C-SNAF4-Cy5 (37° C., 24 h).
Figure 37:
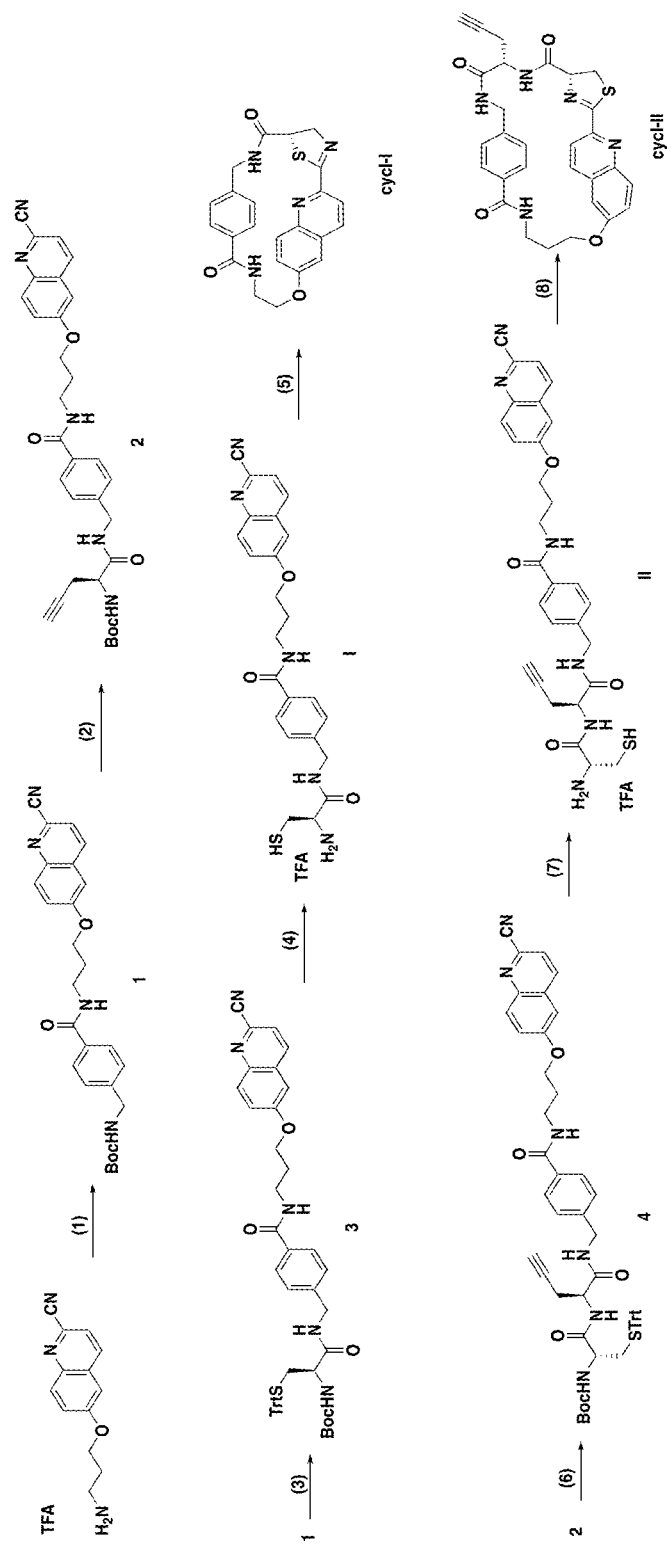
FIG. 37 illustrates Scheme 1. (1) 4-(Boc-aminomethyl) benzoic acid, HBTU, DIPEA, DMF, r.t., 2 h. (2) (i) 1:4 TFA/DCM, r.t., 30 min; (ii) Boc-propargyl-Gly-OH, HBTU, DIPEA, DMF, r.t., 2 h. (3) (i) 1:4 TFA/DCM, r.t., 30 min; (ii) Boc-Cys(Trt)-OH, HBTU, DIPEA, DMF, r.t., 2 h. (4) (i) 1:1:0.05 TFA/DCM/TIPS, r.t. 1 h. (5) PBS, pH=7.4. (6) (i) 1:4 TFA/DCM, r.t., 30 min; (ii) Boc-Cys(Trt)-OH, HBTU, DIPEA, DMF, r.t., 2 h. (7) 1:1:0.05 TFA/DCM/TIPS, r.t. 1 h. (8) PBS, pH=7.4.
Figure 38:
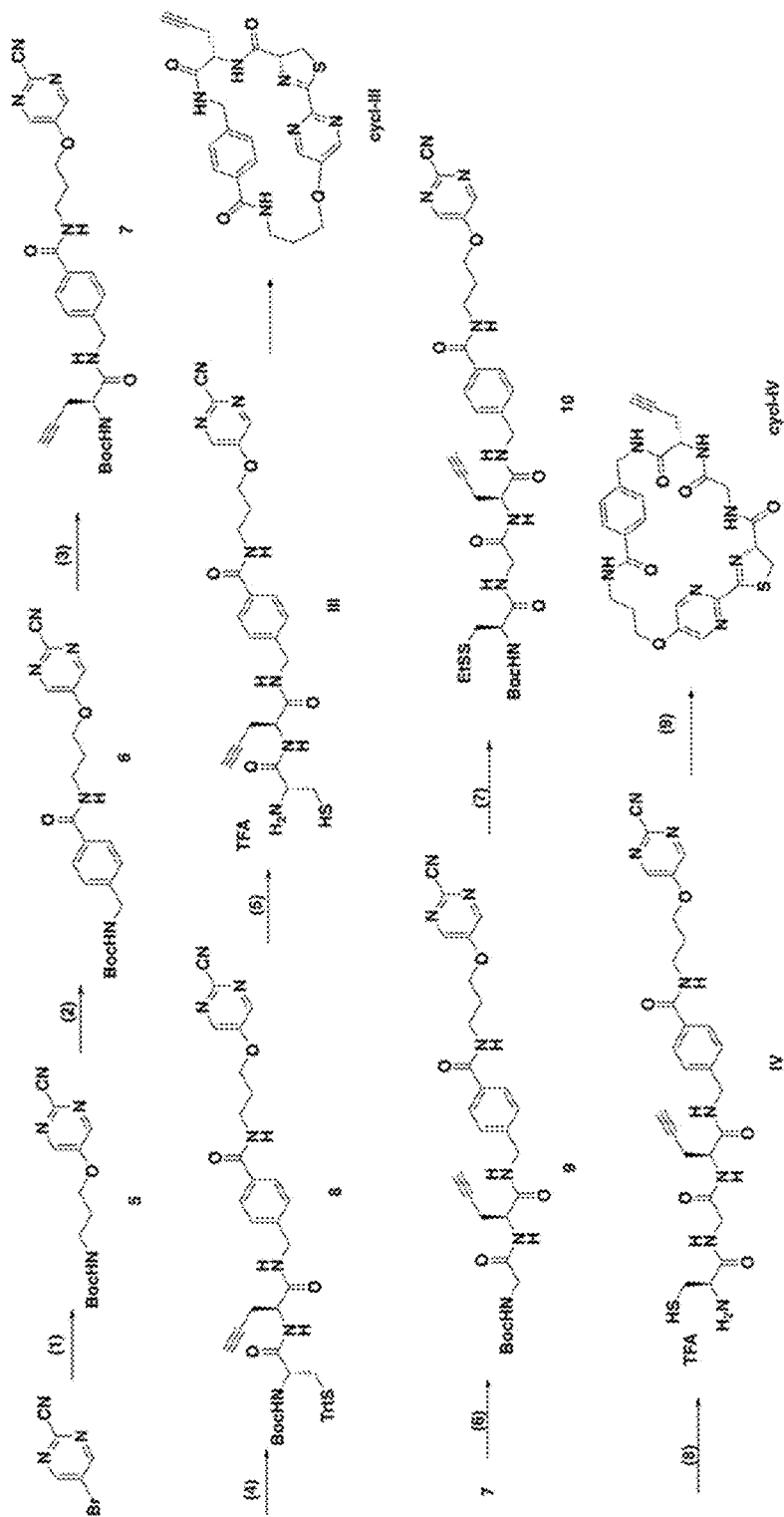
FIG. 38 illustrates Scheme 2. (1) 3-(Boc-amino)-1-propanol, Pd(OAc)$_2$, BINAP, Cs$_2$CO$_3$, reflux, 110° C. (2) (i) 1:4 TFA/DCM, r.t., 30 min; (ii) 4-(Boc-aminomethyl)benzoic acid, HBTU, DIPEA, DMF, r.t., 2 h. (3) (i) 1:4 TFA/DCM, r.t., 30 min; (ii) Boc-propargyl-Gly-OH, HBTU, DIPEA, DMF, r.t., 2 h. (4) (i) 1:4 TFA/DCM, r.t., 30 min; (ii) Boc-Cys(Trt)-OH, HBTU, DIPEA, DMF, r.t., 2 h. (5) (i) 1:1:0.05 TFA/DCM/TIPS, r.t. 1 h. (6) (i) 1:4 TFA/DCM, r.t., 30 min; (ii) Boc-Gly-OH, HBTU, DIPEA, DMF, r.t., 2 h. (7) (i) 1:4 TFA/DCM, r.t., 30 min; (ii) Boc-Cys(SEt)-OH DCHA, HBTU, DIPEA, DMF, r.t., 2 h. (8) (i) 1:4 TFA/DCM, r.t., 30 min; (ii) TCEP, PBS buffer, r.t., 30 min. (9) NaHCO$_3$, pH=7.4. (10) (i) 1:4 TFA/DCM, r.t., 30 min; (ii) Boc-beta-Ala-OH, HBTU, DIPEA, DMF, r.t., 2 h. (11) (i) 1:4 TFA/DCM, r.t., 30 min; (ii) Boc-Cys(SEt)-OHDCHA, HBTU, DIPEA, DMF, r.t., 2 h. (12) (i) 1:4 TFA/DCM, r.t., 30 min; (ii) TCEP, PBS buffer, r.t., 30 min. (13) NaHCO$_3$, pH=7.4. (14) (i) 1:4 TFA/DCM, r.t., 30 min; (ii) 2-methyl-Boc-Cys(SEt)-OHDCHA, HBTU, DIPEA, DMF, r.t., 2 h. (15) (i) 1:4 TFA/DCM, r.t., 30 min; (ii) TCEP, PBS buffer, r.t., 30 min. (16) NaHCO$_3$, pH=7.4.
Figure 39:
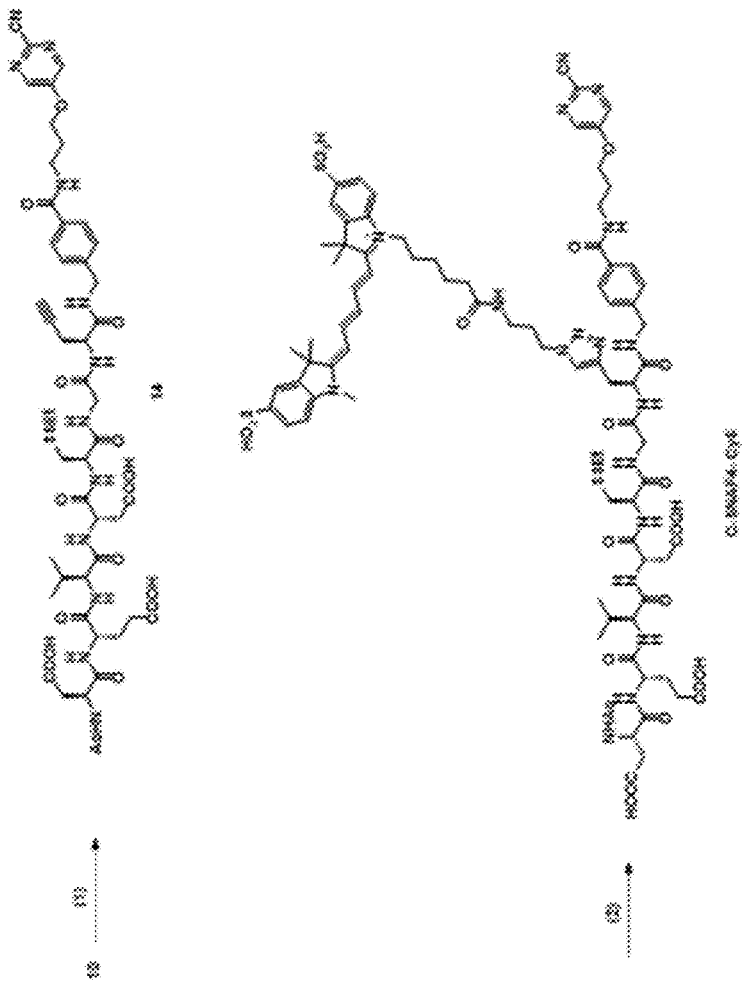
FIG. 39 illustrates Scheme 3. (1) (i) 1:4 TFA/DCM, r.t., 30 min; (ii) Ac-DEVD-OH peptide, HBTU, DIPEA, DMF, r.t., 2 h; (iii) 1:1:0.05 TFA/DCM/TIPS, r.t. 2 h. (2) sulfo-Cy5-azide, CuSO$_4$, sodium ascorbate, DMSO/HEPES.
Figure 40:
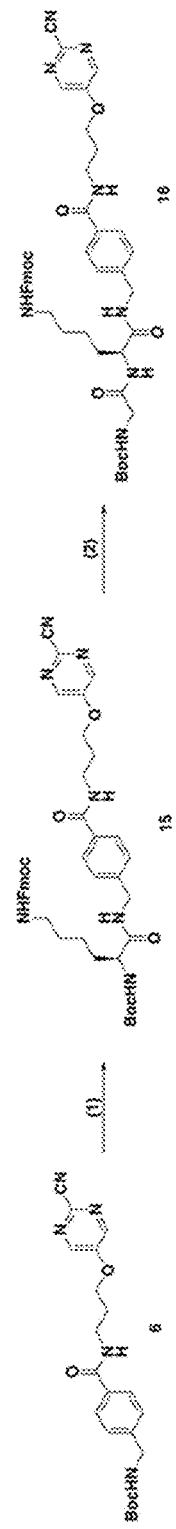
FIG. 40 illustrates Scheme 4. (1) (i) 1:4 TFA/DCM, r.t., 30 min; (ii) Boc-Lys(Fmoc)-OH, HBTU, DIPEA, DMF, r.t., 2 h. (2) (i) 1:4 TFA/DCM, r.t., 30 min; (ii) Boc-Gly-OH, HBTU, DIPEA, DMF, r.t., 2 h. (3) 1:4 TFA/DCM, r.t., 30 min.
Figure 41:
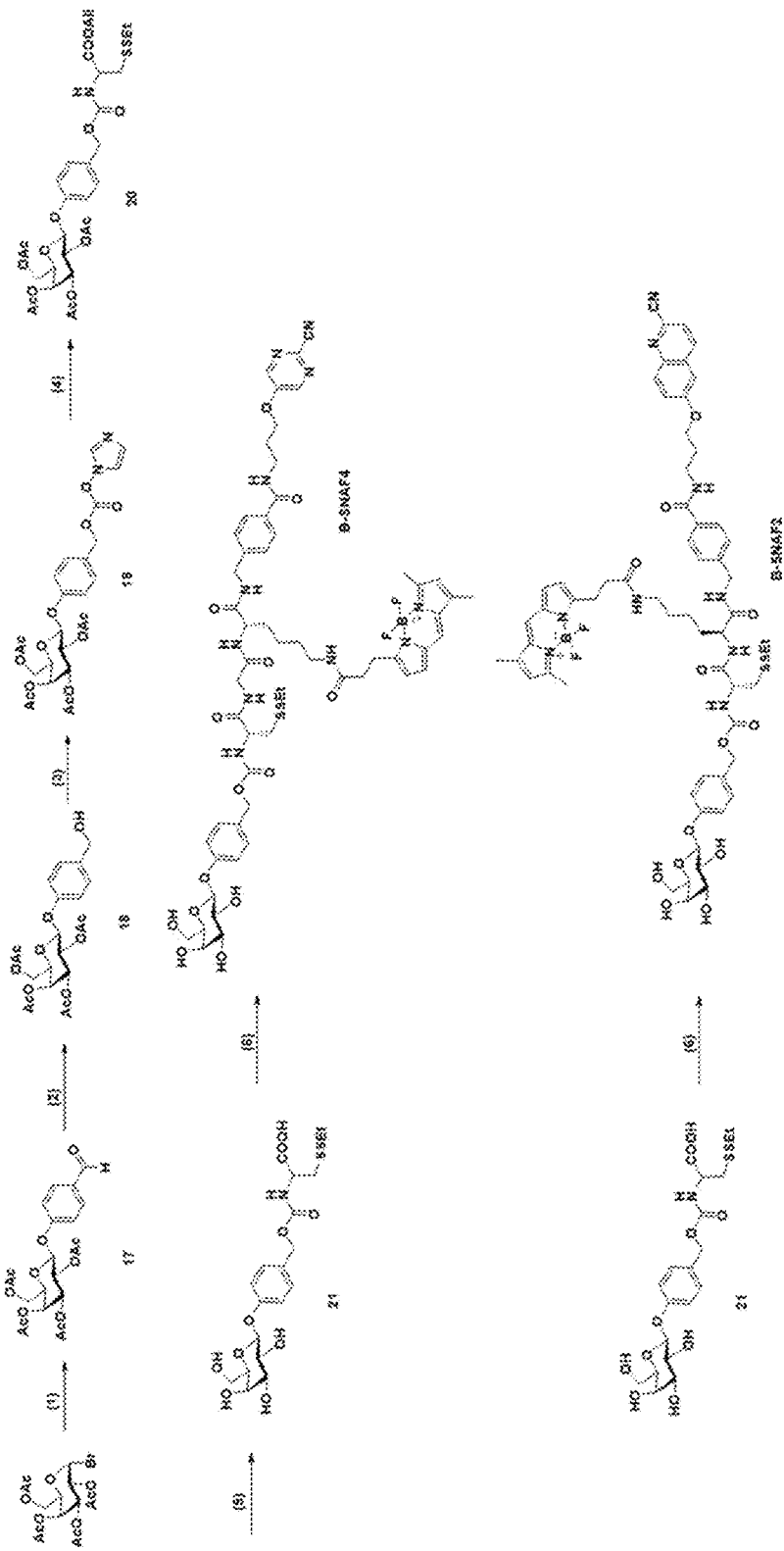
FIG. 41 illustrates Scheme 5. (1) 4-hydroxybenzaldehyde, 1M NaOH, acetone, r.t., 4 h. (2) NaBH$_4$, 4:1 DCM/MeOH, r.t., 1 h. (3) CDI, DCM, r.t., overnight. (4) (i) MeOTf, DCM, r.t., 20 min; (ii) allyl-ester-SEt-Cys-NH$_2$, DIPEA, DMF, r.t., 2 h. (5) (i) Pd(PPh$_3$)$_4$, SiPhH$_3$, DCM, r.t., 1 h; (ii) NaOMe, MeOH, r.t., overnight. (6) (i) 15, 20% TFA/DCM, r.t., 30 min; (ii) HBTU, DIPEA, DMF, r.t., 2 h; (iii) 5% piperidine in DMF, r.t., 20 min; (iv) Bodipy-FL-NHS-ester, DIPEA, DMF, r.t., 30 min.

SANT4 can be applied to image caspase-3/7 activity in human lung cancer. The caspases-sensitive nanoaggregation fluorescent probe C-SNAF4-Cy5 with caspases-3/7 as the target was synthesized. DEVD, a short peptide substrate of the endopeptidase caspase-3/7, and disulfide incorporated into the new scaffold as the masking groups (FIG. 29A). After cleavage of the DEVD by caspases with the presence of glutathione in cells, intramolecular cyclization proceeds between the terminal cysteine and aromatic nitrile will produce Cy5-labeled macrocyclics to afford cycl-SNAF4-Cy5. The probe mechanism was tested in vitro first by incubating C-SNAF4-Cy5 with human recombinant caspase-3 in caspase buffer. The macrocyclic product from the enzymatic reactions were analyzed by HPLC (FIG. 34A) and LC-MS. DLS and TEM analysis of C-SNAF4-Cy5 (20 µM) following incubation with caspase-3 in caspase buffer overnight further confirmed the in situ formation of nanoaggregates with an average size of around 100 nm (FIGS. 29B and 29C). To induce elevated expression of caspase-3 in cells, H460 human non-small cell lung cancer cells were treated with cisplatin (10 µM) for 24 hours following incubation with C-SNAF4-Cy5 (2 µM) at 37° C. for 24 hours. Caspase expression in H460 cells after cisplatin treatment was confirmed by Western blot analysis showing elevated level of caspase-3 expression after cisplatin treatment (FIGS. 35A and 35B). The retention of C-SNAF4-Cy5 in cisplatin treated H460 apoptotic cells was further imaged by fluorescence microscopy. As shown in FIG. 29D, the probe accumulated extensively in cisplatin-treated apoptotic cells, while negligible fluorescence was observed in viable cells without cisplatin treatment. Fluorescence abolishment after pan-caspase inhibitor Z-VAD-fmk (50 µM) treatment further confirmed the activation of C-SNAF4-Cy5 by effector caspases. The toxicity of C-SNAF4-Cy5 was tested in healthy and apoptotic H460 cells using MTS assay. In healthy cells, C-SNAF4-Cy5 did not produce toxicity up to the highest concentration (10 µM) (FIG. 36A). In drug-treated apoptotic cells, the compound did not induce significant added toxicity (FIG. 36B).

The structure-activity relationship of aromatic nitriles and aminothiols and the structural parameters of small molecules that are capable of undergoing target-activated macrocyclization followed by self-assembly to form nanoparticles were investigated. Additional electron delocalization provided by added aromatic ring, electron-withdrawing substituents, and heteroatoms on the aromatic rings have substantial effects on the reactivity of aromatic nitriles for their condensation with aminothiols. Condensation between aromatic nitriles and aminothiols can proceed intramolecularly to form macrocyclics with various ring sizes. These rigid, hydrophobic macrocyclics can further self-assemble into nanoaggregates at a size of around 100 to 250 nm. This work demonstrates that besides the CBT and luciferin moiety, other similar aromatic structures can also undergo macrocyclization and nanoassembly.

To apply the SNAT scaffold to develop a cell imaging probe, both the reaction rate of the aromatic nitrile and the ability in nanoassembly of macrocyclics are important. Other factors like the hydrophobicity also contribute to the performance, as shown by SNAT4 that displayed less non-specific uptake and better contrast than SNAT2 in imaging β-galactosidase activity in LacZ-expressed living cells. The imaging application demonstrated in this work includes fluorescence imaging of protease and galactosidase. By changing the group attached to the cysteine residue in the scaffold, similar probes may be designed to image different enzyme targets. In addition, other imaging tags besides fluorophores may be introduced to the pyrimidine-based scaffold for other imaging modalities, like photoacoustic imaging, magnetic resonance imaging and positron emission tomography imaging. These features further demonstrate the general applicability of this imaging strategy.

Chemical Synthesis

Compound 1

To a solution of 6-(3-aminopropoxy)quinoline-2-carbonitrile (synthesis described previously in Ref 38, 650 mg, 2 mmol) in DMF (10 mL) was added 4-(Boc-aminomethyl) benzoic acid (863 mg, 3.43 mmol), HBTU (1.63 g, 4.3 mmol), and DIPEA (739.3 µL, 5.72 mmol). The reaction was stirred at room temperature for 2 h followed by extraction with ethyl acetate and water. The organic layer was dried over $MgSO_4$ and concentrated in vacuo. The crude product was purified by flash column chromatography ($SiO_2$; 1:2 of ethyl acetate:hexanes to 5% MeOH in DCM) to afford the titled compound 1 (650 mg, 70%). $^1$H NMR (300 MHz, DMSO-$d_6$) δ 8.55 (t, J=5.4 Hz, 1H), 8.47 (d, J=8.4 Hz, 1H), 8.04 (d, J=9.0 Hz, 1H), 7.97 (d, J=8.4 Hz, 1H), 7.80 (d, J=8.0 Hz, 2H), 7.59-7.55 (m, 1H), 7.51 (d, J=2.7 Hz, 1H), 7.46 (t, J=6.0 Hz, 1H), 7.29 (d, J=8.4 Hz, 2H), 4.23 (t, J=6.0 Hz, 2H), 4.23 (t, J=6.0 Hz, 2H), 4.2-4.1 (m, 2H), 2.08 (quint, J=6.4 Hz, 2H), 1.39 (s, 9H). $^{13}$C NMR (75 MHz, DMSO-$d_6$) δ 166.85, 159.48, 156.50 144.35, 144.10, 137.29, 133.66, 131.44, 131.09, 130.62, 127.88, 127.31, 125.45, 124.88, 118.66, 106.92, 78.61, 66.86, 43.81, 36.90, 29.38, 28.93. HRMS(ESI): calc'd for $C_{26}H_{29}N_4O_4^+[(M+H)^+]$: 461.2172; found 461.2183.

Compound 2

(i) 1 (200 mg, 0.434 mmol) in 10 mL of TFA/DCM (1:4) was stirred at room temperature for 30 min before concentrated under reduced pressure. The deprotected amine was precipitated in diethyl ether and used in the next step without further purification. (ii) To a solution of the amine compound from previous step in DMF (10 mL) was added Boc-propargyl-Gly-OH (111 mg, 0.521 mmol), HBTU (247 mg, 0.651 mmol) and DIPEA (151.6 µL, 0.868 mmol). The reaction was stirred at room temperature for 2 h and extracted with ethyl acetate and water. The organic layer was dried over $MgSO_4$ and concentrated in vacuo. The crude product was purified by flash column chromatography ($SiO_2$; 3% MeOH in DCM) to afford the titled compound 2 (215 mg, 89%). $^1$H NMR (400 MHz, CDCl$_3$) δ 8.06 (d, J=8.4 Hz, 1H), 7.94 (d, J=8.4 Hz, 1H), 7.66 (d, J=8.4 Hz, 2H), 7.54 (d, J=8.4 Hz, 1H), 7.41-7.37 (m, 1H), 7.24 (d, J=8.4 Hz, 2H), 7.12 (s, b, 1H), 7.05 (d, J=2.8 Hz, 1H), 6.91 (t, J=1.8 Hz, 1H), 5.44 (s, b, 1H), 4.44 (d, J=6.0 Hz, 2H), 4.34 (s, b, 1H), 4.20 (t, J=6.0 Hz, 2H), 3.67 (q, J=6.0 Hz, 2H), 2.81-2-74 (m, 1H), 2.66-2.59 (m, 1H), 2.19 (quint, J=6.4 Hz, 2H), 2.05 (t, J=6.4 Hz, 1H), 1.40 (s, 9H). $^{13}$C NMR (101 MHz, CDCl$_3$) δ 170.62, 167.57, 159.08, 144.45, 141.72, 135.81, 133.55, 131.51, 130.63, 130.31, 127.51, 127.38, 127.30, 124.65, 123.84, 117.88, 105.55, 80.72, 79.47, 71.90, 66.72, 53.09, 43.09, 37.53, 29.11, 28.34, 22.58. HRMS (ESI): calc'd for $C_{31}H_{34}N_5O_5^+[(M+H)^+]$: 556.2548; found 556.2555.

Compound 3

(i) 1 (40 mg, 0.087 mmol) in 5 mL of TFA/DCM (1:4) was stirred at room temperature for 30 min before concentrated under reduced pressure. The deprotected amine was precipitated in diethyl ether and used in the next step without further purification. (ii) To the solution of the amine compound from previous step in DMF (2 mL) was added Boc-Cys(Trt)-OH (40.3 mg, 0.087 mmol), HBTU (50 mg, 0.13 mmol) and DIPEA (15.2 µL, 0.174 mmol). The reaction was stirred at room temperature for 2 h followed by extraction with ethyl acetate and water. The organic layer was dried over $MgSO_4$ and concentrated in vacuo. The crude product was purified by flash column chromatography ($SiO_2$; 2% to 5% MeOH in DCM) to afford the titled compound 3 (40 mg, 57%). $^1$H NMR (400 MHz, CDCl$_3$) δ 8.09 (d, J=8.8 Hz, 1H), 8.00 (d, J=9.2 Hz, 1H), 7.65 (d, J=8.0 Hz, 2H), 7.58 (d, J=8.4 Hz, 1H), 7.44-7.07 (m, 18H), 7.08 (d, J=4.2 Hz, 1H), 6.69 (t, J=5.6 Hz, 1H), 6.61 (s, b, 1H), 4.88 (d, J=7.6 Hz, 1H), 4.40 (d, J=6.0 Hz, 2H), 4.22 (t, J=6.0 Hz, 2H), 3.88 (s, b, 1H), 3.69 (q, J=6.4 Hz, 2H), 2.76 (dd, J=6.4, 12.4 Hz, 1H), 2.54 (dd, J=6.4, 12.8 Hz, 1H), 2.21 (quint, J=6.0 Hz, 2H), 1.37 (s. 9H). $^{13}$C NMR (101 MHz, CDCl$_3$) δ 170.92, 167.76, 159.06, 144.51, 144.39, 141.81, 135.88, 133.36, 131.60, 130.74, 130.35, 129.61, 128.19, 127.64, 127.28, 127.05, 124.67, 123.92, 117.88, 105.55, 94.53, 80.62, 67.35, 66.73, 53.74, 43.03, 37.66, 33.70, 29.11, 28.33. HRMS (ESI): calc'd for $C_{48}H_{48}N_5O_5S^+[(M+H)^+]$: 806.3357; found 806.3371.

Compound cycl-I. 3

(2 mg, 0.0025 mmol) in 5 mL of TFA/DCM/TIPS (1:1: 0.05) was stirred at room temperature for 1 h before concentrated under reduced pressure. The crude compound I (2 mg) was precipitated in diethyl ether and used in the next step without further purification. Compound I was dissolved in PBS buffer (10 µM) and was added TCEP (20 µM) and NaHCO$_3$ to adjust pH to 7.4. The solution was left at room temperature and progress of the cyclization reaction was monitored by analytical HPLC. $1^{st}$ order rate constant was calculated to be $2\pm0.2\times10^{-4} s^{-1}$. HRMS (ESI): calc'd for $C_{24}H_{23}N_4O_3S^+[(M+H)^+]$: 447.2985; found 447.2941.

Compound 4

(i) 2 (100 mg, 0.18 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (5 mL) was added Boc-Cys(Trt)-OH (100 mg, 216 mmol), HBTU (103 mg, 0.27 mmol) and DIPEA (63 µL, 0.36 mmol). The reaction was stirred at room temperature for 2 h followed by extraction with ethyl acetate and water. The organic layer was dried over $MgSO_4$ and concentrated in vacuo for flash column chromatography ($SiO_2$; 3% MeOH in DCM) to afford the titled compound 4 (147 mg, 90.6%). $^1$H NMR (400 MHz, CDCl$_3$) δ 8.10 (d, J=8.4 Hz, 1H), 8.00 (d, J=8.4 Hz, 1H), 7.65 (d, J=8.4 Hz, 2H), 7.58 (d, J=8.4 Hz, 1H), 7.53 (s, b, 1H), 7.45-7.19 (m, 17H), 7.08 (d, J=2.8 Hz, 1H), 6.81 (t, J=5.6 Hz, 1H), 6.73 (d, J=8 Hz, 1H), 4.84 (d, J=4.8 Hz, 1H), 4.56-4.51 (m, 1H), 4.40-4.36 (m, 2H), 4.21 (t, J=6.0 Hz, 2H), 3.75-3.64 (m, 3H), 2.97-2.89 (m, 2H), 2.73-2.54 (m, 3H), 2.19 (quint, J=6.4 Hz, 2H), 1.98 (t, J=2.4 Hz, 1H), 1.31 (s, 9H). $^{13}$C NMR (101 MHz, CDCl$_3$) δ 170.65, 169.85, 167.76, 159.24, 144.67, 144.27, 142.03, 135.98, 133.47, 131.72, 130.87, 130.49, 129.61, 128.44, 127.70, 127.35, 127.28, 124.81, 124.01, 118.06, 105.72, 81.17, 79.19, 72.30, 67.75, 66.88, 54.55, 51.57, 43.18, 38.84, 37.62, 33.46, 29.30, 28.38, 21.84. HRMS (ESI): calc'd for C$_{53}$H$_{53}$N$_6$O$_6$S$^+$ [(M+H)$^+$]: 901.3722; found 901.3742.

Compound cycl-II

A solution of 4 (5 mg, 0.0055 mmol) in 5 mL of TFA/DCM/TIPS (1:1:0.05) was stirred at room temperature for 1 h before concentrated under reduced pressure. The crude compound II (5 mg) was precipitated in diethyl ether and used in the next step without further purification. To the PBS solution of compound 11 (10 μM) was added TCEP (20 μM) and NaHCO$_3$ to adjust pH to 7.4. The solution was left at room temperature and progress of the cyclization reaction was monitored by analytical HPLC. 1$^{st}$ order rate constant was calculated to be 1.2±0.04×10$^{-3}$s$^{-1}$. HRMS (ESI): calc'd for O$_{29}$H$_{28}$N$_5$O$_4$S$^+$ [(M+H)$^+$]: 542.1857; found 542.1873.

Compound 5

5-Bromopyrimidine-2-carbonitrile (92 mg, 0.5 mmol), Pd(OAc)$_2$ (11.2 mg, 0.05 mmol), BINAP (46.7 mg, 0.075 mmol) and Cs$_2$CO$_3$ (228 mg, 0.7 mmol) in toluene (3 mL) were mixed with 3-(Boc-amino)-1-propanol in 1 mL of toluene. The reaction mixture was refluxed at 110° C. overnight, then cooled to room temperature. After filtered through Celite, the reaction mixture was concentrated under reduced pressure and purified by flash column chromatography (SiO$_2$; 1:4 to 1:2 of ethyl acetate:hexanes) to afford the titled compound 5 (120 mg, 86.3%). $^1$H NMR (400 MHz, CDCl$_3$) δ 8.77 (s, 2H), 4.75 (s, b, 1H), 4.50 (t, J=6.2 Hz, 2H), 3.29 (q, J=6.4 Hz, 2H), 2.02 (quint, J=6.4 Hz, 2H), 1.42 (s, 9H). $^{13}$C NMR (101 MHz, CDCl$_3$) δ 165.88, 162.67, 156.17, 114.93, 103.08, 79.59, 67.03, 37.61, 29.35, 28.60. HRMS (ESI): calc'd for C$_{13}$H$_{19}$N$_4$O$_3$+[(M+H)$^+$]: 279.1444; found 279.1452.

Compound 6

(i) 5 (137 mg, 0.5 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (5 mL) was added 4-(Boc-aminomethyl)benzoic acid (151 mg, 0.6 mmol), HBTU (284 mg, 0.75 mmol) and DIPEA (174.6 μL, 1 mmol). The reaction was stirred at room temperature for 2 h followed by extraction with ethyl acetate and water. The organic layer was dried over MgSO$_4$ and concentrated in vacuo. The crude product was purified by flash column chromatography (SiO$_2$; 2% to 5% MeOH in DCM) to afford the titled compound 6 (183 mg, 89%). $^1$H NMR (300 MHz, DMSO-d$_6$) δ 9.11 (s, 2H), 8.52 (t, J=5.7 Hz, 1H), 7.77 (d, J=8.1 Hz, 2H), 7.46 (t, J=6.3 Hz, 1H), 7.29 (d, J=8.1 Hz, 2H), 4.45 (t, J=6.3 Hz, 2H), 4.16 (d, J=4.5 Hz, 2H), 3.41 (q, J=6.4 Hz, 2H), 2.01 (quint, J=6.4 Hz, 2H), 1.39 (s, 9H). $^{13}$C NMR (75 MHz, DMSO-d$_6$) δ 166.81, 165.83, 164.13, 156.5, 144.09, 133.62, 127.86, 127.32, 116.30, 102.85, 78.61, 67.06, 43.82, 36.67, 29.10, 28.93. HRMS (ESI): calc'd for C$_{21}$H$_{26}$N$_5$O$_4$$^+$[(M+H)$^+$]: 412.1972; found 412.1979.

Compound 7

(i) 6 (90 mg, 0.22 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (5 mL) was added Boc-propargyl-Gly-OH (56 mg, 0.24 mmol), HBTU (125 mg, 0.33 mmol) and DIPEA (77 μL, 0.44 mmol). The reaction was stirred at room temperature for 2 h followed by extraction with ethyl acetate and water. The organic layer was dried over MgSO$_4$ and concentrated in vacuo. The crude product was purified by flash column chromatography (SiO$_2$; 2% MeOH in DCM) to afford the titled compound 7 (98 mg, 87.5%). $^1$H NMR (400 MHz, CDCl$_3$) δ 8.76 (s, 2H), 7.69 (d, J=8.4 Hz, 2H), 7.30 (d, J=8.4 Hz, 2H), 6.93 (s, b, 1H), 6.70 (t, J=6.4 Hz, 1H), 5.35 (s, b, 1H), 4.58 (t, J=6.0 Hz, 2H), 4.51-4.47 (m, 2H), 4.33 (s, 1H), 3.63 (q, J=8.4 Hz, 2H), 2.85-2.78 (m, 1H), 2.67-2.60 (m, 1H), 2.16 (quint, J=6.4 Hz, 2H), 2.08 (t, J=6.4 Hz, 1H), 1.43 (s, 9H). $^{13}$C NMR (101 MHz, CDCl$_3$) δ 170.66, 167.52, 165.78, 162.72, 141.84, 133.65, 127.74, 127.45, 114.89, 103.22, 79.61, 72.10, 67.60, 55.87, 53.24, 43.82, 43.29, 37.53, 28.76, 28.49, 22.62. HRMS (ESI): calc'd for C$_{26}$H$_{31}$N$_6$O$_5$$^+$[(M+H)$^+$]: 507.2341; found 507.2350.

Compound 8

(i) 7 (40 mg, 0.079 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (2 mL) was added Boc-Cys(Trt)-OH (36.6 mg, 0.079 mmol), HBTU (45 mg, 0.12 mmol) and DIPEA (27.6 μL, 0.16 mmol). The reaction was stirred at room temperature for 2 h followed by extraction with ethyl acetate and water. The organic layer was dried over MgSO$_4$ and concentrated in vacuo. The crude product was purified by flash column chromatography (SiO$_2$; 2% to 5% MeOH in DCM) to afford the titled compound 8 (27 mg, 40%). $^1$H NMR (400 MHz, CDCl$_3$) δ 8.78 (s, 2H), 7.67 (d, J=8.4 Hz, 2H), 7.42-7.22 (m, 19H), 6.62 (d, J=7.2 Hz, 1H), 6.54 (t, J=6.4 Hz, 1H), 4.75 (d, J=4.8 Hz, 1H), 4.60-4.54 (m, 3H), 4.47-4.31 (m, 2H), 3.71-3.62 (m, 3H), 3.03-2.96 (m, 1H), 2.76-2.54 (m, 3H), 2.17 (quint, J=6.0 Hz, 2H), 1.30. (s. 9H). $^{13}$C NMR (101 MHz, CDCl$_3$) δ 169.73, 167.56, 165.66, 162.66, 144.13, 142.06, 133.16, 129.52, 128.39, 128.06, 128.04, 127.72, 127.38, 127.28, 127.14, 114.80, 103.17, 81.16, 79.07, 77.16, 72.26, 67.49, 54.47, 51.36, 43.11, 37.41, 28.66, 28.27, 21.68. HRMS (ESI): calc'd for O$_{48}$H$_{50}$N$_7$O$_6$S$^+$ [(M+H)$^+$]: 852.3521, found 852.3532.

Compound cycl-III

A solution of 8 (5 mg, 0.0059 mmol) in 5 mL of TFA/DCM/TIPS (1:1:0.05) was stirred at room temperature for 1 h before concentrated under reduced pressure. The crude compound III was precipitated in diethyl ether and used in the next step without further purification. To a solution of compound III in PBS buffer (10 μM) was added TCEP (20 μM) and NaHCO$_3$ to adjust pH to 7.4. The solution was left at room temperature and progress of the cyclization reaction was monitored by analytical HPLC. 1$^{st}$ order rate constant was calculated to be 9±0.2×10$^{-4}$s$^{-1}$. HRMS: calc'd for O$_{24}$H$_{25}$N$_6$O$_4$S$^+$ [(M+H)$^+$]: 493.1653; found 493.1702.

Compound 9

(i) 7 (130 mg, 0.257 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (3 mL) was added Boc-Gly-OH (54 mg, 0.308 mmol), HBTU (146 mg, 0.386 and DIPEA (90 μL, 0.514 mmol). The reaction was stirred at room temperature for 2 h followed by extraction with ethyl acetate and water. The organic layer was dried over MgSO$_4$ and concentrated in vacuo. The crude product was purified by flash column chromatography (SiO$_2$; 2% to 5% MeOH in DCM) to afford the titled compound 9 (122 mg, 84%). $^1$H NMR (400 MHz, CDCl$_3$) δ 8.74 (s, 2H), 7.68 (s, b, 1H), 7.61 (d, J=8.4 Hz, 2H), 7.21 (d, J=8.4 Hz, 2H), 7.18 (s, b, 1H), 7.12 (s, b, 1H), 5.63 (t, J=6.4 Hz, 1H), 4.64-4.58 (m, 1H), 4.54 (t, J=6.4 Hz, 2H), 4.39 (t, J=6.4 Hz, 2H), 3.77-3.72 (m, 2H), 3.58 (q, J=6.4 Hz, 2H), 2.87-2.77 (m, 1H), 2.66-2.57 (m, 1H), 2.13 (quint, J=6.4 Hz, 2H), 2.07 (t, J=2.8 Hz, 1H), 1.36 (s, 9H). $^{13}$C NMR (101 MHz, CDCl$_3$) δ 170.32, 170.22, 167.98, 165.75, 162.75, 156.87, 141.88, 133.45, 127.61, 127.43, 114.95, 103.13, 80.92, 79.29, 72.30, 67.49, 55.11, 51.67, 44.85, 43.30, 37.39, 28.71, 28.46. HRMS (ESI): calc'd for O$_{28}$H$_{34}$N$_7$O$_6$+[(M+H)$^+$]: 564.2559; found 564.2565.

Compound 10

(i) 9 (138 mg, 0.245 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (3 mL) was added Boc-Cys(SEt)-OH·DCHA (124 mg, 0.270 mmol), HBTU (139 mg, 0.368 mmol) and DIPEA (85.3 μL, 0.490 mmol). The reaction was stirred at room temperature for 2 h, followed by extraction with ethyl acetate and water. The organic layer was dried over MgSO$_4$ and concentrated in vacuo. The crude product was purified by flash column chromatography (SiO$_2$; 2% to 5% MeOH in DCM) to afford the titled compound 10 (170 mg, 96%). $^1$H NMR (400 MHz, CD$_3$OD) δ 8.90 (s, 2H), 7.76 (d, J=8.4 Hz, 2H), 7.38 (d, J=8.4 Hz, 2H), 4.57-4.53 (m, 3H), 4.46 (s, 2H), 4.35-4.31 (m, 1H), 3.98-3.85 (q, J=7.2 Hz, 2H), 3.56 (t, J=6.8 Hz, 2H), 3.13-3.08 (m, 1H), 2.86-2.63 (m, 5H), 2.40 (s, 1H), 2.13 (quint, J=6.4 Hz, 2H), 1.84 (m, 1H), 1.45 (s, 9H), 1.28 (m, 2H). $^{13}$C NMR (101 MHz, CD$_3$OD) δ 173.16, 171.09, 170.41, 168.74, 165.74, 163.05, 142.40, 133.18, 127.32, 127.25, 114.83, 102.91, 79.95, 79.20, 71.49, 66.81, 54.38, 53.36, 52.76, 42.61, 36.71, 32.04, 29.42, 28.55, 27.62, 24.96, 24.29, 13.65. HRMS (ESI): calc'd for C$_{33}$H$_{43}$N$_8$O$_7$S$_2$$^+$ [(M+H)$^+$]: 727.2680; found 727.2691.

Compound cycl-IV 9 (5 mg, 0.007 mmol) in 5 mL of TFA/DCM (1:4) was stirred at room temperature for 30 min before concentrated under reduced pressure. The deprotected amine was precipitated in diethyl ether and used in the next step without further purification. The deprotected amine from previous step was dissolved in PBS buffer to a final concentration of 10 μM and was added TCEP (20 μM) and NaHCO$_3$ to adjust pH to 7.4. The reaction was left at room temperature and progress of the cyclization reaction was monitored by analytical HPLC. 1$^{st}$ order rate constant was calculated to be 2.1±0.07×10$^{-3}$ s$^{-1}$. HRMS (ESI): calc'd for C$_{26}$H$_{28}$N$_7$O$_5$S$^+$ [(M+H)$^+$]: 550.1867; found 550.1889.

Compound 11

(i) 7 (80 mg, 0.158 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (2 mL) was added Boc-beta-Ala-OH (29.9 mg, 0.158 mmol), HBTU (90 mg, 0.237 mmol) and DIPEA (55.2 μL, 0.316 mmol). The reaction was stirred at room temperature for 2 h followed by extraction with ethyl acetate and water. The organic layer was dried over MgSO$_4$ and concentrated in vacuo. The crude product was purified by flash column chromatography (SiO$_2$; 2% to 5% MeOH in DCM) to afford the titled compound 11 (65 mg, 71%). $^1$H NMR (300 MHz, DMSO-d$_6$ with CD$_3$OD as co-solvent) δ 9.11 (s, 2H), 7.77 (d, J=8.4 Hz, 2H), 7.33 (d, J=8.4 Hz, 2H), 4.47-4.40 (m, 3H), 4.33 (s, 2H), 3.40 (t, J=6.8 Hz, 2H), 3.17-3.10 (m, 2H), 2.88 (t, J=2.4 Hz, 1H), 2.63-2.50 (m, 2H), 2.31 (t, J=7.5 Hz, 2H), 2.01 (quint, J=6.4 Hz, 2H), 1.36 (s, 9H). $^{13}$C NMR (75 MHz, DMSO-d$_6$ with CD$_3$OD as co-solvent) δ 171.15, 170.62, 166.70, 165.82, 164.12, 156.14, 143.07, 133.59, 127.81, 127.40, 116.29, 102.85, 81.45, 78.32, 73.69, 67.06, 52.21, 42.42, 37.35, 36.56, 36.23, 29.09, 28.93, 22.39. HRMS (ESI): calc'd for C$_{29}$H$_{36}$N$_7$O$_6$$^+$ [(M+H)$^+$]: 578.2716; found 578.2722.

Compound 12

(i) 11 (40 mg, 0.07 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (1 mL) was added Boc-Cys(SEt)-OH·DCHA (32 mg, 0.07 mmol), HBTU (39.8 mg, 0.105 mmol) and DIPEA (24.4 μL, 0.14 mmol). The reaction was stirred at room temperature for 2 h and was purified by preparative HPLC to afford the titled compound 12 (15 mg, 29%). $^1$H NMR (400 MHz, DMSO-d$_6$) δ 9.10 (s, 2H), 8.64 (t, J=6.0 Hz, 1H), 8.52 (t, J=6.0 Hz, 1H), 8.27 (d, J=8.0 Hz, 1H), 7.97 (t, J=6.0 Hz, 1H), 7.77 (d, J=8.0 Hz, 2H), 7.33 (d, J=8.0 Hz, 2H), 7.08 (d, J=8.4 Hz, 1H), 4.46-4.41 (m, 3H), 4.34 (t, J=6.4 Hz, 2H), 4.16-4.10 (m, 1H), 3.41 (q, J=6.4 Hz, 2H), 3.33-3.19 (m, 2H), 3.03-2.98 (m, 1H), 2.88 (t, J=6.4 Hz, 1H), 2.83-2.76 (m, 2H), 2.70 (q, J=7.2 Hz, 1H), 2.61-2.44 (m, 2H), 2.33 (t, J=6.8 Hz, 2H), 2.01 (quint, J=6.4 Hz, 2H), 1.38 (s, 9H), 1.26-1.20 (m, 3H). $^{13}$C NMR (101 MHz, DMSO-d$_6$) δ 171.24, 170.85, 170.70, 166.76, 165.80, 164.09, 155.92, 143.05, 133.61, 127.79, 127.41, 116.26, 102.83, 81.39, 78.99, 73.67, 67.04, 54.36, 52.37, 42.53, 41.74, 36.66, 36.12, 35.64, 32.18, 29.07, 28.82, 22.44, 14.94. HRMS (ESI): calc'd for C$_{34}$H$_{45}$N$_8$O$_7$S$_2$$^+$ [(M+H)$^+$]: 741.2837; found 741.2847.

Compound cycl-V 12 (5 mg, 0.007 mmol) in 15 mL of TFA/DCM (1:4) was stirred at room temperature for 30 min before concentrated under reduced pressure. The deprotected amine was precipitated in diethyl ether and used in the next step without further purification. The deprotected amine from previous step was dissolved in PBS buffer to a final concentration of 10 μM and was added TCEP (20 μM) and NaHCO$_3$ to adjust pH to 7.4. The solution was left at room temperature and progress of the cyclization reaction was monitored by analytical HPLC. 1$^{st}$ order rate constant was calculated to be 8.0±0.6×10$^{-4}$s$^{-1}$. HRMS (ESI): calc'd for C$_{27}$H$_{30}$N$_7$O$_5$S$^+$ [(M+H)$^+$]: 564.2024; found 564.2041.

Compound 13

9 (131 mg, 0.233 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (1 mL) was added Boc-methyl-Cys(SEt)-OH (69 mg, 0.0233 mmol), HBTU (138.8 mg, 0.35 mmol) and DIPEA (81.4 μL, 0.47 mmol). The reaction was stirred at room temperature for 2 h and was purified by preparative HPLC to afford the titled compound 13 (140 mg, 81%). $^1$H NMR (400 MHz, CDCl$_3$) δ 8.78 (s, 2H), 7.81 (s, b, 1H), 7.64 (d, J=8.0 Hz, 2H), 7.52 (t, J=6.0 Hz, 1H), 7.37 (t, J=6.0 Hz, 1H), 7.28 (d, J=8.0 Hz, 2H), 6.89 (s, b, 1H), 5.62 (s, 1H), 4.66-4.60 (m, 1H), 4.48-4.37 (m, 2H), 4.43 (t, J=4.8 Hz, 2H), 3.88-3.85 (m, 2H), 3.67-3.55 (m, 2H), 3.24 (d, J=14.0 Hz, 1H), 3.11 (d, J=14.0 Hz, 1H), 3.02-2.90 (m, 1H), 2.73-2.65 (m, 3H), 2.15 (quint, J=6.4 Hz, 2H), 1.99 (t, J=4.2 Hz, 1H), 1.43 (s, 9H), 1.39 (s, 3H), 1.30 (m, 3H). $^{13}$C NMR (101 MHz, CD$_3$OD) δ 174.70, 170.38, 169.92, 167.97, 165.77, 162.79, 155.98, 142.27, 133.26, 127.63, 127.37, 114.96, 103.18, 82.04, 80.48, 71.01, 67.48, 60.55, 52.90, 47.16, 44.30, 43.20, 37.41, 33.10, 28.76, 28.62, 22.77, 21.37, 14.43. HRMS (ESI): calc'd for $C_{34}H_{45}N_8O_7S_2^+$ [(M+H)$^+$]: 741.2838; found 741.2847.

Compound cycl-VI 13 (5 mg, 0.007 mmol) in 5 mL of TFA/DCM (1:4) was stirred at room temperature for 30 min before concentrated under reduced pressure. The deprotected amine was precipitated in diethyl ether and used in the next step without further purification. The deprotected amine from previous step was dissolved in PBS buffer to a final concentration of 10 μM and was added TCEP and NaHCO$_3$ to adjust pH to 7.4. The solution was left at room temperature and progress of the cyclization reaction was monitored by analytical HPLC. 1$^{st}$ order rate constant was calculated to 2.7±0.1× 10$^{-3}$s$^{-1}$. HRMS (ESI): calc'd for $C_{27}H_{30}N_7O_5S^+$ [(M+H)$^+$]: 564.2024; found 564.2040.

Compound 14

(i) A solution of 10 (14 mg, 0.019 mmol) in 2 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (1 mL) was added Ac-DEVD-OH (13.2 mg, 0.019 mmol), HBTU (11 mg, 0.029 mmol) and DIPEA (7 μL, 0.038 mmol). The reaction was stirred at room temperature for 2 h followed by extraction with ethyl acetate and water. The organic layer was dried over MgSO$_4$ and concentrated in vacuo. The crude product was used in the next step without further purification. (iii) The crude residue from previous step was dissolved in 5 mL of TFA/DCM/TIPS (1:1:0.05) and was stirred at room temperature for 2 h. The reaction was concentrated under reduced pressure and purified by preparative HPLC to afford the titled compound 14 (8 mg, 37.4%). HRMS (ESI): calc'd for $C_{48}H_{63}N_{12}O_{16}S_2^+$ [(M+H)$^+$]: 1127.3921; found 1127.3923.

C-SNAF4-Cy5

To 14 (1 mg, 0.89 μmop in 0.5 mL of DMSO/0.1 M HEPES buffer (1:4) was added sulfo-Cy5-azide (0.7 mg, 0.89 μmol), CuSO$_4$ (10 μL of 0.1M stock) and sodium ascorbate (2 mg). The reaction was left at room temperature for 1 h before injected into semi-preparative HPLC for purification to afford the final product (0.5 mg, 43%). HRMS (ESI): calc'd for $C_{86}H_{107}N_{16}O_{22}S_4^+$ [(M+H)$^2$+]/2: 926.3353; found 926.3377.

Compound 15

(i) 6 (90 mg, 0.22 mmol) in 5 mL of TFA/DCM (1:4) was stirred at room temperature for 30 min before concentrated under reduced pressure. The deprotected amine was precipitated in diethyl ether and used in the next step without further purification. (ii) To a solution of the deprotected amine from previous step in DMF (3 mL) was added Boc-Lys(Fmoc)-OH (123.7 mg, 0.264 mmol), HBTU (125.2 mg, 0.33 mmol) and DIPEA (77 μL, 0.44 mmol). The reaction was stirred at room temperature for 2 h before extraction with ethyl acetate and water. The organic layer was dried over MgSO$_4$ and concentrated in vacuo. The crude product was purified by flash column chromatography (SiO$_2$; 2% to 5% MeOH in DCM) to afford the titled compound 15 (124 mg, 74%). $^1$H NMR (400 MHz, CDCl$_3$) 8.71 (s, 2H), 7.75 (d, J=7.6 Hz, 2H), 7.68 (d, J=8.4 Hz, 2H), 7.56 (d, J=7.2 Hz, 2H), 7.38 (t, J=7.2 Hz, 2H), 7.31-7.24 (m, 4H), 6.91 (s, b, 1H), 6.75 (t, J=6.0 Hz, 1H), 5.27 (d, J=6.4 Hz, 1H), 5.0 (t, J=6.0 Hz, 1H), 4.53 (t, J=6.4 Hz, 2H), 4.5-4.25 (m, 4H), 4.25-4.00 (m, 2H), 3.61 (q, J=6.4 Hz, 2H), 3.13 (q, J=6.4 Hz, 2H), 2.13 (quint, J=6.4 Hz, 2H), 1.89-1.31 (m, 6H), 1.39 (s, 9H). $^{13}$C NMR (101 MHz, CDCl$_3$) δ 167.56, 165.74, 162.67, 156.94, 144.13, 144.09, 142.13, 141.50, 133.65, 127.93, 127.71, 127.52, 127.28, 125.23, 120.21, 114.90, 103.16, 77.46, 67.51, 66.85, 54.70, 47.42, 43.12, 40.57, 38.84, 37.42, 31.95, 29.73, 28.78, 28.53, 22.71. HRMS (ESI): calc'd for $C_{42}H_{48}N_7O_7+$[(M+H)$^+$]: 762.3600; found 762.3610.

Compound 16. (i) 15 (124 mg, 0.163 mmol) in 5 mL of TFA/DCM (1:4) was stirred at room temperature for 30 min before concentrated under reduced pressure, followed by addition of diethyl ether to precipitate the deprotected amine for the use in the next step without further purification. (ii) To a solution of the deprotected amine from previous step in DMF (3 mL) was added Boc-Gly-OH (34 mg, 0.196 mmol), HBTU (93 mg, 0.245 mmol) and DIPEA (57 μL, 0.33 mmol). The reaction was stirred at room temperature for 2 h and was extracted with ethyl acetate and water. The organic layer was dried over MgSO$_4$ and concentrated in vacuo. The crude material was purified by flash column chromatography (SiO$_2$; 2%-5% MeOH in DCM) to afford the titled compound 16 (107 mg, 80.1%). $^1$H NMR (400 MHz, CD$_3$OD) 8.87 (s, 2H), 7.79-7.75 (m, 4H), 7.63 (d, J=7.6 Hz, 2H), 7.40-7.27 (m, 6H), 4.53 (t, J=6.4 Hz, 2H), 4.42 (s, 2H), 4.38-4.31 (m, 3H), 4.18 (t, J=7.2 Hz, 1H), 3.72 (d, J=3.6 Hz, 2H), 3.54 (t, J=6.4 Hz, 2H), 3.08 (t, J=6.8 Hz, 2H), 2.11 (quint, J=6.4 Hz, 2H), 1.93-1.28 (m, 6H), 1.41 (s, 9H). $^{13}$C NMR (101 MHz, CD$_3$OD) δ 168.81, 165.72, 162.97, 157.73, 157.40, 144.15, 142.58, 141.40, 133.24, 127.58, 127.32, 127.23, 126.95, 124.97, 119.74, 114.74, 102.91, 79.63, 66.70, 66.40, 53.57, 43.57, 42.64, 42.46, 40.23, 36.64, 31.48, 29.28, 28.50, 27.49, 22.79. HRMS (ESI): calc'd for $C_{44}H_{51}N_8O_8+$[(M+H)$^+$]: 819.3815; found 819.3824.

Compound 17. 4-Hydroxybenzaldehyde (89 mg, 0.73 mmol) was dissolved in NaOH solution (1N, 73 μL) and the mixture was added dropwise to acetobromo-α-D-galactose (300 mg, 0.73 mmol) in acetone (2 mL). The reaction was kept under stirring at room temperature for 4 h before the solvent was removed under reduced pressure. The residue was extracted with ethyl acetate and water and the organic layer was dried over MgSO$_4$ and concentrated in vacuo. The crude product was purified by flash column chromatography (SiO$_2$; 1:4 of ethyl acetate: hexanes) to afford the titled compound 17 (170 mg, 51%). $^1$H NMR (400 MHz, CDCl$_3$) δ 9.93 (s, 1H), 7.85 (d, J=8.4 Hz, 2H), 7.11 (d, J=8.4 Hz, 2H), 5.55-5.47 (m, 2H), 5.18-5.12 (m, 2H), 4.25-4.09 (m, 3H), 2.19 (s, 3H), 2.07 (s, 3H), 2.06 (s, 3H), 2.02 (s, 3H). $^{13}$C NMR (101 MHz, CDCl$_3$); δ 191.09, 170.67, 170.50, 170.42, 169.65, 161.57, 132.13, 132.10, 117.02, 98.83, 71.60, 70.96, 68.67, 67.05, 61.67, 21.01, 20.97, 20.95, 20.88. HRMS (ESI): calc'd for $C_{21}H_{24}O_{11}Na^+$[(M+Na)$^+$]: 477.1360; found 477.1367.

Compound 18

To a solution of 17 (250 mg, 0.55 mmol) in 5 mL of DCM/MeOH (4/1) was added NaBH$_4$ (6.2 mg, 0.17 mmol). The reaction kept under stirring at room temperature for 1 h. 5 μL of water was added to quench the remaining NaBH$_4$ and the solvent was evaporated under reduced pressure. The residue was extracted with ethyl acetate and water and the organic layer was dried over MgSO$_4$ and concentrated in vacuo. The crude product (220 mg, 88%) was used without further purification. $^1$H NMR (400 MHz, CDCl$_3$) δ 7.29 (d, J=8.4 Hz, 2H), 6.99 (d, J=8.4 Hz, 2H), 5.50-5.44 (m, 2H), 5.14-5.04 (m, 2H), 4.62 (s, 2H), 4.25-4.06 (m, 4H), 2.18 (s, 3H), 2.07 (s, 3H), 2.06 (s, 3H), 2.01 (s, 3H). $^{13}$C NMR (101 MHz, CDCl$_3$) 170.32, 170.20, 170.06, 169.35, 156.20, 135.86, 128.28, 116.78, 99.49, 70.80, 70.66, 68.50, 66.76, 64.35, 61.22, 20.58, 20.51, 20.50, 20.45. HRMS (ESI): calc'd for $C_{21}H_{27}O_{11}+[(M+H)^+]$: 447.1485; found 447.2941.

Compound 19

To a solution of 18 (220 mg, 0.48 mmol) in 10 ml anhydrous DCM was added carbonyldiimidazole (94.2 mg, 0.58 mmol) and was kept under stirring at room temperature overnight. The reaction was then concentrated and purified by flash column chromatography (SiO$_2$; 1:1 of ethyl acetate: DCM) to afford the titled compound 19 (174 mg, 65.5%). $^1$H NMR (400 MHz, CDCl$_3$) δ 8.12 (s, 1H), 7.41-7.38 (m, 3H), 7.06-7.01 (m, 3H), 5.52-5.46 (m, 2H), 5.37 (s, 2H), 5.13-5.05 (m, 2H), 4.25-4.05 (m, 4H), 2.18 (s, 3H), 2.06 (s, 3H), 2.05 (s, 3H), 2.02 (s, 3H). $^{13}$C NMR (101 MHz, CDCl$_3$) 170.44, 170.41, 170.32, 170.18, 169.46, 157.56, 148.68, 137.21, 130.77, 128.94, 117.25, 117.17, 99.34, 71.18, 70.84, 69.49, 68.64, 66.97, 61.48, 20.83, Compound 20

To a solution of 19 (174 mg, 0.32 mmol) in DCM (1 mL) was added MeOTf (87 µL, 0.79 mmol). The reaction was stirred at room temperature for 20 min before diethyl ether (40 mL) was directly added to precipitate the product. The white solid precipitate was collected through centrifugation and was used immediately without further purification. The solid was dissolved in DMF (1 mL) and was added allyl-ester-SEt-L-cysteine (77.9 mg, 0.352 mmol) and DIPEA (61.5 µL, 0.352 mmol). The reaction was allowed to stir at room temperature for 2 hours before extracted with ethyl acetate and water. The organic layer was dried over MgSO$_4$ and concentrated in vacuo. The crude product was purified by flash column chromatography (SiO$_2$; 1:1 of ethyl acetate: hexanes) to afford the titled compound 20 (140 mg, 62%). $^1$H NMR (400 MHz, CDCl$_3$) δ 7.31 (d, J=8.4 Hz, 2H), 6.98 (d, J=8.4 Hz, 2H), 5.96-5.86 (m, 1H), 5.59 (d, J=7.6 Hz, 1H), 5.51-5.45 (m, 2H), 5.36-5.25 (m, 2H), 5.12-5.02 (m, 4H), 4.71-4.57 (m, 3H), 4.24-4.14 (m, 2H), 4.06 (t, J=6.6 Hz, 1H), 3.17 (t, J=5.3 Hz, 2H), 2.68 (q, J=7.3 Hz, 2H), 2.18 (s, 3H), 2.06 (s, 6H), 2.01 (s, 3H), 1.29 (t, J=7.3 Hz, 3H). $^{13}$C NMR (101 MHz, CDCl$_3$) 170.35, 170.23, 170.15, 170.12, 169.37, 156.86, 155.58, 131.28, 131.09, 129.83, 119.10, 116.88, 99.58, 71.03, 70.78, 68.55, 66.82, 66.59, 66.43, 61.35, 53.42, 40.86, 32.63, 20.73, 20.69, 20.67, 20.59, 14.25. HRMS (ESI): calc'd for $O_{30}N_{40}NO_{14}S_2^+$ [(M+H)$^+$]: 702.1883; found 702.1885.

Compound 21

To a solution of 20 (140 mg, 0.2 mmol) in DCM (1 mL) was added phenylsilane (49 µL, 0.4 mmol) and Pd(PPh$_3$)$_4$ (11.6 mg, 0.01 mmol) and was kept under stirring at room temperature for 1 hour before concentrated under reduced pressure to afford the crude product. The crude product was dissolved in methanol (0.5 mL) and NaOMe was added to adjust the pH to 9. The reaction was allowed to stir at room temperature overnight and was added ion exchange resin (Dowex 50WX8 ion exchange resin) and stirred for 10 min to remove Na$^+$ ions in the solution and to adjust the pH to slightly acidic. The resin was filtered off and the filtrate was concentrated in vacuo. The crude residue was used in the next step without further purification. HRMS (ESI): calc'd for $C_{19}H_{28}NO_{10}S_2^+$ [(M+H)$^+$]: 492.0993; found 492.1009.

B-SNAF4-BDP (i) Compound 16 (15 mg, 0.018 mmol) was dissolved in 2 mL of TFA/DCM (1:4) and stirred at room temperature for 30 min before concentrated under reduced pressure. The deprotected amine was precipitated in diethyl ether and used without further purification. (ii) The crude amine from the previous step was dissolved in DMF (1 mL) and was added 21 (7 mg, 0.014 mmol), HBTU (10 mg, 0.027 mmol) and DIPEA (6.2 µL, 0.035 mmol). The reaction was stirred at room temperature for 2 h before concentrated on high vacuum. The crude residue was used in the next step without further purification. (iii) The crude residue from previous step in 5% piperidine in DMF (1 mL) was stirred at room temperature for 20 min and was subsequently concentrated on high vacuum to afford the crude residue for the use in next step. (iv) To the crude residue from previous step in DMF (1 mL) was added DIPEA (6.2 µL, 0.035 mmol) and BDP-FL-NHS ester (Lumiprobe, 2 mg). The reaction was stirred at room temperature for 30 min and purified by preparative HPLC to afford the titled B-SNAF4-BDP (1.5 mg, 24%). HRMS (ESI): calc'd for $C_{57}H_{71}BF_2N_{11}O_{14}S_2^+$ [(M+H)$^+$]: 1246.4679; found 1246.4694.

B-SNAF2-BDP

B-SNAF2-BDP was synthesized similarly from 21 (5 mg, 0.01 mmol) to yield the titled compound (0.5 mg, 4.2%). HRMS (ESI): calc'd for $C_{60}H_{70}BF_2N_9O_{13}S_2^+$ [(M+H)$^+$]: 1238.4596; found 1238.4652.

General Methods for Measuring Kinetics of Condensation Reactions Between Aromatic Nitriles and Aminothiols: The $2^{nd}$ order rate constants for condensation reactions between aromatic nitriles and aminothiols were measured by using HPLC assays. To solutions of aromatic nitriles (100 µM) in phosphate buffered saline (PBS) (1×, pH=7.4) were added aminothiol (1.0 equiv.), TCEP (2.0 equiv.) and NaHCO$_3$ (3 equiv.). The reaction solutions were kept at room temperature (23° C.) and monitored by HPLC at different time points. The conversion rates were calculated using the peak integrals of aromatic nitriles and the condensation products at 254 nm. Based on $2^{nd}$ order reaction law, 1/[aromatic nitrile] was plotted against time and the slope of the linear regression result gives the $2^{nd}$ order rate constant.

General Methods for Measuring Intramolecular Cyclization Kinetics: The $1^{st}$ order rate constants of intramolecular cyclization of I-VI to produce cycl-I-VI, respectively were measured by HPLC assays adapted from the previously reported assay[38]. To solutions of substrates I-VI in phosphate buffered saline (PBS) (1×, pH=7.4) were added a solution of TCEP (2.0 equiv.) in PBS (freshly prepared and the pH was adjusted to 7.4 by 1 N sodium hydroxide aqueous solution), affording a final concentration of 100 µM for the substrates. The mixture was kept at room temperature (23° C.) and monitored by HPLC at different time points. The concentration of remaining starting material was calculated using the peak integrals of the starting material at 254 nm. Based on first-order reaction law, $\ln([A_t]/[A_0])$ was plotted against time and the slope of the linear regression result gives the first-order rate constant.

DLS Measurements: DLS measurements samples of I-VI were prepared by diluting fresh stock solutions of I-VI (20 mM in DMSO) to 10 µM solutions with HCl aqueous solution to adjust pH to 4. DLS measurements samples of cycl-I-VI were prepared by adding 0.5 µL of freshly prepared stock solutions of 1-VI (20 mM in DMSO), 6 µL saturated sodium bicarbonate solution into 993.5 µL H$_2$O to adjust pH to 7.4.

Cell Culture: NCI-H460 human non-small cell lung cancer cells were culture in RPMI 1640 medium (GIBCO) supplemented with 10% fetal bovine serum (FBS, GIBCO), 100 U/mL penicillin and 100 µg/mL streptomycin (GIBCO). 9L/LacZ and 9L/Luc rat gliosarcoma cells were cultured in Dulbecco's modified eagle medium (GIBCO) supplemented with 10% fetal bovine serum (FBS, GIBCO), 100 U/mL penicillin and 100 µg/mL streptomycin (GIBCO).

In Vitro Validation of B-SNAF2/4-BDP Using HPLC and TEM: B-SNAF2/4-BDP (10 µM) was incubated with β-galactosidase enzyme (1 unit) alone or with β-galactosidase enzyme (1 unit) and TCEP (100 µM) simultaneously in PBS at 37° C. for 2 hours. Aliquots of these solutions were taken out and analyzed by analytical HPLC and DLS.

Measuring Competition Between Intermolecular Condensation and Intramolecular Cyclization: To a solution of SNAT4 (5 µM) in PBS buffer was added TCEP (20 µM), NaHCO$_3$ (100 µM) and various concentrations of L-cysteine (0-200 mM). The reactions were left at room temperature overnight and the resulting mixtures were analyzed by HPLC. The ratios of the two products were measured by comparing integration of the peak areas at 254 nm.

SDS-PAGE Analysis of Interactions Between SNAT2/4 and Intracellular Proteins: HeLa lysate was incubated with disulfide caged SNAT2/4 (100 µM) at 37° C. for 6 hours, followed by subsequent click reaction and HPLC analysis. To perform click reaction, the lysate samples were added Cy5-azide (50 µM), CuSO$_4$ (100 µM), ligand (BimC$_4$A)$_3$ (500 µM) and sodium L-ascorbate (2.5 mM, freshly made). The reaction was kept at 37° C. for 1 hour, followed by ultra-filtration with 10k cutoff to remove excess of Cy5-azide before loaded onto SDS-PAGE (NuPAGE® 4-12% Bis-Tris Gel) according to manufacturer's protocols for electrophoresis at 150 V for 120 min. As a control to evaluate the effectiveness of click reaction, BSA was first labeled with 6-heptynoic NHS ester (100 µM) at pH 8-8.5 at 4° C. for 8 hours followed by click reaction with Cy5-azide and ultrafiltration to remove excess dye. In-gel fluorescence was scanned with Lago-X imaging system followed by staining with Coomassie blue to visualize proteins.

Confocal Microscopy Imaging of 9L/LacZ Cell With B-SNAF2/4-BDP: Cells were incubated with B-SNAF2-BDP or B-SNAF4-BDP (2 µM) at 37° C. for 2 hours and then were then washed three times with cold PBS. The cells were fixed with 4% paraformaldehyde and stained with 2 µM Hoechst 33258 (Sigma) for 10 min. The cells were washed three times with PBS mounted with 2 µM Hoechst 33258 (Sigma) at 37° C. for 20 min. Cells were then fixed and imaged using a confocal laser scanning microscope (Zeiss LSM710; Zeiss America) with DAPI and DsRed filters. The images were processed using the ImageJ software package (National Institutes of Health).

Validation of LacZ Expression By X-gal Staining: Cells were fixed with paraformaldehyde for 15 min at room temperature and were washed with PBS buffer 3 times. The cells were then stained with X-Gal staining solution (1 mg/mL X-Gal, 5 mM K$_4$Fe(CN)$_6$, 5 mM K$_3$Fe(CN)$_6$ and 1 mM MgCl$_2$ in PBS buffer, freshly prepared) at 37° C. overnight. The cells were washed three times with PBS and imaged with light microscope.

In Vitro Validation of C-SNAF4-Cy5 Nanoaggregate Using TEM and DLS: C-SNAF4-Cy5 (20 µM) was incubated with caspase-3 ($2\times10^{-3}$ U mL$^{-1}$, human, recombinant from E. coli, Sigma) in caspase buffer (50 mM HEPES, 100 mM NaCl, 1 mM EDTA, 10 mM TCEP, 10% glycerol and 0.1% CHAPS at pH 7.4) at 37° C. overnight. Aliquots of resulting reaction mixture were then analyzed by DLS and TEM.

Confocal Microscopy Imaging of Cisplatin-treated H460 Cells With C-SNAF4-Cy5: NCI-H460 cells at 70% confluency were either left naïve or treated with cisplatin (10 µM) for 24 hours. After removal of the medium, cells were incubated with 2 µM C-SNAF4-Cy5 at 37° C. for 24 hours. For the inhibition study, cells were first incubated with pan-caspase inhibitor Z-VAD-fmk (50 µM, 30 min) before incubation with C-SNAF4-Cy5. The cells were then washed three times with PBS, mounted with 2 µM Hoechst 33258 (Sigma) at 37° C. for 20 min. After changing medium, cells were fixed and imaged using a confocal laser scanning microscope (Zeiss LSM710; Zeiss America) with DAPI and DsRed filters. The images were processed using the ImageJ software package (National Institutes of Health).

Western Blot Analysis: The procedures for Western blot have been previously described.[1] In brief, H460 cells were lysed in radioimmunoprecipitation (RIPA) assay buffer according to the manufacturer's protocols (Sigma-Aldrich). Samples were centrifuged, the supernatant was collected, and the protein content was determined by BCA Assay (Bio-Rad Inc.). Thirty micrograms of lysate were loaded on NuPAGE gel for electrophoresis at 200 V for 90 min. Wet transfer was performed using the Bio-Rad transfer kit at 300 mA for 90 min. The transferred nitrocellulose membrane was blocked in PBS containing 5% bovine serum albumin and 0.1% Tween-20 for 1 hour. Primary antibody (anti-cleaved caspase-3, Cell Signaling; anti-pro-caspase-3, Cell Signaling; anti-actin, Sigma-Aldrich) incubation (1:2000) was performed in the blocking buffer overnight at 4° C. The membrane was then washed four times with PBS containing 0.1% Tween 20. Secondary antibody incubation (LI-COR donkey anti-mouse IgG IRDye 680 or anti-rabbit IgG IRDye 800CW) was performed in the blocking buffer for 2 hours at room temperature. After washing four times with PBS containing 0.1% Tween 20, the membrane was analyzed using a LI-COR Odyssey imaging system.

Example 3

Methionine Aminopeptidase II Activated Self-Nanoaggregation Probe

The disclosure encompasses embodiments of a methionine aminopeptidase II (MetAP2)-activated self-nanoaggregation tracer for detecting MetAP2 activity in vivo. The expression pattern of MetAP2 in prostate cancer tissue slides and microarrays from 513 patients found the overexpression of MetAP2 in 54% of the low-grade and 59% of the high-grade cancer but none in benign prostatic hyperplasia (BPH). The overexpression of MetAP2 in cancer also prognosticated aggressive disease with a higher chance of biochemical recurrence.

Employing an optimized controlled self-assembly of synthetic small molecule, an MetAP2-activated self-nanoaggregation tracer for detecting MetAP2 activity in vivo was generated. The nanoaggregates derived from the MetAP2 activated self-nanoaggregation tracers were assembled in PC3, DU145 and 22Rv1 cells and were imaged with a post click fluorescent labeling. A fluorine-18 labeled tracer successfully differentiated the MetAP2 activity in human tumor xenografts with a microPET/CT scanner. This non-invasive and highly sensitive MetAP2 sensing tracer, therefore is advantageous for enhancing the risk stratification of prostate cancer at the point of diagnosis. Further, PET tracers that can traverse the cell membrane, and detect and amplify the activity of molecules essential for intrinsic biochemical alterations during cancer initiation and progression is desirable.

Methionine aminopeptidase II (MetAP2) is a cytosolic metalloprotease that catalyzes the co-translational removal of the N-terminus initiator methionine residue from nascent proteins (Li & Chang Proc. Natl. Acad. Sci. U.S.A. (1995) 92: 12357-12361). MetAP2 overexpression indicates a hyperactive protein biosynthesis, is a target for treatment of angiogenesis and is a pathological determinant in the progression of solid tumors (Tucker et al., *Oncogene* (2008) 27: 3967-3976; Sin et al., *Proc. Natl. Acad. Sci. U.S.A.* (1997) 94: 6099-6103; Griffith et al., *Proc. Natl. Acad. Sci. U.S.A.* (1998) 95: 15183-15188). It has now been shown that MetAP2 may serve as a biomarker for PC. Overexpression of MetAP2 was observed in more than half of PC patients which, at the point of diagnosis, also predicted an aggressive disease with a higher chance of biochemical recurrence.

Currently, there have been few successes of intracellular enzyme probing systems characterized in living animals with PET and which must be highly biorthogonal and biocompatible [19, 20]. The present disclosure, however, encompasses methods for a rapid condensation reaction between 6-hydroxy-2-cyanobenzothiazole (CBT) and D-cysteine and a backbone of peptides with 2-cyanopyrimidine that reacts with free cysteine at a much slower reaction rate. This allows an exclusively intramolecular cyclization independent of concentration. In the novel MetAP2 activated self-nanoaggregation tracer (M-SNAT) probes of the disclosure that masks the free cysteine with a methionine residue, upon MetAP2 hydrolysis self-cyclizes and aggregates into nano structures for enhanced retention. A series of in vitro and in vivo studies demonstrated that the MetAP2-controlled self-assembly of small molecules into nanoparticles are advantageous to distinguish MetAP2 activity. The fluorine-18 labeled nanoparticles assembled and retained in tumors were imaged with a PET/CT scanner, thereby providing probes for use in live animals and supports the potential for molecular imaging of MetAP2 for PC diagnosis and risk stratification.

Overexpression of MetAP2 in PC and association with higher chance of biochemical recurrence: The study was initiated by measuring the expression level of MetAP2 in different cell lines including a primary benign human prostate epithelial cell line BS403, ATCC prostate cancer (PC) cell lines PC3, DU145, 22Rv1, and derived tumor xenografts. BS403 was generated as previously described (Goldstein et al., *Nat. Protoc.* (2011) 6: 656-667); PC3 and DU145 were derived from metastasized PC in bone and brain; 22Rv1 was derived from cancerous epithelial cells in primary tumor (Kaighn et al., *Invest. Urol.* (1979) 17: 16-23; Mickey et al., *Cancer Res.* (1977) 37: 4049-4058; Stone et al., *Int. J. Cancer.* (1978) 21:274-281; Sramkoski et al. *In Vitro Cell Dev. Biol. Anim.* (1999) 35: 403-409).

Figure 42A:
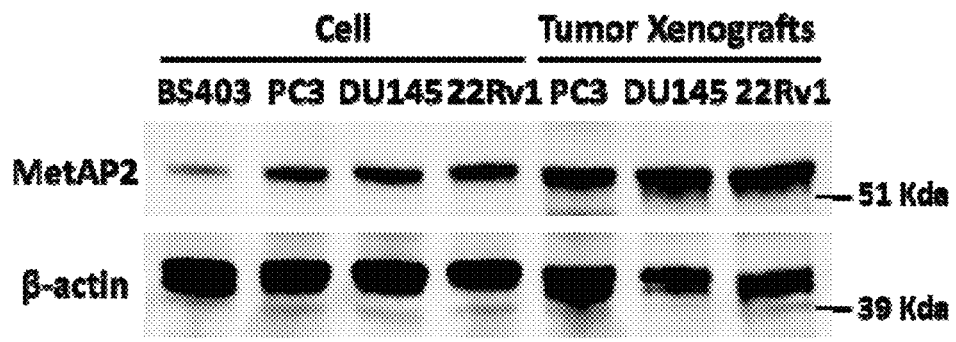
FIGS. 42A-42E illustrate the expression of MetAP2 in cancer cells, tumor xenografts, clinical prostate cancer biopsies and the association with biochemical recurrence.
Figure 42B:
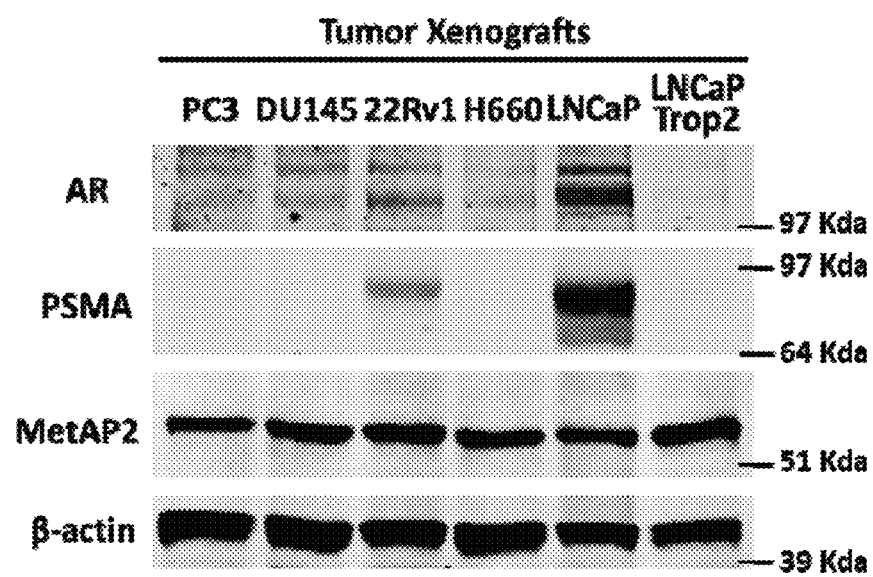

As shown in FIG. 42A, BS403 was expressed at a lower level of MetAP2 than PC3, DU145, or 22Rv1. When developed into tumor xenografts, the MetAP2 expression was further elevated in all 3 PC lines which reflected its role in tumor proliferation and angiogenesis. Unlike androgen receptor (AR) and PSMA, MetAP2 is also highly expressed in neuroendocrine NCI-H660 cells and engineered LNCaP cells that the mimic neuroendocrine phenotype with Trop2 (tumor-associated calcium signal transducer 2) overexpression (FIG. 42B).

Immunohistochemistry (IHC) analysis of tissues slides from PC3, DU145, 22Rv1, NCI-H660, LNCaP and LNCaP-Trop2 xenografts further showed the overexpression of MetAP2 in these PC models. In comparison, PSMA was abundantly expressed only in LNCaP tumor. These results suggested that a raised MetAP2 activity may be universal in PC.

Figure 42C:
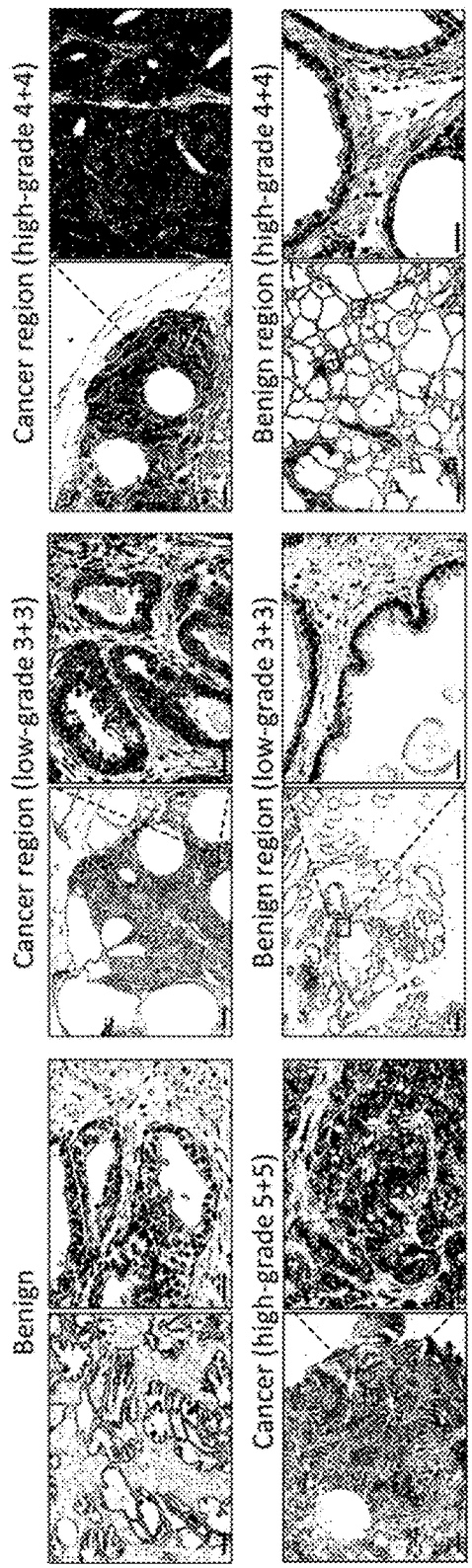

As shown in FIG. 42C, benign tissues express negligible amounts of MetAP2 in closely packed, well-formed large glands. Low-grade cancer (3+3) has recognizable but irregular cribriform glands with an infiltrative pattern; moderate to high MetAP2 staining was observed, especially in cancerous columnar cells around lumen. High-grade cancer exhibits sheets of cancer cells (4+4) and rosette formation with scattered clear vacuoles (5+5). High staining of MetAP2 with high-grade cancers was observed.

Figure 42D:
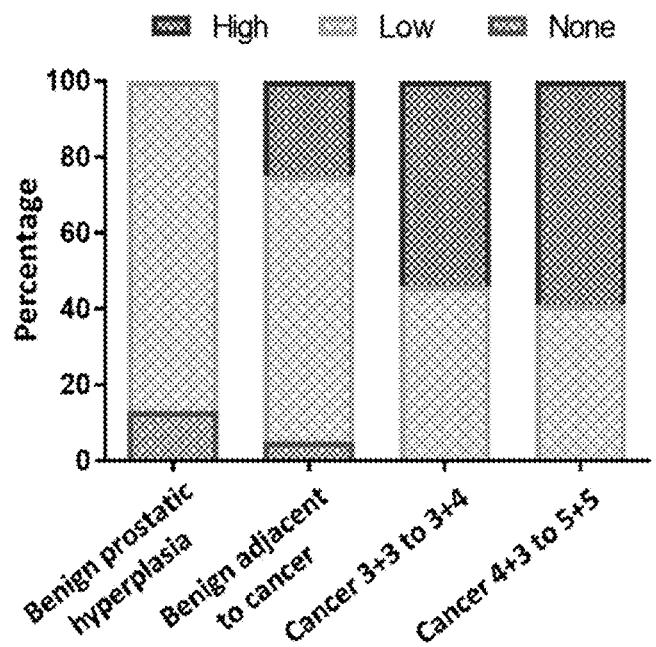

Benign regions in the same tissue slide (3+3, 4+4) have overall low expression. Thus, high staining for MetAP2 (average greater than 2) was found in 25% of the benign tissues adjacent to cancer, 54% of low-grade Gleason grade 3+4) and 59% of high-grade cancer (≤Gleason grade 4+3). For benign prostatic hyperplasia (BPH), there was no high staining (None: 0; low: average>1&≤2) observed (FIG. 42D). The average score of MetAP2 intensity in BPH group was lower than cancer. There were no significant differences between normal adjacent to cancer, low, and high-grade PC statistically).

Figure 42E:
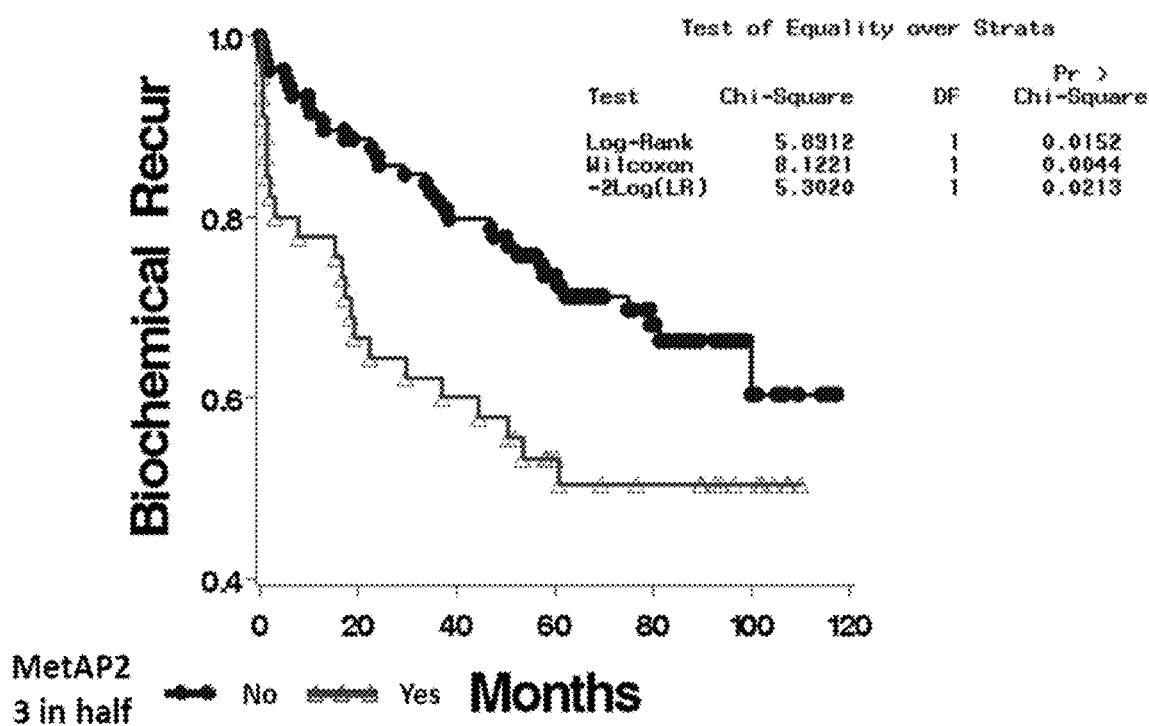

Patients were divided into low and high MetAP2 expression groups and the chance of biochemical recurrence through 10 years was plotted in kaplan-meier curves. As shown in FIG. 42E, when high MetAP2 staining (scored at 3) was identified in at least 2 of 3 biopsy cores from a patient (mostly all 3 cores), the PC tend to be aggressive and doubled the chance of biochemical recurrence at year 5 (60 months, from 25% to 50%). High staining in any of or all the biopsy cores presented similar results. These data suggest that more than half of PCs overexpress MetAP2. The overexpression identified at the point of diagnosis may, therefore, predict aggressive PC with a higher chance of biochemical recurrence. Further, molecular imaging of MetAP2 activity would serve as a prognostic biomarker for disease stratification. Design of MetAP2-sensitive and control probes: Provided are embodiments of an MetAP2-sensitive nanoaggregation tracer (M-SNAT) probe that is biocompatible and undergoes triggered self-assembly through condensation chemistry in vivo.

FIG. 43A illustrates an embodiment of an MetAP2-activated self-assembly molecule design of the disclosure: the small molecule carries a methionine (P1) followed by a cysteine (P2) on the N-terminus, linked to a multi-peptide backbone, and a 2-cyanopyrimidine at the C-terminus. In eukaryotes, the MetAP2 substrates prefer the penultimate residue (P2) with a small nonpolar side chain (e.g. Gly, Ala, Ser, Thr, Val, Cys) (Li & Chang *Proc. Natl. Acad. Sci. U.S.A.* (1995) 92: 12357-12361; Arfin et al., *Proc. Natl. Acad. Sci. U.S.A.* (1995) 92: 7714-7718; Bradshaw et al., *Trends Biochem. Sci.* (1998) 23: 263-267).

Upon intravenous administration, M-SNAT quickly extravasates into tissues. In normal prostatic or BPH tissues, M-SNAT remains mostly intact or partially reduced and diffuses away freely. In cancer cells with high MetAP2 activity, cleavage and release of the P1 methionine residue by MetAP2 as well as the reduction of the disulfide bond by intracellular glutathione (GSH) triggers an intramolecular condensation reaction. Unlike the unprocessed linear compound, the cyclized macromolecules become rigid, hydrophobic, and tend to interact with each other intermolecularly to form nanoaggregates, as shown in FIG. 43B.

Figure 43C:
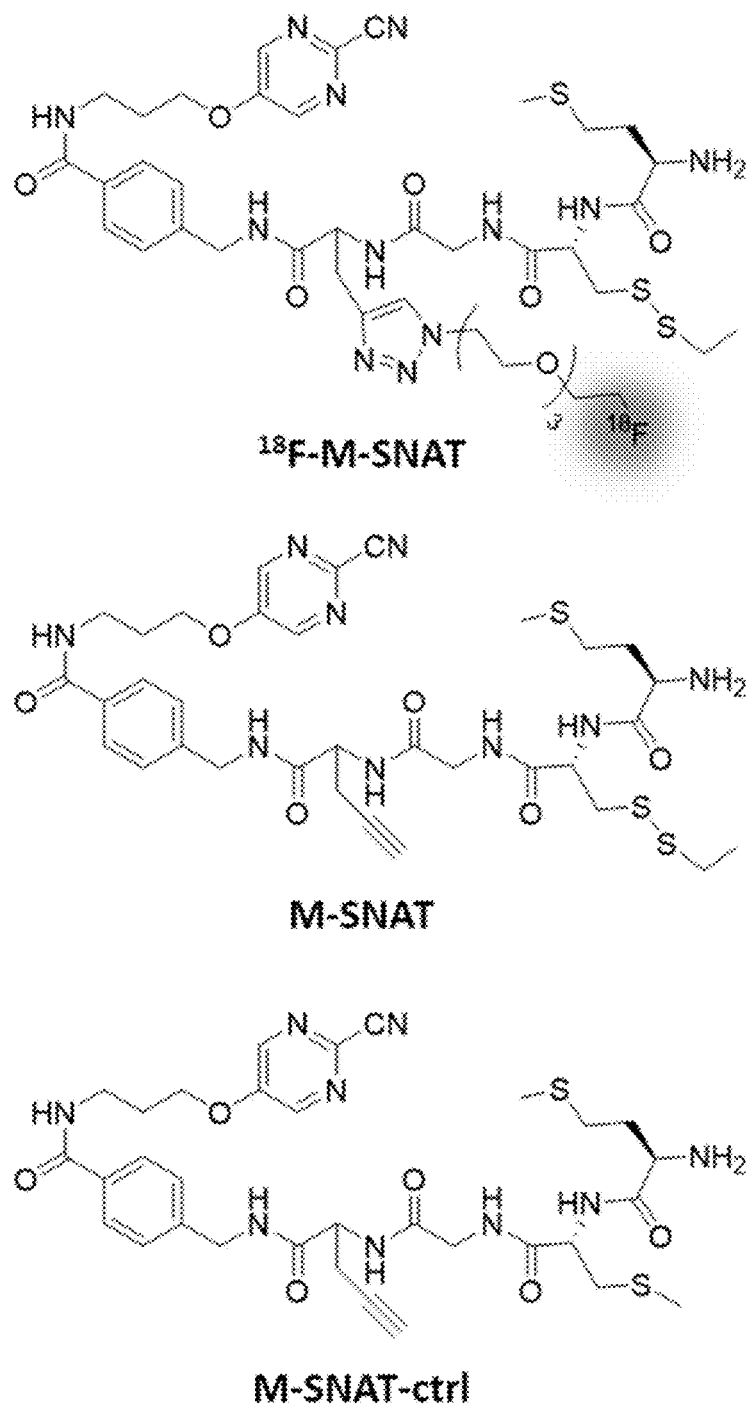
Figure 44A:
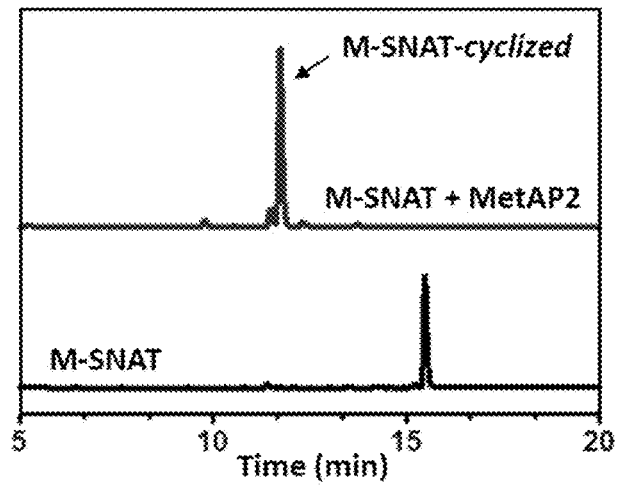
FIGS. 44A-44C illustrate the in vitro characterization of the M-SNAT.
Figure 44B:
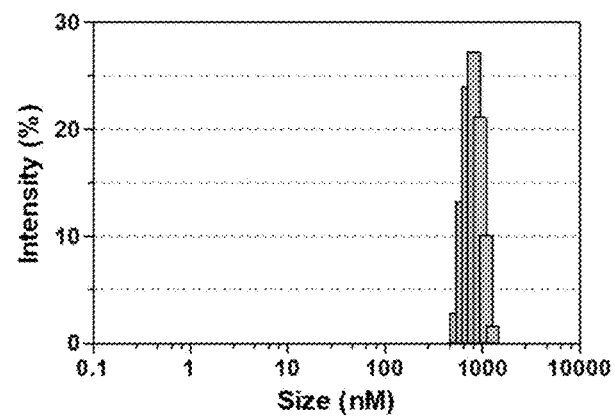
Figure 44C:
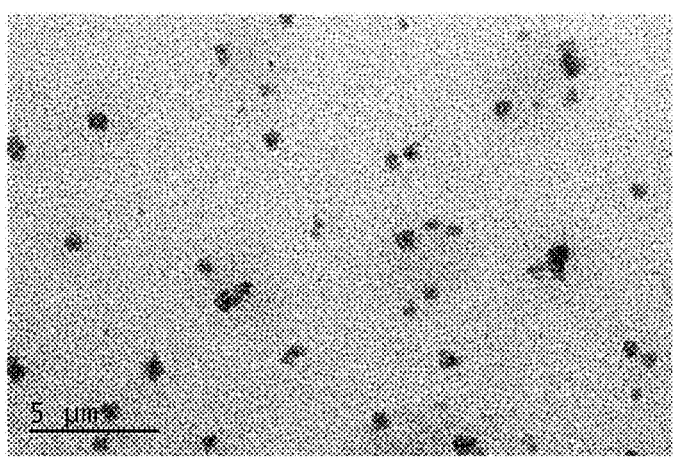

By tagging the probe with a fluorine-18, the location and amounts of the nanoaggregates in vivo can be detected by PET imaging (FIG. 43C, top compound). For in vitro studies, a post-click reaction at the propargylglycine with an azide conjugated far-red fluorophore Cy 5 (Cyanine 5) can be used to detect the aggregated and precipitated M-SNAT in cells (FIG. 43C, middle compound). A control compound M-SNAT-ctrl having a methylated thiol that prevents intramolecular cyclization after methionine cleavage by MetAP2 was used to exam the role of cyclization and aggregation in the activity of M-SNAT (FIG. 43C, bottom compound). Macrocyclization and self-nanoaggregation of M-SNAT in vitro: Macrocyclization of M-SNAT to give M-SNAT-cyclized was monitored in solution using high-performance liquid chromatography (HPLC) and mass spectrometry. On incubation with recombinant human MetAP2 (7.5 μg/ml) in reaction buffer containing 0.1 mM $MgCl_2$, M-SNAT (10 μM; HPLC retention time, $T_R$=15.5 minutes) was converted into M-SNAT-cyclized ($T_R$=11.8 minutes) after 24 h incubation in the presense of tris(2-carboxyethyl)phosphine (TCEP) to mimic the intracellular reducing environment (FIG. 44A). In contrast, M-SNAT-ctrl could not cyclize due to the non-reducible methylated thiol group. Dynamic light scattering (DLS) analysis and transmission electron microscopy (TEM) images showed the formation of nanoparticles with an average diameter of 861 nm (531-1281 nm) (FIGS. 44B and 44C). Thus, MetAP2 catalyzed removal of the methionine residue inducing M-SNAT to undergo intramolecular macrocyclization leading to nanoaggregation.

Figure 45A:
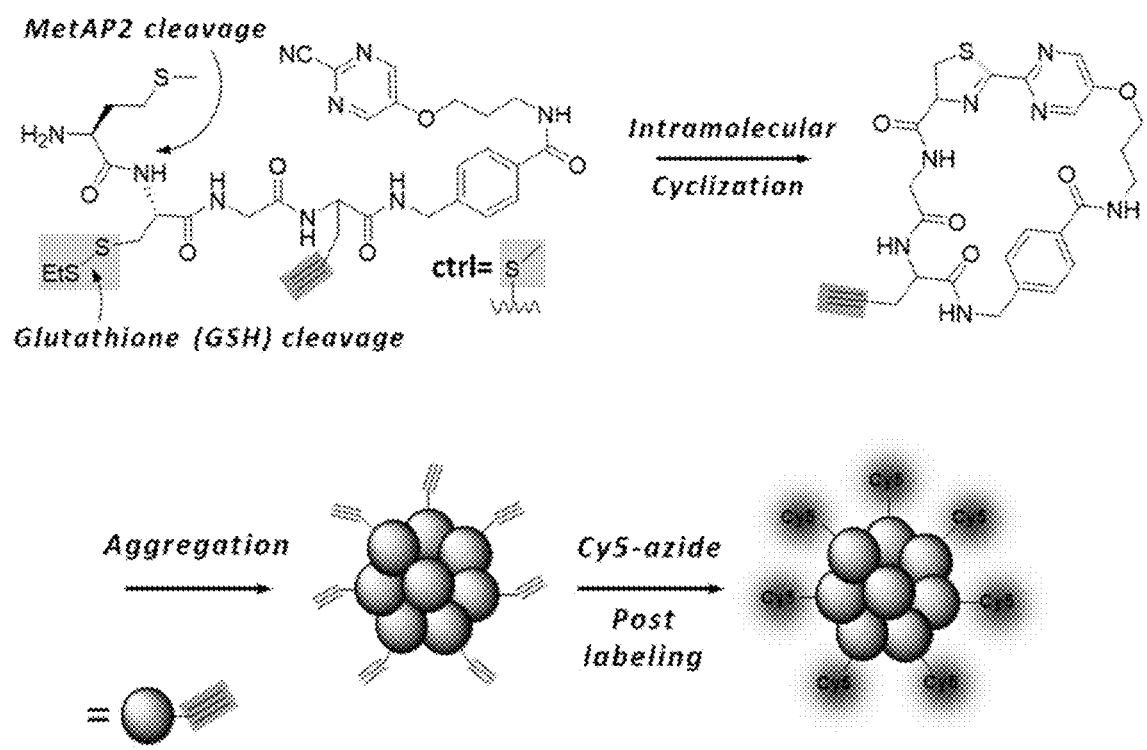
FIGS. 45A and 45B illustrate the imaging of MetAP2 activity with or without TNP-470 in PC3 cells.

Imaging MetAP2 activity in cancer cells: Cell uptake and MetAP2 specific activation of M-SNAT and M-SNAT-ctrl were evaluated in PC3 and DU145 cells with the MetAP2-specific inhibitor TNP-470. Post click fluorescent labeling was performed as illustrated in FIG. 45A to locate the nanoaggregation in cells and avoid the possible interference with probe uptake by pre-conjugating a large Cy5 fluorophore.

Figure 45B:
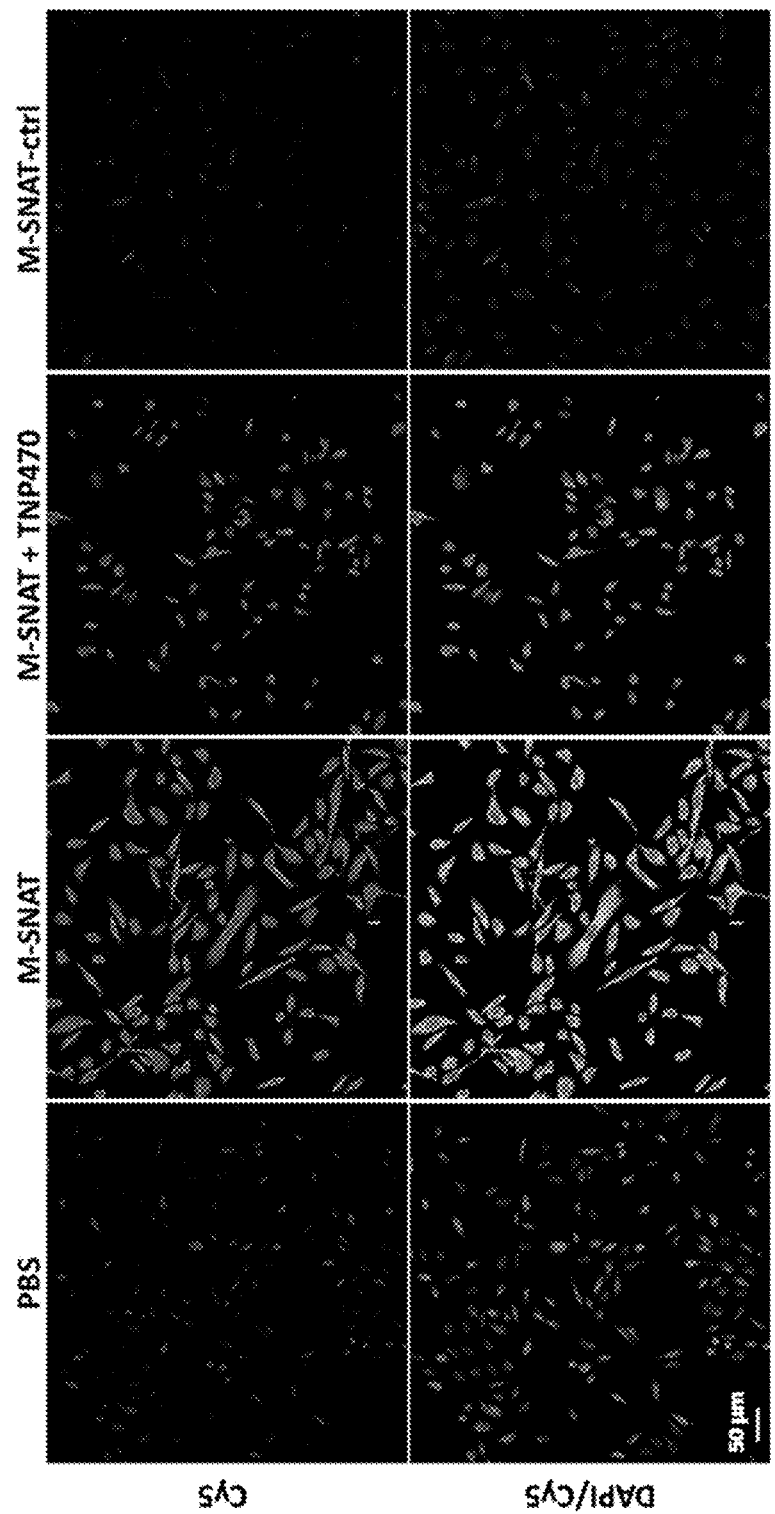

After 24 h incubation, red fluorescence was observed in M-SNAT (20 µM) treated PC3 and DU145 cells but not with M-SNAT-ctrl (20 µM) (FIG. 45B). The accumulation of M-SNAT in DU145 was in a dose-dependent manner. When TNP-470 (2 µM) was added to specifically block MetAP2 activity in cells, the fluorescence in both PC3 and 22Rv1 was significantly reduced (FIG. 45B). Quantitative analysis by flow cytometry revealed a 22.7% inhibition by TNP-470 when PC3 cells were treated, permealized and post-labeled.

To further validate the MetAP2 dependent M-SNAT activation, MetAP2 knockdown (KD) PC3 and 22Rv1 cells were generated (92.4% and 62.6% KD, respectively). The KD itself did not alter cell growth in medium. As with inhibitor studies, much weaker red fluorescence was observed in both PC3 and 22Rv1 KD cells after incubation with M-SNAT for 24 h. These cell studies indicate specific intracellular accumulation of M-SNAT after MetAP2-triggered macrocyclization and aggregation.

Figure 46A:
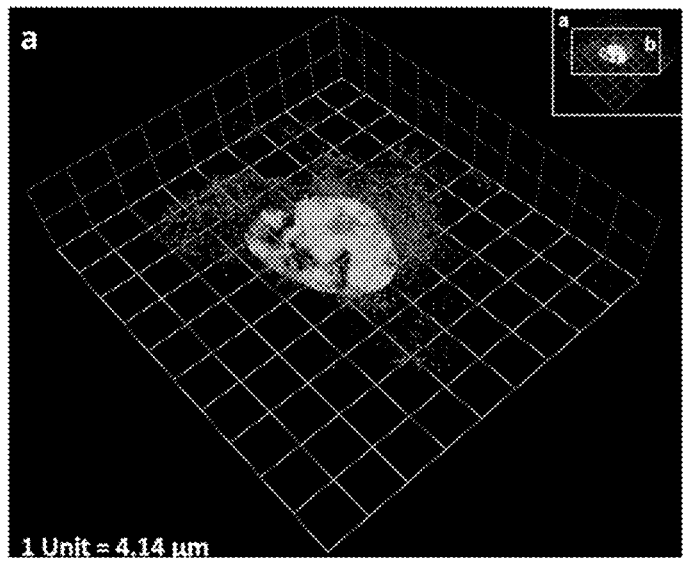
FIGS. 46A-46C illustrate 3D projected Super-Resolution Structured Illumination Microscope (SR-SIM) imaging of cy5 post-labeled self-nanoaggregation of M-SNAT in a single PC3 cell.
Figure 46B:
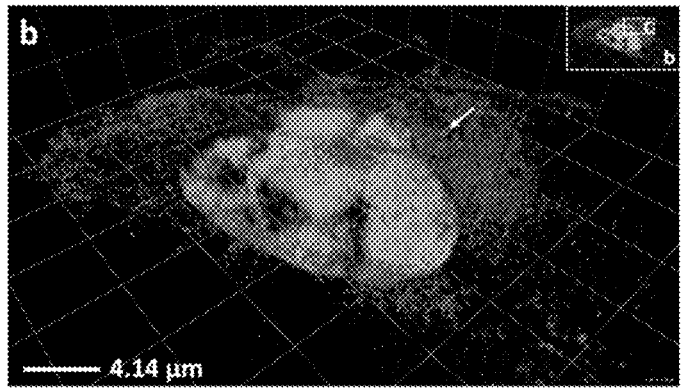
Figure 46C:
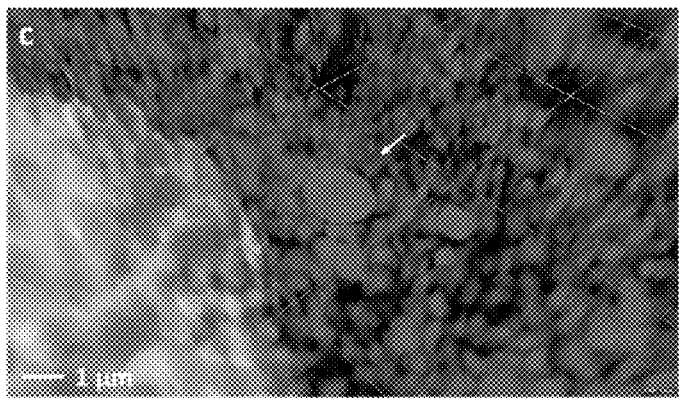

Direct observation of the nanoparticles formed in a single PC3 cell: The 3D structure of the aggregated particles in a single PC3 cell were visualized using a SR-SIM (Superresolution Structured Illumination Microscope) which can achieve both lateral (XY) and axial (Z) resolution at twice the diffraction limit of conventional high-resolution light microscope systems such as confocal (FIG. 46). The size of particles formed in situ varied from a few hundred nanometers to more than one micron, similar to the diameters measured by DLS and TEM (FIGS. 44B and 44C).

The post labeled red fluorescent aggregates occurred throughout the cytoplasm with relatively higher density surrounding nucleus. This distribution represents the activity of MetAP2 in processing newly synthesized peptides from ribosomes and was consistent with association with the rough endoplasmic reticulum adjacent to the nucleus or floating freely through the whole cytoplasm.

Figure 47A:
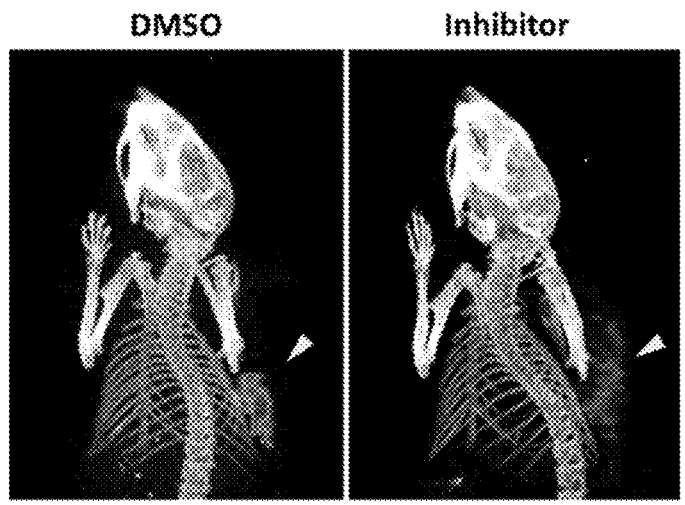
FIGS. 47A-47C illustrate $^{18}$F-M-SNAT PET/CT imaging of a PC3 xenograft mouse model.

PET/CT imaging of MetAP2 activity in tumor: Before applying fluorine-18 labeled M-SNAT ($^{18}$F-M-SNAT) for studies in vivo, the stability of non-radioactive $^{19}$F-M-SNAT was investigated in mouse serum. The ability of $^{18}$F-M-SNAT to indicate MetAP2 activity was assessed in male nude mice bearing subcutaneous PC3 tumors. When the tumors (right shoulder) were grown to 300-500 mm³, PBS with or without TNP-470 were injected subcutaneously at 50 mg/kg at a remote position (lower left on the back) every other day for 4 days and then injected every day for 5 more days. The last injection was 4 h before imaging (FIG. 47A).

Figure 47B:
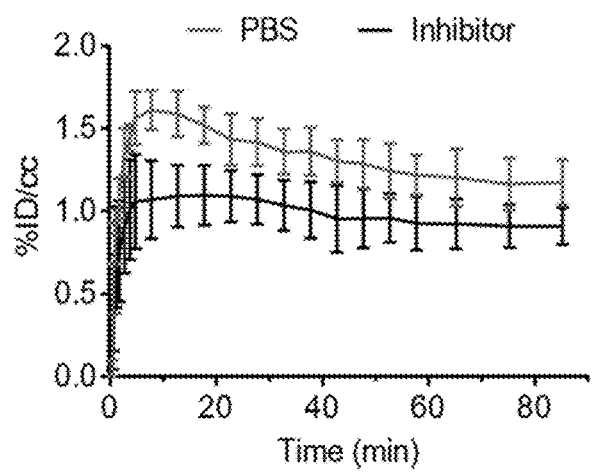
Figure 47C:
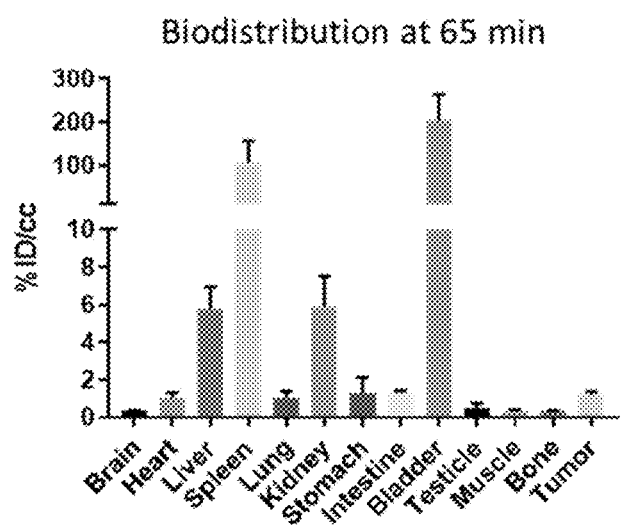

Tumor growth was measured every other day and no significant difference between the inhibitor- or PBS-treated groups was observed because of a low dose of inhibitors injected in a relatively short period of time. On the day of imaging, fluorine-18 was generated using a cyclotron and conjugated to M-SNAT in a rapid two-step chemical synthesis (FIG. 44). About 150 µCi (8.9 pmol)$^{18}$F-M-SNAT were injected to mice intravenously for a programed micro-PET/CT whole body scan through 90 min. As shown in FIG. 47B, PBS-treated tumors showed significantly brighter signals than TNP-470-treated tumors in reconstructed PET/CT images. A rapid uptake to 1.6% of the injected dosage per cc volume (ID/cc) was observed in PBS-treated tumors within 10 min. About 1.3% was retained at 90 min. In comparison, the inhibitor-treated mice hold about 1% ID/cc through the whole scanning period (FIG. 47C). A fast clearance by kidney to bladder was observed. Liver and spleen showed high signal as well, whereas brain, bone and muscle have very low background (FIG. 47D). Tumors were resected 20 h after tracer injection for IHC staining ex vivo.

The expression of MetAP2 in tumors was not affected by TNP-470 so the inhibition was only directed to the methionine hydrolysis. CD31 as a biomarker for neovasculature also had no change, supporting that TNP-470 did not inhibited MetAP2 activity and further suppressed tumor angiogenesis for tracer delivery. Therefore, $^{18}$F-M-SNAT can be utilized to image the MetAP2 activity of individual PC tumors.

What is claimed:
1. A compound having formula:

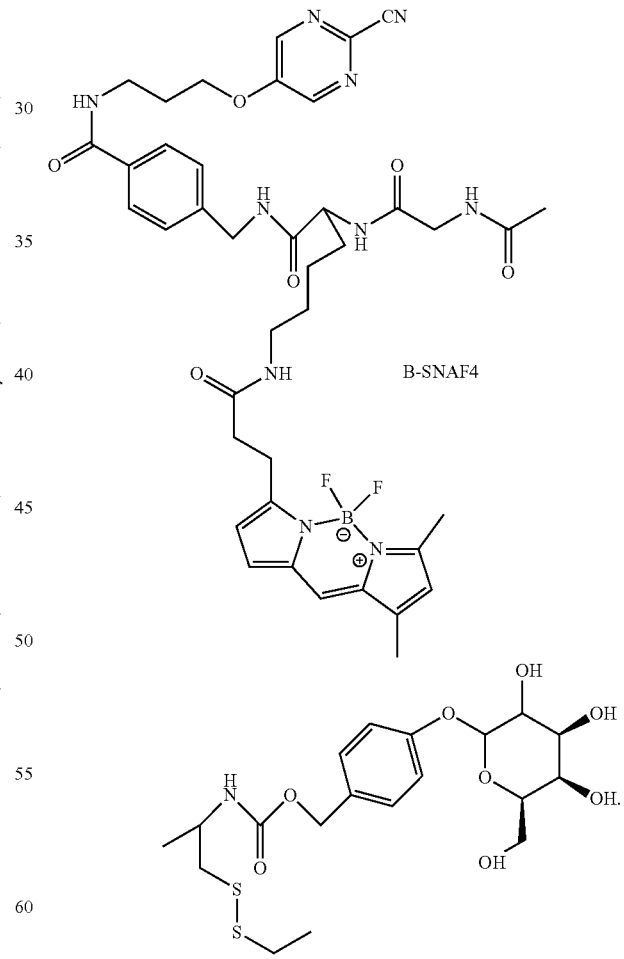

2. A pharmaceutical composition comprising the compound of claim 1 and a pharmaceutically acceptable carrier.

3. A method of imaging nanoaggregates in a subject, the method comprising:

(i) administer to the subject a compound having formula:
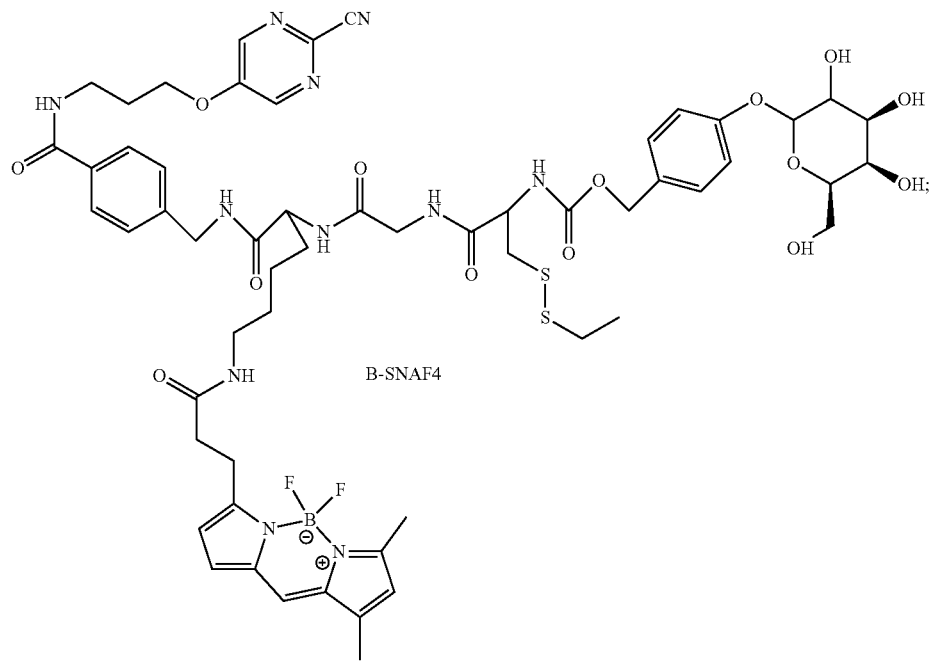 [SMILES: CCSSCC(NC(=O)OCc1ccc(OC2O[C@H](CO)[C@H](O)[C@H](O)C2O)cc1)C(=O)NCC(=O)NC(CCCCNC(=O)CCc1ccc2n1[B-](F)(F)[N+]1=C(C)C=C(C)C1=C2)C(=O)NCc1ccc(C(=O)NCCCOc2cnc(C#N)nc2)cc1]
B-SNAF4
and
(ii) obtaining an image of the nanoaggregates in the subject.
* * * * *